US009828604B2

(12) United States Patent
Hoffmann et al.

(10) Patent No.: US 9,828,604 B2
(45) Date of Patent: Nov. 28, 2017

(54) PHOSPHODIESTERASE 9A AS PROSTATE CANCER MARKER

(75) Inventors: Ralf Hoffmann, Brueggen (DE); Miles Douglas Houslay, Renfrewshire (GB); David James Peter Henderson, Newton Stewart (GB)

(73) Assignees: Koninklijke Philips N.V., Eindhoven (NL); The University Court of the University of Glasgow, Central Scotland (GB)

( * ) Notice: Subject to any disclaimer, the term of this patent is extended or adjusted under 35 U.S.C. 154(b) by 1271 days.

(21) Appl. No.: 13/320,446

(22) PCT Filed: May 11, 2010

(86) PCT No.: PCT/IB2010/052069

§ 371 (c)(1), (2), (4) Date: Nov. 14, 2011

(87) PCT Pub. No.: WO2010/131193

PCT Pub. Date: Nov. 18, 2010

(65) Prior Publication Data

US 2012/0065100 A1 Mar. 15, 2012

(30) Foreign Application Priority Data

May 12, 2009 (EP) .................................... 09159957

(51) Int. Cl.

| | |
|---|---|
| ***C12Q 1/68*** | (2006.01) |
| ***C12N 15/113*** | (2010.01) |
| ***C12N 9/16*** | (2006.01) |
| ***G01N 33/574*** | (2006.01) |

(52) U.S. Cl.

CPC ............ *C12N 15/1137* (2013.01); *C12N 9/16* (2013.01); *C12Q 1/6886* (2013.01); *G01N 33/57434* (2013.01); *C12Q 2600/106* (2013.01); *C12Q 2600/112* (2013.01); *G01N 2800/52* (2013.01)

(58) Field of Classification Search

CPC .................................................. G01N 33/574

USPC ............................................................ 506/9

See application file for complete search history.

(56) References Cited

U.S. PATENT DOCUMENTS

| | | | |
|---|---|---|---|
| 2006/0025457 A1 | 2/2006 | Muller | |
| 2006/0269546 A1 | 11/2006 | Srivastava | |
| 2008/0269157 A1 | 10/2008 | Srivastava | |

FOREIGN PATENT DOCUMENTS

| | | |
|---|---|---|
| WO | 9929873 A1 | 6/1999 |
| WO | 2004042389 A2 | 5/2004 |
| WO | 2004053492 A1 | 6/2004 |
| WO | 2004053493 A1 | 6/2004 |
| WO | 2004053495 A1 | 6/2004 |
| WO | 2004053494 A1 | 6/2006 |

OTHER PUBLICATIONS

Strausberg et al, in Microarrays and Cancer Research, 2002, Warrington et al (eds.), Eaton Publishing, Westborough, MA, pp. xi-xvi.*

Notterman et al, in Microarrays and Cancer Research, 2002, Warrington et al (eds.), Eaton Publishing, Westborough, MA, pp. 81-111.*

Gretarsdottir et al, "The gene encoding phosphodiesterase 4D confers risk of ischemic stroke", Nautre Genetics Advance Online Publication, published online Sep. 23, 2003, pp. 1-8.*

Zhang, Lingzhi et al "Cyclic Nucleotide Phosphodiesterase Profiling Reveals Increased Expression of Phosphodiesterase 7B in Chrinic Lymphocytic Leukemia", Proceedings of the National Academy of Sciences of the United States of America, vol. 105, No. 49, Dec. 2008, pp. 19532-19537.

Ellington, Andrew D. et al "In Vitro Selection of RNA Molecules that Bind Specific Ligands" Nature, vol. 346, Aug. 30, 1990, pp. 818-822.

"Identification and Distribution of Different mRNA Variants Produced by Differential Splicing in the Human Phosphodiesterase 9A Gene" Rentero et al, Biochemical and Biophysical Research Communications 301 (2003) p. 686-692.

"A Hierarchical Network of Transcription Factors Governs Androgen . . . " Wang et al , Molecular Cell 27, Aug. 3, 2007 p. 380-392.

Baillie GS, Adams DR, Bhari N, Houslay TM, Vadrevu S, Meng D, Li X, Dunlop A, Milligan G, Bolger GB, Klussmann E, Houslay MD (2007) Mapping binding sites for the PDE4D5 cAMP-specific phosphodiesterase to the N- and C-domains of beta-arrestin using spot-immobilized peptide arrays. Biochem J 404: 71-80.

(Continued)

*Primary Examiner* — James Martinell

(57) ABSTRACT

The present invention relates to phosphodiesterase 9A (PDE9A) for use as a marker for prostate cancer, and the use of PDE9A as a marker for diagnosing, detecting, monitoring or prognosticating prostate cancer or the progression of prostate cancer. The present invention also relates to a composition for diagnosing, detecting, monitoring or prognosticating prostate cancer or the progression of prostate cancer, a corresponding method and immunoassay, a method for diagnosing, monitoring or prognosticating hormone-resistant prostate cancer vs. hormone-sensitive prostate cancer, a corresponding immunoassay, a method of data acquisition, an immunoassay for diagnosing, detecting, monitoring or prognosticating prostate cancer or the progression of prostate cancer, a method of identifying an individual for eligibility for prostate cancer therapy, an immunoassay for stratifying an individual or cohort of individuals with a prostate cancer disease, an immunoassay for stratifying an individual with prostate cancer. The present invention further envisages pharmaceutical compositions and their use for the treatment of prostate cancer, in particular hormone-resistant prostate cancer.

4 Claims, 13 Drawing Sheets

(56) References Cited

OTHER PUBLICATIONS

Baillie GS, Houslay MD (2005) Arrestin times for compartmentalised cAMP signalling and phosphodiesterase-4 enzymes. Curr Opin Cell Biol 17: 129-134.
Baillie GS, Sood A, McPhee I, Gall I, Perry SJ, Lefkowitz RJ, Houslay MD (2003) beta-Arrestin-mediated PDE4 cAMP phosphodiesterase recruitment regulates beta-adrenoceptor switching from Gs to Gi. Proc Natl Acad Sci U S A 100: 940-945.
Bolger GB, Baillie GS, Li X, Lynch MJ, Herzyk P, Mohamed A, Mitchell LH, McCahill A, Hundsrucker C, Klussmann E, Adams DR, Houslay MD (2006) Scanning peptide array analyses identify overlapping binding sites for the signalling scaffold proteins, beta-arrestin and RACK1, in cAMP-specific phosphodiesterase PDE4D5. Biochem J 398: 23-36.
Bos JL (2006) Epac proteins: multi-purpose cAMP targets. Trends in biochemical sciences 31: 680-686.
Conti M, Beavo J (2007) Biochemistry and physiology of cyclic nucleotide phosphodiesterases: essential components in cyclic nucleotide signaling. Annu Rev Biochem 76: 481-511.
D'Sa C, Tolbert LM, Conti M, Duman RS (2002) Regulation of cAMP-specific phosphodiesterases type 4B and 4D (PDE4) splice variants by cAMP signaling in primary cortical neurons. Journal of neurochemistry 81: 745-757.
Houslay MD (2001) PDE4 cAMP-specific phosphodiesterases. Prog Nucleic Acid Res Mol Biol 69: 249-315.
Houslay MD, Adams DR (2003) PDE4 cAMP phosphodiesterases: modular enzymes that orchestrate signalling cross-talk, desensitization and compartmentalization. Biochem J 370: 1-18.
Houslay MD, Baillie GS, Maurice DH (2007) cAMP-Specific phosphodiesterase-4 enzymes in the cardiovascular system: a molecular toolbox for generating compartmentalized cAMP signaling. Circ Res 100: 950-966.
Houslay MD, Milligan G (1997) Tailoring cAMP-signalling responses through isoform multiplicity. Trends in biochemical sciences 22: 217-224.
Houslay MD, Schafer P, Zhang KY (2005) Keynote review: phosphodiesterase-4 as a therapeutic target. Drug Discov Today 10: 1503-1519.
Lugnier C (2006) Cyclic nucleotide phosphodiesterase (PDE) superfamily: a new target for the development of specific therapeutic agents. Pharmacol Ther 109: 366-398.
Lynch MJ, Baillie GS, Mohamed A, Li X, Maisonneuve C, Klussmann E, van Heeke G, Houslay MD (2005) RNA silencing identifies PDE4D5 as the functionally relevant cAMP phosphodiesterase interacting with beta arrestin to control the protein kinase A/AKAP79-mediated switching of the beta2-adrenergic receptor to activation of ERK in HEK293B2 cells. J Biol Chem 280: 33178-33189.
McCahill A, Campbell L, McSorley T, Sood A, Lynch MJ, Li X, Baillie GS, Houslay MD (2008) In cardiac myocytes, cAMP elevation triggers the down-regulation of transcripts and promoter activity for cyclic AMP phosphodiesterase-4A10 (PDE4A10). . Cell Signal:, 20: 2071.
McCahill A, McSorley T, Huston E, Hill EV, Lynch MJ, Gall I, Keryer G, Lygren B, Tasken K, van Heeke G, Houslay MD (2005) In resting COS1 cells a dominant negative approach shows that specific, anchored PDE4 cAMP phosphodiesterase isoforms gate the activation, by basal cyclic AMP production, of AKAP-tethered protein kinase A type II located in the centrosomal region. Cell Signal, 17: 1158.
Monaco L, Vicini E, Conti M (1994) Structure of two rat genes coding for closely related rolipram-sensitive cAMP phosphodiesterases. Multiple mRNA variants originate from alternative splicing and multiple start sites. J Biol Chem 269: 347-357.
Rena G, Begg F, Ross A, MacKenzie C, McPhee I, Campbell L, Huston E, Sullivan M, Houslay MD (2001) Molecular cloning, genomic positioning, promoter identification, and characterization of the novel cyclic amp-specific phosphodiesterase PDE4A10. Mol Pharmacol 59: 996-1011.
Smith FD, Langeberg LK, Scott JD (2006) The where's and when's of kinase anchoring. Trends in biochemical sciences 31: 316-323.
Smith KJ, Baillie GS, Hyde EI, Li X, Houslay TM, McCahill A, Dunlop AJ, Bolger GB, Klussmann E, Adams DR, Houslay MD (2007) 1H NMR structural and functional characterisation of a cAMP-specific phosphodiesterase-4D5 (PDE4D5) N-terminal region peptide that disrupts PDE4D5 interaction with the signalling scaffold proteins, beta-arrestin and RACK1. Cell Signal 19: 2612-2624.
Tasken K, Aandahl EM (2004) Localized effects of cAMP mediated by distinct routes of protein kinase A. Physiol Rev 84: 137-167.
Taylor SS, Yang J, Wu J, Haste NM, Radzio-Andzelm E, Anand G (2004) PKA: a portrait of protein kinase dynamics. Biochim Biophys Acta 1697: 259-269.
Terrin A, Di Benedetto G, Pertegato V, Cheung YF, Baillie G, Lynch MJ, Elvassore N, Prinz A, Herberg FW, Houslay MD, Zaccolo M (2006) PGE(1) stimulation of HEK293 cells generates multiple contiguous domains with different [cAMP]: role of compartmentalized phosphodiesterases. The Journal of cell biology 175: 441-451.
Tilley DD, Maurice DH (2005) Vascular smooth muscle cell phenotype-dependent phosphodiesterase 4D short form expression: role of differential histone acetylation on cAMP-regulated function. Mol Pharmacol 68: 596-605.
Vicini E, Conti M (1997) Characterization of an intronic promoter of a cyclic adenosine 3',5'-monophosphate (cAMP)-specific phosphodiesterase gene that confers hormone and cAMP inducibility. Molecular endocrinology (Baltimore, Md 11: 839-850.
Wallace DA, Johnston LA, Huston E, MacMaster D, Houslay TM, Cheung YF, Campbell L, Millen JE, Smith RA, Gall I, Knowles RG, Sullivan M, Houslay MD (2005) Identification and characterization of PDE4A11, a novel, widely expressed long isoform encoded by the human PDE4A cAMP phosphodiesterase gene. Mol Pharmacol 67: 1920-1934.
Wang D, Deng C, Bugaj-Gaweda B, Kwan M, Gunwaldsen C, Leonard C, Xin X, Hu Y, Unterbeck A, De Vivo M (2003) Cloning and characterization of novel PDE4D isoforms PDE4D6 and PDE4D7. Cell Signal 15: 883-891.
Willoughby D, Baillie GS, Lynch MJ, Ciruela A, Houslay MD, Cooper DM (2007) Dynamic regulation, desensitization, and cross-talk in discrete subcellular microdomains during beta2-adrenoceptor and prostanoid receptor cAMP signaling. J Biol Chem 282: 34235-34249.
Willoughby D, Cooper DM (2007) Organization and Ca2+ regulation of adenylyl cyclases in cAMP microdomains. Physiol Rev 87: 965-1010.

* cited by examiner

FIGURE 1

| Sample | Origine | Androgen Response | AR expression | PSA expression | AR sequence |
|---|---|---|---|---|---|
| LNCaP 8 hr - (no R1881 treatment) | Lymph node | AD/AS | Yes | Yes | T877A |
| LNCaP 8 hr + R1881 | Lymph node | AD/AS | Yes | Yes | T877A |
| PC3 | Bone | AI | No | No | n/a |
| DU145 | Brain | AI | No | No | n/a |
| VCaP 8 hr - (no R1881 treatment) | Vertebra | AI/AS | Yes | Yes | Wt |
| VCaP 8 hr + R1881 | Vertebra | AI/AS | Yes | Yes | Wt |
| DuCaP 8 hr - (no R1881 treatment) | Vertebra | AI/AS | Yes | Yes | Wt |
| DuCaP 8 hr + R1881 | Vertebra | AI/AS | Yes | Yes | Wt |
| PC-EW | Primary | AS | Yes | Yes | Wt |
| PC82 | Primary | AS | Yes | Yes | Wt |
| PC133 | Primary | AI | No | No | n/a |
| PC135 | Primary | AI | No | No | n/a |
| PC295 | Primary | AD | Yes | Yes | Wt |
| PC310 | Lymph node | AD | Yes | Yes | Wt |
| PC324 | Primary | AI | No | No | n/a |
| PC339 | Bone | AI | No | No | n/a |
| PC374 | Primary | AI | No | No | n/a |

PHOSPHODIESTERASE 9A AS PROSTATE CANCER MARKER

FIELD OF THE INVENTION

The present invention relates to phosphodiesterase 9A (PDE9A) for use as a marker for prostate cancer, and the use of PDE9A as a marker for diagnosing, detecting, monitoring or prognosticating prostate cancer or the progression of prostate cancer. The present invention also relates to a composition for diagnosing, detecting, monitoring or prognosticating prostate cancer or the progression of prostate cancer, a corresponding method and immunoassay, a method for diagnosing, monitoring or prognosticating hormone-resistant prostate cancer vs. hormone-sensitive prostate cancer, a corresponding immunoassay, a method of data acquisition, an immunoassay for diagnosing, detecting, monitoring or prognosticating prostate cancer or the progression of prostate cancer, a method of identifying an individual for eligibility for prostate cancer therapy, an immunoassay for stratifying an individual or cohort of individuals with a prostate cancer disease, an immunoassay for stratifying an individual with prostate cancer. The present invention further envisages pharmaceutical compositions and their use for the treatment of prostate cancer, in particular hormone-resistant prostate cancer.

BACKGROUND OF THE INVENTION

Cancer is a class of diseases in which a group of cells display uncontrolled growth, invasion and sometimes metastasis. These three malignant properties of cancers differentiate them from benign tumors, which are self-limited, do not invade or metastasize. Among men, the three most commonly diagnosed cancers are prostate, lung and colorectal cancer in developed countries. Particularly prostate cancer is the most common malignancy in European males. In 2002 in Europe, an estimated 225,000 men were newly diagnosed with prostate cancer and about 83,000 died from this disease.

Certain phosphodiesterases have been associated with cancer development. For instance, phosphodiesterase PDE7 has been shown to be linked to chronic lymphocytic leukemia (Zhang L et al., PNAS, 2008, 105(49): 19532-7). Yet, for many cancer types or cancer progression forms there is no adequate marker molecule available.

Prostate cancer, for example, is traditionally diagnosed via the serum level of prostate-specific antigen (PSA). However, PSA is not prostate cancer-specific and can be raised in other circumstances, leading to a large number of false-positives (cancer is not found in around 70% of men with raised PSA levels who undergo biopsy). Furthermore, there will be an unpredictable number of false-negatives who later develop prostate cancer in the presence of a "normal" PSA test.

Therefore, there is a need for the provision of a new and effective, alternative diagnosis perspective for the detection, monitoring and prognostication of prostate cancer.

SUMMARY OF THE INVENTION

The present invention addresses this need and provides means and methods which allow the diagnosis and detection of prostate cancer.

The above objective is accomplished by phosphodiesterase 9A (PDE9A) for use as a prostate cancer marker.

Phosphodiesterase 9A is shown by the present inventors to be down-regulated in prostate cancer cell lines and patient derived prostate tissue. PDE9A is, thus, considered as a biomarker for prostate cancer prediction and a decision tool for the stratification of certain cancer surveillance regimes, as well as the prognosis and monitoring of prostate cancer progression. In particular, it was demonstrated by the present inventors that PDE9A is down-regulated in hormone-resistant human-derived prostate cell lines as well as corresponding human tissue samples. Diagnostic methods and uses based on PDE9A as a prostate cancer marker can, thus, advantageously be employed for (i) detecting and diagnosing life-threatening prostate cancer forms, (ii) prognosticating life-threatening prostate cancer forms, (iii) monitoring of cancer progression towards life-threatening prostate cancer forms, and (iv) distinguishing between indolent and life-threatening cancer forms.

In another aspect the present invention relates to a composition for diagnosing, detecting, monitoring or prognosticating prostate cancer or the progression of prostate cancer, comprising a nucleic acid affinity ligand and/or a peptide affinity ligand for the PDE9A expression product or protein.

In a preferred embodiment of the present invention said composition comprises a nucleic acid affinity ligand or peptide affinity ligand which is modified to function as a contrast agent.

In a further preferred embodiment of the present invention said composition comprises a set of oligonucleotides specific for the PDE9A expression product, a probe specific for the PDE9A expression product, an aptamer specific for the PDE9A expression product or protein, an antibody specific for the PDE9A protein and/or an antibody variant specific for the PDE9A protein.

In a further aspect the present invention relates to the use of PDE9A as a marker for diagnosing, detecting, monitoring or prognosticating prostate cancer or the progression of prostate cancer.

In another aspect the present invention relates to a method for detecting, diagnosing, monitoring or prognosticating prostate cancer or the progression of prostate cancer comprising the step of determining the level of PDE9A.

In another aspect the present invention relates to a method for diagnosing, monitoring or prognosticating hormone-resistant prostate cancer or the progression towards hormone-resistant prostate cancer, wherein said method discriminates between a hormone-sensitive and a hormone-resistant prostate cancer, comprising the steps of (a) determining the level of PDE9A in a sample;

(b) determining the level of expression of a reference gene in a sample;

(c) normalizing the measured expression level of PDE9A to the expression of the reference gene; and (d) comparing the normalized expression level with a predetermined cutoff value chosen to exclude hormone-sensitive prostate cancer, wherein a normalized expression level below the cutoff value is indicative of a hormone-resistant prostate cancer, wherein said cutoff value is between about 2 and 15, preferably about 5.

In another aspect the present invention relates to a method of data acquisition comprising at least the steps of:

(a) testing in an individual for expression of PDE9A; and (b) comparing the expression as determined in step (a) to a control level.

In a further preferred embodiment of the present invention the diagnosing, detecting, monitoring prognosticating or data acquisition is to be carried out on a sample obtained from an individual.

In another aspect the present invention relates to an immunoassay for detecting, diagnosing, monitoring or prognosticating prostate cancer or the progression of prostate cancer comprising at least the steps of:

(a) testing in a sample for the expression of PDE9A, (b) testing in a control sample for the expression of PDE9A, (c) determining the difference in expression of PDE9A of steps (a) and (b); and (d) deciding on the presence or stage of prostate cancer or the progression of prostate cancer based on the results obtained in step (c), wherein said testing steps are based on the use of an antibody specifically binding to PDE9A.

In another aspect the present invention relates to an immunoassay for discriminating between a hormone-sensitive and a hormone-resistant prostate cancer, comprising the steps of:

(a) determining the level of PDE9A in a sample;

(b) determining the level of expression of a reference gene in a sample;

(c) normalizing the measured expression level of PDE9A to the expression of the reference gene; and (d) comparing the normalized expression level with a predetermined cutoff value to exclude hormone-sensitive prostate cancer, wherein a normalized expression level below the cutoff value is indicative of a hormone-resistant prostate cancer, wherein said cutoff value is between about 2 and 15, preferably about 5.

In another aspect the present invention relates to a method of identifying an individual for eligibility for prostate cancer therapy comprising:

(a) testing in a sample obtained from an individual for the expression of PDE9A;

(b) testing in said sample for the expression of a reference gene and/or testing in a control sample for the expression of PDE9A;

(c) classifying the levels of expression of step (a) relative to levels in control samples of PDE9A of step (b); and (d) identifying the individual as eligible to receive a prostate cancer therapy where the individual's sample is classified as having an altered level of PDE9A expression.

In yet another aspect the present invention relates to an immunoassay for stratifying an individual or cohort of individuals with a prostate cancer disease comprising:

(a) testing in a sample obtained from an individual for the expression of PDE9A;

(b) testing in said sample for the expression of a reference gene and/or testing in a control sample for the expression of PDE9A;

(c) determining the difference in expression of PDE9A of step (a) and the expression of PDE9A and/or the reference gene in step (b); and (d) stratifying an individual or cohort of individuals to prostate cancer therapy based on the results obtained in step (c), where the individual's sample has an altered level of PDE9A expression.

In a further preferred embodiment of the present invention said testing or determining of the expression is accomplished, or additionally accomplished, by the measurement of nucleic acid or protein levels or by the determination of the biological activity of PDE9A, or of the reference gene.

In a further preferred embodiment of the present invention said method or immunoassay comprises the additional step of comparing the measured nucleic acid or protein levels or the measured biological activity to a control level.

In a further preferred embodiment of the present invention said reference gene is a housekeeping gene, particularly preferred GAPDH or PBGD, or a different phosphodiesterase, particularly preferred PDE4D5.

In a further preferred embodiment of the present invention said method or immunoassay comprises the additional step of determining the level of prostate specific antigen (PSA).

In a further preferred embodiment of the present invention in said method or immunoassay as defined above, an individual classified or tested with an increased level of PDE9A expression and an increased level of PSA of more than about >2.5 ng/ml up to about 10 ng/ml is identified as suffering from a malignant, hormone sensitive prostate cancer; and an individual classified or tested with a decreased level of PDE9A expression and an increased level of PSA of more than about >10 ng/ml is identified as suffering from hormone resistant prostate cancer.

In a further preferred embodiment of the present invention the sample as mentioned above is a tissue sample, a urine sample, a urine sediment sample, a blood sample, a saliva sample, a semen sample, a sample comprising circulating tumor cells, or a sample containing prostate secreted exosomes.

In yet another aspect the present invention relates to a stimulatory pharmaceutical composition comprising at least one element selected from the group of:

(a) a compound directly stimulating or modulating the activity of PDE9A, preferably an allosteric agonist of PDE9A enzymatic activity;

(b) a compound indirectly stimulating or modulating the activity of PDE9A;

(c) the PDE9A protein or a biologically active equivalent thereof;

(d) a nucleic acid encoding and expressing PDE9A;

(e) a miRNA inhibitor specific for PDE9A miRNAs;

(f) a demethylation agent; and (g) a phosphodiesterase displacement factor.

As phosphodiesterase 9A is down-regulated in disease-associated cell lines, PDE9A itself and agents modifying or stimulating PDE9A, modifying or stimulating PDE9A expression or modifying or stimulating PDE9A interactions can advantageously be used as medicaments. Thus, by counteracting the observed down-regulation process, PDE9A and/or PDE9A modification agents may be used as a medicament, e.g. as a medicament counteracting all or some of the effects associated with a low PDE9A expression or its down-regulation.

In a further aspect the present invention relates to a stimulatory pharmaceutical composition for the treatment or prevention of prostate cancer comprising at least one element selected from the group of:

(a) a compound directly stimulating or modulating the activity of PDE9A, preferably an allosteric agonist of PDE9A enzymatic activity;

(b) a compound indirectly stimulating or modulating the activity of PDE9A;

(c) the PDE9A protein or a biologically active equivalent thereof;

(d) a nucleic acid encoding and expressing PDE9A;

(e) a miRNA inhibitor specific for PDE9A miRNAs;

(f) a demethylation agent; and (g) a phosphodiesterase displacement factor.

As phosphodiesterase 9A is down-regulated in prostate cancer cell lines, PDE9A itself and agents modifying or stimulating PDE9A or modifying or stimulating PDE9A expression or modifying or stimulating PDE9A interactions can advantageously be used as medicaments for the treatment of cancer, in particular for the treatment of prostate cancer. Thus, by counteracting the observed down-regulation process, PDE9A and/or PDE9A modification agents may be used as a medicament counteracting the low PDE9A expression and/or the PDE9A down-regulation in cancerous cells, in particular prostate cancer cells.

In yet another aspect the present invention relates to an inhibitory pharmaceutical composition comprising at least one element selected from the group of:

(a) a compound directly inhibiting the activity of PDE9A, preferably an antagonist of PDE9A enzymatic activity;

(b) a compound indirectly inhibiting the activity of PDE9A;

(c) a dominant negative form of the PDE9A protein or a biologically active equivalent thereof;

(d) a nucleic acid encoding and expressing a dominant negative form of PDE9A;

(e) a miRNA specific for PDE9A;

(f) a PDE9A antisense molecule;

(g) a siRNA specific for PDE9A;

(h) an aptamer specific for the PDE9A expression product or for the PDE9A protein;

(i) a small molecule or peptidomimetic capable of specifically binding to the PDE9A protein; and (j) an antibody specific for the PDE9A protein and/or an antibody variant specific for the PDE9A protein.

In a preferred embodiment of the present invention either said inhibitory or said stimulatory pharmaceutical composition said is to be used for the treatment of prostate cancer in dependence of the expression level of PDE9A, wherein said level of expression is determined and/or monitored according to the steps of (a) determining the level of PDE9A in a sample;

(b) determining the level of expression of a reference gene in a sample; and (c) normalizing the measured expression level of PDE9A to the expression of the reference gene.

In a further, particularly preferred embodiment of the present invention for increased and/or increasing levels of PDE9A said inhibitory pharmaceutical composition is to be administered, and for decreased and/or decreasing levels of PDE9A said stimulatory pharmaceutical composition is to be administered.

In another aspect the present invention relates to a method of treatment or prevention of cancer, in particular prostate cancer, comprising the administration of (a) a compound directly stimulating or modulating the activity of PDE9A, preferably an allosteric agonist of PDE9A enzymatic activity;

(b) a compound indirectly stimulating or modulating the activity of PDE9A;

(c) the PDE9A protein or a biologically active equivalent thereof;

(d) a nucleic acid encoding and expressing PDE9A;

(e) a miRNA inhibitor specific for PDE9A miRNAs;

(f) a demethylation agent; and/or (g) a phosphodiesterase displacement factor to an individual.

In a preferred embodiment of the present invention said phosphodiesterase displacement factor as mentioned above is a peptide, a peptidomimetic, a small molecule, an antibody or an aptamer.

In another preferred embodiment of the present invention said prostate cancer is hormone-resistant prostate cancer.

These and other characteristics, features and objectives of the present invention will become apparent from the following detailed description, taken in conjunction with the accompanying figures and examples, which demonstrate by way of illustration the principles of the invention.

The description is given for the sake of example only, without limiting the scope of the invention.

BRIEF DESCRIPTION OF THE DRAWINGS

FIG. 1 gives an overview over the samples tested on expression levels. AD means "androgen dependent", AS stands for "androgen sensitive" and AI means "androgen independent". Samples "LNCaP" through "DuCaP" are cell lines, samples "PC-EW" through "PC374" are xenografts.

DETAILED DESCRIPTION OF EMBODIMENTS

Figure 2:
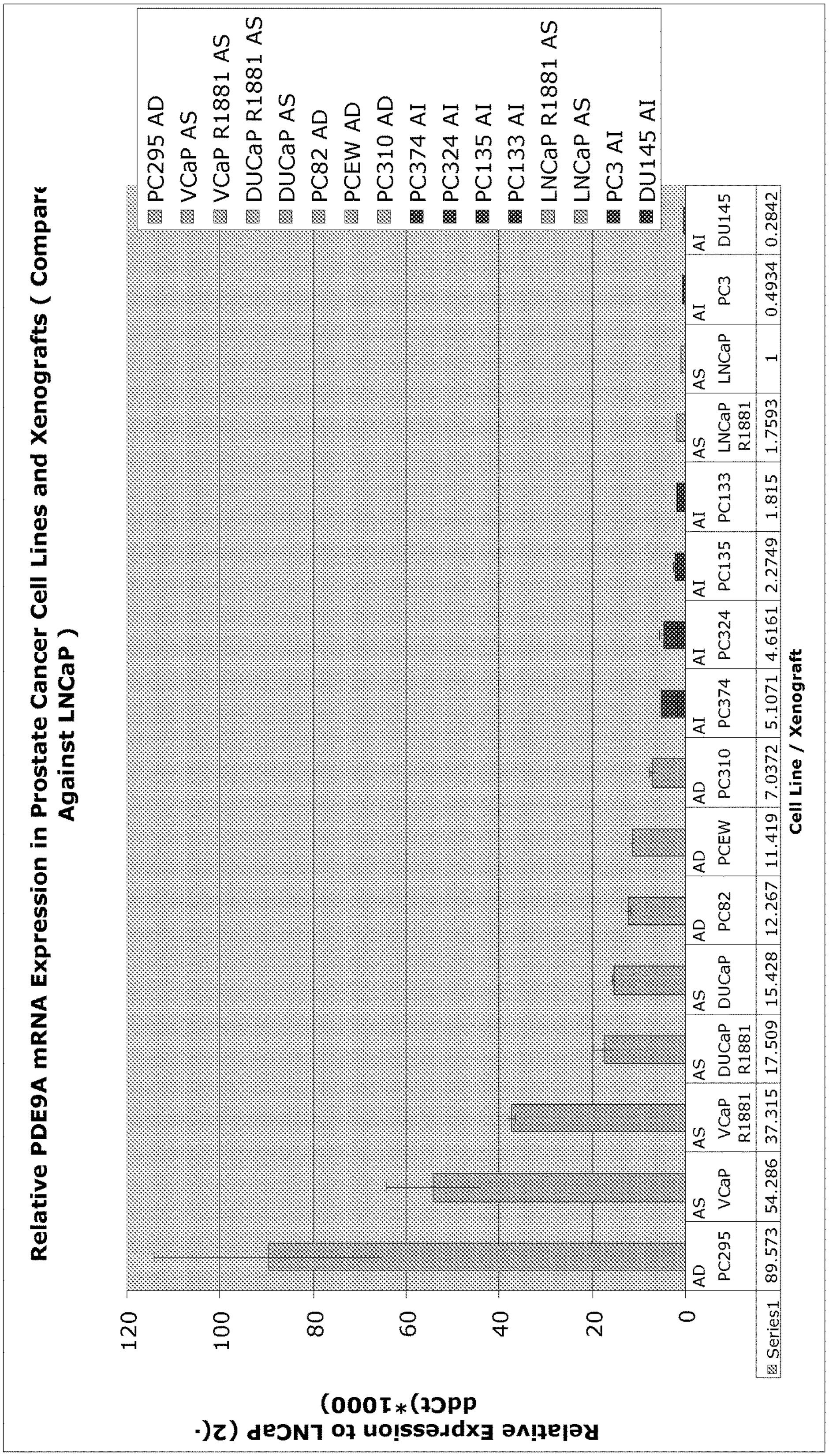
FIG. 2 depicts the relative PDE9A mRNA expression in prostate cancer cell lines and xenografts compared against LNCaP.
Figure 3:
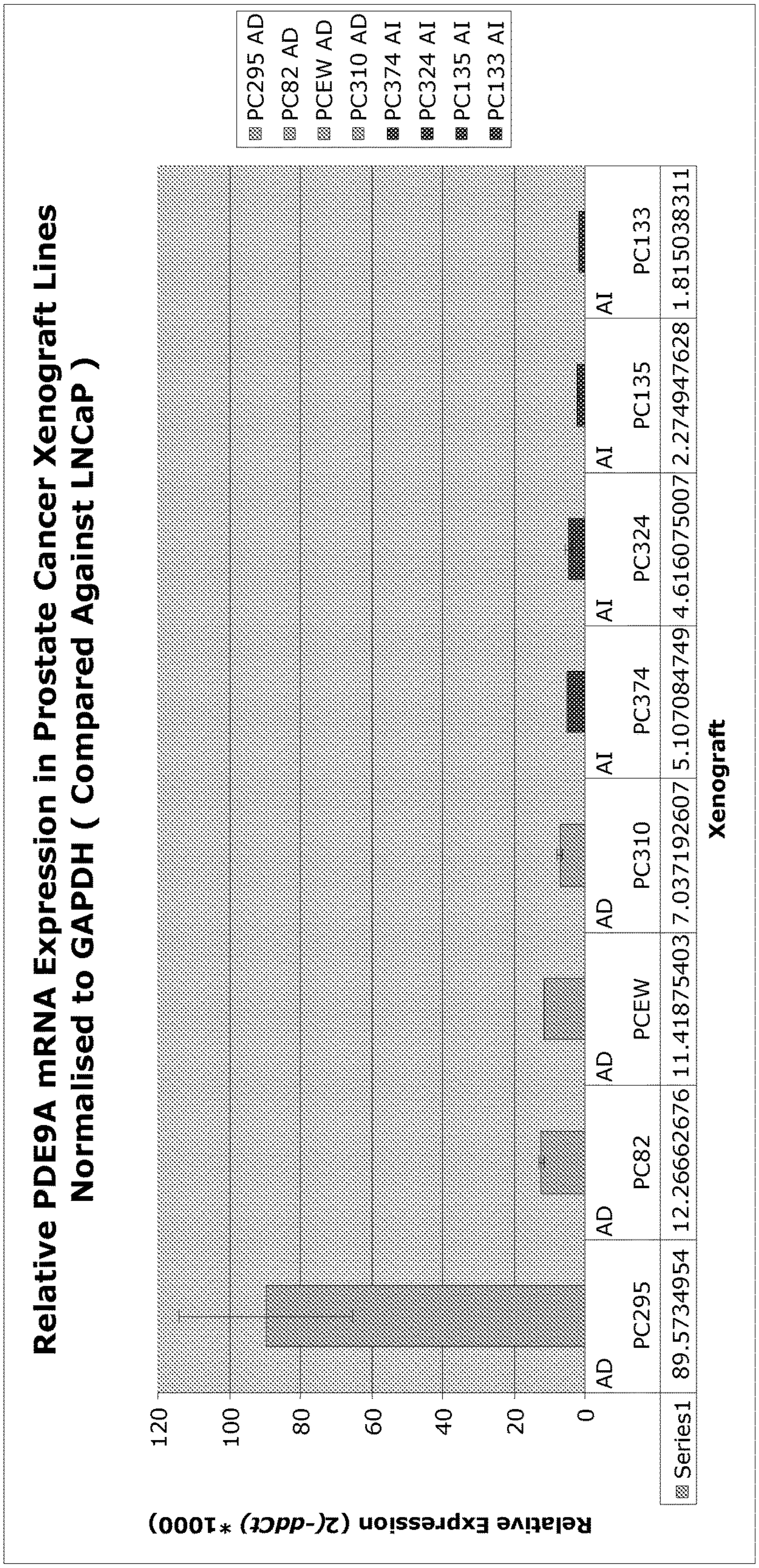
FIG. 3 depicts the relative PDE9A mRNA expression in prostate cancer xenograft lines normalized to GAPDH compared to LNCaP.
Figure 4:
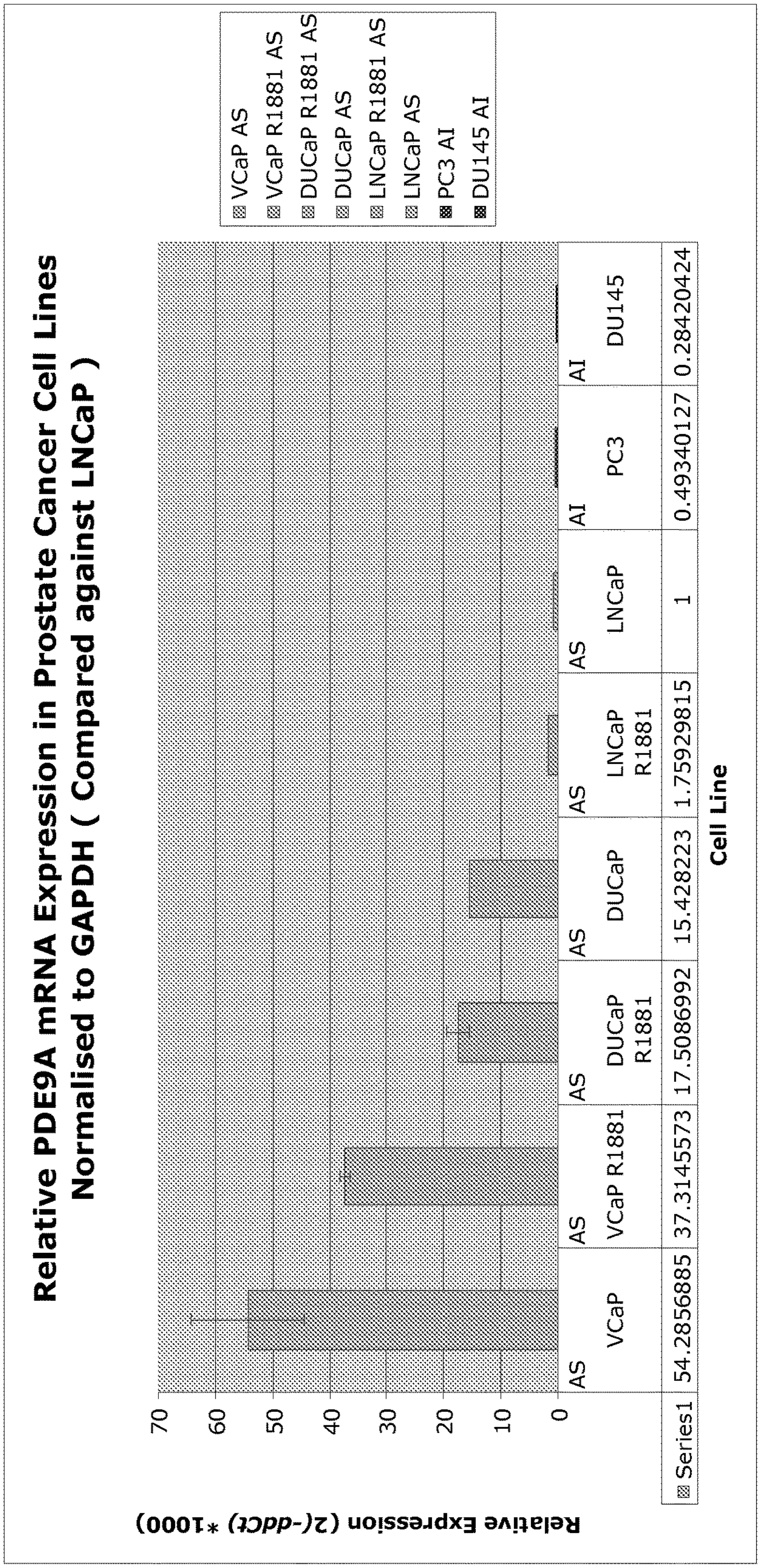
FIG. 4 depicts the relative PDE9A mRNA expression in prostate cancer cell lines normalized to GAPDH compared to LNCaP.
Figure 5:
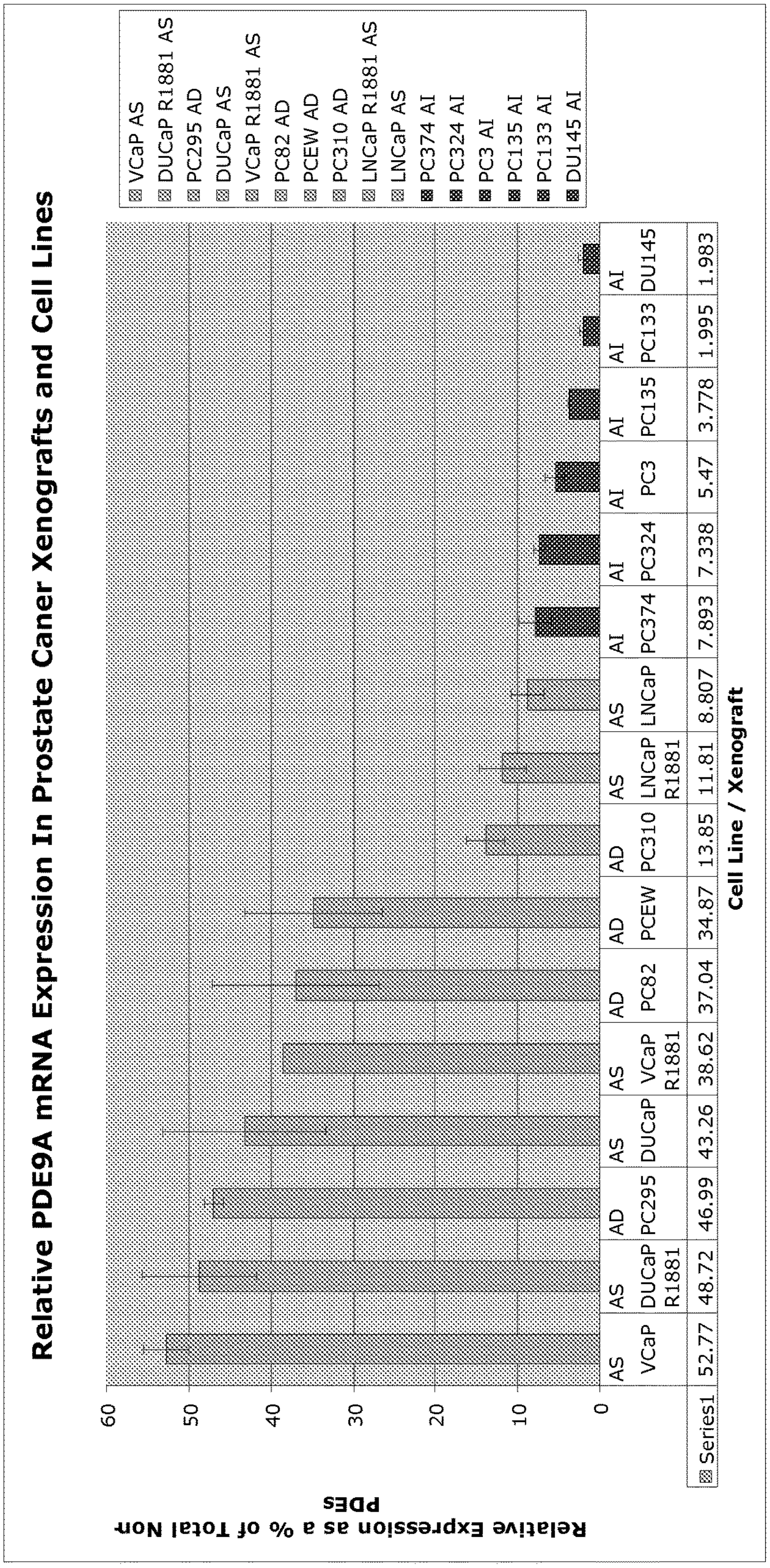
FIG. 5 shows the relative PDE9A mRNA expression in prostate cancer xenografts and cell lines.
Figure 6:
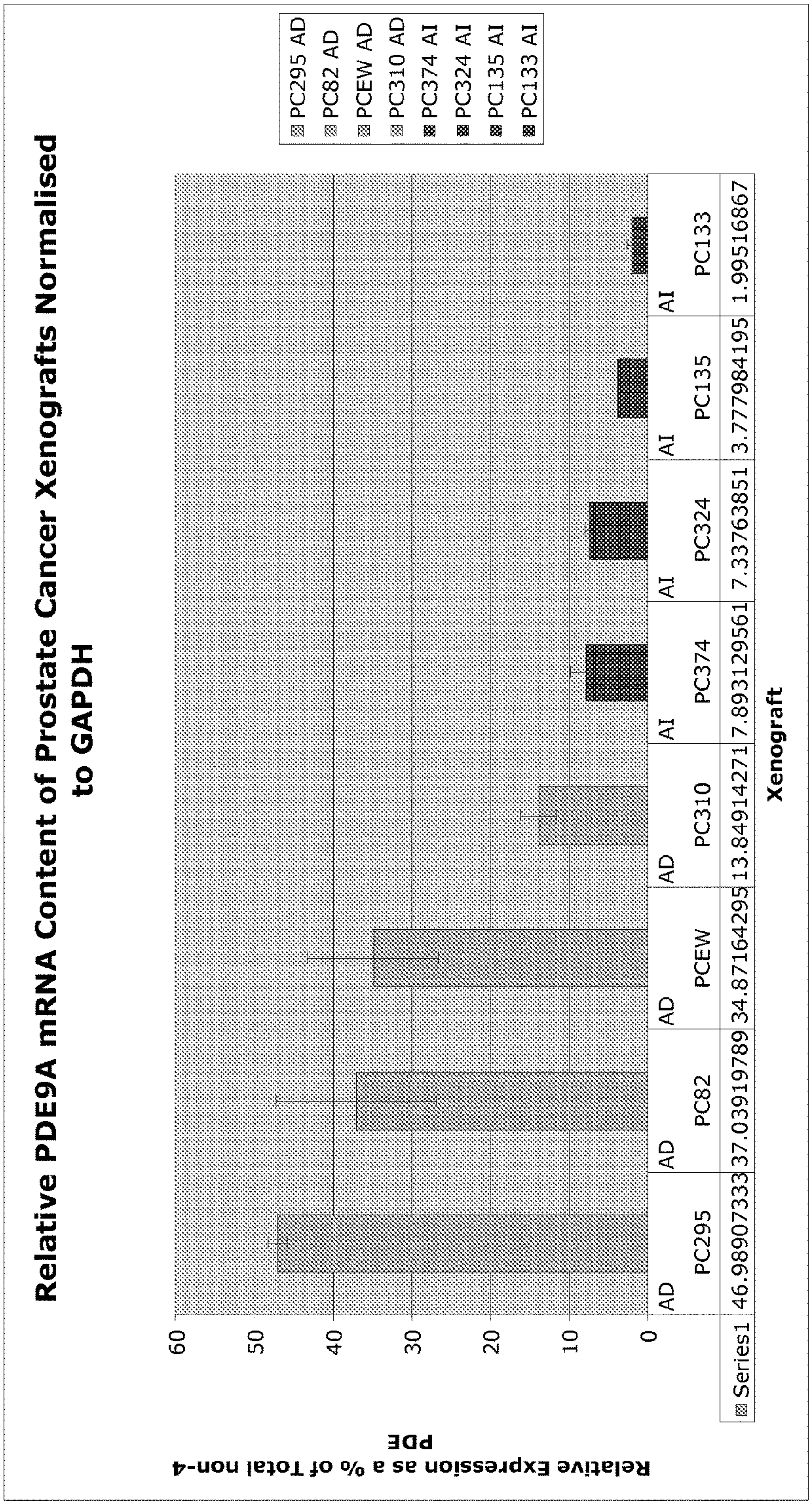
FIG. 6 shows the PDE9A mRNA content in prostate cancer xenografts normalized to GAPDH.
Figure 7:
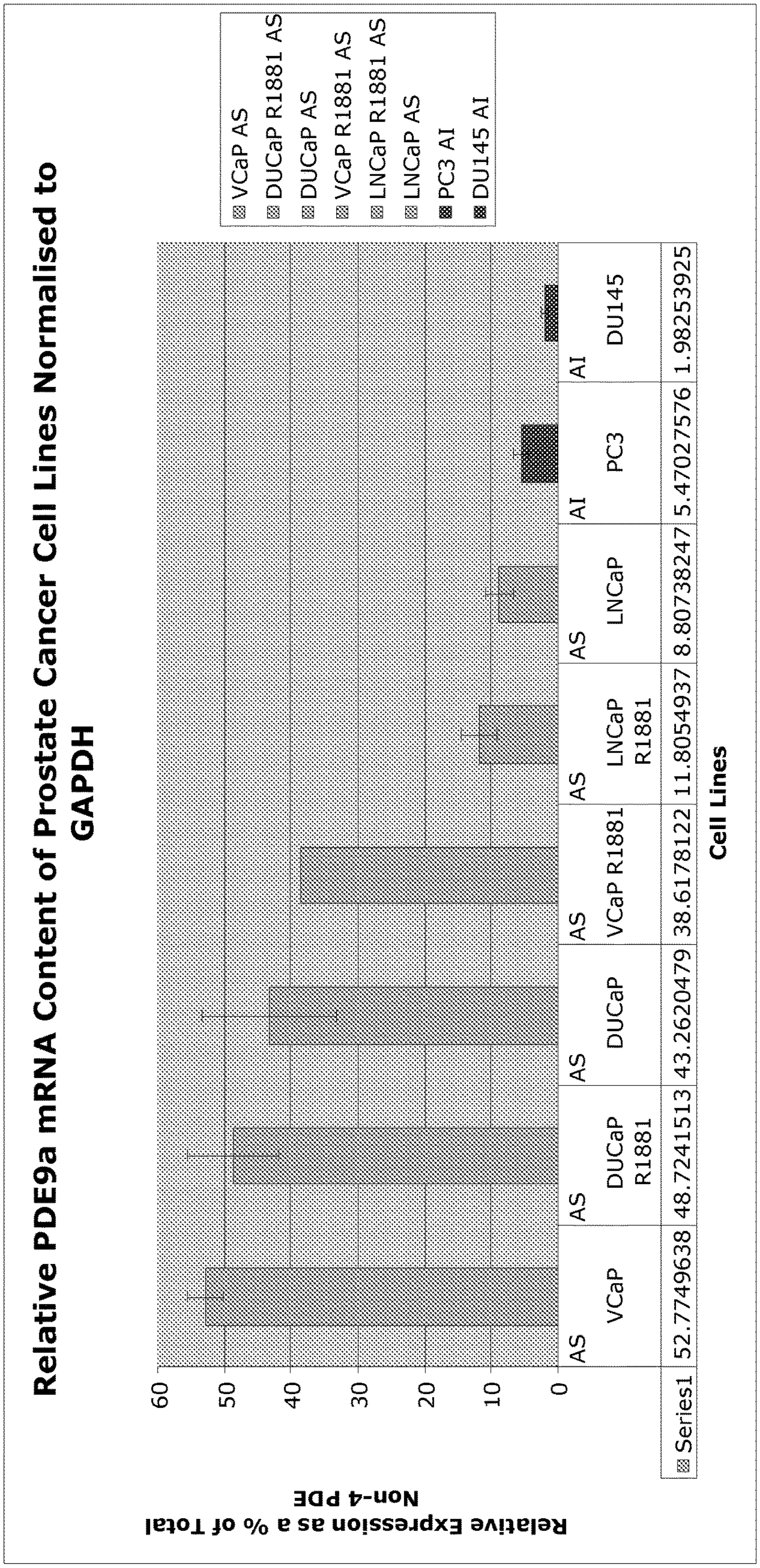
FIG. 7 shows the PDE9A content of prostate cancer cell lines normalized to GAPDH.

The inventors have found that PDE9A is strongly down-regulated in certain prostate cancer-associated cell types and human patient tissues and can, hence, be used as biomarker for prostate cancer. PDE9A as well as agents modifying PDE9A or modifying PDE9A expression can further be used as medicaments, in particular for the treatment of prostate cancer.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, proteins, bacteria, vectors, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect phosphodiesterase 9A (PDE9A) for use as a prostate cancer marker. The term "phosphodiesterase 9A" or "PDE9A" relates to all splice variants of the human phosphodiesterase PDE9A, i.e. the human phosphodiesterase PDE9A gene, preferably to the sequences as defined in Genbank Accession No: NM_002606 (version NM_002606.2, GI:48762716 as of 9 Mar. 2009) showing transcript variant 1 of PDE9A, Genbank Accession No: NM_001001567 (version NM_001001567.1, GI:48762717 as of 9 Mar. 2009) showing transcript variant 2 of PDE9A, Genbank Accession No: NM_001001568 (version NM_001001568.1, GI:48762719 as of 9 Mar. 2009) showing transcript variant 3 of PDE9A, Genbank Accession No: NM_001001569 (version NM_001001569.1, GI:48762721 as of 9 Mar. 2009) showing transcript variant 4 of PDE9A, Genbank Accession No: NM_001001570 (version NM_001001570.1, GI:48762723 as of 9 Mar. 2009) showing transcript variant 5 of PDE9A, Genbank Accession No: NM_001001571 (version NM_001001571.1, GI:48762725 as of 9 Mar. 2009) showing transcript variant 6 of PDE9A, Genbank Accession No: NM_001001572 (version NM_001001572.1, GI:48762727 as of 9 Mar. 2009) showing transcript variant 7 of PDE9A, Genbank Accession No: NM_001001573 (version NM_001001573.1, GI:48762729 as of 9 Mar. 2009) showing transcript variant 8 of PDE9A, Genbank Accession No: NM_001001574 (version NM_001001574.1, GI:48762731 as of 9 Mar. 2009) showing transcript variant 9 of PDE9A, Genbank Accession No: NM_001001575 (version NM_001001575.1, GI:48762733 as of 9 Mar. 2009) showing transcript variant 10 of PDE9A, Genbank Accession No: NM_001001576 (version NM_001001576.1, GI:48762735 as of 9 Mar. 2009) showing transcript variant 11 of PDE9A, Genbank Accession No: NM_001001577 (version NM_001001577.1, GI:48762737 as of 9 Mar. 2009) showing transcript variant 12 of PDE9A, Genbank Accession No: NM_001001578 (version NM_001001578.1, GI:48762739 as of 9 Mar. 2009) showing transcript variant 13 of PDE9A, Genbank Accession No: NM_001001579 (version NM_001001579.1, GI:48762741 as of 9 Mar. 2009) showing transcript variant 14 of PDE9A, Genbank Accession No: NM_001001580 (version NM_001001580.1, GI:48762743 as of 9 Mar. 2009) showing transcript variant 15 of PDE9A, Genbank Accession No: NM_001001581 (version NM_001001581.1, GI:48762745 as of 9 Mar. 2009) showing transcript variant 16 of PDE9A, Genbank Accession No: NM_001001582 (version NM_001001582.1, GI:48762747 as of 9 Mar. 2009) showing transcript variant 17 of PDE9A, Genbank Accession No: NM_001001583 (version NM_001001583.1, GI:48762749 as of 9 Mar. 2009) showing transcript variant 18 of PDE9A, Genbank Accession No: NM_001001584 (version NM_001001584.2, GI:209954812 as of 26 Mar. 2009) showing transcript variant 19 of PDE9A and Genbank Accession No: NM_001001585 (version NM_001001585.1, GI:48762753 as of 9 Mar. 2009) showing transcript variant 20 of PDE9A.

More preferably the term relates to the nucleotide sequences as set forth in SEQ ID NOs: 1 to 20, which correspond to the sequences of the above indicated Genbank Accession numbers of PDE9A transcript variants 1 to 20, and the corresponding amino acid sequences as set forth in SEQ ID NOs: 21 to 40, which correspond to the sequences of the above indicated Genbank Accession numbers of PDE9A polypeptides encoded by transcript variants 1 to 20. The term also comprises nucleotide sequences showing a high degree of homology to PDE9A, e.g. nucleic acid sequences being at least 75%, 80%, 85%, 90%, 91%, 92%, 93%, 94%, 95%, 96%, 97%, 98% or 99% identical to any of the sequences as set forth in SEQ ID NOs: 1 to 20, or amino acid sequences being at least 75%, 80%, 85%, 90%, 91%, 92%, 93%, 94%, 95%, 96%, 97%, 98% or 99% identical to any of the sequences as set forth in any of SEQ ID NOs: 21 to 40, or nucleic acid sequences encoding amino acid sequences being at least 75%, 80%, 85%, 90%, 91%, 92%, 93%, 94%, 95%, 96%, 97%, 98% or 99% identical to any of the sequences as set forth in SEQ ID NOs: 21 to 40, or amino acid sequences being encoded by nucleic acid sequences being at least 75%, 80%, 85%, 90%, 91%, 92%, 93%, 94%, 95%, 96%, 97%, 98% or 99% identical to any of the sequences as set forth in SEQ ID NOs: 1 to 20.

The term "human phosphodiesterase PDE9A gene", "PDE9A gene" or "PDE9A marker gene" as used herein relates to the gene encoding phosphodiesterase 9A. Preferably, the term relates to a gene expressing phosphodiesterase 9A as splice variants 1 to 20, e.g. the specific exon combination as defined in Genbank Accession No: NM_002606 (version NM_002606.2, GI:48762716 as of 9 Mar. 2009) or as set forth in SEQ ID NO: 1, Genbank Accession No: NM_001001567 (version NM_001001567.1, GI:48762717 as of 9 Mar. 2009) or as set forth in SEQ ID NO: 2, Genbank Accession No: NM_001001568 (version NM_001001568.1, GI:48762719 as of 9 Mar. 2009) or as set forth in SEQ ID NO: 3, Genbank Accession No: NM_001001569 (version NM_001001569.1, GI:48762721 as of 9 Mar. 2009) or as set forth in SEQ ID NO: 4, Genbank Accession No: NM_001001570 (version NM_001001570.1, GI:48762723 as of 9 Mar. 2009) or as set forth in SEQ ID NO: 5, Genbank Accession No: NM_001001571 (version NM_001001571.1, GI:48762725 as of 9 Mar. 2009) or as set forth in SEQ ID NO: 6, Genbank Accession No: NM_001001572 (version NM_001001572.1, GI:48762727 as of 9 Mar. 2009) or as set forth in SEQ ID NO: 7, Genbank Accession No: NM_001001573 (version NM_001001573.1, GI:48762729 as of 9 Mar. 2009) or as set forth in SEQ ID NO: 8, Genbank Accession No: NM_001001574 (version NM_001001574.1, GI:48762731 as of 9 Mar. 2009) or as set forth in SEQ ID NO: 9, Genbank Accession No: NM_001001575 (version NM_001001575.1, GI:48762733 as of 9 Mar. 2009) or as set forth in SEQ ID NO: 10, Genbank Accession No: NM_001001576 (version NM_001001576.1, GI:48762735 as of 9 Mar. 2009) or as set forth in SEQ ID NO: 11, Genbank Accession No: NM_001001577 (version NM_001001577.1, GI:48762737 as of 9 Mar. 2009) or as set forth in SEQ ID NO: 12, Genbank Accession No: NM_001001578 (version NM_001001578.1, GI:48762739 as of 9 Mar. 2009) or as set forth in SEQ ID NO: 13, Genbank Accession No: NM_001001579 (version NM_001001579.1, GI:48762741 as of 9 Mar. 2009) or as set forth in SEQ ID NO: 14, Genbank Accession No: NM_001001580 (version NM_001001580.1, GI:48762743 as of 9 Mar. 2009) or as set forth in SEQ ID NO: 15, Genbank Accession No: NM_001001581 (version NM_001001581.1, GI:48762745 as of 9 Mar. 2009) or as set forth in SEQ ID NO: 16, Genbank Accession No: NM_001001582 (version NM_001001582.1, GI:48762747 as of 9 Mar. 2009) or as set forth in SEQ ID NO: 17, Genbank Accession No: NM_001001583 (version NM_001001583.1, GI:48762749 as of 9 Mar. 2009) or as set forth in SEQ ID NO: 18, Genbank Accession No: NM_001001584 (version NM_001001584.1, GI:48762751 as of 9 Mar. 2009) or as set forth in SEQ ID NO: 19 and Genbank Accession No: NM_001001585 (version NM_001001585.1, GI:48762753 as of 9 Mar. 2009) or as set forth in SEQ ID NO: 20

The term also relates to DNA molecules derived from mRNA transcripts encoding phosphodiesterase 9A spliced as variants 1 to 20, preferably cDNA molecules.

The term "marker" or "PDE9A marker", as used herein, relates to a gene, genetic unit or sequence (a nucleotide sequence or amino acid or protein sequence) as defined herein above, whose expression level is modified, preferably decreased, in a cancerous cell or in cancerous tissue or in any type of sample comprising cancerous cells or cancerous tissues or portions or fragments thereof, in comparison to a control level or state. The term also refers to any expression product of said genetic unit or sequence, in particular to a PDE9A mRNA transcript, a polypeptide encoded by a PDE9A transcript or variants or fragments thereof, as well as homologous derivatives thereof as described herein above. The term "expression level" as used herein refers to the amount of PDE9A transcript and/or PDE9A protein derivable from a defined number of cells or a defined tissue portion, preferably to the amount of PDE9A transcript and/or PDE9A protein obtainable in a standard nucleic acid (e.g. RNA) or protein extraction procedure. Suitable extraction methods are known to the person skilled in the art.

The term "control level" (or "control state"), as used herein, relates to an expression level which may be determined at the same time and/or under similar or comparable conditions as the test sample by using (a) sample(s) previously collected and stored from a subject/subjects whose disease state, e.g. non-cancerous, is/are known. The term "disease state" or "cancerous disease state" relates to any state or type of cellular or molecular condition between a non-cancerous cell state and (including) a terminal cancerous cell state. Preferably, the term includes different cancerous proliferation/developmental stages or levels of tumor development in the organism between (and excluding) a non-cancerous cell state and (including) a terminal cancerous cell state. Such developmental stages may include all stages of the TNM (Tumor, Node, Metastasis) classification system of malignant tumors as defined by the UICC, e.g. stages 0 and I to IV. The term also includes stages before TNM stage 0, e.g. developmental stages in which cancer biomarkers known to the person skilled in the art show a modified expression or expression pattern.

The expression level as mentioned above may preferably be the expression level of PDE9A as defined herein above.

Alternatively or additionally, the expression level may also be the expression level of any other suitable gene or genetic element expressed in a cell, preferably in the context of PDE9A, e.g. the expression level of another phosphodiesterase, the expression level of a housekeeping gene, e.g. GAPDH or PBGD.

The term “cancerous” relates in the context of the present invention to a cancerous disease state as defined herein above. A preferred control level in the context of cancerous controls is the expression of PDE9A in malignant, hormone-sensitive prostate tumors.

The term “non-cancerous” relates in the context of the present invention to a condition in which neither benign nor malign proliferation can be detected. Suitable means for said detection are known in the art. A preferred control level in the context of non-cancerous controls is the expression of PDE9A in normal, i.e. healthy or non-cancerous tissue or the expression of PDE9A in benign prostate tumor tissue. The term “benign prostate tumor” as used herein refers to a prostate tumor which lacks all three of the malignant properties of a cancer, i.e. does not grow in an unlimited, aggressive manner, does not invade surrounding tissues, and does not metastasize. Typically, a benign prostate tumor implies a mild and non-progressive prostate neoplastic or swelling disease lacking the invasive properties of a cancer. Furthermore, benign prostate tumors are typically encapsulated, and thus inhibited in their ability to behave in a malignant manner. A benign tumor or a healthy condition may be determined by any suitable, independent molecular, histological or physiological method known to the person skilled in the art.

Alternatively, the control level may be determined by a statistical method based on the results obtained by analyzing previously determined expression level(s) of the PDE9A marker gene of the present invention in samples from subjects whose disease state is known. Furthermore, the control level can be derived from a database of expression patterns from previously tested subjects or cells. Moreover, the expression level of the marker genes of the present invention in a biological sample to be tested may be compared to multiple control levels, whose control levels are determined from multiple reference samples. It is preferred to use a control level determined from a reference sample derived from a tissue type similar to that of the patient-derived biological sample. It is particularly preferred to use sample(s) derived from a subject/subjects whose disease state is non-cancerous as defined herein above, i.e. which present a health condition in which neither benign nor malign proliferation can be detected. In another embodiment of the present invention, the control level can be determined from a reference sample derived from a subject who has been diagnosed to suffer from prostate cancer, e.g. from hormone-independent or hormone-resistant prostate cancer.

Alternatively, reference samples may comprise material derived from cell lines, e.g. immortalized cancer cell lines, or be derived from tissue xenografts. Preferably, material derived from prostate cancer cell lines or material derived from tissue xenografts with human prostate tissue, in particular with benign and tumor-derived human prostate tissue, may be comprised in a reference sample according to the present invention. Examples of preferred cancer cell lines comprise cells lines PC346P, PC346B, LNCaP, VCaP, DuCaP, PC346C, PC3, DU145, PC346CDD, PC346Flu1, PC346Flu2. Examples of preferred xenografts comprise PC295, PC310, PC-EW, PC82, PC133, PC135, PC324 and PC374. Preferably an entire panel of cell lines and xenografts may be used, e.g. the human PC346 panel. Further preferred are cell lines and xenografts as described in Marques et al., 2006, Eur. Urol., 49(2):245-57.

In a further, preferred alternative, reference samples may be derived from patient tissues, or tissue panels or tissue collections obtained in clinical environments. The samples may, for example, be obtained from male patients undergoing surgery. The samples may be derived from any suitable tissue type, e.g. from prostate tissue or lymph nodes. Preferred examples of patient tissue collections are from surgical procedures (e.g., prostatectomy).

Moreover, it is preferred to use the standard value of the expression levels of the PDE9A marker of the present invention in a population with a known disease state. The standard value may be obtained by any method known in the art. For example, a range of mean±2 SD (standard deviation) or mean±3 SD may be used as standard value.

Furthermore, the control level may also be determined at the same time and/or under similar or comparable conditions as the test sample by using (a) sample(s) previously collected and stored from a subject/subjects whose disease state is/are known to be cancerous, i.e. who have independently been diagnosed to suffer from a certain cancer type, e.g. from prostate cancer, in particular hormone-dependent, hormone-sensitive or hormone-resistant prostate cancer.

In the context of the present invention, a control level determined from a biological sample that is known not to be cancerous is called “normal control level”. If the control level is determined from a cancerous biological sample, e.g. a sample from a subject for which prostate cancer, in particular hormone-dependent, hormone-sensitive or hormone-resistant cancer was diagnosed independently, it may be designated as “cancerous control level”.

The term “prostate cancer” relates to a cancer of the prostate gland in the male reproductive system, which occurs when cells of the prostate mutate and begin to multiply out of control. Typically, prostate cancer is linked to an elevated level of prostate-specific antigen (PSA). In one embodiment of the present invention the term “prostate cancer” relates to a cancer showing PSA levels above 4.0. In another embodiment the term relates to cancer showing PSA levels above 2.0. The term “PSA level” refers to the concentration of PSA in the blood in ng/ml.

The term “hormone-dependent prostate cancer” means that the growth and/or proliferation of prostate cancer or prostate cancer cell lines is dependent on male sex hormone stimulation.

The term “hormone-sensitive prostate cancer” means that the growth and proliferation of prostate cancer or prostate cancer cell lines is sensitive on male sex hormone stimulation. The term “sensitive” relates to situations in which the prostate cancer or prostate cancer cell line shows a biochemical or cellular reaction pattern in the presence of male sex hormones, but does need a male sex hormone for growth and/or proliferation.

The term “hormone-resistant prostate cancer” means that the growth and proliferation of prostate cancer or prostate cancer cell lines is resistant to male sex hormone stimulation. The term also relates to a late prostate cancer developmental stage which is no longer amenable to an administration of anti-hormones, preferably anti-androgens as defined herein above. The term “male sex hormone” as used herein refers to an androgen, preferably to testosterone, androstenedione, dihydrotestosterone, dehydroepiandrosterone, androstenediol or androsterone.

In a further aspect the present invention relates to the use of PDE9A as a marker for diagnosing, detecting, monitoring or prognosticating prostate cancer or the progression of prostate cancer.

The term "diagnosing prostate cancer" as used herein means that a subject or individual may be considered to be suffering from prostate cancer, when the expression level of the PDE9A marker of the present invention is modified, preferably reduced or down-regulated, compared to a control level as defined herein above, preferably if compared to the normal control level as defined herein above. The term "diagnosing" also refers to the conclusion reached through that comparison process.

The term "modified" or "modified expression level" in the context of the present invention thus denotes a change in the expression level. Expression levels are deemed to be "changed" when the PDE9A gene expression, e.g. in a sample to be analyzed, differs by, for example, 5%, 6%, 7%, 8%, 9%, 10%, 15%, 20%, 25%, 30%, 40%, 50%, or more than 50% from a control level, or at least 0.1 fold, at least 0.2 fold, at least 1 fold, at least 2 fold, at least 5 fold, or at least 10 fold or more in comparison to a control level. The control level may either be a normal control level or a cancerous control level as defined herein above. If a comparison with a cancerous control level is to be carried out, an additional comparison with a normal control level is preferred. Such an additional comparison allows for the determination of a tendency of the modification, i.e. an increase or a decrease of the expression level is observed.

The term "modified" relates preferably to a decrease or down-regulation of the expression level of the PDE9A marker or a complete inhibition of the PDE9A marker expression if a test sample is compared to a control level. The control level may either be a normal control level or a cancerous control level as defined herein above. In a preferred embodiment of the present invention the control level is a cancerous control level derived from, or associated with hormone-dependent prostate tumors or tissues, more preferably derived from or associated with hormone-sensitive prostate tumors or tissues. The term "reduced expression level" or "down-regulated expression level" or "decrease of expression level" (which may be used synonymously) in the context of the present invention thus denotes a reduction of the expression level of PDE9A between a situation to be analyzed, e.g. a situation derivable from a patient's sample, and a reference point, which could either be a normal control level or cancerous control level derivable from any suitable cancer stage known to the person skilled in the art, preferably a hormone-dependent prostate tumor stage, more preferably a hormone-sensitive prostate tumor stage. Expression levels are deemed to be "reduced" or "down-regulated" when the PDE9A gene expression decreases by, for example, 5%, 6%, 7%, 8%, 9%, 10%, 15%, 20%, 25%, 30%, 40%, 50%, or more than 50% from a control level, or at least 0.1 fold, at least 0.2 fold, at least 1 fold, at least 2 fold, at least 5 fold, or at least 10 fold or more in comparison to a control level, preferably in comparison to a hormone-dependent or hormone-sensitive prostate tumor control.

In a further embodiment, an additional similarity in the overall gene expression pattern between a sample obtained from a subject and a reference as defined herein above, which is cancerous, indicates that the subject is suffering from a cancer. In another embodiment of the present invention, the diagnosis may be combined with the elucidation of additional cancer biomarker expression levels. For example, the expression of biomarkers like PSA may be tested.

A cancer, in particular a prostate cancer, may be considered as being diagnosed when the expression level of the PDE9A marker of the present invention is modified, preferably reduced or down-regulated, compared to a control level as defined herein above, e.g. the normal control level as defined herein above.

In a particularly preferred embodiment a prostate cancer may considered as being diagnosed if the PDE9A expression level, as defined herein above, is decreased by a value of between 20% to 80%, preferably by a value of 30%, 40%, 50%, 60% or 70% in a test sample in comparison to a control level, preferably in comparison to a control expression level derived from a hormone-dependent tumor control, more preferably a hormone-sensitive prostate tumor control. In a further preferred embodiment a hormone-resistant prostate cancer may be considered as being diagnosed if the PDE9A expression level, as defined herein above, is decreased by a value of between 20% to 90%, preferably by a value of 30%, 40%, 50%, 60%, 70% or 80% in a test sample in comparison to a control level. The control level may either be a normal control level or a cancerous control level, preferably derivable from a hormone-dependent or hormone-sensitive prostate cancer.

The term "detecting prostate cancer" as used herein means that the presence of a cancerous disease or disorder in an organism may be determined or that a cancerous disease or disorder may be identified in an organism. The determination or identification of a cancerous disease or disorder may be accomplished by a comparison of the expression level of the PDE9A marker of the present invention and the normal control level as defined herein above. A cancer, in particular a prostate cancer, may be detected when the expression level of the PDE9A marker is similar to a cancerous control level as defined herein above. In a preferred embodiment of the present invention a prostate cancer may be detected if the expression level of the PDE9A marker is similar to a cancerous control level of an established prostate cancer cell or cell line, e.g. a prostate cancer cell line as mentioned herein above.

The term "monitoring prostate cancer" as used herein relates to the accompaniment of a diagnosed or detected cancerous disease or disorder, e.g. during a treatment procedure or during a certain period of time, typically during 2 months, 3 months, 4 months, 6 months, 1 year, 2 years, 3 years, 5 years, 10 years, or any other period of time. The term "accompaniment" means that states of disease as defined herein above and, in particular, changes of these sates of disease may be detected by comparing the expression level of the PDE9A marker of the present invention in a sample to a normal or a cancerous control level as defined herein above, preferably a control expression level derived from a hormone-dependent tumor control, more preferably a hormone-sensitive prostate tumor control in any type of periodical time segment, e.g. every week, every 2 weeks, every month, every 2, 3, 4, 5, 6, 7, 8, 9, 10, 11 or 12 month, every 1.5 year, every 2, 3, 4, 5, 6, 7, 8, 9 or 10 years, during any period of time, e.g. during 2 weeks, 3 weeks, 1, 2, 3, 4, 5, 6, 7, 8, 9, 10, 11, 12 months, 1.5, 2, 3, 4, 5, 6, 7, 8, 9, 10, 15 or 20 years, respectively. The cancerous control level may be derived from samples corresponding to different stages of cancer development, e.g. stages 0 and I to IV of the TNM classification system. In a preferred embodiment of the present invention the term relates to the accompaniment of a diagnosed prostate cancer, more preferably of a hormone-dependent and a hormone-sensitive prostate cancer. In a further embodiment the monitoring may also be used for the accompaniment of hormone-resistant prostate cancer, e.g. during a treatment procedure. The monitoring may also include the detection of the expression of additional genes or genetic elements, e.g. housekeeping genes like GAPDH or PBGD, or other phosphodiesterases, preferably PDE4D5.

The term "prognosticating prostate cancer" as used herein refers to the prediction of the course or outcome of a diagnosed or detected cancerous disease, e.g. during a certain period of time, during a treatment or after a treatment. The term also refers to a determination of chance of survival or recovery from a disease, as well as to a prediction of the expected survival time of a subject. A prognosis may, specifically, involve establishing the likelihood for survival of a subject during a period of time into the future, such as 6 months, 1 year, 2 years, 3 years, 5 years, 10 years or any other period of time.

The term "progression of prostate cancer" as used herein relates to a switch between different stages of prostate cancer development, e.g. stages 0 and I to IV of the TNM classification, or any other stage or sub-stage, starting from a healthy condition up to a terminal cancer scenario. Typically such switches are accompanied by a modification of the expression level of PDE9A, preferably a decrease, in a test sample in comparison to a previous test sample from the same individual, e.g. in comparison to a sample derived from a hormone-dependent prostate tumor or tumor control or a hormone-sensitive prostate tumor or tumor control. A progression of prostate cancer may be considered as being detected or diagnosed if the PDE9A expression level, as defined herein above, is decreased by a value of between 3% to 50%, preferably by a value of 10%, 15%, 20% or 25% in a test sample in comparison to a previous test sample from the same individual. The modification may be detected over any period of time, preferably over 1, 2, 3, 4, 5, 6, 7, 8, 9, 10, 11, 12 months, 1.5, 2, 3, 4, 5, 6, 7, 8, 9, 10, 15 or 20 years, i.e. the value indicated above may be calculated by comparing the expression level of PDE9A at a first point in time and at a second point in time after the above indicated period of time. The progression may, in a specific embodiment, be a progression towards hormone-resistant prostate cancer.

In a particularly preferred embodiment of the present invention the term "progression of prostate cancer" relates to a switch from a hormone-dependent prostate cancer state to a hormone-sensitive prostate cancer state, to a switch from a hormone-sensitive prostate cancer state to a hormone-resistant prostate cancer state or from a hormone-dependent or hormone-sensitive prostate cancer state to a hormone-resistant prostate cancer state.

A progression from a hormone-dependent or hormone-sensitive prostate cancer state to a hormone-resistant prostate cancer state may be considered as being detected or diagnosed if the PDE9A expression level, as defined herein above, is decreased by a value of between 3% to 50%, preferably by a value of 10%, 15%, 20% or 25% in a test sample in comparison to a previous test sample from the same individual, which has been diagnosed as suffering from a hormone-sensitive or hormone-dependent prostate cancer. The progression may also be considered to be detected if the comparison is carried out with test samples from other individuals, test samples from tissue collections, values from databases etc.

The modification may be detected over any period of time, preferably over 1, 2, 3, 4, 5, 6, 7, 8, 9, 10, 11, 12 months, 1.5, 2, 3, 4, 5, 6, 7, 8, 9, 10, 15 or 20 years, i.e. the value indicated above may be calculated by comparing the expression level of PDE9A at a first point in time and at a second point in time after the above indicated period of time.

In a further embodiment the present invention relates to the diagnosis and detection of a predisposition for developing prostate cancer, more preferably hormone-resistant prostate cancer. A "predisposition for developing prostate cancer" and in particular a "predisposition for developing hormone-resistant prostate cancer" in the context of the present invention is a state of risk of developing prostate cancer, in particular hormone-resistant prostate cancer. Preferably a predisposition for developing hormone-resistant prostate cancer may be present in cases in which the PDE9A expression level as defined herein above is below a cancerous control level as defined herein above, e.g. a reference expression level derived from tissues or samples of a subject which evidently suffers from hormone-sensitive prostate cancer. The term "below" as used herein means that the expression level of PDE9A is decreased by about 40% to 80% in comparison to a cancerous control level, preferably decreased by about 50%.

Alternatively, a predisposition for developing prostate cancer in the context of the present invention may be present in situations in which the PDE9A expression level as defined herein above given and in which further, alternative cancer markers, e.g. PSA, show no modification of expression level or the expression pattern. Suitable further cancer markers are known to the person skilled in the art.

Thus, a predisposition for prostate cancer, in particular hormone-resistant prostate cancer, may be considered as being diagnosed or detected if one of the above depicted situations is observed.

The difference between the expression levels of a test biological sample and a control level can be normalized to the expression level of further control nucleic acids, e.g. housekeeping genes whose expression levels are known not to differ depending on the cancerous or non-cancerous state of the cell. Exemplary control genes include inter alia (β-actin, glycerinaldehyde 3-phosphate dehydrogenase (GAPDH), porphobilinogen deanimase (PBGD) and ribosomal protein P1. The normalization may also be carried out with other phosphodiesterases, preferably with a human phosphodiesterase showing an unaltered expression pattern in different tumor stages. A preferred phosphodiesterase is PDE4D5 or any other isoform of the PDE4D family, e.g. PDE4D1, PDE4D2, PDE4D3, PDE4D4, PDE4D6, PDE4D8 or PDE4D9.

In the context of the present invention, the terms "diagnosing" and "prognosticating" are also intended to encompass predictions and likelihood analyses. PDE9A as a marker may accordingly be used clinically in making decisions concerning treatment modalities, including therapeutic intervention or diagnostic criteria such as a surveillance for the disease. According to the present invention, an intermediate result for examining the condition of a subject may be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

A subject or individual to be diagnosed, monitored or in which a prostate cancer, a progression of prostate cancer or predisposition for prostate cancer is to be detected or prognosticated according to the present invention is an animal, preferably a mammal, more preferably a human being.

Particularly preferred is the use of molecular imaging tools as known to the person skilled in the art, e.g. magnetic resonance imaging (MRI) and/or magnetic photon resonance imaging (MPI) technology in the context of using PDE9A as a marker for diagnosing, detecting, monitoring or prognosticating prostate cancer of the progression of prostate cancer. For example, PDE9A may be used as a marker for diagnosing, detecting, monitoring or prognosticating prostate cancer or the progression of prostate cancer in approaches like MRI or MPI that allows for online detection of the diagnostic marker within a human subject.

In a further aspect the present invention relates to a composition for diagnosing, detecting, monitoring or prognosticating prostate cancer or the progression of prostate cancer or a predisposition for prostate cancer in an individual. The composition according to the present invention may comprise a nucleic acid or peptide affinity ligand for the PDE9A expression product or protein.

The term "nucleic acid affinity ligand for the PDE9A expression product" as used herein refers to a nucleic acid molecule being able to specifically bind to a PDE9A transcript or a DNA molecule derived from derived from splice variants 1 to 20 of PDE9A, even more preferably to the DNA sequence depicted in SEQ ID NOs: 1 to 20 or to the complementary DNA sequence of the sequence depicted in SEQ ID NOs: 1 to 20 or a corresponding RNA molecule. The nucleic acid affinity ligand may also be able to specifically bind to a DNA sequence being at least 75%, 80%, 85%, 90%, 91%, 92%, 93%, 94%, 95%, 96%, 97%, 98% or 99% identical to any of the sequences as set forth in SEQ ID NOs: 1 to 20 or a DNA sequence encoding an amino acid sequence being at least 75%, 80%, 85%, 90%, 91%, 92%, 93%, 94%, 95%, 96%, 97%, 98% or 99% identical to any of the sequences as set forth in SEQ ID NOs: 21 to 40 or to any fragments of said sequences.

The term "peptide affinity ligand for the PDE9A protein" as used herein refers to a peptide molecule being able to specifically bind to a PDE9A protein. The peptide molecule may preferably be able to specifically bind to a protein or polypeptide comprising the amino acid sequence as set forth in SEQ ID NOs: 21 to 40. The peptide affinity ligand may also be able to specifically bind to a protein or polypeptide comprising an amino acid sequence encoded by a DNA sequence being at least 75%, 80%, 85%, 90%, 91%, 92%, 93%, 94%, 95%, 96%, 97%, 98% or 99% identical to any of the sequences as set forth in SEQ ID NOs: 1 to 20 or to a protein or polypeptide comprising an amino acid sequence being at least 75%, 80%, 85%, 90%, 91%, 92%, 93%, 94%, 95%, 96%, 97%, 98% or 99% identical to any of the sequences as set forth in SEQ ID NOs: 21 to 40 or to any fragments of said sequences. The term "peptide" refers to any type of amino acid sequence comprising more than 2 amino acids, e.g. polypeptide structures, protein structures or functional derivatives thereof. Furthermore, the peptide may be combined with further chemical moieties or functionalities.

The term "expression product" as used herein refers to a PDE9A transcript or an mRNA molecule generated by the expression of the PDE9A gene. More preferably, the term relates to a processed PDE9A transcript as defined herein above, e.g. via the sequences as set forth in SEQ ID NO: 1 to 20.

In a preferred embodiment of the present invention the composition of the present invention comprises nucleic acid and peptide affinity ligands selected from the group consisting of a set of oligonucleotides specific for the PDE9A expression product, a probe specific for the PDE9A expression product, an aptamer specific for the PDE9A expression product or for the PDE9A protein, an antibody specific for the PDE9A protein and an antibody variant specific for the PDE9A protein.

The composition of the present invention may, for example, comprise a set of oligonucleotides specific for the PDE9A expression product and/or a probe specific for the PDE9A expression product. The term "oligonucleotide specific for the PDE9A expression product" as used herein refers to a nucleotide sequence which is complementary to the sense- or antisense-strand of splice variants 1 to 20 of PDE9A. Preferably, the oligonucleotide is complementary to the DNA sequence depicted in SEQ ID NOs: 1 to 20 or to the complementary DNA sequence of the sequence depicted in SEQ ID NOs: 1 to 20. The oligonucleotide sequence may also be complementary to a DNA sequence being at least 75%, 80%, 85%, 90%, 91%, 92%, 93%, 94%, 95%, 96%, 97%, 98% or 99% identical to any of the sequences as set forth in SEQ ID NOs: 1 to 20 or a DNA sequence encoding an amino acid sequence being at least 75%, 80%, 85%, 90%, 91%, 92%, 93%, 94%, 95%, 96%, 97%, 98% or 99% identical to any of the sequences as set forth in SEQ ID NOs: 21 to 40.

The oligonucleotide may have any suitable length and sequence known to the person skilled in the, as derivable from the sequence of any one of SEQ ID NOs: 1 to 20, or its complement. Typically, the oligonucleotide may have a length of between 8 and 60 nucleotides, preferably of between 10 and 35 nucleotides, more preferably a length of 11, 12, 13, 14, 15, 16, 17, 18, 19, 20, 21, 22, 23, 24, 25, 26, 27, 28, 29, 30, 31, 32 or 33 nucleotides. Oligonucleotide sequences specific for the PDE9A expression product may be defined with the help of software tools known to the person skilled in the art.

In a further embodiment of the present invention the oligonucleotide sequences may be complementary to sequences localized in the conserved region of PDE9A, preferably between exon 10 and exon 22 of the PDE9A gene, more preferably to sequences localized in the boundary between exon 19 and exon 20 of the PDE9A gene or to sequences localized in exon 19, 20 or 21 of the PDE9A gene solely, even more preferably to sequences between exon 20 on the one side, and all nucleotides of exon 21 on the other side.

For instance, an oligonucleotide usable as a forward primer may be localized in exon 19 of the PDE9A gene and the oligonucleotide usable as a reverse primer may be localized in exon 20 of the PDE9A gene. In a preferred embodiment an oligonucleotide usable as a forward primer may be complementary to a sequence localized on exon 20, and an oligonucleotide usable as a reverse primer may be complementary to a sequence localized on exon 21.

In a preferred embodiment of the present invention the set of oligonucleotides has the sequences as set forth in SEQ ID NO: 41 and SEQ ID NO: 42. Further preferred are the oligonucleotides having or comprising the sequence as set forth in SEQ ID NO: 45 and/or SEQ ID NO: 46.

The term "probe specific for the PDE9A expression product" as used herein means a nucleotide sequence which is complementary to the sense- or antisense-strand of splice variants 1 to 20 of PDE9A. Preferably, the probe is complementary to the DNA sequence depicted in any one of SEQ ID NOs: 1 to 20 or to the complementary DNA sequence of the sequence depicted in SEQ ID NOs: 1 to 20. The probe sequence may also be complementary to a DNA sequence being at least 75%, 80%, 85%, 90%, 91%, 92%, 93%, 94%, 95%, 96%, 97%, 98% or 99% identical to any of the sequences as set forth in SEQ ID NOs: 1 to 20 or a DNA sequence encoding an amino acid sequence being at least 75%, 80%, 85%, 90%, 91%, 92%, 93%, 94%, 95%, 96%, 97%, 98% or 99% identical to any of the sequences as set forth in SEQ ID NOs: 21 to 40.

The probe may have any suitable length and sequence known to the person skilled in the, as derivable from the sequence of SEQ ID NOs: 1 to 20 or its complement. Typically, the probe may have a length of between 6 and 300 nucleotides, preferably of between 15 and 60 nucleotides, more preferably a length of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. Probe sequences specific for the PDE9A expression product may be defined with the help of software tools known to the person skilled in the art.

In a further embodiment of the present invention the probe sequence may be complementary to a sequence localized in the conserved region of PDE9A, preferably between exon 10 and exon 22 of the PDE9A gene. More preferably the probe sequence may be complementary to sequences localized in the boundary between exon 19 and exon 20 of the PDE9A gene or to sequences localized in exon 19, 20 or 21 of the PDE9A gene solely, even more preferably the probe sequence may be complementary to sequences between exon 20 on the one side, and all nucleotides of exon 21 on the other side. In a preferred embodiment an oligonucleotide usable as a probe may be complementary to a sequence localized between the last 16 bases of exon 20 and the first 5 bases of exon 21 of the PDE9A gene.

If the probe is to be used for quantitative PCR reactions, e.g. real time PCR, the probe may be designed such that it is localized at a position in between the binding positions of a forward and reverse primer. Preferably, the probe may be designed such that it is localized in the proximity of one of the primer oligonucleotides. More preferably, it may be localized in the proximity of the forward primer.

In a preferred embodiment of the present invention the probe has the sequence as set forth in SEQ ID NO: 43 or SEQ ID NO: 47.

The composition of the present invention may additionally or alternatively comprise an aptamer specific for the PDE9A expression product or protein. The term "aptamer specific for the PDE9A expression product" as used herein refers to a short nucleic acid molecule, e.g. RNA, DNA, PNA, CNA, HNA, LNA or ANA or any other suitable nucleic acid format known to the person skilled in the art, being capable of specifically binding to splice variants 1 to 20 of PDE9A, preferably the DNA molecule derived from splice variants 1 to 20 of PDE9A. More preferably, the nucleic acid aptamer molecule may specifically bind to a DNA sequence depicted in SEQ ID NOs: 1 to 20 or a double stranded derivative thereof. The nucleic acid aptamer according to the present invention may also bind to an RNA molecule corresponding to the PDE9A transcript, preferably an RNA molecule corresponding to the DNA sequence as set forth in SEQ ID NOs: 1 to 20.

The nucleic acid aptamer may further be capable of specifically binding to a DNA sequence being at least 75%, 80%, 85%, 90%, 91%, 92%, 93%, 94%, 95%, 96%, 97%, 98% or 99% identical to any of the sequences as set forth in SEQ ID NOs: 1 to 20 or a DNA sequence encoding an amino acid sequence being at least 75%, 80%, 85%, 90%, 91%, 92%, 93%, 94%, 95%, 96%, 97%, 98% or 99% identical to any of the sequences as set forth in SEQ ID NOs: 21 to 40 or RNA molecules corresponding to these sequences.

Specificity of the nucleic acid aptamer to splice variants 1 to 20 of PDE9A may be conferred by a specific binding to sequences solely present in said splice variants.

Nucleic acid aptamers may be generated according to any suitable method known to the person skilled in the art, e.g. by in vitro selection or SELEX methods. Preferably, nucleic acid aptamers may be generated and/or designed according to the guidance provided in Ellington and Szostak, 1990, Nature, 346:818-822. A nucleic acid aptamer according to the present invention may further be combined with additional moieties, e.g. with interacting portions like biotin or enzymatic functionalities like ribozyme elements.

The term "aptamer specific for the PDE9A protein" as used herein refers to a short peptide capable of interacting and specifically binding the PDE9A protein. The peptide aptamer may preferably be able to specifically bind to a protein or polypeptide comprising the amino acid sequence as set forth in SEQ ID NOs: 21 to 40. The peptide aptamer may also be able to specifically bind to a protein or polypeptide comprising an amino acid sequence encoded by a DNA sequence being at least 75%, 80%, 85%, 90%, 91%, 92%, 93%, 94%, 95%, 96%, 97%, 98% or 99% identical to any of the sequences as set forth in any one of SEQ ID NOs: 1 to 20 or to a protein or polypeptide comprising an amino acid sequence being at least 75%, 80%, 85%, 90%, 91%, 92%, 93%, 94%, 95%, 96%, 97%, 98% or 99% identical to any of the sequences as set forth in any one of SEQ ID NOs: 21 to 40. Typically, a peptide aptamer is a variable peptide loop, comprising for example, 10 to 20 amino acids. In the context of the present invention the peptide aptamer may preferably be attached at one or both ends to a scaffold structure. The scaffold structure may be any molecule, preferably a protein, which has good solubility properties. Suitable scaffold molecules would be known to the person skilled in the art. A preferred scaffold molecule to be used in the context of the present invention is the bacterial protein thioredoxin-A. The aptamer peptide loop may preferably be inserted within a reducing active site of the scaffold molecule. Alternatively, staphylococcal protein A and domains thereof and derivatives of these domains, such as protein Z or lipocalins may be used as scaffold structures in the context of the present invention.

Peptide aptamers may be generated according to any suitable method known to the person skilled in the art, e.g. via yeast two-hybrid approaches.

In another preferred embodiment of the present invention the composition may comprise, or may additionally comprise, an antibody specific for the PDE9A protein, preferably a monoclonal or polyclonal antibody. Also preferred are antibody variants or fragments like a single chain antibody, a diabody, a minibody, a single chain Fv fragment (sc(Fv)), a $sc(Fv)_2$ antibody, a Fab fragment or a $F(ab')_2$ fragment based on a monoclonal PDE9A specific antibody, a small modular immunopharmaceutical (SMIP), a binding-domain immunoglobulin fusion protein, a camelized antibody, a $V_{HH}$ containing antibody etc. The antibody may be mono-, bi-, tri- or multivalent. The antibody may be of any origin, e.g. a murine, human, or chimeric, or a humanized murine antibody. In a specific embodiment of the present invention commercially available anti-PDE9A antibodies like H00005152-M01 (Abnova Taiwan Corp) or NBP1-00641 (Novas Biologicals, Inc.) may be comprised in the composition or may be used diagnostically.

Antibodies may be produced according to any suitable method known to the person skilled in the art. Polyclonal antibodies may be produced by immunization of animals with the antigen of choice, whereas monoclonal antibodies of defined specificity may be produced using, for instance, the hybridoma technology developed by Köhler and Milstein (Köhler and Milstein, 1976, Eur. J. Immunol., 6: 511-519).

An affinity ligand, as described herein above, may be labeled with various markers or may be detected by a secondary affinity ligand, labeled with various markers, to allow detection, visualization and/or quantification. This can be accomplished using any suitable labels, which can be conjugated to the affinity ligand capable of interaction with the PDE9A expression product or the PDE9A protein or to any secondary affinity ligand, using any suitable technique or methods known to the person skilled in the art. The term "secondary affinity ligand" refers to a molecule which is capable of binding to the affinity ligand as defined herein above (i.e. a "primary affinity ligand" if used in the context of a system with two interacting affinity ligands). The binding interaction is preferably a specific binding.

Examples of labels that can be conjugated to a primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin).

In a particularly preferred embodiment an affinity ligand to be used as a probe, in particular a probe specific for the PDE9A expression product as defined herein above, may be labeled with a fluorescent label like 6-FAM, HEX, TET, ROX, Cy3, Cy5, Texas Red or Rhodamine, and/or at the same time with a quenching label like TAMRA, Dabcyl, Black Hole Quencher, BHQ-1 or BHQ-2. A variety of other useful fluorescents and chromophores are described in Stryer, 1968, Science, 162:526-533. Affinity ligands may also be labeled with enzymes (e.g. horseradish peroxidase, alkaline phosphatase, beta-lactamase), radioisotopes (e.g. $^{3}H$, $^{14}C$, $^{32}P$, $^{33}P$, $^{35}S$, $^{125}I$, $^{11}C$, $^{13}N$, $^{15}O$, $^{18}F$, $^{64}Cu$, $^{62}Cu$, $^{124}I$, $^{76}Br$, $^{82}Rb$, $^{68}Ga$ or $^{18}F$) or particles (e.g. gold).

The different types of labels may be conjugated to an affinity ligand using various chemistries, e.g. the amine reaction or the thiol reaction. However, other reactive groups than amines and thiols can also be used, e.g. aldehydes, carboxylic acids and glutamine.

In a preferred embodiment of the present invention the nucleic acid affinity ligand or peptide affinity ligand of the present invention may be modified to function as a contrast agent.

The term "contrast agent" as used herein refers to a molecular compound that is capable of specifically interacting with the PDE9A marker and which can be detected by an apparatus positioned outside the human or animal body. Preferably, such contrast agents are suitable for use in magnetic resonance imaging (MRI) or magnetic photon imaging (MPI). The term "specifically interacting" refer to the property of a molecular compound to preferentially interact with the PDE9A marker on the cell surface of cells being present within the human or animal body over other proteins that are expressed by such cells. Preferred contrast agents which may also be designated as contrast agent compositions will be capable of specifically detecting molecules having the nucleotide sequence of any one of SEQ ID NOs: 1 to 20 or the amino acid sequence of any one of SEQ ID NOs: 21 to 40 or derivatives or homologous variants thereof as defined herein above. Preferred contrast agents are aptamers specific for the PDE9A expression product or for a PDE9A protein as defined herein above as well as antibodies specific for a PDE9A protein as defined herein above.

Contrast agents, aside from their property of being capable of specifically recognizing the PDE9A marker will in addition typically comprise a further molecule which is detectable by the specific detection technology used. The term "modified to function" as used herein thus refers to any suitable modifications known to the person skilled in the art, which may be necessary in order to allow the use of the contrast agent in molecular imaging methods, in particular in MRI or MPI. For example, if fluorescent spectroscopy is used as a detection means, such molecules may comprise fluorophores as detectable marker molecules that can be excited at a specific wavelength. Alternatively, a radioactive label, e.g. a radioisotope as described herein above may be employed. With respect to preferred contrast agents in accordance with the invention that are suitable for MRI, the contrast agents such as the above described antibodies may comprise a marker molecule which is detectable by MRI. Such detectable labels include e.g. USPIOS and 19Fluor.

In a specific embodiment of the present invention a composition may additionally comprise accessory ingredients like PCR buffers, dNTPs, a polymerase, ions like bivalent cations or monovalent cations, hybridization solutions, secondary affinity ligands like, e.g. secondary antibodies, detection dyes and any other suitable compound or liquid necessary for the performance of a detection based on any of the affinity ligands or contrast agents as defined herein above, which is known to the person skilled in the art.

In another aspect the present invention relates to the use of a nucleic acid or peptide affinity ligand for the PDE9A expression product or protein, as defined herein above, for the preparation of a composition for diagnosing, detecting, monitoring or prognosticating prostate cancer or the progression of prostate cancer or a predisposition for prostate cancer in an individual, as described herein above.

In a preferred embodiment the present invention relates to the use of a set of oligonucleotides specific for the PDE9A expression product and/or a probe specific for the PDE9A expression product, as defined herein above, for the preparation of a composition for diagnosing, detecting, monitoring or prognosticating prostate cancer or the progression of prostate cancer or a predisposition for prostate cancer in an individual, as described herein above. In another preferred embodiment the present invention relates to the use of an aptamer specific for the PDE9A expression product or protein, as defined herein above, for the preparation of a composition for diagnosing, detecting, monitoring or prognosticating prostate cancer or the progression of prostate cancer or a predisposition for prostate cancer in an individual, as described herein above.

In a further preferred embodiment the present invention relates to the use of an antibody specific for the PDE9A protein or an antibody variant specific for the PDE9A protein, as defined herein above, for the preparation of a composition for diagnosing, detecting, monitoring or prognosticating prostate cancer or the progression of prostate cancer or a predisposition for prostate cancer in an individual, as described herein above.

In a preferred embodiment of the present invention a composition as defined herein above is a diagnostic composition.

In another aspect the present invention relates to a diagnostic kit for detecting, diagnosing, monitoring or prognosticating prostate cancer or the progression of prostate cancer or a predisposition for prostate cancer, comprising a set of oligonucleotides specific for the PDE9A expression product, a probe specific for the PDE9A expression product and/or an aptamer specific for the PDE9A expression product or protein and/or an antibody specific for the PDE9A protein and an antibody variant specific for the PDE9A protein.

Typically, the diagnostic kit of the present invention contains one or more agents allowing the specific detection of PDE9A as defined herein above. The agents or ingredients of a diagnostic kit may, according to the present invention, be comprised in one or more containers or separate entities. The nature of the agents is determined by the method of detection for which the kit is intended. Where detection at the PDE9A mRNA expression level, i.e. via the PDE9A expression product, is intended, the agents to be comprised may be a set of oligonucleotides specific for the PDE9A expression product and/or a probe specific for the PDE9A expression product as defined herein above, which may be optionally labeled according to methods known in the art, e.g. with labels described herein above. In addition or alternatively an aptamer specific for the PDE9A expression production may be comprised. Where detection is at the PDE9A protein level is intended, the agents to be comprised may be antibodies or compounds containing an antigen-binding fragment of an antibody or antibody variants specific for the PDE9A protein, as described herein above. In addition or alternatively an aptamer specific for the PDE9A protein may be comprised. Alternatively, a diagnostic kit may comprise a contrast agent as defined herein above.

The presence of specific proteins may also be detected using other compounds that specifically interact with PDE9A, e.g. specific substrates or ligands.

Preferably, a diagnostic kit of the present invention contains detection reagents for PDE9A expression product or the PDE9A protein. Such detection reagents comprise, for example, buffer solutions, labels or washing liquids etc. Furthermore, the kit may comprise an amount of a known nucleic acid molecule or protein, which can be used for a calibration of the kit or as an internal control. Typically, a diagnostic kit for the detection of PDE9A expression products may comprise accessory ingredients like a PCR buffers, dNTPs, a polymerase, ions like bivalent cations or monovalent cations, hybridization solutions etc. A diagnostic kit for the detection of PDE9A proteins may also comprise accessory ingredients like secondary affinity ligands, e.g. secondary antibodies, detection dyes and any other suitable compound or liquid necessary for the performance of a protein detection based known to the person skilled in the art. Such ingredients are known to the person skilled in the art and may vary depending on the detection method carried out. Additionally, the kit may comprise an instruction leaflet and/or may provide information as to the relevance of the obtained results.

In another aspect the present invention relates to a method for detecting, diagnosing, monitoring or prognosticating prostate cancer or the progression of prostate cancer in an individual comprising at least the step of determining the level of PDE9A in a sample. The term "determining the level of PDE9A" refers to the determination of the presence or amount of PDE9A expression products, e.g. PDE9A transcript(s), and/or the determination of the presence and/or amount of PDE9A protein(s). The term "level of PDE9A" thus means the presence or amount of PDE9A expression products, e.g. PDE9A transcript(s), and/or the determination of the presence or amount of PDE9A protein(s). The determination of the presence or amount of PDE9A expression products, e.g. PDE9A transcript(s) or PDE9A protein(s) may be accomplished by any means known in the art.

In a preferred embodiment of the present invention the determination of the presence or amount of PDE9A expression products, e.g. PDE9A transcript(s) and/or of PDE9A protein(s), is accomplished by the measurement of nucleic acid or protein levels or by the determination of the biological activity of PDE9A. Thus, the PDE9A expression level(s) may be determined by a method involving the detection of an mRNA encoded by the PDE9A gene, the detection of a PDE9A protein encoded by a PDE9A transcript and/or the detection of the biological activity of a PDE9A protein.

For example, the measurement of the nucleic acid level of PDE9A expression may be assessed by separation of nucleic acid molecules (e.g. RNA or cDNA) obtained from the sample in agarose or polyacrylamide gels, followed by hybridization with PDE9A specific oligonucleotide probes as defined herein above. Alternatively, the expression level may be determined by the labeling of nucleic acid obtained from the sample followed by separation on a sequencing gel. Nucleic acid samples may be placed on the gel such that patient and control or standard nucleic acid are in adjacent lanes. Comparison of expression levels may be accomplished visually or by means of a densitometer. Methods for the detection of mRNA or expression products are known to the person skilled in the art. Typically, Northern blot analysis may be used for such a purpose.

Alternatively, the nucleic acid level of PDE9A expression may be detected in a DNA array or microarray approach. Typically, sample nucleic acids derived from subjects to be tested are processed and labeled, preferably with a fluorescent label. Subsequently, such nucleic acid molecules may be used in a hybridization approach with immobilized capture probes corresponding to the PDE9A marker gene of the present invention or known biomarker or cancer marker genes. Suitable means for carrying out microarray analyses are known to the person skilled in the art.

In a standard setup a DNA array or microarray comprises immobilized high-density probes to detect a number of genes. The probes on the array are complementary to one or more parts of the sequence of the marker gene, or to the entire coding region of the marker gene. In the present invention, any type of PDE9A associated polynucleotide may be used as probe for the DNA array, as long as the polynucleotide allows for a specific distinction between PDE9A expression and the expression of other genes. Typically, cDNAs, PCR products, and oligonucleotides are useful as probes. Preferably, a probe involving the specific portions of splice variants 1 to 20 of PDE9A may be used as a probe. In addition to the determination of the PDE9A expression also the determination of the expression of other genes, e.g. additional biomarker or cancer marker genes may be accomplished.

A DNA array- or microarray-based detection method typically comprises the following steps: (1) Isolating mRNA from a sample and optionally converting the mRNA to cDNA, and subsequently labeling this RNA or cDNA. Methods for isolating RNA, converting it into cDNA and for labeling nucleic acids are described in manuals for micro array technology. (2) Hybridizing the nucleic acids from step 1 with probes for the marker genes. The nucleic acids from a sample can be labeled with a dye, such as the fluorescent dyes Cy3 (red) or Cy5 (blue). Generally a control sample is labeled with a different dye. (3) Detecting the hybridization of the nucleic acids from the sample with the probes and determining at least qualitatively, and more particularly quantitatively, the amounts of mRNA in the sample for PDE9A and/or additional marker genes investigated. The difference in the expression level between sample and control can be estimated based on a difference in the signal intensity. These can be measured and analyzed by appropriate software such as, but not limited to the software provided for example by Affymetrix.

There is no limitation on the number of probes corresponding to the marker genes used, which are spotted on a DNA array. Also, a marker gene can be represented by two or more probes, the probes hybridizing to different parts of a gene. Probes are designed for each selected marker gene. Such a probe is typically an oligonucleotide comprising 5-50 nucleotide residues. Longer DNAs can be synthesized by PCR or chemically. Methods for synthesizing such oligonucleotides and applying them on a substrate are well known in the field of micro-arrays. Genes other than the marker genes may be also spotted on the DNA array. For example, a probe for a gene whose expression level is not significantly altered may be spotted on the DNA array to normalize assay results or to compare assay results of multiple arrays or different assays.

Alternatively, the nucleic acid level of PDE9A expression may be detected in a quantitative RT-PCR approach, preferably in a real-time PCR approach following the reverse transcription of the PDE9A mRNA transcript. Typically, as first step, a transcript is reverse transcribed into a cDNA molecule according to any suitable method known to the person skilled in the art. A quantitative or real-time PCR approach may subsequently be carried out based on a first DNA strand obtained as described above.

Preferably, Taqman or Molecular Beacon probes as principal FRET-based probes of this type may be used for quantitative PCR detection. In both cases, the probes, preferably PDE9A probes as defined herein above, serve as internal probes which are used in conjunction with a pair of opposing primers that flank the target region of interest, preferably a set of PDE9A oligonucleotides as defined herein above. Upon amplification of a target segment, the probe may selectively bind to the products at an identifying sequence in between the primer sites, thereby causing increases in FRET signaling relative to increases in target frequency.

Preferably, a Taqman probe to be used for a quantitative PCR approach according to the present invention may comprises a PDE9A oligonucleotide as defined above of about 22 to 30 bases that is labeled on both ends with a FRET pair. Typically, the 5' end will have a shorter wavelength fluorophore such as fluorescein (e.g. FAM) and the 3' end is commonly labeled with a longer wavelength fluorescent quencher (e.g. TAMRA) or a non-fluorescent quencher compound (e.g. Black Hole Quencher). It is preferred that the probes to be used for quantitative PCR, in particular the PDE9A probes as defined herein above, have no guanine (G) at the 5' end adjacent to the reporter dye in order to avoid quenching of the reporter fluorescence after the probe is degraded.

A Molecular Beacon probe to be used for a quantitative PCR approach according to the present invention preferably uses FRET interactions to detect and quantify a PCR product, with each probe having a 5' fluorescent-labeled end and a 3' quencher-labeled end. This hairpin or stem-loop configuration of the probe structure comprises preferably a stem with two short self-binding ends and a loop with a long internal target-specific region of about 20 to 30 bases.

Alternative detection mechanisms which may also be employed in the context of the present invention are directed to a probe fabricated with only a loop structure and without a short complementary stem region. An alternative FRET-based approach for quantitative PCR which may also be used in the context of the present invention is based on the use of two hybridization probes that bind to adjacent sites on the target wherein the first probe has a fluorescent donor label at the 3' end and the second probe has a fluorescent acceptor label at its 5' end.

The measurement of protein levels of the PDE9A protein or of any fragments, homologues or derivates derived thereof may be carried out via any suitable detection technique known in the art. Preferably, the protein level of PDE9A and derivatives thereof may be determined immunologically, e.g. by using an antibody specific for the PDE9A protein, preferably an antibody as defined herein above. Alternatively, antibody variants or fragments as defined herein above may be used. The present invention also envisages the use of peptide affinity ligands like aptamers specific for the PDE9A protein as defined herein above.

Determination of the protein levels of the PDE9A protein can be accomplished, for example, by the separation of proteins from a sample on a polyacrylamide gel, followed by identification of the PDE9A protein using specifically binding antibodies in a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. The analysis of 2D SDS-PAGE gels can be performed by determining the intensity of protein spots on the gel, or can be performed using immune detection. In other embodiments, protein samples are analyzed by mass spectroscopy.

Within the context of the present invention PDE9A specific antibodies may be placed on a support and be immobilized. Proteins derived from samples or tissues to be analyzed may subsequently be mixed with the antibodies. A detection reaction may then be carried out, e.g. with a second affinity ligand as defined herein above, preferably with a specific antibody.

Immunological tests which may be used in the context of the present invention, in particular for the diagnostic purposes of the present invention, include, for example, competitive and non-competitive assay systems using techniques such as western blots, radioimmunoassay like RIA (radio-linked immunoassay), ELISA (enzyme linked immunosorbent assay), "sandwich" immunoassays, immunoprecipitation assays, precipitin reactions, gel diffusion precipitin reactions, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays, electrochemiluminescence immunoassay (ECLIA) and protein A immunoassays. Such assays are routine and well known to the person skilled in the art.

Furthermore, the binding affinity of an antibody to an antigen and the off-rate of an antibody-antigen interaction may be determined by competitive binding assays. One example of a competitive binding assay is a radioimmunoassay comprising the incubation of labeled antigen (e.g., $^{3}H$ or $^{125}I$) with a suitable antibody in the presence of increasing amounts of unlabeled antigen, and the detection of the antibody bound to the labeled antigen. The affinity of the antibody of interest for a particular antigen and the binding off-rates may be determined from the data by any suitable analysis approach, e.g. by a scatchard plot analysis. Competition with a second antibody may also be determined using radioimmunoassays. In this case, the antigen may be incubated with a suitable antibody conjugated to a labeled compound (e.g., $^{3}H$ or $^{125}I$) in the presence of increasing amounts of an unlabeled second antibody.

In addition, aptamers specific for the PDE9A protein, preferably as defined herein above, may be used in a method of detecting PDE9A proteins. Such aptamers may preferably be labeled in order to allow the detection of a protein-ligand interaction.

The determination of the biological activity of PDE9A may be carried out by employing molecular or enzymatic assays specific to the corresponding function or functions of PDE9A. Preferably, a readout system based on the conversion of cGMP by phosphodiesterase may be used. Suitable techniques would be known to the person skilled in the art. In a further preferred embodiment, an assay for the determination of the biological activity of PDE9A may be carried out in combination with the inhibition of the activity of other PDE9 isoforms and/or other PDEs, preferably other PDEs capable of performing the conversion of cGMP. Such an inhibition of the activity may be carried out by any suitable means known to the person skilled in the art, preferably via the use of suitable antisense nucleotides, siRNA molecules or miRNA molecules, more preferably via specifically hybridizing antisense nucleotides, specific siRNA or miRNA molecules as well as molecules like BAY 73-6691, Zaprinast, SCH51866, Sildenafil and Vardenafil.

In a further preferred embodiment the biological activity of PDE9A may be tested with the help of specific PDE9A inhibitors. The use of such inhibitors may, for example, be combined with a readout system based on the conversion of the cGMP substrate. Typical PDE9A inhibitors to be used comprise antisense molecules, siRNA molecules or miRNA molecules.

The level of PDE9A may also be detected in methods involving histological or cell-biological procedures. Typically, visual techniques, such as light microscopy or immunofluorescence microscopy, as well as flow cytometry or luminometry may be used. The presence of PDE9A protein in a cell may, for instance, be detected or determined by removing cells to be tested from samples as defined herein above. Also tissue sections or biopsy samples may be used for these methods. Subsequently, affinity ligands for PDE9A may be applied, preferably antibodies or aptamers. Typically, such affinity ligands are labeled, preferably with fluorescent labels as defined herein above. Such a procedure allows for the detection of PDE9A, for its quantification and, in addition, allows to determine the distribution and relative level of expression thereof.

Such procedures involve the use of visualization methods. Suitable visualization methods are known to the person skilled in the art. Typical methods to be used comprise fluorometric, luminometric and/or enzymatic techniques. Fluorescence is normally detected and/or quantified by exposing fluorescent labels to light of a specific wavelength and thereafter detecting and/or quantifying the emitted light of a specific wavelength. The presence of a luminescently tagged affinity ligand may be detected and/or quantified by luminescence developed during a chemical reaction. Detection of an enzymatic reaction is due to a color shift in the sample arising from chemical reaction.

In a further, preferred embodiment the level of PDE9A may be determined by suitable molecular imaging techniques, e.g. magnetic resonance imaging (MRI) or magnetic photon imaging (MPI), and/or by using suitable contrast agents, e.g. contrast agents as defined herein above.

In a further, preferred embodiment a method for detecting, diagnosing, monitoring or prognosticating prostate cancer or the progression of prostate cancer of the present invention comprises the additional step of comparing the measured nucleic acid or protein levels or the measured biological activity to a control level. The term "control level" as used herein refers to the expression of the PDE9A marker or other suitable markers in a cancerous control or non-cancerous control, as defined herein above. The status, nature, amount and condition of the control level may be adjusted according to the necessities. Preferably a non-cancerous control level may be used. The term "comparing" as used herein refers to any suitable method of assessing, calculating, evaluating or processing of data.

In yet another embodiment as a further, additional step a decision on the presence or stage of prostate cancer or the progression of prostate cancer may be based on the results of the comparison step. A prostate cancer may be diagnosed or prognosticated or a progression of prostate cancer may be diagnosed or prognosticated in said method according to the corresponding definitions provided herein above in the context of PDE9A as prostate cancer marker.

In another embodiment the present invention relates to a method for detecting, diagnosing, monitoring or prognosticating prostate cancer or the progression of prostate cancer comprising at least the steps of:

(a) testing in at least one sample obtained from at least one individual suspected to suffer from prostate cancer for expression of the PDE9A expression product or the PDE9A protein;

(b) testing in at least one control sample obtained from at least one individual not suffering from cancer for the expression of the PDE9A expression product or the PDE9A protein;

(c) determining the difference in the expression of steps (a) and (b); and (d) deciding on the presence or stage of prostate cancer or the progression of prostate cancer based on the results obtained in step (c).

In one embodiment, steps a), b), c) and/or d) of this method of diagnosis may be performed outside the human or animal body, e.g. in samples obtained from a patient or individual.

In another aspect the present invention relates to a method for diagnosing, monitoring or prognosticating hormone-resistant prostate cancer or the progression towards hormone-resistant prostate cancer, wherein said method discriminates between a hormone-sensitive and a hormone-resistant prostate cancer, comprising the steps of (a) determining the level of PDE9A in a sample;

(b) determining the level of expression of a reference gene in a sample;

(c) normalizing the measured expression level of PDE9A to the expression of the reference gene; and (d) comparing the normalized expression level with a predetermined cutoff value chosen to exclude hormone-sensitive prostate cancer, wherein a normalized expression level below the cutoff value is indicative of a hormone-resistant prostate cancer. wherein said cutoff value between about 2 and 15, preferably about 5.

The level of PDE9A may be determined on the nucleic acid, protein or activity level as described herein above. Preferred is the determination of the amount of PDE9A transcript(s) and/or protein. In addition the level of a reference gene in a sample may be determined. The term "reference gene" as used herein refers to any suitable gene, e.g. to any steadily expressed and continuously detectable gene, gene product, expression product, protein or protein variant in the organism of choice. The term also includes gene products such as expressed proteins, peptides, polypeptides, as well as modified variants thereof. The invention hence also includes reference proteins derived from a reference gene. Also encompassed are all kinds of transcripts derivable from the reference gene as well as modifications thereof or secondary parameters linked thereto. Alternatively or additionally, other reference parameters may also be used for reference purposes, e.g. metabolic concentrations, cell sizes etc.

The expression may be preferably be carried out in the same sample, i.e. the level of PDE9A and of the reference gene is determined in the same sample. If the testing is carried out in the same sample, a single detection or a multiplex detection approach as described herein may be performed. Preferably, for a multiplex detection the oligonucleotides and probes having the sequence of SEQ ID NO: 7, 8 and 9 or the sequence of SEQ ID NO: 45, 46 and 47 may be used. For the performance of the multiplex detection the concentration of primers and/or probe oligonucleotides may be modified. Furthermore, the concentration and presence of further ingredients like buffers, ions etc. may be modified, e.g. increased or decreased in comparison to manufacturers' indications.

In a specific embodiment of the present invention, the expression of more than one reference gene or steadily expressed gene may be determined. E.g. the expression of 2, 3, 4, 5, 6, 7, 8, 9, 10, 12, 15, 20, 30 or more reference genes may be determined. The results of such measurements may be either calculated separately, or may be combined in order to obtain an average expression index. Furthermore, pattern of reference gene expression may be determined and/or used as basis for subsequent steps. Such pattern may be based on known expression behaviors of genes in certain cancer, in particular prostate cancer stages or states.

Furthermore, expression results may be compared to already known results from reference cases or databases. The comparison may additionally include a normalization procedure in order to improve the statistical relevance of the results.

In an alternative embodiment of the present invention, instead of determining the level of expression of a reference gene in a sample, the expression of a further cancer marker or non-steadily expressed gene may be determined. For example, the expression of a gene, which is known to be reduced during hormone-resistant prostate cancer, or which is known to be increased during hormone-sensitive prostate cancer, may be determined.

In a further embodiment, also both expression determinations may be carried out, i.e. the determination of expression of a reference gene and of a further cancer or biomarker gene.

Expression results may be normalized according to any suitable method known to the person skilled in the art, e.g. according to normalization statistical methods like the standard score, Student's T-test, studentized residual test, standardized moment text, or coeffizient variation test. Typically, such tests or corresponding formula, which would be known to the person skilled in the art, would be used to standardize expression data to enable differentiation between real variations in gene expression levels and variations due to the measurement processes.

Based on the expression results obtained in steps (a) and (b) and/or the normalized results obtained in step (c) a comparison with a cutoff value for PDE9A expression may be carried out. The cutoff value below which the expression level of PDE9A is indicative of a hormone-resistant prostate cancer, thereby excluding hormone-sensitive prostate cancer or tumor forms, is between about 2 and 15, 2 and 14.5, 2 and 14, 2 and 13.5, 2 and 13, 2 and 12.5, 2 and 12, 2 and 11.5, 2 and 11, 2 and 10.5, 2 and 10, 2 and 9.5, 2 and 9, 2 and 8.5, 2 and 8, 2 and 7.5, 2 and 7, 2 and 6.5, 2 and 6, 2 and 5.5, 2 and 5 or 2.5 and 15, 3 and 15, 3.5 and 15, 4 and 15, 4.5 and 15, 5 and 15, 5 and 15. More preferred is a cutoff value of about 5, e.g. 4.9, 4.8, 4.7, 4.6, 4.5, 4.4, 4.3, 4.2, 4.1 or 5.9, 5.8, 5.7, 5.6, 5.5, 5.4, 5.3, 5.2, 5.1.

In a particularly preferred embodiment, said cutoff is to be used with a housekeeping gene as reference gene. Even more preferably, said cutoff is to be used with GAPDH and/or PBGD as reference gene.

In another aspect the present invention relates to a method for diagnosing, monitoring or prognosticating malignant, hormone-sensitive prostate cancer or the progression towards malignant, hormone-sensitive prostate cancer, wherein said method discriminates between a non-cancerous stage, preferably a healthy stage and a malignant, hormone-sensitive prostate cancer, comprising the steps of (a) determining the level of PDE9A, (b) determining the level of expression of a reference gene in a sample;

(c) normalizing the measured expression level of PDE9A to the expression of the reference gene; and comparing the normalized expression level with a predetermined cutoff value chosen to exclude benign prostate tumor, wherein a normalized expression level above the cutoff value is indicative of a malignant, hormone-sensitive prostate cancer, wherein said cutoff value is between 1.5 and 3, preferably about 2. The method may be carried out as described herein above. In the context of this method the employment of PDE4D5 as reference gene is preferred. Further, particularly preferred is the performance of multiplex detection reactions with suitable oligonucleotides and probes, e.g. with oligonucleotides and probes having the sequence of SEQ ID NO: 45, 46 and 47 (PDE9A) together with oligonucleotides and probes having the sequence of SEQ ID NO: 48, 49 and 50 (PDE4D5). For the performance of the multiplex detection the concentration of primers and/or probe oligonucleotides may be modified. Furthermore, the concentration and presence of further ingredients like buffers, ions etc. may be modified, e.g. increased or decreased in comparison to manufacturers' indications.

Based on the expression results obtained in steps (a) and (b) and/or the normalized results obtained in step (c) a comparison with a cutoff value for PDE9A expression may be carried out. The cutoff value below which the expression level of PDE9A is indicative of a healthy situation, i.e. the absence of prostate cancer, thereby excluding hormone-sensitive prostate cancer or tumor forms, is between about 1.5 and 3, 1.75 and 3, 2 and 3, 2.25 and 3, 2.5 and 3, 2.75 and 3. More preferred is a cutoff value of about 2, e.g. 1.9, 1.8, 1.7, 1.6, 1.5, 2.9, 2.8, 2.7, 2.6, 2.5, 2.4, 2.3, 2.2, 2.1

"A sample" as used herein may be the same sample or a similar sample used for the detection of the level of PDE9A and of the reference gene. Preferred is the employment of the same sample.

In addition to the determination of a reference gene in the same sample, also a control sample may be analyzed. In this context the analysis comprises the detection of the expression of PDE9A in the control sample. The control is preferably a healthy tissue or a tissue derived from a benign prostate tumor.

The cutoff value may be a cutoff value for PDE9A in blood samples, e.g. serum or plasma samples, urine samples or urine sediment samples etc. as described herein below.

If the measured and/or normalized PDE9A expression is above the indicated cutoff value this may be seen as an indication that the individual suffers from a prostate cancer, in particular from a hormone dependent or hormone sensitive prostate cancer.

In a preferred embodiment of the present invention the cutoff value is a cutoff value for PDE9A in blood samples, e.g. serum or plasma samples, urine samples or urine sediment samples. In a particularly preferred embodiment of the present invention the cutoff value is a cutoff value for the PDE9A protein or polypeptide or any derivative thereof as defined herein above in a urine sample. In another particularly preferred embodiment of the present invention the cutoff value is a cutoff value for the PDE9A protein or polypeptide or any derivative thereof as defined herein above in cells contained in urine or exosomes secreted from cells contained in urine. In an even more preferred embodiment of the present invention the cutoff value is a cutoff value for the PDE9A protein or polypeptide or any derivative thereof as defined herein above in a urine sediment sample and cells contained in a urine sediment sample, or exosomes secreted from cells contained in a urine sediment sample.

If the measured and/or normalized PDE9A expression is above the indicated cutoff value this may be seen as an indication that the individual does not suffer from a hormone-resistant prostate cancer. The value may additionally indicate that the individual suffers from a prostate cancer other than hormone-resistant prostate cancer, in particular hormone-dependent prostate cancer or hormone-sensitive prostate cancer.

In another aspect the present invention relates to a method of data acquisition comprising at least the steps of:

(a) testing in an individual for expression of PDE9A; and (b) comparing the expression as determined in step (a) to a control level.

The testing for expression of PDE9A may be carried out according to steps as defined herein above. Preferably the testing may be carried out as measurement of nucleic acid or protein levels of PDE9A or by determining the biological activity of PDE9A, more preferably according to the herein above described options for such measurements. The testing may be carried out in an individual, i.e. in vivo, or outside the individual, i.e. ex vivo or in vitro. The term "control level" as used in the context of the method of data acquisition refers to the expression of the PDE9A marker or other suitable markers in a cancerous control or non-cancerous control, as defined herein above. The status, nature, amount and condition of the control level may be adjusted according to the necessities. Preferably a non-cancerous control level may be used. More preferably, a control level derived from hormone-sensitive prostate cancer stages may be used. A comparison of the expression to a control level may be carried out according to any suitable method of assessing, calculating, evaluating or processing of data and particularly aims at the detection of differences between two data sets. A statistical evaluation of the significance of the difference may further be carried out. Suitable statistical methods are known to the person skilled in the art. Obtained data and information may be stored, accumulated or processed by suitable informatics or computer methods or tools known to the person skilled in the art and/or be presented in an appropriate manner in order to allow the practitioner to use the data for one or more subsequent deduction or conclusion steps.

In another aspect the present invention relates to an immunoassay for detecting, diagnosing, monitoring or prognosticating prostate cancer or the progression of prostate cancer comprising at least the steps of:

(a) testing in a sample obtained from an individual for the expression of PDE9A, (b) testing in a control sample for the expression of PDE9A, (c) determining the difference in expression of PDE9A of steps (a) and (b); and (d) deciding on the presence or stage of prostate cancer or the progression of cancer based on the results obtained in step (c).

The immunoassay is preferably based on the use of an antibody specifically binding to PDE9A, e.g. one or more of the PDE9A antibodies mentioned herein. Alternatively, the immunoassay may be carried out or combined with any other suitable agent. For example, the assay may be combined with the detection of nucleic acids, or enzymatic testing methods as described herein.

In a further aspect the present invention relates to an immunoassay for discriminating between a hormone-sensitive and a hormone-resistant prostate cancer, comprising the steps of (a) determining the level of PDE9A in a sample;

(b) determining the level of expression of a reference gene in a sample;

(c) normalizing the measured expression level of PDE9A to the expression of the reference gene; and (d) comparing the normalized expression level with a predetermined cutoff value chosen to exclude hormone-sensitive prostate cancer, wherein a normalized expression level below the cutoff value is indicative of a hormone-resistant prostate cancer, wherein said cutoff value is between about 2 and 15. Preferably, the cutoff value is about 5.

The level of PDE9A may preferably be determined on the protein or activity level as described herein above. Preferred is the determination of the amount of PDE9A protein with the help of PDE9A specific antibodies, e.g. one or more of the PDE9A antibodies mentioned herein. Alternatively, the immunoassay may be carried out with any other suitable agent or be combined with the determination of other entities. For example, the assay may be combined with the detection of the presence or amount of nucleic acids, or enzymatic testing methods as described herein.

In addition the level of a reference gene as defined herein above in a sample may be determined. For the detection of a reference gene the amount of the gene's expression product (i.e. protein) may be determined, preferably with the help of one or more suitable antibodies known to the person skilled in the art. Alternatively, the determination of the reference gene may be carried out with any other suitable agent or be combined with the detection of the presence or amount of nucleic acids, or enzymatic testing methods as described herein.

Based on the expression results obtained in steps (a) and (b) and/or the normalized results obtained in step (c) a comparison with a cutoff value for PDE9A expression may be carried out. The cutoff value below which the expression level of PDE9A is indicative of a hormone-resistant prostate cancer, thereby excluding hormone-sensitive prostate cancer or tumor forms in the immunoassay is between about 2 and 15, 2 and 14.5, 2 and 14, 2 and 13.5, 2 and 13, 2 and 12.5, 2 and 12, 2 and 11.5, 2 and 11, 2 and 10.5, 2 and 10, 2 and 9.5, 2 and 9, 2 and 8.5, 2 and 8, 2 and 7.5, 2 and 7, 2 and 6.5, 2 and 6, 2 and 5.5, 2 and 5 or 2.5 and 15, 3 and 15, 3.5 and 15, 4 and 15, 4.5 and 15, 5 and 15, 5 and 15. More preferred is a cutoff value of about 5, e.g. 4.9, 4.8, 4.7, 4.6, 4.5, 4.4, 4.3, 4.2, 4.1 or 5.9, 5.8, 5.7, 5.6, 5.5, 5.4, 5.3, 5.2, or 5.1.

The cutoff value may be a cutoff value for PDE9A in blood samples, e.g. serum or plasma samples, urine samples or urine sediment samples etc. as described herein below.

If the measured and/or normalized PDE9A expression is above the indicated cutoff value this may be seen as an indication that the individual is does not suffer from a hormone-resistant prostate cancer. The value may additionally indicate that the individual suffers from a prostate cancer other than hormone-resistant prostate cancer, in particular hormone-dependent prostate cancer or hormone-sensitive prostate cancer.

In another aspect the present invention relates to an immunoassay for discriminating between a non-cancerous stage, preferably a healthy stage and a malignant, hormone-sensitive prostate cancer, comprising the steps of (a) determining the level of PDE9A, (b) determining the level of expression of a reference gene in a sample;

(c) normalizing the measured expression level of PDE9A to the expression of the reference gene; and comparing the normalized expression level with a predetermined cutoff value chosen to exclude benign prostate tumor, wherein a normalized expression level above the cutoff value is indicative of a malignant, hormone-sensitive prostate cancer, wherein said cutoff value is between 1.5 and 3, preferably about 2. The level of PDE9A may preferably be determined on the protein or activity level as described herein above. Preferred is the determination of the amount of PDE9A protein with the help of PDE9A specific antibodies, e.g. one or more of the PDE9A antibodies mentioned herein. Alternatively, the immunoassay may be carried out with any other suitable agent or be combined with the determination of other entities. For example, the assay may be combined with the detection of the presence or amount of nucleic acids, or enzymatic testing methods as described herein.

In addition the level of a reference gene as defined herein above in a sample may be determined. For the detection of a reference gene the amount of the gene's expression product (i.e. protein) may be determined, preferably with the help of one or more suitable antibodies known to the person skilled in the art. Alternatively, the determination of the reference gene may be carried out with any other suitable agent or be combined with the detection of the presence or amount of nucleic acids, or enzymatic testing methods as described herein.

Based on the expression results obtained in steps (a) and (b) and/or the normalized results obtained in step (c) a comparison with a cutoff value for PDE9A expression may be carried out. The cutoff value below which the expression level of PDE9A is indicative of a healthy situation, i.e. the absence of prostate cancer, thereby excluding hormone-sensitive prostate cancer or tumor forms, is between about 1.5 and 3, 1.75 and 3, 2 and 3, 2.25 and 3, 2.5 and 3, 2.75 and 3. More preferred is a cutoff value of about 2, e.g. 1.9, 1.8, 1.7, 1.6, 1.5, 2.9, 2.8, 2.7, 2.6, 2.5, 2.4, 2.3, 2.2, or 2.1.

The cutoff value may be a cutoff value for PDE9A in blood samples, e.g. serum or plasma samples, urine samples or urine sediment samples etc. as described herein below.

If the measured and/or normalized PDE9A expression is above the indicated cutoff value this may be seen as an indication that the individual suffers from a prostate cancer, in particular from a hormone dependent or hormone sensitive prostate cancer.

In a further aspect the present invention relates to a method of identifying an individual for eligibility for prostate cancer therapy comprising:

(a) testing in a sample obtained from an individual for the expression of PDE9A;

(b) testing in said sample for the expression of a reference gene and/or testing in a control sample for the expression of PDE9A;

(c) classifying the levels of expression of step (a) relative to levels of step (b); and (d) identifying the individual as eligible to receive a prostate cancer therapy where the individual's sample is classified as having an altered level of PDE9A expression.

The level of PDE9A may be determined on the nucleic acid, protein or activity level as described herein above. Preferred is the determination of the amount of PDE9A transcript(s) and/or protein. In addition the level of a reference gene as described herein above in a sample may be determined. Testing for the expression of a reference gene may be carried out in the same sample used for the determination of PDE9A. If the testing is carried out in the same sample, a single detection or a multiplex detection approach may be performed. Preferably, for a multiplex detection the oligonucleotides and probes having the sequence of SEQ ID NO: 7, 8 and 9 may be used. For the performance of the multiplex detection the concentration of primers and/or probe oligonucleotides may be modified. Furthermore, the concentration and presence of further ingredients like buffers, ions etc. may be modified, e.g. increased or decreased in comparison to manufacturers' indications. Alternatively, the testing for the expression of a reference gene may be carried out in a different sample, preferably a control sample as defined herein above. Preferably, such a control sample may be a control sample from the same individual as the test sample, or a control sample derived from a different source or individual. The control sample may further be either a sample derived from the same tissue, preferably prostate tissue, or be derived from a different tissue type. Examples of preferred alternative tissue types are stromal prostate tissue, bladder epithelial tissue and urethra epithelial tissue Furthermore, the testing of the test sample for the expression of a reference gene and the testing of control sample for the expression of PDE9A may be combined.

In a further embodiment the control sample may also be tested for the expression of the reference gene. In case more than one sample was tested for the expression of a reference gene, the obtained expression results may be compared and/or averaged or normalized according to any suitable statistical method known to the person skilled in the art.

The term "classifying the levels of expression of step (a) relative to levels of step (b)" as used herein means that the expression in a test sample for PDE9A and the expression in a control sample for PDE9A are compared, e.g. after normalization against a suitable normalization references. According to the outcome of the comparison the test sample is indicated as providing a similar expression as the control sample, an increased expression in comparison to the control sample, or an reduced expression in comparison to the control sample. The term further means that the expression in a test sample for PDE9A and the expression in the same test sample for a reference gene are compared, e.g. after normalization against a further gene as normalization reference. According to the outcome of the comparison the test sample is indicated as providing a similar expression as the reference gene, an increased expression in comparison to the reference gene, or an reduced expression in comparison to the reference gene.

According to the classification of the expression results an individual may be considered to be eligible for a prostate cancer therapy when the PDE9A expression levels are reduced. The term "altered" as used herein either refers to a reduced or an increased PDE9A expression level. The expression level is deemed to be "reduced" when the PDE9A gene expression in the test sample is decreased by, for example, 5%, 6%, 7%, 8%, 9%, 10%, 15%, 20%, 25%, 30%, 40%, 50%, or more than 50% in comparison to the PDE9A expression in a control sample, or at least 0.1 fold, at least 0.2 fold, at least 1 fold, at least 2 fold, at least 5 fold, or at least 10 fold or more in comparison to the PDE9A expression in a control sample; or when the PDE9A gene expression is decreased by, for example, 5%, 6%, 7%, 8%, 9%, 10%, 15%, 20%, 25%, 30%, 40%, 50%, or more than 50% in comparison to the expression of a reference gene in a control sample, or at least 0.1 fold, at least 0.2 fold, at least 1 fold, at least 2 fold, at least 5 fold, or at least 10 fold or more decreased in comparison to the expression of a reference gene. In a specific embodiment, the expression of a reference gene may also be normalized or adjusted to the expression of additional genes or markers, e.g. housekeeping genes. Similarly, the PDE9A expression level is deemed to be "increased" when the PDE9A gene expression in the test sample is elevated by, for example, 5%, 6%, 7%, 8%, 9%, 10%, 15%, 20%, 25%, 30%, 40%, 50%, or more than 50% in comparison to the PDE9A expression in a control sample, or at least 0.1 fold, at least 0.2 fold, at least 1 fold, at least 2 fold, at least 5 fold, or at least 10 fold or more in comparison to the PDE9A expression in a control sample; or when the PDE9A gene expression is elevated by, for example, 5%, 6%, 7%, 8%, 9%, 10%, 15%, 20%, 25%, 30%, 40%, 50%, or more than 50% in comparison to the expression of a reference gene in a control sample, or at least 0.1 fold, at least 0.2 fold, at least 1 fold, at least 2 fold, at least 5 fold, or at least 10 fold or more elevated in comparison to the expression of a reference gene. In a specific embodiment, the expression of a reference gene may also be normalized or adjusted to the expression of additional genes or markers, e.g. housekeeping genes.

In a further aspect the present invention relates to an immunoassay for stratifying an individual or cohort of individuals with a prostate cancer disease comprising:

(a) testing in a sample obtained from an individual for the expression of PDE9A;

(b) testing in said sample for the expression of a reference gene and/or testing in a control sample for the expression of PDE9A;

(c) determining the difference in expression of PDE9A of step (a) and the expression of PDE9A and/or the reference gene in step (b); and (d) stratifying an individual or cohort of individuals to prostate cancer therapy based on the results obtained in step (c), where the individual's sample has an altered level of PDE9A expression.

The testing of the expression of PDE9A may preferably be carried out via the determination of the amount of PDE9A protein or the determination of the PDE9A activity level as described herein above. Preferred is the determination of the amount of PDE9A protein with the help of PDE9A specific antibodies, e.g. one or more of the PDE9A antibodies mentioned herein. Alternatively, the immunoassay may be carried out with any other suitable agent or be combined with the determination of other entities. For example, the assay may be combined with the detection of the presence or amount of nucleic acids, or enzymatic testing methods as described herein. In addition the level of a reference gene as described herein above in a sample may be determined. Testing for the expression of a reference gene may be carried out in the same sample used for the determination of PDE9A. If the testing is carried out in the same sample, a single detection or a parallel or multiplex detection approach may be performed. Preferably, for a parallel or multiplex detection differently labeled primary or secondary antibodies may be used.

Alternatively, the testing for the expression of a reference gene may be carried out in a different sample, preferably a control sample as defined herein above. Preferably, such a control sample may be a control sample from the same individual as the test sample, or a control sample derived from a different source or individual. The control sample may further be either a sample derived from the same tissue, preferably prostate tissue, or be derived from a different tissue type. Examples of preferred alternative tissue types are stromal prostate tissue, bladder epithelial tissue and urethra epithelial tissue.

Furthermore, the testing of the test sample for the expression of a reference gene and the testing of control sample for the expression of PDE9A may be combined.

In a further embodiment the control sample may also be tested for the expression of the reference gene. In case more than one sample was tested for the expression of a reference gene, the obtained expression results may be compared and/or averaged or normalized according to any suitable statistical method known to the person skilled in the art.

The term "determining the difference in expression of PDE9A of step (a) and the expression of PDE9A and/or the reference gene in step (b)" as used herein means that the expression in a test sample for PDE9A and the expression in a control sample for PDE9A are compared, e.g. after normalization against a suitable normalization references. According to the outcome of the comparison the test sample is indicated as providing a similar expression as the control sample, an increased expression in comparison to the control sample, or an reduced expression in comparison to the control sample. The term further means that alternatively or additionally the expression in a test sample for PDE9A and the expression in the same test sample for a reference gene are compared, e.g. after normalization against a further gene as normalization reference. According to the outcome of the comparison the test sample is indicated as providing a similar expression as the reference gene, or a difference in the expression. The difference may be either an increased expression in comparison to the reference gene, or a reduced expression in comparison to the reference gene.

The term "stratifying an individual or cohort of individuals to prostate cancer therapy" as used herein means that an individual is identified as pertaining to a group of similar individuals, whose optimal therapy form is a prostate cancer therapy, preferably a therapy against hormone-resistant prostate cancer in accordance with the outcome of the expression test as described herein above, in particular in accordance with encountered difference in the PDE9A expression level and a reference gene or the PDE9A expression level in different samples. According to the determination of the expression difference an individual may be identified as pertaining to a group of similar individuals whose optimal therapy form is prostate cancer therapy when the PDE9A expression levels are altered, i.e. reduced or increased. The expression level is deemed to be "reduced" when the PDE9A gene expression in the test sample is decreased by, for example, 5%, 6%, 7%, 8%, 9%, 10%, 15%, 20%, 25%, 30%, 40%, 50%, or more than 50% in comparison to the PDE9A expression in a control sample, or at least 0.1 fold, at least 0.2 fold, at least 1 fold, at least 2 fold, at least 5 fold, or at least 10 fold or more in comparison to the PDE9A expression in a control sample; or when the PDE9A gene expression is decreased by, for example, 5%, 6%, 7%, 8%, 9%, 10%, 15%, 20%, 25%, 30%, 40%, 50%, or more than 50% in comparison to the expression of a reference gene in a control sample, or at least 0.1 fold, at least 0.2 fold, at least 1 fold, at least 2 fold, at least 5 fold, or at least 10 fold or more decreased in comparison to the expression of a reference gene. In a specific embodiment, the expression of a reference gene may also be normalized or adjusted to the expression of additional genes or markers, e.g. housekeeping genes. Similarly, the PDE9A expression level is deemed to be "increased" when the PDE9A gene expression in the test sample is elevated by, for example, 5%, 6%, 7%, 8%, 9%, 10%, 15%, 20%, 25%, 30%, 40%, 50%, or more than 50% in comparison to the PDE9A expression in a control sample, or at least 0.1 fold, at least 0.2 fold, at least 1 fold, at least 2 fold, at least 5 fold, or at least 10 fold or more in comparison to the PDE9A expression in a control sample; or when the PDE9A gene expression is elevated by, for example, 5%, 6%, 7%, 8%, 9%, 10%, 15%, 20%, 25%, 30%, 40%, 50%, or more than 50% in comparison to the expression of a reference gene in a control sample, or at least 0.1 fold, at least 0.2 fold, at least 1 fold, at least 2 fold, at least 5 fold, or at least 10 fold or more elevated in comparison to the expression of a reference gene. In a specific embodiment, the expression of a reference gene may also be normalized or adjusted to the expression of additional genes or markers, e.g. housekeeping genes.

An individual being considered to be eligible for a prostate cancer therapy or being stratified to prostate cancer therapy as described herein above may receive any suitable therapeutic prostate cancer treatment known to the person skilled the art. Typically, an individual considered to be eligible for prostate cancer therapy, or stratified to a corresponding treatment group, due to reduced PDE9A expression may be deemed to be suffering from a hormone-resistant prostate cancer or be prone to develop a hormone-resistant prostate cancer in the future, e.g. within the next 1 to 24 months. A correspondingly identified or stratified individual may be treated with a pharmaceutical composition according to the present invention, e.g. as defined herein below. In a further embodiment a correspondingly identified individual may be treated with a pharmaceutical composition according to the present invention in combination with an additional cancer therapy. The term "additional cancer therapy" refers to any types of cancer therapy known to the person skilled in the art. Preferred are cancer therapy forms known for hormone-resistant prostate cancer. The term includes, for example, all suitable forms of chemotherapy, radiation therapy, surgery, antibody therapies etc.

Alternatively, a correspondingly identified or stratified individual may also be treated solely with one or more cancer therapies such as a chemotherapy, radiation therapy, surgery, antibody therapies etc. Preferred are cancer therapies typically used for prostate cancer, more preferred cancer therapies used for hormone-resistant prostate cancer.

In a further embodiment of the present invention the classification method for eligibility or the immunoassay for stratification as described herein above may also be used for monitoring the treatment of an individual, e.g. an individual being classified as suffering from a hormone-resistant prostate cancer. The monitoring process may be carried out as expression determination over a prolonged period of time, e.g. during or after treatment sessions, for 1, 2, 3, 4, 5, 6, 7, 8, 9, 10 weeks, 1, 2, 3, 4, 5, 6, 7, 8, 9, 10 months, or 1, 2, 3 or more years. The determination steps may be carried out in suitable intervals, e.g. every week, 2 weeks, 3 weeks, every month, 2 months, 3 months, 6 months, 12 months etc.

In a further embodiment of the present invention any treatment scheme as mentioned herein above may be adjusted, e.g. enforced or attenuated, or altered in any suitable manner in correspondence with the results of the monitoring process.

The testing for expression of PDE9A may be carried out according to steps as defined herein above. Preferably, the testing may be carried out as measurement of protein levels of PDE9A, more preferably according to the herein above described options for such measurements. As controls or control samples controls as defined herein above may be used. In a particularly preferred embodiment the testing steps may be based on the use of an antibody specifically binding to PDE9A, e.g. a commercially available anti-PDE9A antibody like H00005152-M01 or NBP1-00641. A cancer may be diagnosed or prognosticated or a progression of cancer may be diagnosed or prognosticated in said immunoassay or an individual may be identified for eligibility for prostate cancer, or an individual or cohort of individuals may be stratified in an immunoassay according to the corresponding definitions provided herein above in the context of the PDE9A as cancer marker. Accordingly, said testing or determining of the expression of PDE9A may be accomplished, or may additionally be accomplished, by the measurement of nucleic acid or protein levels or by the determination of the biological activity of PDE9A. Similar measurements may be carried out with respect to the reference gene.

In a particularly preferred embodiment of the present invention the reference gene is a housekeeping gene or a different phosphodiesterase. In human organisms, examples of "housekeeping genes" include inter alia β-actin, glycerinaldehyde 3-phosphate dehydrogenase (GAPDH), porphobilinogen deanimase (PBGD), and ribosomal protein P1. Apart from these genes any other suitable gene may be used as a house-keeping gene, as long as the gene shows an expression or transcription on a steady, non-modified level, in particular during different stages of cancer development, more preferably during different stages of prostate cancer development, more preferably during the transition of hormone-sensitive prostate cancer to hormone-resistant prostate cancer states. Particularly preferred is the gene or transcript or expression product or protein of GAPDH. Further particularly preferred is the gene or transcript or expression product or protein of PBGD. Expression data of a housekeeping gene may be obtained from one or more samples of the same individual or from more individuals, e.g. 2, 3, 4, 5, 6, 7, 8, 9, 10, 20, 50, 100, 1000, 5,000, 10,000 or more. Expression data may also be obtained from databases or from data collections available to the person skilled in the art.

The term "different phosphodiesterase" as used herein refers to other phosphodiesterases which are not PDE9A. Such phosphodiesterases, to be suitable as reference genes, should be steadily expressed and provide a continuously detectable gene product, expression product, protein or protein variant in the organism of choice. Particularly preferred are phosphodiesterases of the PDE4D family, e.g. PDE4D1, PDE4D2, PDE4D3, PDE4D4, PDE4D5, PDE4D6, PDE4D8 and PDE4D9. More preferred is the PDE4D5 phosphodiesterase.

Accordingly normalization and/or comparison with GAPDH, PBGD and in particular PDE4D5 may preferably be used for the above described cutoff based diagnosis methods and immunoassays, the methods of identifying or the immunoassays for discriminating or stratifying individuals. Corresponding determination steps may either be carried out in separate reactions, or, particularly preferred in multiplex reactions. For the performance of the multiplex detection the concentration of primers and/or probe oligonucleotides may be modified. Furthermore, the concentration and presence of further ingredients like buffers, ions etc. may be modified, e.g. increased or decreased in comparison to manufacturers' indications.

In a further embodiment of the present invention the method of identifying an individual for eligibility for prostate cancer therapy based on the expression of PDE9A as described herein above may further be combined with one or more similar identification methods, based on the expression of one or more different biomarkers. Preferred is the determination of the level of prostate specific antigen (PSA). Thus, if the level of PSA is encountered to be between about 2 and 10 ng/ml, e.g. about 2, 3, 4, 5, 6, 7, 8, 9 or 10 ng/ml, an individual may be considered to be suffering from a malignant, hormone sensitive prostate cancer, or be likely to develop malignant, hormone sensitive prostate cancer in the near future, i.e. within the next 1, 2, 3, 4, 5, 6 months. If the level of PSA is encountered to be above 10 n/ml, e.g. 11, 12, 15, 20 etc., an individual may be considered to be suffering from a hormone resistant prostate cancer, or be likely to develop hormone resistant prostate cancer in the near future, In a preferred embodiment of the present invention the diagnosing, detecting, monitoring or prognosticating as mentioned above is to be carried out on a sample obtained from an individual. The term "sample obtained from an individual" as used herein relates to any biological material obtained via suitable methods known to the person skilled in the art from an individual. The sample used in the context of the present invention should preferably be collected in a clinically acceptable manner, more preferably in a way that nucleic acids (in particular RNA) or proteins are preserved.

The biological samples may include body tissues and fluids, such as blood, sweat, sputum or saliva, semen and urine, as well as feces or stool samples. Furthermore, the biological sample may contain a cell extract derived from or a cell population including an epithelial cell, preferably a cancerous epithelial cell or an epithelial cell derived from tissue suspected to be cancerous. Even more preferably the biological sample may contain a cell population derived from a glandular tissue, e.g. the sample may be derived from the prostate of a male individual. Additionally, cells may be purified from obtained body tissues and fluids if necessary, and then used as the biological sample.

Samples, in particular after initial processing, may be pooled. However, also non-pooled samples may be used.

In a specific embodiment of the present invention the content of a biological sample may also be submitted to an enrichment step. For instance, a sample may be contacted with ligands specific for the cell membrane or organelles of certain cell types, e.g. prostate cells, functionalized for example with magnetic particles. The material concentrated by the magnetic particles may subsequently be used for detection and analysis steps as described herein above or below.

In a specific embodiment of the invention, biopsy or resections samples may be obtained and/or used. Such samples may comprise cells or cell lysates.

Furthermore, cells, e.g. tumor cells, may be enriched via filtration processes of fluid or liquid samples, e.g. blood, urine, sweat etc. Such filtration processes may also be combined with enrichment steps based on ligand specific interactions as described herein above.

In a particularly preferred embodiment of the present invention a sample may be a tissue sample, a urine sample, a urine sediment sample, a blood sample, a saliva sample, a semen sample, a sample comprising circulating tumor cells, or a sample containing prostate secreted exosomes.

In yet another aspect the present invention relates to a stimulatory pharmaceutical composition comprising at least one element selected from the group consisting of: (a) a compound directly stimulating or modulating the activity of PDE9A, preferably an allosteric agonist of PDE9A enzymatic activity; (b) a compound indirectly stimulating or modulating the activity of PDE9A; (c) the PDE9A protein or a biologically active equivalent thereof; (d) a nucleic acid encoding and expressing PDE9A; (e) a miRNA inhibitor specific for PDE9A miRNAs; (f) a demethylation agent; and (g) a phosphodiesterase displacement factor, preferably a peptide, a peptidomimetic, a small molecule, an antibody or an aptamer.

The term "a compound directly stimulating or modulating the activity of PDE9A" as used herein refers to a compound which is capable of increasing the activity of PDE9A to degrade cGMP by a direct interaction with PDE9A. Such a compound may be any direct interactor of PDE9A, which has positive influence on the catalytic activity of PDE9A. Such a compound may preferably be an allosteric agonist of the catalytic activity of PDE9A, e.g. a homotropic allosteric modulator. Preferred allosteric agonists of PDE9A are cGMP or cGMP analogs. Other directly stimulating compounds envisaged by the present invention are ions, preferably biologically active mono- and bivalent cations like $Ca^{2+}$, $Mg^{2+}$.

The term "a compound indirectly stimulating or modulating the activity of PDE9A" as used herein refers to a compound which is capable of increasing the activity of PDE9A to degrade cGMP by an interaction with a direct interactor of PDE9A ("indirect interactor") or via an indirect working pathway not involving an interaction with PDE9A. Such a compound may be any direct interactor of an interactor of PDE9A. The effect conveyed by the direct interactor of an interactor of PDE9A may be either positive if the interactor of PDE9A itself has a positive effect on the activity of PDE9A, or negative, if the interactor of PDE9A has a negative effect on the activity of PDE9A. Typically positively working indirect interactors may stimulate the agonistic effect of direct interactors, e.g. provoke the increase of concentration of allosterically working compounds like cGMP or analogs thereof by inhibiting cGMP degrading processes not conferred by PDE9A, by raising the cGMP production etc.

Alternatively, such positively working indirect integrators may provoke a modification of the binding behavior of directly binding proteins, leading to an increased PDE9A activity. Typically negatively working indirect interactors may have an inhibitory effect on inhibitors of PDE9A. Examples of such interactors are enzymatic activities degrading PDE9A inhibitors, or proteins capable of binding and quenching PDE9A inhibitors. Alternatively, such interactors may inhibit activities leading to a degradation of PDE9A, e.g. proteinase inhibitors. Further examples and their implementation would be known to the person skilled in the art.

Alternatively, an indirect stimulation of the PDE9A activity may be conveyed by compounds activating, protecting or sustaining the expression of the endogenous PDE9A gene. Examples of such compounds are PDE9A specific transcription factors, PDE9A specific mRNA stabilizing activities or PDE9A splice factors. Further examples and their implementation would be known to the person skilled in the art.

The "PDE9A protein" may be a PDE9A protein as defined herein above. In particular, it may be a protein being encoded by splice variants 1 to 20 of the human phosphodiesterase 9A, more preferably it may have the amino acid sequence as defined in Genbank Accession No: NM_002606 (version NM_002606.2, GI:48762716 as of 9 Mar. 2009), Genbank Accession No: NM_001001567 (version NM_001001567.1, GI:48762717 as of 9 Mar. 2009), Genbank Accession No: NM_001001568 (version NM_001001568.1, GI:48762719 as of 9 Mar. 2009), Genbank Accession No: NM_001001569 (version NM_001001569.1, GI:48762721 as of 9 Mar. 2009), Genbank Accession No: NM_001001570 (version NM_001001570.1, GI:48762723 as of 9 Mar. 2009), Genbank Accession No: NM_001001571 (version NM_001001571.1, GI:48762725 as of 9 Mar. 2009), Genbank Accession No: NM_001001572 (version NM_001001572.1, GI:48762727 as of 9 Mar. 2009), Genbank Accession No: NM_001001573 (version NM_001001573.1, GI:48762729 as of 9 Mar. 2009), Genbank Accession No: NM_001001574 (version NM_001001574.1, GI:48762731 as of 9 Mar. 2009), Genbank Accession No: NM_001001575 (version NM_001001575.1, GI:48762733 as of 9 Mar. 2009), Genbank Accession No: NM_001001576 (version NM_001001576.1, GI:48762735 as of 9 Mar. 2009), Genbank Accession No: NM_001001577 (version NM_001001577.1, GI:48762737 as of 9 Mar. 2009), Genbank Accession No: NM_001001578 (version NM_001001578.1, GI:48762739 as of 9 Mar. 2009), Genbank Accession No: NM_001001579 (version NM_001001579.1, GI:48762741 as of 9 Mar. 2009), Genbank Accession No: NM_001001580 (version NM_001001580.1, GI:48762743 as of 9 Mar. 2009), Genbank Accession No: NM_001001581 (version NM_001001581.1, GI:48762745 as of 9 Mar. 2009), Genbank Accession No: NM_001001582 (version NM_001001582.1, GI:48762747 as of 9 Mar. 2009), Genbank Accession No: NM_001001583 (version NM_001001583.1, GI:48762749 as of 9 Mar. 2009), Genbank Accession No: NM_001001584 (version NM_001001584.1, GI:48762751 as of 9 Mar. 2009) or Genbank Accession No: NM_001001585 (version NM_001001585.1, GI:48762753 as of 9 Mar. 2009) and even more preferably it may have the amino acid sequences as set forth in any of SEQ ID NOs: 21 to 40.

The "PDE9A protein" as used in this context also comprises amino acid sequences being at least 60%, 70%, 75%, 80%, 85%, 90%, 91%, 92%, 93%, 94%, 95%, 96%, 97%, 98% or 99% identical to any of the sequences as set forth in SEQ ID NOs: 21 to 40 and amino acid sequences being encoded by nucleotide sequences being at least 60%, 70%, 75%, 80%, 85%, 90%, 91%, 92%, 93%, 94%, 95%, 96%, 97%, 98% or 99% identical to any of the sequences as set forth in SEQ ID NOs: 1 to 20. Homologous variants of PDE9A, in particular those mentioned above, preferably have PDE9A functionality, i.e. are capable of degrading cGMP. In a further embodiment of the invention the homologous variants of PDE9A may additionally have a similar or identical localization pattern as PDE9A within a cell or within a tissue type.

In a further preferred embodiment the region or homology between the homologous variants of PDE9A and PDE9A may be confined to the C-terminal part of the protein. For instance, the homologous variant may comprise an N-terminal domain being present in PDE9A and a remainder of the protein having a degree of homology to PDE9A as indicated herein above. The N-terminal portion of the homologous variant may comprise amino acids 1 to 120, 1 to 110, 1 to 100, 1 to 90, 1 to 80, 1 to 70, 1 to 60, 1 to 50, 1 to 40, 1 to 30, 1 to 20 or 1 to 10 derived from PDE9A.

The term "biologically active equivalent of PDE9A" as used herein refers to a PDE9A protein which is capable of performing all or a majority of PDE9A functions. Preferably, it relates to proteins being capable of degrading cGMP. In a further embodiment of the invention the biologically active equivalents of PDE9A may additionally or alternatively have a similar or identical localization pattern as PDE9A within a cell or within a tissue type. Biologically active equivalents of PDE9A may also comprise PDE9A variants as defined herein above.

PDE9A or biologically active equivalents of PDE9A according to the present invention may be produced recombinantly by any suitable method known to the person skilled in the art. The present invention, thus, also encompasses methods for the production of PDE9A or biologically active equivalents of PDE9A.

Accordingly, the present invention contemplates vectors containing the polynucleotides encoding PDE9A or biologically active equivalents of PDE9A as defined herein above, host cells, and the production of PDE9A or biologically active equivalents of PDE9A by recombinant techniques.

A suitable vector may be, for example, a phage, plasmid, viral, or retroviral vector. Retroviral vectors may be replication competent or replication defective. In the latter case, viral propagation generally will occur only in complementing host cells. Polynucleotides encoding PDE9A or biologically active equivalents of PDE9A may be joined to a vector or carrier containing a selectable marker for propagation in a host. A corresponding polynucleotide insert may be operatively linked to an appropriate promoter, such as the phage lambda PL promoter, the *E. coli* lac, trp, phoA and tac promoters, the SV40 early and late promoters and promoters of retroviral LTRs, or the PSA promoter. Other suitable promoters are known to the person skilled in the art. The expression constructs may further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The polypeptides or proteins may be glycosylated or may be non-glycosylated or may otherwise by modified. In addition, polypeptides or proteins may also include an initial modified methionine residue, in some cases as a result of host-mediated processes. Furthermore, the polypeptide, protein or peptide may be modified by acetylation, pegylation, hesylation, formylation, phosphorylation, amidation, derivatization by known protecting/blocking groups, specific chemical cleavage, proteolytic cleavage, a linkage to a cellular ligand or other protein or hapylation, i.e. a fusion with a glycine-rich homo-amino-acid polymer (HAP), etc. Such modifications may be carried out by suitable techniques known to the person skilled in the art. Additionally, the polypeptide, peptide or variant may contain one or more non-classical amino acids.

In addition, PDE9A or biologically active equivalents of PDE9A of the invention can be chemically synthesized using techniques known in the art, e.g. by using a peptide synthesizer.

The "nucleic acid encoding and expressing PDE9A" comprised in the stimulatory pharmaceutical composition as defined herein above refers to any suitable carrier element comprising an expressible PDE9A gene. Preferably, such a carrier element may comprise the sequence as defined in Genbank Accession No: NM_002606 (version NM_002606.2, GI:48762716 as of 9 Mar. 2009), Genbank Accession No: NM_001001567 (version NM_001001567.1, GI:48762717 as of 9 Mar. 2009), Genbank Accession No: NM_001001568 (version NM_001001568.1, GI:48762719 as of 9 Mar. 2009), Genbank Accession No: NM_001001569 (version NM_001001569.1, GI:48762721 as of 9 Mar. 2009), Genbank Accession No: NM_001001570 (version NM_001001570.1, GI:48762723 as of 9 Mar. 2009), Genbank Accession No: NM_001001571 (version NM_001001571.1, GI:48762725 as of 9 Mar. 2009), Genbank Accession No: NM_001001572 (version NM_001001572.1, GI:48762727 as of 9 Mar. 2009), Genbank Accession No: NM_001001573 (version NM_001001573.1, GI:48762729 as of 9 Mar. 2009), Genbank Accession No: NM_001001574 (version NM_001001574.1, GI:48762731 as of 9 Mar. 2009), Genbank Accession No: NM_001001575 (version NM_001001575.1, GI:48762733 as of 9 Mar. 2009), Genbank Accession No: NM_001001576 (version NM_001001576.1, GI:48762735 as of 9 Mar. 2009), Genbank Accession No: NM_001001577 (version NM_001001577.1, GI:48762737 as of 9 Mar. 2009), Genbank Accession No: NM_001001578 (version NM_001001578.1, GI:48762739 as of 9 Mar. 2009), Genbank Accession No: NM_001001579 (version NM_001001579.1, GI:48762741 as of 9 Mar. 2009), Genbank Accession No: NM_001001580 (version NM_001001580.1, GI:48762743 as of 9 Mar. 2009), Genbank Accession No: NM_001001581 (version NM_001001581.1, GI:48762745 as of 9 Mar. 2009), Genbank Accession No: NM_001001582 (version NM_001001582.1, GI:48762747 as of 9 Mar. 2009), Genbank Accession No: NM_001001583 (version NM_001001583.1, GI:48762749 as of 9 Mar. 2009), Genbank Accession No: NM_001001584 (version NM_001001584.1, GI:48762751 as of 9 Mar. 2009) or Genbank Accession No: NM_001001585 (version NM_001001585.1, GI:48762753 as of 9 Mar. 2009), more preferably the nucleotide sequences as set forth in SEQ ID NOs: 1 to 20. Such a carrier element may also comprises nucleotide sequences showing a high degree of homology to PDE9A, e.g. nucleic acid sequences being at least 60%, 70%, 75%, 80%, 85%, 90%, 91%, 92%, 93%, 94%, 95%, 96%, 97%, 98% or 99% identical to any of the sequences as set forth in SEQ ID NOs: 1 to 20 or nucleic acid sequences encoding amino acid sequences being at least 60%, 70%, 75%, 80%, 85%, 90%, 91%, 92%, 93%, 94%, 95%, 96%, 97%, 98% or 99% identical to any of the sequences as set forth in SEQ ID NOs: 21 to 40. Alternatively, the carrier may comprise the genomic sequence of PDE9A, preferably the sequence as defined in Genbank Accession No: AB017602 (version AB017602.1, GI:6681700 as of 24 Mar. 2009), which corresponds to SEQ ID NO: 44. More preferably, the carrier may comprise the genomic sequence of PDE9A as defined in SEQ ID NO: 44.

Furthermore, biologically active equivalents of PDE9A as defined herein above may be comprised in a carrier of the present invention.

The polynucleotide encoding PDE9A may preferably be joined to a vector containing a selectable marker for propagation in a human cell. In a preferred embodiment the polynucleotide insert may be operatively linked to a PSA promoter.

In one embodiment of the present invention nucleic acids encoding and expressing PDE9A as defined herein above may be provided via living therapeutics. The term "living therapeutic" means that PDE9A or biologically active equivalents of PDE9A as defined herein above are expressed in any suitable live carrier. Accordingly, the present invention relates to corresponding polynucleotides which are suitable for expression in a living cell. The present invention also relates to vectors containing such polynucleotides, appropriate host cells, and the production of polypeptides by recombinant techniques in said host cells.

The term "live carrier" relates to any appropriate living host cell or virus known to the person skilled in the art. Representative examples of appropriate hosts include, but are not limited to, bacterial cells such as *Escherichia coli* or *Lactobacillus*, fungal cells, such as yeast cells, protozoa, insect cells, or animal cells. Preferably, the term relates to attenuated bacteria, attenuated fungal cells or attenuated protozoa. Representative examples of appropriate viruses include viruses of the group of adenoviruses, retrovirues or lentiviruses, preferably attenuated viruses of the group of adenoviruses, retroviruses or lentiviruses. In a preferred embodiment, probiotic bacterial cells, in particular probiotic *Escherichia coli* or *Lactobacillus* cells may be used. More preferably, cells of *Escherichia coli* Nissle 1973 and even more preferably cells of *Lactobacillus casei* or *Lactobacillus zeae* 393 may be used.

The "miRNA inhibitor specific for PDE9A miRNA" comprised in the stimulatory pharmaceutical composition as defined herein above refers to a nucleic acid molecule encoding a nucleic acid sequence complementary to a PDE9A miRNA or microRNA molecule. The term "complementary" as used herein refers to a perfect complementary between the miRNA inhibitor nucleic acid (sense molecule) and the miRNA (antisense molecule) without any mismatch, as well as situations in which the nucleic acid contains any base mismatches and/or additional or missing nucleotides in comparison to the miRNA molecule. In other embodiments, the two molecules comprise one or more base mismatches or differ in their total numbers of nucleotides (due to additions or deletions). In further embodiments, the "complementary" miRNA inhibitor nucleic acid molecule comprises at least ten contiguous nucleotides showing perfect complementarity with a sequence comprised in the miRNA molecule.

Typically miRNA inhibitor nucleic acid molecules are naturally occurring DNA- or RNA molecules or synthetic nucleic acid molecules comprising in their sequence one or more modified nucleotides which may be of the same type or of one or more different types.

It is, for example, envisaged by the present invention that such a miRNA inhibitor nucleic acid molecule comprises at least one ribonucleotide backbone unit and at least one deoxyribonucleotide backbone unit. Furthermore, the miRNA inhibitor nucleic acid molecule may contain one or more modifications of the RNA backbone into 2'-O-methyl group or 2'-O-methoxyethyl group (also referred to as "2'-O-methylation"), which prevented nuclease degradation in the culture media and, importantly, also prevented endonucleolytic cleavage by the RNA-induced silencing complex nuclease, leading to irreversible inhibition of the miRNA. Another possible modification, which is functionally equivalent to 2'-O-methylation, involves locked nucleic acids (LNAs) representing nucleic acid analogs containing one or more LNA nucleotide monomers, as defined herein above.

Another class of silencers of miRNA expression to be used in the context of the present invention comprises chemically engineered oligonucleotides named "antagomirs", which represent single-stranded RNA molecules conjugated to cholesterol. The molecules may comprise between 19 and 25 nucleotides. Preferably, the molecule comprises 20, 21, 22, 23 or 24 nucleotides. More preferably, the molecule comprises 23 nucleotides (further details may be derived from Krutzfeldt et al., 2005, Nature, 438: 685-689).

In another embodiment of the present invention miRNA inhibitors as defined herein above may be provided in the form of expression vectors to be introduced into tissue or cells. Alternatively, such vectors may also be introduced in living therapeutics as defined herein above.

Typically, RNAs may be produced from transgenes provided in the form of transfection or transient expression vectors or carriers. For instance, competitive miRNA inhibitors may be provided as transcripts expressed from strong promoters, containing more than one, preferably multiple, tandem binding sites to a microRNA of interest. A "microRNA sponge" as described in Ebert et al., 2007, Nat. Methods, 4: 721-726 is an illustrative, non-limiting example of this technique.

The "demethylation agent" comprised in the stimulatory pharmaceutical composition as defined herein above refers to an agent capable of demethylating chromatine structures, preferably promoter regions, more preferably the PDE9A promoter. Examples of demethylation agents to be used in the context of the present invention are 5-aza-2'-deoxycytidine and 5-azacytidine, which reactivate genes inappropriately silenced by structural chromatin changes that involve DNA methylation and which can reverse these changes and, therefore, restore principal cellular pathways. This typically results in gene re-expression and reversion of some aspects of the transformed state. 5-azacytidine and 5-aza-2'-deoxycytidine typically inactivate DNA cytosine C5-methyltransferases through the formation of stable complexes between the 5-aza-2'-deoxycytidine residues in DNA and the enzyme, thereby mimicking a stable transition state intermediate when bound to the methyltransferase enzyme.

A further agent, which may be comprised in a stimulatory pharmaceutical composition according to the present invention, either per se or in combination with 5-aza-2'-deoxycytidine and/or 5-azacytidine, is trichostatin A (TSA).

The "phosphodiesterase displacement factor" comprised in the stimulatory pharmaceutical composition as defined herein above refers to a compound which is capable of disturbing or disrupting the interaction of phosphodiesterases, in particular PDE9A, with interacting partner or interactors. Such a process may ultimately lead to an association of PDEs, in particular PDE9A, with different interaction partners than before and, in consequence, to a redistribution of PDEs. Such new interaction partners may sequester PDE, in particular PDE9A, and correspondingly modify cellular behaviors, e.g. provoke influences on receptor binding or other downstream activities. Examples of protein partners which may be involved in such a displacement reaction and/or are capable of sequestering PDE, in particular PDE9A are anchoring proteins like AKAPs, scaffold proteins like DISC1, beta-arrestin or RACK1, regulatory proteins like XAP2/AIP/ARA9, proteins like PKA-R subunits or EPACs or receptors like the beta1-adrenoceptor, as well as enzymes like ERK.

Preferred phosphodiesterase displacement factors are peptides, peptidomimetics, small molecules, antibodies and aptamers.

A "peptide" in the context of a phosphodiesterase displacement factor refers to a stretch of amino acids present in or representing the phosphodiesterase molecule, in particular PDE9A, or an interacting or sequestering protein as defined herein above. The stretch of amino acids comprised in the peptide may have a length of 5 to 100 amino acids, preferably of 10 to 50 amino acids, more preferably of 20 to 30 amino acids. The stretches may be entirely identical to the PDE or interactor protein or a portion thereof or may comprise sequence variations. For example, the peptide sequence may comprise modified amino acid residues at up to 25% of all positions, preferably modifications which do not change the structural properties or the binding properties of the molecule. The amino acid sequence present in the peptide may alternatively represent spatial domains of the PDE or interactor protein and correspondingly comprise a juxtaposition of amino acid stretches which are not adjoined in the primary sequence of the molecules.

A "peptidomimetic" in the context of a phosphodiesterase displacement factor refers is a small protein-like chain designed to mimic a peptide. Such a peptidomimetic may arise from a modification of an existing peptide, e.g. a peptide as defined herein above, in order to alter the molecule's properties. A peptidomimetic may arise from a modification which changes the molecule's stability or binding capability. These modifications typically involve changes to the peptide that will not occur naturally. For example, a peptidomimetic according to the present invention may have altered peptide backbones or may comprise non-natural amino acids. Preferably, a peptidomimetic according to the present invention may represent a phosphodiesterase molecule, in particular PDE9A, or an interacting or sequestering protein as defined herein above.

In one embodiment of the present invention a peptidomimetic may block the interaction between PDE, in particular PDE9A, and its interactor. In another embodiment of the present invention a peptidomimetic may enhance the interaction between PDE, in particular PDE9A, and its interactor.

Methods and techniques for the preparation of peptidomimetics as well as assays for the testing of peptidomimetics are known to the person skilled in the art.

A "small molecules" in the context of a phosphodiesterase displacement factor refers to a small organic compound that is preferably biologically active, i.e. a biomolecule, but is preferably not a polymer. Such an organic compound may have any suitable form or chemical property. The compound may be a natural compound, e.g. a secondary metabolites or an artificial compound, which has been designed and generated de novo. In one embodiment of the present invention a small molecule is capable of blocking the interaction between PDE, in particular PDE9A, and its interactor. In another embodiment of the present invention a small molecule may enhance the interaction between PDE, in particular PDE9A, and its interactor. Methods and techniques for the identification and preparation of small molecules as well as assays for the testing of small molecules are known to the person skilled in the art.

An "antibody" or an "aptamer" in the context of a phosphodiesterase displacement factor refers to a PDE9A specific antibody or antibody variant or fragment as defined herein above, or to a PDE9A specific aptamer as defined herein above, having the capability of disturbing or disrupting the interaction between PDE, in particular PDE9A, and one or more of its interactors. Alternatively, the terms may also refer to antibodies or aptamers binding to any one or more of the PDE9A interactors as described herein above, having likewise the capability of disturbing or disrupting the interaction between PDE, in particular PDE9A, and one or more of its interactors. Methods for the production or testing of antibodies or aptamers have been described herein above and/or are known to the person skilled in the art.

In an embodiment of the invention the stimulatory pharmaceutical composition may further comprise additional compounds being active against cancer cells, e.g. cytotoxic compounds or other chemotherapeutic or radiotherapeutic compounds as known to the person skilled in the art.

In yet another aspect the present invention relates to an inhibitory pharmaceutical composition comprising at least one element selected from the group consisting of: (a) a compound directly inhibiting the activity of PDE9A, preferably an antagonist of PDE9A enzymatic activity; (b) a compound indirectly inhibiting the activity of PDE9A; (c) a dominant negative form of the PDE9A protein or a biologically active equivalent thereof; (d) a nucleic acid encoding and expressing a dominant negative form of PDE9A; (e) a miRNA specific for PDE9A; (f) a PDE9A antisense molecule; (g) a siRNA specific for PDE9A; (h) an aptamer specific for the PDE9A expression product or for the PDE9A protein; (i) a small molecule or peptidomimetic capable of specifically binding to the PDE9A protein; and (j) an antibody specific for the PDE9A protein and/or an antibody variant specific for the PDE9A protein.

The term "a compound directly inhibiting the activity of PDE9A" as used herein refers to a compound which is capable of decreasing the activity of PDE9A. Such a compound may be any direct interactor of PDE9A, which has negative influence on the catalytic activity of PDE9A. Such a compound may preferably be an antagonist of the catalytic activity of PDE9A.

The term "a compound indirectly inhibiting the activity of PDE9A" as used herein refers to a compound which is capable of decreasing the activity of PDE9A by an interaction with a direct interactor of PDE9A ("indirect interactor") or via an indirectly working pathway not involving an interaction with PDE9A. Such a compound may be any direct interactor of an interactor of PDE9A. The effect conveyed by the direct interactor of an interactor of PDE9A may be either negative if the interactor of itself has a negative effect on the activity of PDE9A, or negative, if the interactor PDE9A has a positive effect on the activity of PDE9A.

Particularly preferred are inhibitors of phosphodiesterases, in particular any of the herein mentioned PDE9 isoforms. Examples of suitable phosphodiesterase inhibitors which may singularly or in any combination be included in an inhibitory pharmaceutical composition according to the present invention are: BAY 73-669, SCH51866 and Zaprinast. Further examples of suitable inhibitors are known to the person skilled in the art and are also envisaged by the present invention. Details on the structure, effectivity, suitable formulations etc. of the inhibitors would also be known to the person skilled in the art and/or can be derived from suitable text books or publications, e.g. Joseph A. Beavo, Sharron H. Francis, Miles D Houslay, Cyclic Nucleotide Phosphodiesterase in Health and Disease, CRC Press 2006.

The inhibitor compounds as defined above may be formulated, dosed, used or administered according to the herein provided details. In particular, the following Table of inhibitors may be used for the determination of necessary IC50 concentrations and Manufacturer:

Table of inhibitors (examples):

| Compound | IC 50 | Manufacturer |
|---|---|---|
| BAY 73-669 | 55 nM | Sigma-Aldrich |
| SCH 51866 | | |
| ZAPRINAST | | Tocris |

Alternatively, such negatively working indirect integrators may provoke a modification of the binding behavior of directly binding proteins, leading to a decreased activity of PDE9A. Typically negatively working indirect interactors may have an inhibitory effect on activators of PDE9A. Examples of such interactors are enzymatic activities degrading activators of PDE9A, or proteins capable of binding and quenching activators of PDE9A. Alternatively, such interactors may positively modulate activities leading to a degradation of PDE9A, e.g. proteinases. Further examples and their implementation would be known to the person skilled in the art.

Alternatively, an indirect inhibition of the activity of PDE9A may be conveyed by compounds deactivating, interfering or disrupting the expression of the endogenous gene(s) of PDE9A. Examples of such compounds are specific interactors of transcription factors of PDE9A that inhibit and/or preclude binding of transcription factors and the basal transcription machinery to the promoters of the PDE9A gene, specific destabilizing activities of the mRNA(s) of PDE9A or factors inhibiting the splicing factors specific for PDE9A. Further examples and their implementation would be known to the person skilled in the art.

A "nucleic acid encoding and expressing a dominant negative form of a protein of a tumor marker" as used herein refers to any nucleic acid capable of expressing a mutant form of a naturally occurring protein or polypeptide. Thus the term refers to a nucleic acid encoding (a) variant(s) of PDE9A, which comprises an antimorphic modification, in particular which adversely affects PDE9A. Typically, such a behavior may occur if the antimorphic variant can interact with PDE9Abut blocks some aspect of its function. Preferably, such variants may comprise or lack specific domains of PDE9A, e.g. one or more protein-protein interacting or dimerization domains, complex assembly domains, one or more membrane-associated domains etc.

The term "miRNA specific for PDE9A" refers to a short single-stranded RNA molecule of typically 18-27 nucleotides in length, which regulate gene expression of PDE9A. miRNAs are encoded by genes from whose DNA they are transcribed but are not translated into a protein. In a natural context miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). After integration into an active RISC complex, miRNAs may base pair with their complementary mRNA molecules and inhibit translation or may induce mRNA degradation by the catalytically active members of the RISC complex, e.g. argonaute proteins. Mature miRNA molecules are typically at least partially complementary to mRNA molecules corresponding to the expression product of the present invention, and fully or partially down-regulate gene expression. Preferably, miRNAs according to the present invention may be 100% complementary to their target sequences. Alternatively, they may have 1, 2 or 3 mismatches, e.g. at the terminal residues or in the central portion of the molecule. miRNA molecules according to the present invention may have a length of between about 18 to 27 nucleotides, e.g. 18, 19, 20, 21, 22, 23, 24, 25, 26 or 27 nucleotides. Preferred are 21 to 23 mers.

miRNAs having 100% complementarity may preferably be used for the degradation of nucleic acids according to the present invention, whereas miRNAs showing less than 100% complementarity may preferably be used for the blocking of translational processes.

The term "PDE9A antisense molecule" refers to nucleic acids corresponding to the sequences comprised in SEQ ID NO: 1 or 6 or the complementary strand thereof. Preferably, the antisense molecule of the invention comprises a sequence complementary to at least a portion of a PDE9A expression product according to the present invention. While antisense molecules complementary to the coding region sequence of PDE9A may be used, those complementary to the transcribed and untranslated region are preferred.

Generally, antisense technology can be used to control, i.e. reduce or terminate gene expression through antisense DNA or RNA, or through triple-helix formation. In one embodiment, an antisense molecule may be generated internally by the organism, for example intracellularly by transcription from an exogenous sequence. A vector or a portion thereof may be transcribed, producing an antisense nucleic acid of the invention. Such a vector would contain a sequence encoding the antisense nucleic acid of the invention. Such a vector can remain episomal or become chromosomally integrated, as long as it can be transcribed to produce the desired antisense molecule. Corresponding vectors can be constructed by recombinant DNA technology methods known to the person skilled in the art. Vectors can be plasmid, viral, or others known in the art, used for replication and expression in vertebrate cells, e.g. vectors as defined herein above.

In another embodiment, the antisense molecule may be separately administered. As an example, the 5' coding portion of a PDE9A nucleic acid according to the present invention may be used to design an antisense RNA or DNA oligonucleotide of from about 6 to 50 nucleotides in length. Preferably, the oligonucleotide is at least 10 nucleotides, at least 17 nucleotides, at least 25 nucleotides or at least 50 nucleotides in length.

The antisense nucleic acids of the invention typically comprise a sequence complementary to at least a portion of an RNA transcript of a gene of interest. However, absolute complementarity, although preferred, is not required. A sequence "complementary to at least a portion of an RNA transcript" as referred to herein, means a sequence having sufficient complementarity to be able to hybridize with the RNA, forming a stable duplex triplex formation in the case of double stranded antisense nucleic acids. The ability to hybridize will depend on both the degree of complementarity and the length of the antisense nucleic acid. Generally, the larger the hybridizing nucleic acid, the more base mismatches with a RNA sequence of the invention it may contain and still form a stable duplex or triplex. A person skilled in the art can ascertain a tolerable degree of mismatch by use of standard procedures to determine the melting point of the hybridized complex.

Preferably antisense molecules complementary to the 5' end of the transcript, e.g., the 5' untranslated sequence up to and including the AUG initiation codon may be used in for the inhibition of translation. In a further preferred embodiment, sequences complementary to the 3' untranslated sequences of mRNAs may also be used.

An antisense molecule according to the present invention may be DNA or RNA or chimeric mixtures or derivatives or modified versions thereof, single-stranded or double-stranded. An antisense molecule, preferably an antisense olignucleotide or any further antisense nucleic acid molecule according to the present invention or a siRNA molecule according to the present invention can be modified at the base moiety, sugar moiety, or phosphate backbone, for example, to improve stability of the molecule, hybridization, etc. The molecule may include other appended groups such as peptides (e.g., for targeting host cell receptors in vivo), or agents facilitating transport across the cell membrane or the blood-brain barrier hybridization triggered cleavage agents or intercalating agents. The molecule may accordingly be conjugated to another molecule, e.g., a peptide, hybridization triggered cross-linking agent, transport agent, hybridization-triggered cleavage agent, etc.

The antisense molecule or antisense oligonucleotide, miRNA- or siRNA molecule, may comprise at least one modified base moiety which is selected from the group including 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethyl-aminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methyl guanine, 3-methyl cytosine, 5-methylcytosine, N6-adenine, 7-methyl guanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6 isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The molecule may also comprise at least one modified sugar moiety selected from the group including, but not limited to, arabinose, 2-fluoroarabinose, xylulose, and hexose. In another embodiment, the molecule comprises alternatively or additionally at least one modified phosphate backbone, e.g. a phosphorothioate, a phosphorodithioate, a phosphoramidothioate, a phosphoramidate, a phosphordiamidate, a methylphosphonate, an alkyl phosphotriester, and a formacetal or analog thereof.

In another embodiment, the antisense molecule, e.g. the antisense oligonucleotide may be an alpha-anomeric oligonucleotide, i.e. an oligonucleotide which forms specific double-stranded hybrids with complementary RNA in which the strands run parallel to each other.

The term "siRNA specific for PDE9A" refers to a particular type of antisense-molecules, namely small inhibitory RNA duplexes that induce the RNA interference (RNAi) pathway to negatively regulate gene expression of the tumor marker according to Table 1. These siRNA molecules can vary in length and may be between about 18-28 nucleotides in length, e.g. have a length of 18, 19, 20, 21, 22, 23, 24, 25, 26, 27 or 28 nucleotides. Preferably, the molecule has a length of 21, 22 or 23 nucleotides. The siRNA molecule according to the present invention may contain varying degrees of complementarity to their target mRNA, preferably in the antisense strand. siRNAs may have unpaired overhanging bases on the 5' or 3' end of the sense strand and/or the antisense strand. The term "siRNA" includes duplexes of two separate strands, as well as single strands that can form hairpin structures comprising a duplex region. Preferably the siRNA may be double-stranded wherein the double-stranded siRNA molecule comprises a first and a second strand, each strand of the siRNA molecule is about 18 to about 23 nucleotides in length, the first strand of the siRNA molecule comprises nucleotide sequence having sufficient complementarity to the target RNA via RNA interference, and the second strand of said siRNA molecule comprises nucleotide sequence that is complementary to the first strand.

Methods for designing suitable siRNAs directed to a given target nucleic acid are known to person skilled in the art.

The term "aptamer specific for the expression product or specific for the protein of PDE9A" as used herein refers to (a) short peptide(s) capable of interacting and specifically binding the PDE9A protein(s). The peptide aptamer(s) may preferably be able to specifically bind to (a) protein(s) or polypeptide(s) comprising (the) amino acid sequence as set forth in SEQ ID NO: 2. The peptide aptamer(s) may also be able to specifically bind to (a) protein(s) or polypeptide(s) comprising (an) amino acid sequence(s) encoded by (a) DNA sequence(s) being at least 75%, 80%, 85%, 90%, 91%, 92%, 93%, 94%, 95%, 96%, 97%, 98% or 99% identical to the sequence as set forth in SEQ ID NOs: 2 or to a protein or polypeptide comprising an amino acid sequence being at least 75%, 80%, 85%, 90%, 91%, 92%, 93%, 94%, 95%, 96%, 97%, 98% or 99% identical to the sequence as set forth in SEQ ID NO: 2. Typically, (a) peptide aptamer(s) is/are a variable peptide loop, comprising for example, 10 to 20 amino acids. In the context of the present invention the peptide aptamer(s) may preferably be attached at one or both ends to a scaffold structure. The scaffold structure may be any molecule, preferably a protein, which has good solubility properties. Suitable scaffold molecules would be known to the person skilled in the art. A preferred scaffold molecule to be used in the context of the present invention is the bacterial protein thioredoxin-A. The aptamer peptide loop may preferably be inserted within a reducing active site of the scaffold molecule. Alternatively, staphylococcal protein A and domains thereof and derivatives of these domains, such as protein Z or lipocalins may be used as scaffold structures in the context of the present invention. Peptide aptamers may be generated according to any suitable method known to the person skilled in the art, e.g. via yeast two-hybrid approaches.

In a preferred embodiment the above mentioned peptide aptamer is capable to bind to a PDE9A protein or polypeptide, preferably protein or polypeptide corresponding to SEQ ID NO: 2 and to reduce the biological activity and/or the enzymatic activity of these/this protein(s) by at least 10%, 20%, 30%, 40%, 50%, 60%, 70%, 80%, 90%, 95% or by at least 98% or 99% when compared to a control level obtained from an untreated sample.

A "small molecule capable of specifically binding to the PDE9A protein" as used herein refers to a small organic compound that is preferably biologically active, i.e. a biomolecule, but is preferably not a polymer. Such an organic compound may have any suitable form or chemical property. The compound may be a natural compound, e.g. a secondary metabolites or an artificial compound, which has been designed and generated de novo. In an embodiment of the present invention a small molecule is capable of blocking the interaction between PDE, in particular PDE9A, and its interactor. Methods and techniques for the identification and preparation of small molecules as well as assays for the testing of small molecules are known to the person skilled in the art.

The term "peptidomimetic capable of specifically binding to the PDE9A protein" in the context of the present invention refers to a small protein-like chain designed to mimic a peptide and capable of binding to the PDE9A protein. Such a peptidomimetic may arise from a modification of an existing peptide, e.g. a peptide or peptide aptamer as defined herein above, in order to alter the molecule's properties. A peptidomimetic may arise from a modification which changes the molecule's stability or binding capability. These modifications typically involve changes to the peptide that will not occur naturally. For example, a peptidomimetic according to the present invention may have altered peptide backbones or may comprise non-natural amino acids. Preferably, a peptidomimetic according to the present invention may represent a phosphodiesterase molecule, in particular PDE9A, or an interacting or sequestering protein. In an embodiment of the present invention a peptidomimetic may block the interaction between PDE, in particular PDE9A, and its interactor. Methods and techniques for the preparation of peptidomimetics as well as assays for the testing of peptidomimetics are known to the person skilled in the art.

A inhibitory pharmaceutical composition according to the present invention may also comprise an antibody specific for the PDE9A protein and/or an antibody variant specific for the PDE9A protein, e.g. an antibody or antibody variant as defined herein above.

In a preferred embodiment such an antibody or antibody fragment may be capable of inhibiting the biological activity and/or enzymatic activity of PDE9A.

The skilled person would also be aware of the possibility to target and destroy malignant, hormone-sensitive prostate cancer cells and tissue by virtue of conjugated antibodies specific for PDE9A. Thus, in a specific embodiment of the present invention the antibody or fragment thereof as defined herein above may be conjugated to a therapeutic or cytotoxic agent. The term "therapeutic agent" refers to any compound, drug, small molecule or medicament, which is able to confer a therapeutic effect to a cell, a tissue or the entire organism. Examples of such agents are known to the person skilled in the art. The term "cytotoxic agent" refers to any compound, drug, small molecule which is able to confer a toxic effect to a cell or a tissue. Such agents may, for example, comprise compounds which activate endogenous cytotoxic effector systems, as well as radioisotopes, holotoxins, modified toxins, catalytic subunits of toxins, or any molecules or enzymes not normally present in or on the surface of a cell that under defined conditions cause the cell's death. The term may also include radioisotopes known in the art, additional antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. The term also refers to cytotoxic produgs. By "cytotoxic prodrug" is meant a non-toxic compound that is converted by an enzyme, normally present in the cell, into a cytotoxic compound. Cytotoxic prodrugs that may be used according to the invention include glutamyl derivatives of benzoic acid mustard alkylating agent, phosphate derivatives of etoposide or mitomycin C, cytosine arabinoside, daunorubisin, and phenoxyacetamide derivatives of doxorubicin.

In a further embodiment the present invention also envisages screening procedures and methods for the identification of an aptamer specific for the PDE9A expression product or protein, a compound directly stimulating or modulating the activity of PDE9A, an allosteric agonist of PDE9A enzymatic activity, a miRNA inhibitor specific for PDE9A miRNA, an antagomir, a PDE9A specific demethylation agent, a PDE9A specific phosphodiesterase displacement factor, a PDE9A specific peptidomimetic, and a PDE9A specific small molecule or drug as defined herein above. Such screening procedures may comprise the steps of (a) producing cells which express the PDE9A as a polypeptide either as secreted protein or on the cell membrane or as intracellular component, (b) contacting the polypeptide produced in step (a) with a test sample potentially containing an interacting molecule, e.g. an aptamer specific for the PDE9A protein, a compound directly stimulating or modulating the activity of PDE9A, a compound directly stimulating or modulating the activity of PDE9A, an allosteric agonist of PDE9A enzymatic activity, a PDE9A specific phosphodiesterase displacement factor, a PDE9A specific peptidomimetic or a PDE9A specific small molecule or drug; and (c) indentifying an interacting molecule by observing binding and/or inhibition or modulation of the activity of PDE9A.

Alternatively, such screening procedures may comprise the steps of (a) contacting a test sample potentially containing a directly or indirectly interacting molecule, e.g. an aptamer specific for the PDE9A transcript, a miRNA inhibitor specific for PDE9A miRNA, an antagomir, a PDE9A specific demethylation agent, a PDE9A specific phosphodiesterase displacement factor, a PDE9A specific peptidomimetic or a PDE9A specific small molecule or drug with one or more cells which express the PDE9A as a transcript, (b) detecting the expression level of said sequence; and (c) indentifying an interacting molecule by observing binding or a modulation or reduction of the expression level of PDE9A.

The present invention also encompasses an aptamer specific for the PDE9A expression product or protein, a compound directly stimulating or modulating the activity of PDE9A, an allosteric agonist of PDE9A enzymatic activity, a miRNA inhibitor specific for PDE9A miRNA, an antagomir, a PDE9A specific demethylation agent, a PDE9A specific phosphodiesterase displacement factor, a PDE9A specific peptidomimetic, and a PDE9A specific small molecule or drug obtainable or obtained by a screening procedure or method as described herein above.

In a further aspect the present invention relates to a stimulatory pharmaceutical composition as defined herein above for the treatment or prevention of cancer, in particular for the treatment of prostate cancer.

Further, in yet another aspect, the present invention relates to the use of (a) a compound directly stimulating or modulating the activity of PDE9A, preferably an allosteric agonist of PDE9A enzymatic activity; (b) a compound indirectly stimulating or modulating the activity of PDE9A; (c) the PDE9A protein or a biologically active equivalent thereof; (d) a nucleic acid encoding and expressing PDE9A; (e) a miRNA inhibitor specific for PDE9A miRNAs; (f) a demethylation agent; and/or (g) a phosphodiesterase displacement factor, preferably a peptide, a peptidomimetic, a small molecule, an antibody or an aptamer for the preparation of a stimulatory pharmaceutical composition for the treatment or prevention of cancer, in particular prostate cancer, preferably the treatment of hormone-resistant prostate cancer.

In another aspect the present invention relates to a method of treatment or prevention of cancer, in particular prostate cancer, preferably the treatment of hormone-resistant prostate cancer comprising the administration of (a) a compound directly stimulating or modulating the activity of PDE9A, preferably an allosteric agonist of PDE9A enzymatic activity; (b) a compound indirectly stimulating or modulating the activity of PDE9A; (c) the PDE9A protein or a biologically active equivalent thereof; (d) a nucleic acid encoding and expressing PDE9A; (e) a miRNA inhibitor specific for PDE9A miRNAs; (f) a demethylation agent; and/or (g) a phosphodiesterase displacement factor, preferably a peptide, a peptidomimetic, a small molecule, an antibody or an aptamer to an individual, in particular to an individual suffering from cancer or being prognosticated to develop cancer.

In a further preferred embodiment said inhibitory pharmaceutical composition as defined above or said stimulatory pharmaceutical composition as defined above may be used for the treatment of prostate cancer in dependence of the expression level of PDE9A, wherein said level of expression is determined and/or monitored according to the steps of (a) determining the level of PDE9A in a sample;

(b) determining the level of expression of a reference gene in a sample; and (c) normalizing the measured expression level of PDE9A to the expression of the reference gene. The level of PDE9A may be determined on the nucleic acid, protein or activity level as described herein above. Preferred is the determination of the amount of PDE9A transcript(s) and/or protein. In addition the level of a reference gene as defined herein above in a sample may be determined. A preferred reference gene in the context of this embodiment is PDE4D5, as described herein above.

The term "in dependence of the expression level of PDE9A" means that the choice for the administration of an inhibitory pharmaceutical composition or a stimulatory pharmaceutical composition may be made after the level of PDE9A in a sample has been determined, preferably in comparison to a reference gene like PDE4D5.

In a particularly preferred embodiment of the present invention for increased and/or increasing levels of PDE9A an inhibitory pharmaceutical composition according to the present invention is to be administered, and for decreased and/or decreasing levels of PDE9A a stimulatory pharmaceutical composition according to the present invention is to be administered.

The term "increased" as used in this context means that the level of PDE9A gene expression in a test sample is elevated by, for example, 5%, 6%, 7%, 8%, 9%, 10%, 15%, 20%, 25%, 30%, 40%, 50%, or more than 50% in comparison to the PDE9A expression in a control sample, or at least 0.1 fold, at least 0.2 fold, at least 1 fold, at least 2 fold, at least 5 fold, or at least 10 fold or more in comparison to the PDE9A expression in a control sample; or when the PDE9A gene expression is elevated by, for example, 5%, 6%, 7%, 8%, 9%, 10%, 15%, 20%, 25%, 30%, 40%, 50%, or more than 50% in comparison to the expression of a reference gene in a control sample, or at least 0.1 fold, at least 0.2 fold, at least 1 fold, at least 2 fold, at least 5 fold, or at least 10 fold or more elevated in comparison to the expression of a reference gene. In a specific embodiment, the expression of a reference gene may also be normalized or adjusted to the expression of additional genes or markers, e.g. housekeeping genes. As a preferred control sample or reference point a non-cancerous control, healthy tissue, tissue or cells derived from a healthy individual or benign tumor tissues or data derived therefrom etc. may be used. Alternatively any other control sample or control point may also be used.

The term "increasing" refers to correspondingly determined expression values which tend to augment over a certain period of time, i.e. which become higher after repeated determination steps, e.g. every 4 weeks, 6 weeks, two months, 4 months, 6 months, 8 months, 12 months, 1.5 years, 2 years, 2.5 years etc. An "increasing" PDE9A expression level may accordingly be elevated by 0.5 to more than 100% in every testing session, preferably be elevated by 10%, 20%, 30%, 40%, 50% etc. The increase itself depends on the frequency of testing and the significance may accordingly be adjusted, as the person skilled in the art would be aware of In a preferred embodiment an increased or increasing PDE9A level may be determined in the early stages of prostate cancer development, i.e. up to tumor stage of hormone-sensitive prostate cancer has. Alternatively, histological determinations may provide independent information on the staging of a prostate tumor. In dependence of such an independent determination a benign prostate tumor stage or a hormone-dependent tumor stage may be diagnosed. In this situation an increased or increasing PDE9A level (in comparison to a non-cancerous or healthy control or stage) may trigger the administration of an inhibitory pharmaceutical composition according to the present invention.

Alternatively, the level of PSA may be additionally be determined. In case a low PSA level of below 2.0-3.0 ng/ml is encountered an increased or increasing level of PDE9A may trigger the administration of an inhibitory pharmaceutical composition according to the present invention.

The term "decreased" as used in this context means that the level of PDE9A gene expression in a test sample is reduced by, for example, 5%, 6%, 7%, 8%, 9%, 10%, 15%, 20%, 25%, 30%, 40%, 50%, or more than 50% in comparison to the PDE9A expression in a control sample, or at least 0.1 fold, at least 0.2 fold, at least 1 fold, at least 2 fold, at least 5 fold, or at least 10 fold or more in comparison to the PDE9A expression in a control sample; or when the PDE9A gene expression is decreased by, for example, 5%, 6%, 7%, 8%, 9%, 10%, 15%, 20%, 25%, 30%, 40%, 50%, or more than 50% in comparison to the expression of a reference gene in a control sample, or at least 0.1 fold, at least 0.2 fold, at least 1 fold, at least 2 fold, at least 5 fold, or at least 10 fold or more decreased in comparison to the expression of a reference gene. In a specific embodiment, the expression of a reference gene may also be normalized or adjusted to the expression of additional genes or markers, e.g. housekeeping genes. As a preferred control sample or reference point a cancerous control, in particular a hormone-sensitive or hormone-dependent prostate cancer tissue or data derived therefrom etc. may be used. Alternatively any other control sample or control point may also be used.

The term "decreasing" refers to correspondingly determined expression values which tend to become lower over a certain period of time, i.e. which become lower after repeated determination steps, e.g. every 4 weeks, 6 weeks, two months, 4 months, 6 months, 8 months, 12 months, 1.5 years, 2 years, 2.5 years etc. An "increasing" PDE9A expression level may accordingly be elevated by 0.5 to more than 100% in every testing session, preferably be elevated by 10%, 20%, 30%, 40%, 50% etc. The decrease itself depends on the frequency of testing and the significance may accordingly be adjusted, as the person skilled in the art would be aware of.

In a preferred embodiment a decreased or decreasing PDE9A level may be determined after an increase of PDE9A up to tumor stage of hormone-sensitive prostate cancer has already been determined. Alternatively, histological determinations may provide independent information on the staging of a prostate tumor. In dependence of such an independent determination a hormone-sensitive tumor stage may be diagnosed. In this situation a decreased or decreasing PDE9A level (in comparison to the starting tumor stage) may trigger the administration of a stimulatory pharmaceutical composition according to the present invention.

Alternatively, the level of PSA may be additionally be determined. In case a PSA level of about 20 ng/ml and/or higher is encountered a decreased or decreasing level of PDE9A may trigger the administration of a stimulatory pharmaceutical composition according to the present invention.

In a further specific embodiment the present invention envisages a method of monitoring the development of prostate cancer, which encompasses the determination of PDE9A, preferably in combination with the determination of a reference gene as described herein above, over a certain period of time, i.e. after repeated determination steps, e.g. every 4 weeks, 6 weeks, two months, 4 months, 6 months, 8 months, 12 months, 1.5 years, 2 years, 2.5 years, 3 years, 4 years or any other suitable period of time etc. The method may provide data showing an increase or decrease of the level of PDE9A in comparison to controls, e.g. non-cancerous controls, cancerous controls or to earlier data obtained from the same individual. These data may be used to depict or develop a PDE9A expression curve over time. With the help of suitable statistical methods known to the person skilled in the art the position within said curve may be determined. In dependence of the position within said curve, i.e. in an augmenting portion or a falling portion of said curve, the presence or future development of hormone-dependent/hormone-sensitive prostate cancer or hormone-resistant prostate cancer may be diagnosed. Correspondingly, either the use of inhibitory pharmaceutical compositions according to the present invention, or stimulatory pharmaceutical compositions according to the present invention is envisaged. Preferably, any such determination may be combined with the determination of secondary biomarkers, e.g. markers for prostate cancer, in particular PSA. In case of low PSA levels (up to 4.0 to 10.0 ng/ml) the PDE9A data may be analysed with respect to early prostate cancer, i.e. benign or hormone-dependent/hormone-sensitive prostate cancer. In case of higher PSA levels (higher than about 4.0 to 10.0 ng/ml, more preferably higher than about 20 ng/ml) the PDE9A data may be analysed with respect to more advanced prostate cancer, i.e. hormone-resistant prostate cancer.

A pharmaceutical composition according to the present invention may be administered to a patient, subject or individual with the help of various delivery systems known to the person skilled in the art, e.g., via encapsulation in liposomes, microparticles, microcapsules, recombinant cells capable of expressing the compound, receptor-mediated endocytosis, construction of a nucleic acid as part of a retroviral or other vector, etc. Methods of introduction may be topical, enteral or parenteral and may include intradermal, intramuscular, intraperitoneal, intravenous, subcutaneous, intranasal, inhalational, epidural, and oral routes. The composition may be administered by any convenient route, for example by infusion or bolus injection, by absorption through epithelial or mucocutaneous linings (e.g., oral mucosa, rectal and intestinal mucosa, etc.) or by inhalation and may be administered together with other biologically active agents. Administration can be systemic or local. A preferred method of local administration is by direct injection.

In another embodiment the pharmaceutical composition may be delivered directly to internal organs, body cavities and the like by use of imaging devices used to guide an injecting needle directly to the site of interest. The pharmaceutical composition may also be administered to disease sites at the time of surgical intervention. In yet another embodiment, the composition can be delivered in a controlled release system.

Preferably the pharmaceutical composition is in a form, which is suitable for oral, local or systemic administration. In a preferred embodiment the pharmaceutical composition is administered locally, orally or systemically.

In a specific embodiment of the present invention the stimulatory or inhibitory pharmaceutical composition may be administered after an immunoassay for stratifying an individual, or a method of identifying an individual for eligibility for prostate cancer as described herein above has been carried out, in particular upon the classification of an individual as having a reduced level of PDE9A.

In a further embodiment the pharmaceutical composition comprises a therapeutically effective amount of the ingredients of the pharmaceutical composition of the present invention as defined herein above and a pharmaceutically acceptable carrier. The term "pharmaceutically acceptable" means approved by a regulatory agency or other generally recognized pharmacopeia for use in animals, and more particularly in humans. The term "carrier" refers to a diluent, adjuvant, excipient, or vehicle with which the therapeutic is administered. Such a carrier is pharmaceutically acceptable, i.e. is non-toxic to a recipient at the dosage and concentration employed.

Generally, the ingredients are supplied either separately or mixed together in unit dosage form, for example, as a dry lyophilised powder or water free concentrate in a hermetically sealed container such as an ampoule or sachette indicating the quantity of active agent.

The pharmaceutical composition of the invention can be formulated as neutral or salt forms.

Preferably, the pharmaceutical composition may be administered directly or in combination with any suitable adjuvant known to the person skilled in the art. The composition of the present invention can be administered to an animal, preferably to a mammal. "Mammal" as used herein is intended to have the same meaning as commonly understood by one of ordinary skill in the art. Particularly, "mammal" encompasses human beings.

The term "administered" means administration of a therapeutically effective dose of the aforementioned composition. By "therapeutically effective amount" is meant a dose that produces the effects for which it is administered, preferably this effect is induction and enhancement of PDE9A. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The concentration of the active ingredients or compounds of a pharmaceutical composition according to the present invention may be further adjusted to the intended dosage regimen, the intended usage duration, the exact amount and ratio of all ingredients of the composition and further factors and parameter known to the person skilled in the art.

The active agents or compounds according to the present invention may be administered alone or in combination with other treatments. In a preferred embodiment the pharmaceutical composition of the present invention may be administered in combination with an anti-hormone treatment, e.g. an anti-androgen treatment.

The pharmaceutical composition of the present invention can also comprise any suitable preservative known to the person skilled in the art.

Furthermore, the preparations according to the invention may also comprise compounds, which have an antioxidative, free-radical scavenger, antierythematous, antiinflammatory or antiallergic action, in order to supplement or enhance their action.

In another preferred embodiment of the present invention active components of the pharmaceutical composition as defined herein above may be fused to a suitable carrier protein, e.g. to Ig Fc receptor proteins or polymeric Ig receptors. Preferably PDE9A or biologically active equivalents thereof as defined herein above may be provided as fusion proteins. The fusion partner may be provided at the N- or C-terminus.

If the pharmaceutical composition according to the present invention is to be administered in the form of a live cell or living therapeutic as defined herein above, transformed and prepared cells may be administered to a patient in any suitable form known to the person skilled in the art. Preferably living therapeutics may be administered in the form of a composition comprising a microorganism, e.g. a *Lactobacillus* as described above, in an amount between $10^2$ to $10^{12}$ cells, preferably $10^3$ to $10^8$ cells.

In a further preferred embodiment of the present invention the ratio between two or more ingredients in the pharmaceutical composition or medicament may be suitably adjusted according to the skilled person's knowledge.

Suitable assays may optionally be employed to help identify optimal ratios and/or dosage ranges for ingredients of pharmaceutical compositions of the present invention. The precise dose and the ratio between the ingredients of the pharmaceutical composition as defined herein above to be employed in the formulation will, inter alia, depend on the route of administration, and the exact type of disease or disorder, and should be decided according to the judgment of the practitioner and each patient's circumstances. Effective doses or ingredient ratios may be extrapolated from dose-response curves derived from in vitro or (animal) model test systems.

A typical dose can be, for example, in the range of 0.001 to 1000 μg; however, doses below or above this exemplary range are envisioned, especially considering the aforementioned factors.

In another aspect the present invention relates to a medical kit comprising the ingredient of an inhibitory or stimulatory pharmaceutical composition according to the present invention. Preferably, the present invention relates to a medical kit for the treatment or prevention of cancer, in particular prostate cancer, preferably hormone-resistant prostate cancer comprising at least one element selected from the group consisting of: (a) a compound directly stimulating or modulating the activity of PDE9A, preferably an allosteric agonist of PDE9A enzymatic activity; (b) a compound indirectly stimulating or modulating the activity of PDE9A; (c) the PDE9A protein or a biologically active equivalent thereof; (d) a nucleic acid encoding and expressing PDE9A; (e) a miRNA inhibitor specific for PDE9A miRNAs; (f) a demethylation agent; and (g) a phosphodiesterase displacement factor.

A medical kit that can be used in the context of the administration of the pharmaceutical composition as defined herein above. In particular, a kit according to the present invention may be used for the treatment or prevention of cancer, in particular prostate cancer, preferably hormone-resistant prostate cancer.

The ingredients of a medical kit may, according to the present invention, be comprised in one or more containers or separate entities. They may preferably be formulated as pharmaceutical compositions or medicaments, more preferably they may be formulated as has been described herein above in the context of the pharmaceutical compositions of the present invention, e.g. they may comprise suitable pharmaceutical carriers etc. Particularly preferred are formulations for topical administration as mentioned herein above in the context of pharmaceutical compositions of the invention. The medical kit according to the present invention may optionally also comprise a documentation which indicates the use or employment of the medical kit and its components. Preferably, instructions comprised in the medical kit of the present invention may comprise recommended treatment options, dosage regimens etc. The medical kit may also comprise an instruction leaflet and/or may provide additional information on the use, dosage etc.

The medical kit of the present invention may be administered to a patient according to any suitable dosage regimen known to the person skilled in the art. The medical kit or kit components may preferably be given once a week, more preferably 2 times, 3 times, 4 times, 5 times or 6 times a week and most preferably daily and or 2 times a day or more often, unless otherwise indicated. During progression of the treatment the dosages may be given in much longer time intervals and in need can be given in much shorter time intervals, e.g., several times a day. In a preferred case a response to the treatment may be monitored using herein described methods and further methods known to those skilled in the art and dosages may accordingly be optimized, e.g., in time, amount and/or composition. Progress can be monitored by periodic assessment. It is also envisaged that a stimulatory medical kit is employed in co-therapy approaches, i.e. in co-administration with other medicaments or drugs, for example antibiotics, antiviral medicaments or IgG or IgA immunoglobulins, anticancer medicaments and, preferably, anti-hormone medicaments, more preferably anti-androgens as mentioned herein above.

In a further, specific aspect the present invention relates to a kit comprising ingredients for the determination of the expression of PDE9A as defined herein above together with ingredients of a medical kit for the treatment of prostate cancer, in particular hormone-resistant prostate cancer as defined herein above.

In a further, particularly preferred embodiment of the present invention the cancer to be diagnosed, detected, monitored or prognosticated or whose progression is diagnosed, detected, monitored or prognosticated or which is to be treated with a pharmaceutical composition as mentioned above or by a method of treatment according to the present invention is prostate cancer.

In another particularly preferred embodiment of the present invention the cancer to be diagnosed, detected, monitored or prognosticated or whose progression is diagnosed, detected, monitored or prognosticated or which is to be treated with a stimulatory pharmaceutical composition as mentioned above or by a method of treatment according to the present invention is hormone-resistant prostate cancer. The term "hormone-resistant prostate cancer" means that the growth and proliferation of prostate cancer or prostate cancer cell lines is resistant to male sex hormone stimulation. The term also relates to a late prostate cancer developmental stage which is no longer amenable to an administration of anti-hormones, preferably anti-androgens as defined herein above.

Typically, prostate cancer progression is accompanied by a shift in reliance on endocrine controls to paracrine and eventually autocrine controls and that this complex process is believed to be the result of changes which occur at molecular levels of cellular control. Due to the possibility of metastatic spread of tumors at this stage hormone-resistant prostate cancers are a prime target for diagnosis and treatments according to the present invention, in particular according to the above provided embodiments.

The following examples and figures are provided for illustrative purposes. It is thus understood that the example and figures are not to be construed as limiting. The skilled person in the art will clearly be able to envisage further modifications of the principles laid out herein.

EXAMPLES

Example 1—Quantitative RT-PCR Assay

From the cell lines and human tissue xenografts depicted in FIG. 1 (see also for further details Marques et al., 2006, Eur. Urol., 49(2):245-57) RNA was isolated and transcribed by standard procedures into cDNA. The prepared cDNAs of samples LNCaP" through "DuCaP" which are cell lines and samples "PC-EW" through "PC374" which are xenografts were tested on expression levels of PDE9A.

qRT-PCR: Materials and Methods

RNA samples were treated with DNase to ensure there was no DNA contamination. Prior to cDNA synthesis RNA samples were treated with DnaseI (In Vitrogen) for 30 min at 37° C. 1 μg of the RNA sample was then treated with Superscript Vilo (In Vitrogen) to synthesize the first strand DNA for qPCR analysis as per manufacturer's guidelines. DNA samples were then treated with RnaseH1 30 min at 37° C.

Resulting DNA was diluted to a final concentration of 50-60 ng/μl, of which 5 μl was added to each reaction well of a 96-well optical reaction plate.

Quantitative PCR reactions were performed using an ABI Prism 7300 machine in a reaction volume of 15 μl according to the following protocol:

7.5 μl Platinum qPCR SuperMix-UDG with ROX (In Vitrogen)
2.2 μl nuclease free water
0.1 μl 100 pmol/μl Probe
0.1 μl 100 pmol/μl Forward Primer
0.1 μl 100 pmol/μl Reverse Primer Total volume in each reaction well was 15 μl including cDNA.

The PCR itself was run over 40 cycles under the following program:

| Stage | Repetitions | Temperature (° C.) | Time |
|---|---|---|---|
| 1 | 1 | 50 | 2 seconds |
| 2 | 1 | 95 | 2 minutes |
| 3 | 40 | 95 | 15 seconds |
| | | 60 | 1 minute |

qRT-PCR Primers and Probes (TAQMAN)

The following oligonucleotide primers and probes were used for RT-PCR on PDE9A:

Forward Primer 5'-CGAGGAGCTGAAGCGGATA-3' (SEQ ID NO: 41), Reverse Primer 5'-CCCCAGACGT-CAAGCTGTC-3' (SEQ ID NO: 42) giving rise to a product of the length 71.

As probe the sequence 5'-TGACGCCATGAAAGAGT-TACA-3' (SEQ ID NO: 43) was used.

The probe-set was designed to target the conserved C-terminal regions of the PDE iso form. The amplicon was designed to be within the optimal range for Taqman assays on ABI Prism technology. All assays were performed in quadruplicate to maximise data integrity. A GAPDH reference probe was also included to which all consecutive data were referenced against.

qRT-PCR: Data Analysis

A −ddCt approach was carried out in order to normalize and compare different RT-PCR experiments. Ct values were obtained by manual threshold observation where each probe-set was amplifying exponentially at a comparable efficiency. In particular, the following steps were carried out:

1.) The difference in cycle number (Ct) between reference and gene of interest (GAPDH subtracted from Gene of interest) was calculated to give the experimental sample (ES) dCt.

2.) One sample was selected as standard to be compared against (LNCaP) (C) and its dCt was calculated.

3.) The change in cycle number difference could be derived by dCt(ES)−dCt(C)=ddCt 4.) The final comparable expression values could be derived by 2-ddCt in order to take into account the doubling of DNA after each cycle, hence showing the amount of mRNA in comparison to LNCaP.

This operation gave a value in comparison to LNCaP (which will have the value of 1), i.e. any value >1 was considered to be an increase in expression, a value of <1 was considered to be a decrease in expression.

It was accordingly assumed that the extension efficiencies of all the PCR reactions are within a certain range, resulting in a value of 1.

Percentage Approach to Normalize and Compare Different RT-PCR Experiments

For each probe-set a Ct (cycle number) value was obtained. This was generated by finding a baseline which intersected the amplification curves during their exponential phase. The baselines were generated dynamically according to the curves obtained in each experiment. The Ct (intersect or cycle) values of the GOIs were then subtracted from the Ct value of the GAPDH standard.

According to the formula Ct(GAPDH)−Ct(GOI)=dCt, given that GOI Ct values are always larger than the reference gene the dCt value resulted in negative numbers, i.e. a −dCt value.

Based on the doubling effect of each cycle and the absolute values were determined according to the Comparative Expression Value=2−dCt.

Due to the very small values gained from this calculation the value multiplied by 1000 for handling purposes.

Expression levels for PDE9A obtained by this approach are depicted in FIGS. 2 to 7.

The results presented in FIGS. 2 to 7 show that the transcription of PDE9A in human prostate cancer cell lines and tissues is dependent on the status of the Androgen Receptor activity in a given cell type. In case of presence of AR and sensitivity of a cell to androgen/hormone stimulation significant PDE9A transcription can be observed whereas on the absence of active AR the PDE9A transcription is very minimal.

Example 2—Quantitative RT-PCR Assay with Human Tissue Samples

The relative gene expression of human PDE9A was evaluated in prostate cancer tissues derived from patients with hormone-sensitive/responsive vs. hormone-refractory/castration-resistant patients.

Materials and Methods

Details on the samples used in the qPCR measurements of PDE gene expression experiment are given in Table 1, below:

TABLE 1

Patient information used in the experiment

| Tissue1 | Type of Tissue | Gleason score | Age at treatment | Hormone Refractory sample |
|---|---|---|---|---|
| Prostate | TURP | 3 + 4 | 60 | yes |
| Prostate | TURP | 4 + 4 | 68 | no |
| Prostate | TURP | 4 + 4 | 49 | no |
| Prostate | TURP | 4 + 4 | 64 | no |
| Prostate | TURP | 6 | 71 | yes |
| Prostate | TURP | 7 | 75 | yes |
| Prostate | TURP | 4 + 4 | 77 | yes |
| Prostate | TURP | 3 + 3 | 67 | no |
| Prostate | TURP | 4 + 3 | 66 | yes |
| Prostate | TURP | 5 + 4 | 76 | yes |
| Prostate | TURP | 3 + 5 | 70 | yes |
| Prostate | TURP | 4 + 4 | 82 | no |
| Prostate | TURP | 5 + 3 | 90 | yes |
| Prostate | TURP | 4 + 4 | 66 | no |

All samples were derived from male patients (ages at treatment 49-90). The column "Tissue" defines the tissue that has been taken during surgery, either prostate tissue, or lymph nodes for staging. The column "Type of Tissue" describes the approach of tissue resection. If not otherwise indicated the tissue was resected during prostate surgery (prostatectomy). TURP is defined as Trans Urethral Resection of the Prostate.

This cDNA panel includes 6 derived from patients with hormone-sensitive prostate cancer, and 8 samples derived from patients with hormone-refractory prostate cancer.

```
Primer and probe sequences used for human
PDE9A:
sense primer sequence:
                                    (SEQ ID NO: 45)
GCAGAGCGACCGTGAGAAG

antisense primer sequence:
                                    (SEQ ID NO: 46)
AGGACAAACTTGATGAACCCAATC

probe sequence:
                                    (SEQ ID NO: 47)
CCTGTGGCACCGTTCATGGACCGAGACTCACAGG
(FAM-labeled).
```

The PDE9A specific primers were premixed with the FAM probes to perform quantitative, real-time PCR (qPCR), and used in a 1:20 dilution according to manufacturer's description (PrimerDesign, UK). The human cDNA samples (see Tables 1 & 2 for details on the sample descriptions that we used for the study) are arranged in standard, qPCR-ready, 96-well microtiter (MT) plates.

16 tissue samples, derived from 16 different patients were arranged per 96-well MT plate, with each of the 16 wells used per plate containing ca 2-3 ng of RNA reverse transcribed cDNA.

To each of the used well of the MT plate 15 μL Applied Biosystems' GeneAmp mastermix (2×), 13.5 μL RNAse/DNAse free water and 2 μL PrimerDesign PerfectProbe primermix (PrimerDesign, UK) were added. All samples were analyzed with the following PCR protocol: 2 min at 50° C., 10 min at 95° C., 15 sec at 95° C., 30 sec at 50° C. while recording fluorescence, 15 sec at 72° C. and the last three steps repeated 50 times.

For all calculations relative gene expression values, the following procedure was used: $C_T$ values of 40 or higher or below 16 were excluded for poor quality reasons. (The genes examined here had an average $C_T$-value of ~33).

To normalize the $C_T$ values, we used the following approach: we converted $C_T$ values to relative gene copy number based on calibration curves. The calibration curves were independently measured on different dilutions of cDNA. Subsequently we normalized the PDE-9a expression by dividing the PDE-9a copy number by the average copy number of the household genes (Glycerinaldehyd-3-phosphat-Dehydrogenase (GAPDH), and Porphobilinogen Deaminase (PBGD))

Relative Expression of Human PDE9A in Human Prostate Tissues (Hormone-Responsive vs. Hormone-Resistant) Including Lymph Node Resected Tissue Samples The gene expression level of the human PDE9A isoform was determined on human prostate tissues as described above. The relative expression levels were determined in tow defined prostate tissues ("hormone-responsive", "hormone-refractory"). For an initial investigation of the human PDE9A expression status we included only primary prostate cancer samples, i.e., all samples derived from lymph node resections were dismissed.

Figure 8:
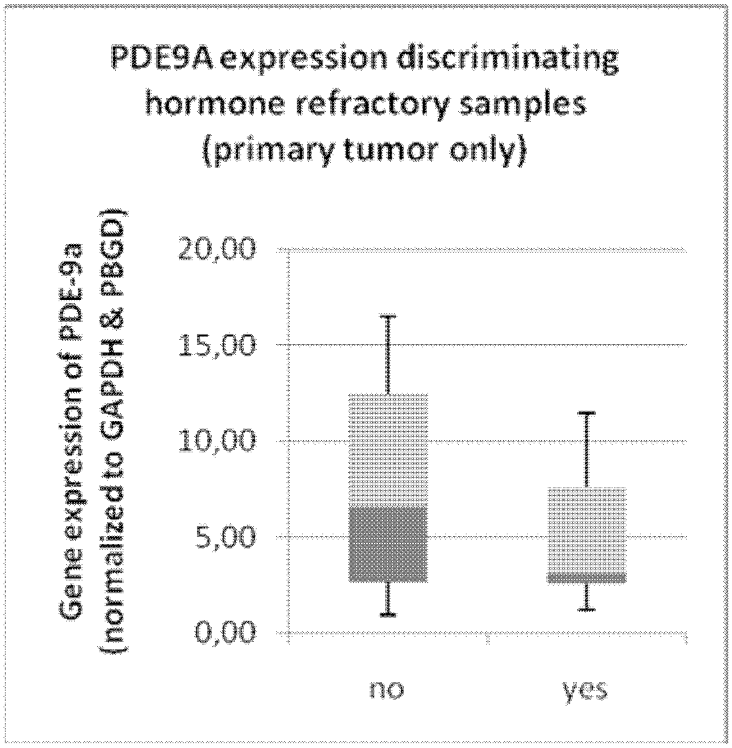
FIG. 8 shows the relative gene expression of human PDE9A in human patient tissue samples. Information is derived from 16 different samples in total, as depicted in Table 1. Sample group "no" is defined as hormone-responsive primary prostate tumors, Sample group "yes" is defined as hormone-resistant prostate tumors. Indicated are the individual relative expression values for human PDE9A on human prostate tissues. The results were normalized to the expression of GAPDH and PBGD. The median of the data relative data measurements is indicated for each patient group.
Figure 9:
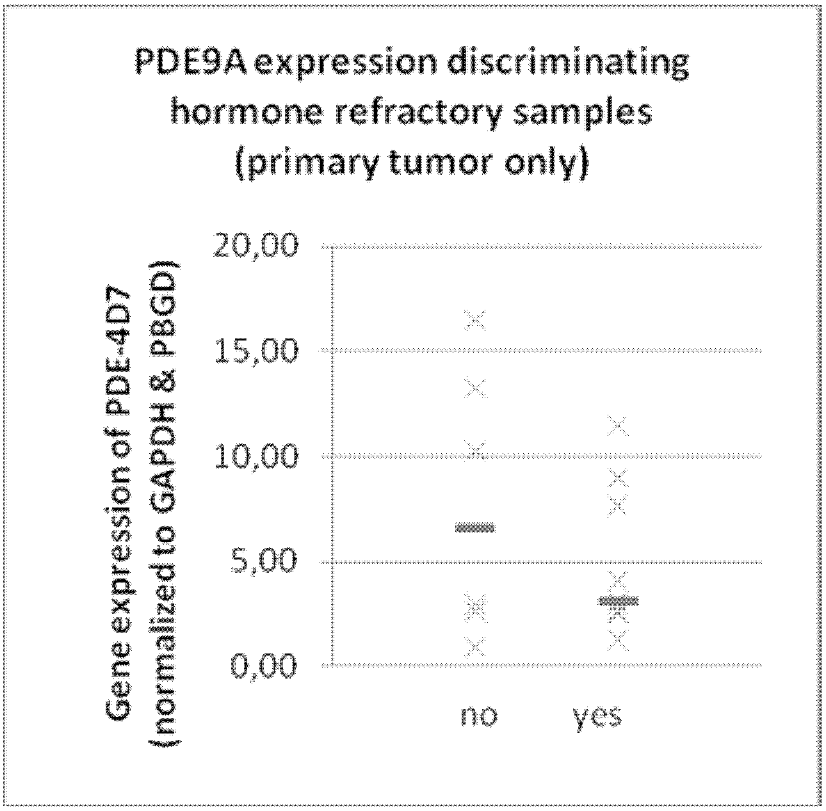
FIG. 9 shows the relative gene expression of human PDE9A in human patient tissue samples. Information is derived from 16 different samples in total, as depicted in Table 1 (including the lymph node resected tissues). Sample group "no" is defined as hormone-responsive primary prostate tumors, Sample group "yes" is defined as hormone-resistant prostate tumors. The results were normalized to the expression of GAPDH and PBGD. The figure shows a box plot of the individual data relative expression measurements for human PDE9A, whereby the box includes 75% of all measurements. The median relative expression value is indicated as the border between the two colored boxes.

As can be derived from FIGS. 8 and 9, the PDE9A expression in the hormone-resistant prostate tumors is generally decreased compared to hormone-responsive prostate tumors. It can, hence, be concluded that decreased levels of cAMP/cGMP-PDE activity is advantageous for enhanced cell proliferation. It has been long speculated that next to Androgen Receptor gene mutations or gene amplification, the activation of other cellular signaling pathways can support the transition of hormone-responsive to hormone-independent cell growth. The cAMP-PKA pathway is one of the pathways that have been implicated in that transition of hormone related growth. The change in PDE9A expression from hormone-sensitive to hormone-refractory human prostate tissue supports this view.

Example 3—Detection of PDE9A and PDE4D5 in Quantitative RT-PCR Assays with Human Tissue Samples (Origene's Human Prostate Cancer Tissue Panels I and II)

The relative gene expression of human PDE9A and human PDE4D5 as reference gene was evaluated various patient panels.

Materials and Methods

Details on the samples used in the qPCR measurements of PDE gene expression experiment are given in Tables 2 and 3, below:

TABLE 2

Origene's Human Prostate Cancer Tissue panel I (HPRT501, Origene Inc):

| gender | age | tissue | appearance | diagnosis | tumorgrade | normal | lesion | tumor |
|---|---|---|---|---|---|---|---|---|
| Male | 67 | Prostate/Prostate | Normal | Adenocarcinoma of prostate | Gleason Score: 3 + 4 = 7/10 | 100 | 0 | 0 |
| Male | 68 | Prostate/Prostate | Normal | Adenocarcinoma of prostate | Gleason Score: 4 + 3 = 7/10 | 100 | 0 | 0 |
| Male | 53 | Prostate/Prostate | Normal | Adenocarcinoma of prostate | Gleason Score: 3 + 3 = 6/10 | 100 | 0 | 0 |
| Male | 65 | Prostate/Prostate | Normal | Adenocarcinoma of prostate | Gleason Score: 3 + 3 = 6/10 | 100 | 0 | 0 |
| Male | 48 | Prostate/Prostate | Normal | Adenocarcinoma of prostate | Gleason Score: 3 + 3 = 6/10 | 100 | 0 | 0 |
| Male | 68 | Prostate/Prostate | Normal | Adenocarcinoma of prostate | Gleason Score: 3 + 3 = 6/10 | 100 | 0 | 0 |
| Male | 76 | Prostate/Prostate | Normal | Adenocarcinoma of prostate | Gleason Score: 4 + 3 = 7/10 | 100 | 0 | 0 |
| Male | 60 | Prostate/Prostate | Lesion | Adenocarcinoma of prostate | Gleason Score: 3 + 3 = 6/10 | 0 | 100 | 0 |
| Male | 70 | Prostate/Prostate | Lesion | Carcinoma of bladder | AJCC G3: Poorly differentiated | 0 | 100 | 0 |
| Male | 74 | Prostate/Prostate | Lesion | Adenocarcinoma of prostate | Gleason Score: 3 + 3 = 6/10 | 0 | 100 | 0 |
| Male | 66 | Prostate/Prostate | Lesion | Adenocarcinoma of prostate | Gleason Score: 4 + 3 = 7/10 | 0 | 100 | 0 |
| Male | 72 | Prostate/Prostate | Lesion | Adenocarcinoma of prostate | Gleason Score: 3 + 4 = 7/10 | 0 | 0 | 100 |
| Male | 63 | Prostate/Prostate | Lesion | Adenocarcinoma of prostate | Gleason Score: 3 + 4 = 7/10 | 25 | 75 | 0 |
| Male | 55 | Prostate/Prostate | Lesion | Adenocarcinoma of prostate | Gleason Score: 3 + 4 = 7/10 | 0 | 100 | 0 |
| Male | 70 | Prostate/Prostate | Lesion | Adenocarcinoma of prostate | Gleason Score: 3 + 4 = 7/10 | 0 | 100 | 0 |
| Male | 68 | Prostate/Prostate | Lesion | Adenocarcinoma of prostate | Gleason Score: 3 + 3 = 6/10 | 0 | 100 | 0 |
| Male | 66 | Prostate/Prostate | Lesion | Adenocarcinoma of prostate | Gleason Score: 2 + 2 = 4/10 | 0 | 100 | 0 |
| Male | 76 | Prostate/Prostate | Lesion | Adenocarcinoma of prostate | Not Reported | 0 | 100 | 0 |
| Male | 71 | Prostate/Prostate | Lesion | Adenocarcinoma of prostate | Gleason Score: 3 + 4 = 7/10 | 0 | 100 | 0 |
| Male | 56 | Prostate/Prostate | Lesion | Adenocarcinoma of prostate | Gleason Score: 3 + 4 = 7/10 | 0 | 100 | 0 |
| Male | 61 | Prostate/Prostate | Lesion | Adenocarcinoma of prostate | Gleason Score: 4 + 3 = 7/10 | 0 | 100 | 0 |
| Male | 63 | Prostate/Prostate | Tumor | Adenocarcinoma of prostate | Gleason Score: 3 + 4 = 7/10 | 25 | 15 | 60 |
| Male | 70 | Prostate/Prostate | Tumor | Adenocarcinoma of prostate | Gleason Score: 3 + 3 = 6/10 | 25 | 5 | 70 |
| Male | 68 | Prostate/Prostate | Tumor | Adenocarcinoma of prostate | Gleason Score: 3 + 3 = 6/10 | 30 | 0 | 65 |
| Male | 61 | Prostate/Prostate | Tumor | Adenocarcinoma of prostate | Gleason Score: 3 + 3 = 6/10 | 10 | 0 | 70 |
| Male | 59 | Prostate/Prostate | Tumor | Adenocarcinoma of prostate | Gleason Score: 4 + 5 = 9/10 | 10 | 0 | 80 |
| Male | 61 | Prostate/Prostate | Tumor | Adenocarcinoma of prostate | Gleason Score: 3 + 4 = 7/10 | 5 | 0 | 85 |
| Male | 63 | Prostate/Prostate | Tumor | Adenocarcinoma of prostate | Gleason Score: 3 + 4 = 7/10 | 5 | 0 | 80 |
| Male | 53 | Prostate/Prostate | Lesion | Adenocarcinoma of prostate | Gleason Score: 4 + 3 = 7/10 | 0 | 100 | 0 |
| Male | 66 | Prostate/Prostate | Lesion | Adenocarcinoma of prostate | Gleason Score: 3 + 5 = 8/10 | 0 | 100 | 0 |
| Male | 61 | Prostate/Prostate | Lesion | Adenocarcinoma of prostate | Gleason Score: 4 + 3 = 7/10 | 0 | 100 | 0 |
| Male | 65 | Prostate/Prostate | Lesion | Adenocarcinoma of prostate | Gleason Score: 4 + 4 = 8/10 | 0 | 100 | 0 |
| Male | 64 | Prostate/Prostate | Lesion | Adenocarcinoma of prostate | Gleason Score: 3 + 4 = 7/10 | 0 | 100 | 0 |
| Male | 48 | Prostate/Prostate | Tumor | Adenocarcinoma of prostate | Gleason Score: 4 + 5 = 9/10 | 5 | 0 | 75 |

TABLE 2-continued

| Origene's Human Prostate Cancer Tissue panel I (HPRT501, Origene Inc): | | | | | | | | |
|---|---|---|---|---|---|---|---|---|
| gender | age | tissue | appearance | diagnosis | tumorgrade | normal | lesion | tumor |
| Male | 65 | Prostate/Prostate | Tumor | Adenocarcinoma of prostate | Gleason Score: 4 + 4 = 8/10 | 0 | 0 | 90 |
| Male | 61 | Prostate/Prostate | Tumor | Adenocarcinoma of prostate | Gleason Score: 4 + 4 = 8/10 | 10 | 0 | 80 |
| Male | 51 | Prostate/Prostate | Lesion | Carcinoma of bladder, urothelial | AJCC G4: Undifferentiated | 0 | 100 | 0 |
| Male | 76 | Prostate/Prostate | Lesion | Hyperplasia of prostate, atypical | NULL | 0 | 100 | 0 |
| Male | 62 | Prostate/Prostate | Lesion | Hyperplasia of prostate | NULL | 0 | 100 | 0 |
| Male | 72 | Prostate/Prostate | Lesion | Hyperplasia of prostate | NULL | 0 | 100 | 0 |
| Male | 71 | Prostate/Prostate | Lesion | Hyperplasia of prostate | NULL | 0 | 100 | 0 |
| Male | 76 | Prostate/Prostate | Lesion | Glandular hyperplasia of prostate | NULL | 0 | 100 | 0 |
| Male | 71 | Prostate/Prostate | Lesion | Hyperplasia of prostate | NULL | 0 | 100 | 0 |
| Male | 76 | Prostate/Prostate | Lesion | Hyperplasia of prostate | NULL | 45 | 55 | 0 |
| Male | 76 | Prostate/Prostate | Lesion | Hyperplasia of prostate | NULL | 0 | 100 | 0 |
| Male | 56 | Prostate/Prostate | Lesion | Hyperplasia of prostate | NULL | 0 | 100 | 0 |
| Male | 85 | Prostate/Prostate | Lesion | Adenoma of prostate | NULL | 0 | 100 | 0 |
| Male | 72 | Prostate/Prostate | Lesion | Hyperplasia of prostate | NULL | 0 | 100 | 0 |

TABLE 3

| Origene's Human Prostate Cancer Tissue panel II (HPRT502, Origene Inc) | | | | | | | | |
|---|---|---|---|---|---|---|---|---|
| gender | age | tissue | appearance | sample diagnosis from pathology verification | tumor grade | normal | lesion | tumor |
| Male | 53 | Prostate/Prostate | Normal | Within normal limits | Not Applicable | 100 | 0 | 0 |
| Male | 48 | Prostate/Prostate | Normal | Within normal limits | Not Applicable | 100 | 0 | 0 |
| Male | 68 | Prostate/Prostate | Normal | Within normal limits | Not Applicable | 100 | 0 | 0 |
| Male | 76 | Prostate/Prostate | Normal | Within normal limits | Not Applicable | 100 | 0 | 0 |
| Male | 53 | Prostate/Prostate | Normal | Within normal limits | Not Applicable | 100 | 0 | 0 |
| Male | 68 | Prostate/Prostate | Normal | Within normal limits | Not Applicable | 100 | 0 | 0 |
| Male | 74 | Prostate/Prostate | Normal | Within normal limits | Not Applicable | 100 | 0 | 0 |
| Male | 72 | Prostate/Prostate | Normal | Within normal limits | Not Applicable | 100 | 0 | 0 |
| Male | 62 | Prostate/Prostate | Tumor | Adenocarcinoma of prostate | Gleason Score: 3 + 3 = 6/10 | 50 | 0 | 50 |
| Male | 54 | Prostate/Prostate | Tumor | Adenocarcinoma of prostate | Gleason Score: 3 + 3 = 6/10 | 20 | 0 | 60 |
| Male | 56 | Prostate/Prostate | Tumor | Adenocarcinoma of prostate | Gleason Score: 3 + 4 = 7/10 | 0 | 25 | 75 |
| Male | 56 | Prostate/Prostate | Tumor | Adenocarcinoma of prostate | Gleason Score: 3 + 3 = 6/10 | 10 | 0 | 90 |
| Male | 55 | Prostate/Prostate | Tumor | Adenocarcinoma of prostate | Gleason Score: 3 + 4 = 7/10 | 45 | 0 | 40 |
| Male | 63 | Prostate/Prostate | Tumor | Adenocarcinoma of prostate | Gleason Score: 3 + 4 = 7/10 | 20 | 0 | 80 |
| Male | 53 | Prostate/Prostate | Tumor | Adenocarcinoma of prostate | Gleason Score: 3 + 3 = 6/10 | 40 | 0 | 60 |
| Male | 64 | Prostate/Prostate | Tumor | Adenocarcinoma of prostate | Gleason Score: 3 + 4 = 7/10 | 0 | 0 | 90 |
| Male | 68 | Prostate/Prostate | Tumor | Adenocarcinoma of prostate | Gleason Score: 3 + 4 = 7/10 | 0 | 0 | 95 |
| Male | 63 | Prostate/Prostate | Tumor | Adenocarcinoma of prostate | Gleason Score: 3 + 3 = 6/10 | 60 | 0 | 40 |
| Male | 66 | Prostate/Prostate | Tumor | Adenocarcinoma of prostate | Gleason Score: 3 + 4 = 7/10 | 0 | 5 | 60 |
| Male | 70 | Prostate/Prostate | Tumor | Adenocarcinoma of prostate | Gleason Score: 3 + 4 = 7/10 | 25 | 0 | 65 |
| Male | 65 | Prostate/Prostate | Tumor | Adenocarcinoma of prostate | Gleason Score: 3 + 4 = 7/10 | 0 | 30 | 70 |
| Male | 64 | Prostate/Prostate | Tumor | Adenocarcinoma of prostate | Gleason Score: 3 + 3 = 6/10 | 0 | 0 | 90 |
| Male | 54 | Prostate/Prostate | Tumor | Adenocarcinoma of prostate | Gleason Score: 4 + 3 = 7/10 | 30 | 0 | 40 |
| Male | 64 | Prostate/Prostate | Tumor | Adenocarcinoma of prostate | Gleason Score: 3 + 4 = 7/10 | 0 | 0 | 80 |
| Male | 62 | Prostate/Prostate | Tumor | Adenocarcinoma of prostate | Gleason Score: 4 + 3 = 7/10 | 0 | 0 | 95 |
| Male | 62 | Prostate/Prostate | Tumor | Adenocarcinoma of prostate | Gleason Score: 4 + 3 = 7/10 | 0 | 0 | 90 |
| Male | 61 | Prostate/Prostate | Tumor | Adenocarcinoma of prostate | Gleason Score: 3 + 4 = 7/10 | 0 | 0 | 90 |
| Male | 62 | Prostate/Prostate | Tumor | Adenocarcinoma of prostate | Gleason Score: 3 + 5 = 8/10 | 0 | 0 | 80 |
| Male | 53 | Prostate/Prostate | Tumor | Adenocarcinoma of prostate | Gleason Score: 3 + 4 = 7/10 | 0 | 0 | 90 |
| Male | 58 | Prostate/Prostate | Tumor | Adenocarcinoma of prostate | Gleason Score: 4 + 3 = 7/10 | 0 | 0 | 90 |
| Male | 57 | Prostate/Prostate | Tumor | Adenocarcinoma of prostate | Gleason Score: 4 + 5 = 9/10 | 0 | 60 | 40 |
| Male | 65 | Prostate/Prostate | Tumor | Adenocarcinoma of prostate | Gleason Score: 3 + 3 = 6/10 | 0 | 55 | 45 |
| Male | 53 | Prostate/Prostate | Tumor | Adenocarcinoma of prostate | Gleason Score: 3 + 3 = 6/10 | 0 | 0 | 95 |
| Male | 61 | Prostate/Prostate | Tumor | Adenocarcinoma of prostate | Gleason Score: 3 + 4 = 7/10 | 0 | 0 | 90 |
| Male | 73 | Prostate/Prostate | Tumor | Adenocarcinoma of prostate | Gleason Score: 3 + 4 = 7/10 | 0 | 0 | 90 |
| Male | 52 | Prostate/Prostate | Tumor | Adenocarcinoma of prostate | Gleason Score: 4 + 4 = 8/10 | 0 | 0 | 85 |
| Male | 64 | Prostate/Prostate | Tumor | Adenocarcinoma of prostate | Gleason Score: 4 + 3 = 7/10 | 0 | 0 | 90 |
| Male | 54 | Prostate/Prostate | Tumor | Adenocarcinoma of prostate | Gleason Score: 5 + 4 = 9/10 | 0 | 0 | 90 |
| Male | 61 | Prostate/Prostate | Tumor | Adenocarcinoma of prostate | Gleason Score: 3 + 2 = 5/10 | 20 | 0 | 80 |
| Male | 61 | Prostate/Prostate | Lesion | Hyperplasia of prostate | Gleason Score: 4 + 3 = 7/10 | 0 | 100 | 0 |
| Male | 54 | Prostate/Prostate | Tumor | Adenocarcinoma of prostate | Gleason Score: 4 + 3 = 7/10 | 0 | 0 | 80 |
| Male | 62 | Prostate/Lymph node | Tumor | Adenocarcinoma of prostate, metastatic | Not Reported | 0 | 0 | 95 |
| Male | 64 | Prostate/Prostate | Tumor | Adenocarcinoma of prostate | Gleason Score: 4 + 3 = 7/10 | 0 | 0 | 90 |
| Male | 87 | Prostate/Prostate | Tumor | Adenocarcinoma of prostate | Gleason Score: 5 + 4 = 9/10 | 0 | 0 | 80 |
| Male | 76 | Prostate/Prostate | Tumor | Adenocarcinoma of prostate | Gleason Score: 3 + 4 = 7/10 | 0 | 0 | 90 |
| Male | 71 | Prostate/Prostate | Tumor | Adenocarcinoma of prostate | Gleason Score: 2 + 3 = 5/10 | 0 | 0 | 80 |
| Male | 77 | Prostate/Prostate | Tumor | Adenocarcinoma of prostate | Gleason Score: 4 + 4 = 8/10 | 10 | 0 | 90 |
| Male | 83 | Prostate/Prostate | Tumor | Adenocarcinoma of prostate | Gleason Score: 5 + 4 = 9/10 | 40 | 0 | 60 |

The Origene's Human Prostate Cancer Tissue panels I and II used for the experiments described in the following comprises samples which are all derived from male patients (ages 48-87). The column "tissue" defines the tissue that has been taken during surgery. The column "appearance" indicates the pathological status of the tissue section that was used to isolate RNA, and that was finally used for qPCR measurements. "Normal" in that context means normal, adjacent tissue (NAT), which is a tissue taken from surgical material (commonly, by Radical Prostatectomy or TURP (Trans Urethral Resection of the Prostate)) but which appears with normal/healthy morphology and histology and is therefore used as a control. The definition of "Lesion" is as follows: Non-neoplastic tissue that is not normal, in that there is some type of pathological diagnostic abnormality (but no tumor). This includes histopathologies such as inflammation or benign hyperplasia (examples: Colitis, Crohn's disease, Endometriosis, Emphysema, Bronchitis). "Tumor" is defined as neoplastic tissue that could either be benign or malignant based on pathology diagnosis (e.g. Adenoma, Adenocarcinoma, Sarcoma). The column "diagnosis" describes the scheduled reason for surgery (e.g., bladder cancer for patient 9, but prostate cancer tissue was taken as well). Column "tumor grade" describes the Gleason Score if applicable (i.e., in case of tumor tissue). Columns "normal', "lesion", and "tumor" define the percentage of corresponding tissue found in histology within the tissue section used for RNA isolation. Origene's Human Prostate Cancer Tissue panel I includes 7 normal samples (normal adjacent tissue, NAT), 11 hyperplasia samples (BPH—Benign prostate hyperplasia), 20 lesion samples, and 10 prostate tumor samples. Of the tumor samples, 7 are from tumors that had a Gleason score of 7 or higher. Origene's Human Prostate Cancer Tissue panel II includes 8 normal samples (normal adjacent tissue), 1 hyperplasia sample (BPH—Benign prostate hyperplasia), and 39 prostate tumor samples. Of the tumor samples, 10 originate from donors ranked with Gleason score of up to 6, and 29 are from tumors that had a Gleason score of 7 or higher.

```
Primer sequences used for human
PDE4D5:
sense primer sequence:
                                    (SEQ ID NO: 48)
GCAGCATGAGAAGTCCAAGA,

antisense primer sequence:
                                    (SEQ ID NO: 49)
TGTATGTGCCACCGTGAAAC

probe sequence:
                                    (SEQ ID NO: 50)
TCGGTTTCTCCCAAGCTCTCTCCAGTGAT AAACCGA
(FAM-labeled).

Primer and probe sequences used for human
PDE9A:
sense primer sequence:
                                    (SEQ ID NO: 45)
GCAGAGCGACCGTGAGAAG

antisense primer sequence:
                                    (SEQ ID NO: 46)
AGGACAAACTTGATGAACCCAATC

probe sequence:
                                    (SEQ ID NO: 47)
CCTGTGGCACCGTTCATGGACCGAGACTCACAGG
(FAM-labeled).
```

The PDE9A specific primers were premixed with the FAM probes to perform quantitative, real-time PCR (qPCR), and used in a 1:20 dilution according to manufacturer's description (PrimerDesign, UK). The human cDNA samples (see Tables 2 and 3, supra, for details on the sample descriptions) were arranged in standard, qPCR-ready, 96-well microtiter (MT) plates. 48 tissue samples, derived from 48 different patients are arranged per 96-well MT plate, with each of the 48 wells used per plate containing ca 2-3 ng of RNA reverse transcribed cDNA.

The cDNA content of each well was normalized based on qPCR on a 'house-keeping' gene like beta-actin, GAPDH, beta-2-microglubolin, such that further normalization of cDNA content was not required.

To each of the used well of the MT plate 15 μL Applied Biosystems' GeneAmp mastermix (2×), 13.5 μL RNAse/DNAse free water and 2 μL PrimerDesign PerfectProbe primermix (PrimerDesign, UK) were added. All samples were analyzed with the following PCR protocol: 2 min at 50° C., 10 min at 95° C., 15 sec at 95° C., 30 sec at 50° C. while recording fluorescence, 15 sec at 72° C. and the last three steps repeated 50 times. For all calculations relative gene expression values, the following procedure was used: $C_T$ values of 40 or higher or below 16 were excluded for poor quality reasons. (The genes examined here had an average $C_T$-value of ~32). To normalize the $C_T$ values across different qPCR plates, the median $C_T$ value of the "normal" tissue samples was calculated, and the relative expression values for the "lesion", "hyperplasia" as well as "tumor" samples relative to this value were determined by calculating the ratio between $C_T$ values of "lesion", "hyperplasia" as well as "tumor" samples and the $C_T$ value of "normal" tissue samples. Typically this resulted in relative expression values of ~1. In case the gene expression was analyzed multiple times (using multiple plates of the same panel), the relative expression values of each individual sample were averaged.

Relative Expression of Human PDE9A in Human Prostate Tissue

The gene expression level of the human PDE-9a isoform was determined on human prostate tissues as described above. The relative expression levels were determined in four defined prostate tissues ("Normal", "Lesion", "Hyperplasia", "Tumor"). The depicted expression levels for the groups "Lesion", "Hyperplasia", and "Tumor" were calculated as outlined above as a normalized value by forming the ratio of $C_T$ values for each individual patient tissue of groups "Lesion", "Hyperplasia", "Tumor" against the median $C_T$ value of the group "Normal". The same was done for each individual patient tissue of the group "Normal" such that the median expression value for this group is 1.

A Student's t-test was performed to see whether human PDE9A gene expression is on average significantly elevated in different tumor tissues compared against normal prostate tissue. The p-values derived from the pair-wise comparison were: T-test of Normal vs. Tumor: p=0.02.

Figure 10:
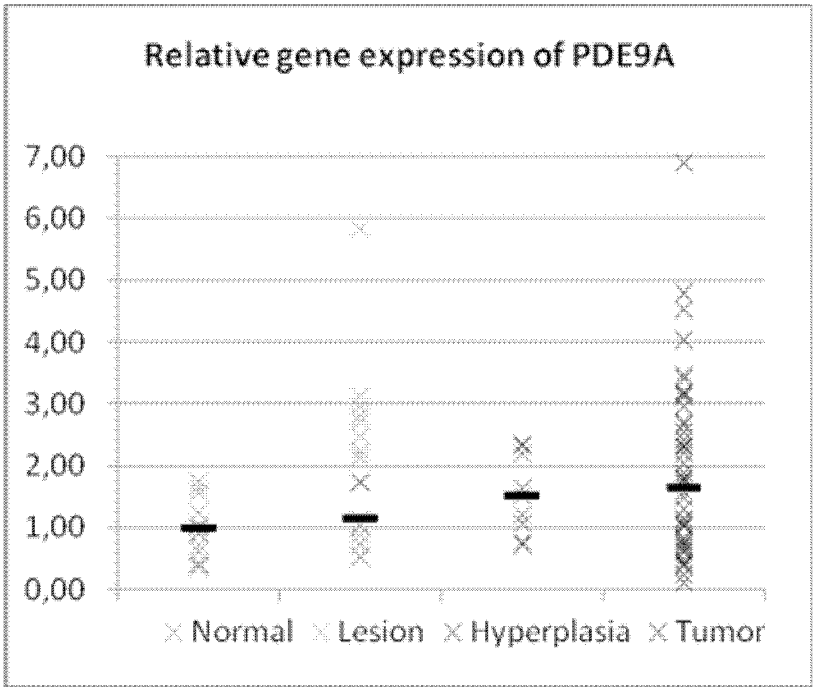
FIG. 10 shows the relative gene expression of PDE9A in 96 different samples derived from Origene HPRT panels I and II. Indicated are the individual relative expression values for human PDE9A on human prostate tissues and the median of the data relative data measurements is indicated for each patient group.
Figure 11:
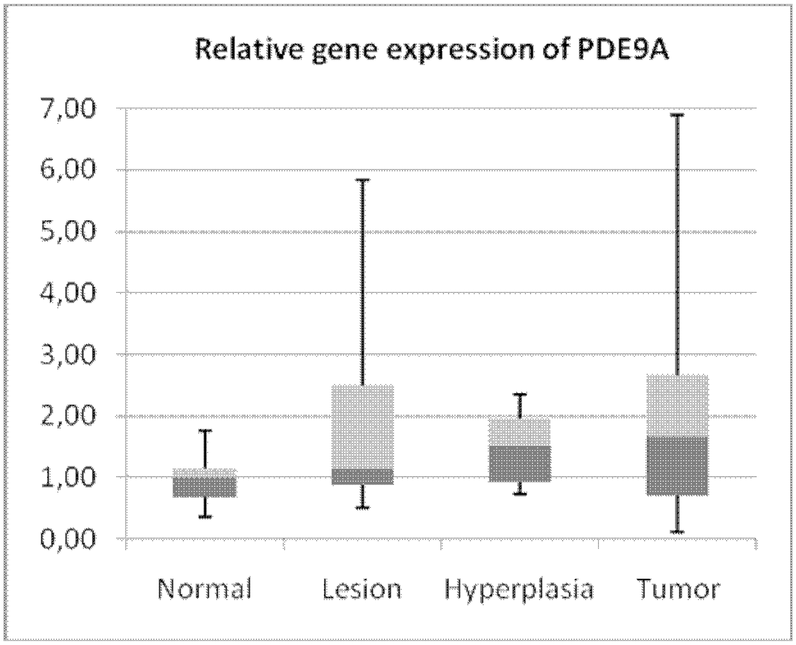
FIG. 11 shows the relative gene expression of PDE9A in 96 different samples derived from Origene HPRT panels I and II. The figure shows a box plot of the individual data relative expression measurements for human PDE9A, whereby the box includes 75% of all measurements. The median relative expression value is indicated as the border between the two grey-colored boxes.

As can be derived from FIGS. 10 and 11, a different expression for human PDE9A could be detected for different tumor tissues compared against normal prostate tissue.

Receiver-Operator-Curve (ROC) Analysis of PDE9A Expression

Figure 12:
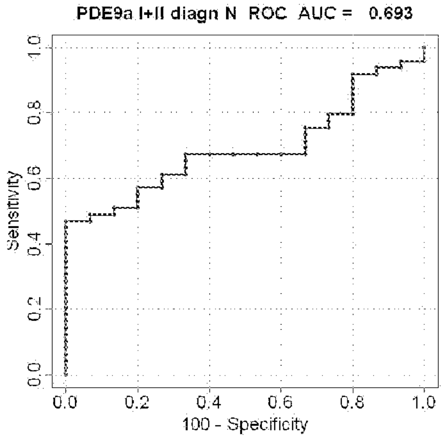
FIG. 12 shows the ROC curve representations of PDE9A gene expression on human prostate tissue samples indicating AUC for the pair-wise comparisons Normal (N) versus Tumor.

Subsequently, a Receiver-Operator-Curve (ROC) analysis was performed to determine the AUC (Area Under Curve) for different pair-wise comparisons. The Receiver Operating Characteristic curves of PDE9A gene expression to assess diagnostic power are shown in FIG. 12. The ROC analysis provided evidence that a discrimination between normal and malignant prostate tissue is possible based on the measurement of the expression of human PDE9A.

The Prostate PDE-Index (PPI)—Relative Expression of Human PDE9A in Human Prostate Tissue Normalized Against Human PDE4D5 to Effectively Discriminate Between Benign and Malignant Prostate Diseases The gene expression level of the human PDE9A and human PDE4D5 iso forms were determined on human prostate tissues as described above. The relative expression levels were determined in four defined prostate tissues ("Normal", "Lesion", "Hyperplasia", "Tumor"). The relative expression level of PDE9A was calculated by subtracting the individual $C_T$ values PDE9A from the individual $C_T$ values for PDE4D5. Typically, this leads to a distribution of the "Normal" expression values around 0 (between −1 and +1). Further, the optimal cutoff value between non-tumor ("Normal", "Lesion", "Hyperplasia") and tumor ("Tumor") samples is such between −1 and +1.

This approach advantageously allows the comparison of PDE9A $C_T$ values against an internal control, namely PDE4D5. It is therefore not necessary to normalize samples of relevant clinical patient groups against a number of normal samples that may not always be available in a real testing setting. This test can be run as a simple assay with human PDE4D5 as an internal reference control to form the Prostate PDE-Index which is defined as delta $(C_{T\,[human\ PDE4D5]}-C_{T\,[human\ PDE9A]})$.

A Student's t-test was performed to see whether human delta $(C_{T\,[human\ PDE4D5]}-C_{T\,[human\ PDE9A]})$ gene expression is on average significantly elevated in different tumor tissues compared against normal prostate tissue. The p-values derived from the pair-wise comparison were: T-test of Normal vs. Tumor: p=0.024.

Figure 13:
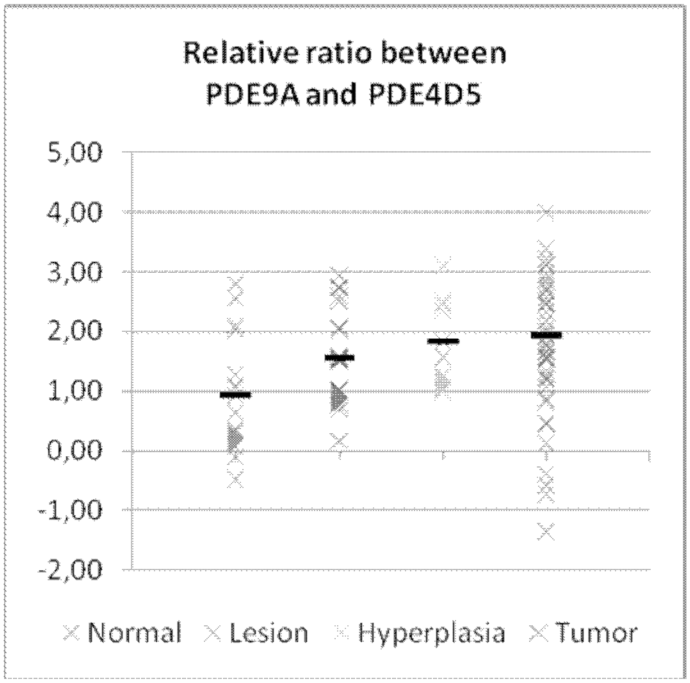
FIG. 13 shows the Prostate PDE-Index (PPI), i.e. the relative gene expression of delta ($C_{T\ [human\ PDE4D5]}-C_{T\ [human\ PDE9A]}$). $C_T$ values of human PDE9a were subtracted from $C_T$ values of human PDE4D5 for each individual tissue sample tested. Information was derived from 96 different samples in total, measured on Origene HPRT panels I and II (see Examples). The FIG. shows individual relative expression values for human delta ($C_{T\ [human\ PDE4D5]}-C_{T\ [human\ PDE9A]}$) on human prostate tissues. The median of the data relative data measurements is indicated for each patient group.
Figure 14:
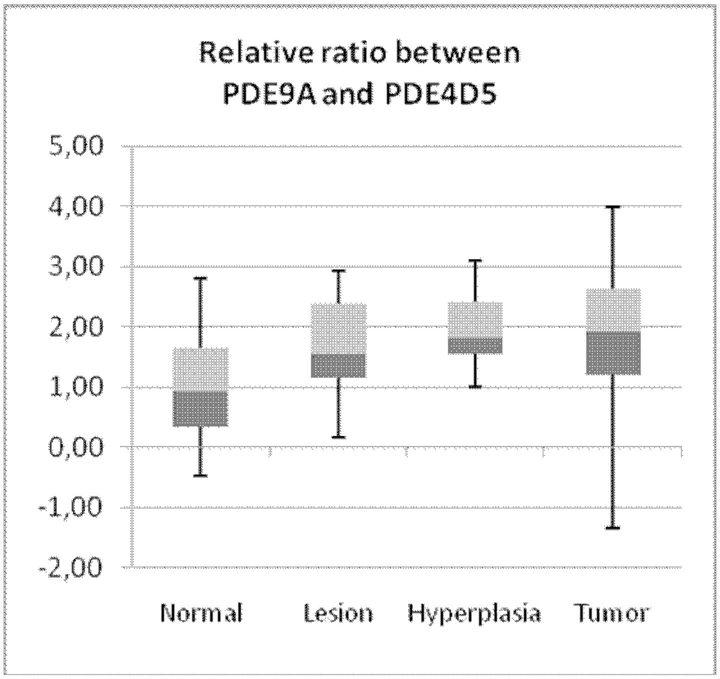
FIG. 14 shows the Prostate PDE-Index (PPI), i.e. the relative gene expression of delta ($C_{T\ [human\ PDE4D5]}-C_{T\ [human\ PDE9A]}$). $C_T$ values of human PDE9a were subtracted from $C_T$ values of human PDE4D5 for each individual tissue sample tested. Information was derived from 96 different samples in total, measured on Origene HPRT panels I and II (see Examples). The FIG. shows a box plot of the individual data relative expression measurements for human delta ($C_{T\ [human\ PDE4D5]}-C_{T\ [human\ PDE9A]}$), whereby the box includes 75% of all measurements. The median relative expression value is indicated as the border between the two grey-colored boxes.

As can be derived from FIGS. 13 and 14, a significant different expression for human PDE9A could be detected for different tumor tissues compared against normal prostate tissue.

Receiver-Operator-Curve (ROC) Analysis of PDE9A Expression

Figure 15:
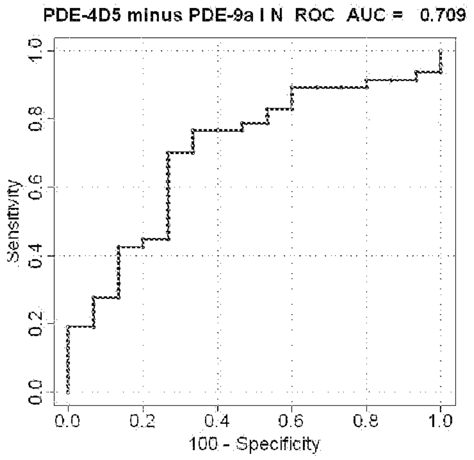
FIG. 15 depicts a Receiver Operating Characteristic (ROC) curve of delta ($C_{T\ [human\ PDE4D5]}-C_{T\ [human\ PDE9A]}$) gene expression to assess diagnostic power. Shown is the ROC curve representation of the PDE9A gene expression on human prostate tissue samples indicating AUC for the pair-wise comparisons Normal (N) versus Tumor.

Subsequently, a Receiver-Operator-Curve (ROC) analysis was performed to determine the AUC (Area Under Curve) for different pair-wise comparisons. The Receiver Operating Characteristic curves of PDE9A gene expression to assess diagnostic power are shown in FIG. 15. The ROC analysis provided evidence that a discrimination between normal and malignant prostate tissue is possible based on the measurement of the expression of human PDE9A.

The present application comprises the following additional embodiments:

Item 1: Phosphodiesterase 9A (PDE9A) for use as a marker for cancer.

Item 2: A composition for diagnosing, detecting, monitoring or prognosticating cancer or the progression of cancer, comprising a nucleic acid affinity ligand and/or a peptide affinity ligand for the PDE9A expression product or protein.

Item 3: The composition of item 2, wherein said nucleic acid affinity ligand or peptide affinity ligand is modified to function as a contrast agent.

Item 4: The composition of item 2, wherein said affinity ligand is a set of oligonucleotides specific for the PDE9A expression product, a probe specific for the PDE9A expression product, an aptamer specific for the PDE9A expression product or for the PDE9A protein, an antibody specific for the PDE9A protein and/or an antibody variant specific for the PDE9A protein.

Item 5: Use of PDE9A as a marker for diagnosing, detecting, monitoring or prognosticating cancer or the progression of cancer.

Item 6: A method for detecting, diagnosing, monitoring or prognosticating cancer or the progression of cancer comprising at least the step of determining the level of PDE9A in a sample.

Item 7: The method of item 6, wherein the determining step is accomplished by the measurement of nucleic acid or protein levels or by the determination of the biological activity of PDE9A.

Item 8: The method of item 7, wherein said method comprises the additional step of comparing the measured nucleic acid or protein levels or the measured biological activity to a control level.

Item 9: A method of data acquisition comprising at least the steps of:

(a) testing in an individual for expression of PDE9A; and (b) comparing the expression as determined in step (a) to a control level.

Item 10: The use of item 2 or the method of any one of items 6 to 9, wherein the diagnosing, detecting, monitoring, prognosticating or data acquisition is to be carried out on a sample obtained from an individual.

Item 11: An immunoassay for detecting, diagnosing, monitoring or prognosticating cancer or the progression of cancer comprising at least the steps (a) testing in a sample obtained from an individual for the expression of PDE9A, (b) testing in a control sample for the expression of PDE9A, (c) determining the difference in expression of PDE9A of steps (a) and (b); and (d) deciding on the presence or stage of cancer or the progression of cancer based on the results obtained in step (c), wherein said testing steps are based on the use of an antibody specifically binding to PDE9A.

Item 12: The use or method of item 10 or the immunoassay of item 11, wherein said sample is a tissue sample, a urine sample, a urine sediment sample, a blood sample, a saliva sample, a semen sample, or a sample comprising circulating tumor cells.

Item 13: A pharmaceutical composition comprising at least one element selected from the group of:

(a) a compound directly stimulating or modulating the activity of PDE9A, preferably an allosteric agonist of PDE9A enzymatic activity;

(b) a compound indirectly stimulating or modulating the activity of PDE9A;

(c) the PDE9A protein or a biologically active equivalent thereof;

(d) a nucleic acid encoding and expressing PDE9A;

(e) a miRNA inhibitor specific for PDE9A miRNAs;

(f) a demethylation agent; and (g) a phosphodiesterase displacement factor, preferably a peptide, a peptidomimetic, a small molecule, an antibody or an aptamer.

Item 14: A pharmaceutical composition for the treatment or prevention of cancer comprising at least one element selected from the group of:

(a) a compound directly stimulating or modulating the activity of PDE9A, preferably an allosteric agonist of PDE9A enzymatic activity;

(b) a compound indirectly stimulating or modulating the activity of PDE9A;

(c) the PDE9A protein or a biologically active equivalent thereof;

(d) a nucleic acid encoding and expressing PDE9A;

(e) a miRNA inhibitor specific for PDE9A miRNAs;

(f) a demethylation agent; and (g) a phosphodiesterase displacement factor preferably a peptide, a peptidomimetic, a small molecule, an antibody or an aptamer.

Item 15: Use of (a) a compound directly stimulating or modulating the activity of PDE9A, preferably an allosteric agonist of PDE9A enzymatic activity;

(b) a compound indirectly stimulating or modulating the activity of PDE9A;

(c) the PDE9A protein or a biologically active equivalent thereof;

(d) a nucleic acid encoding and expressing PDE9A;

(e) a miRNA inhibitor specific for PDE9A miRNAs;

(f) a demethylation agent; and/or (g) a phosphodiesterase displacement factor, preferably a peptide, a peptidomimetic, a small molecule, an antibody or an aptamer, for the preparation of a pharmaceutical composition for the treatment or prevention of cancer.

Item 16: The phosphodiesterase of item 1, the composition of any one of items 2 to 4, the use of item 5, 10 or 12, the method of any one of item 6 to 10 or 12, the immunoassay of item 11 or 12, the pharmaceutical composition of item 13 or 14, or the use of item 15, wherein said cancer is prostate cancer.

Item 17: The phosphodiesterase, use, composition, method, immunoassay, or pharmaceutical composition of item 16, wherein said prostate cancer is hormone-resistant prostate cancer.

The invention claimed is:

1. A method for monitoring an expression level of PDE9A in a patient, comprising the steps of (a) determining a measured expression level of PDE9A in a sample obtained from the patient by using SEQ ID NOs:43 and 47 specific for the cDNA of the PDE9A transcript;

(b) determining the level of expression of two or more reference genes in the sample, at least one being PDE4D5 detected with SEQ ID NO:50;

(c) normalizing the measured expression level of PDE9A to the expression levels of the reference genes; and (d) comparing the normalized expression level of PDE9A with a predetermined cutoff value, wherein said cutoff value is between 2 and 15 ng/ml, wherein the sample is selected from the group consisting of a prostate tissue sample, a urine sample, a urine sediment sample, a blood sample, a saliva sample, a semen sample, a sample comprising circulating tumor cells, and a sample containing prostate secreted exosomes.

2. The method of claim 1, wherein said reference genes are selected from β-actin, glycerinaldehyde 3-phosphate dehydrogenase (GAPDH), porphobilinogen deanimase (PBGD), ribosomal protein P1, PDE4D1, PDE4D2, PDE4D3, PDE4D4, PDE4D5, PDE4D6, PDE4D8, and PDE4D9.

3. The method of claim 2 wherein an individual classified or tested with an increased level of PDE9A expression and an increased level of PSA of more than about >2.5 ng/ml up to about 10 ng/ml is identified as suffering from a malignant, hormone sensitive prostate cancer; and wherein an individual classified or tested with a decreased level of PDE9A expression and an increased level of PSA of more than about >10 ng/ml is identified as suffering from hormone resistant prostate cancer.

4. The method of claim 1, wherein the method comprises the additional step of determining the level of prostate specific antigen (PSA).

* * * * *

SEQUENCE LISTING

```
<160> NUMBER OF SEQ ID NOS: 50

<210> SEQ ID NO 1
<211> LENGTH: 2103
<212> TYPE: DNA
<213> ORGANISM: Homo sapiens
<300> PUBLICATION INFORMATION:
<308> DATABASE ACCESSION NUMBER: Genbank / NM_002606.2
<309> DATABASE ENTRY DATE: 2008-10-24
<313> RELEVANT RESIDUES IN SEQ ID NO: (1)..(2103)

<400> SEQUENCE: 1

tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga aggtaatctt cagcaagtac tgcaactcca gcgacatcat ggacctgttc    180

tgcatcgcca ccggcctgcc tcggaacacg accatctccc tgctgaccac cgacgacgcc    240

atggtctcca tcgaccccac catgcccgcg aattcagaac gcactccgta caaagtgaga    300

cctgtggcca tcaagcaact ctccgctggt gtcgaggaca agagaaccac aagccgtggc    360

cagtctgctg agagaccact gagggacaga cgggttgtgg gcctggagca gccccggagg    420

gaaggagcat ttgaaagtgg acaggtagag cccaggccca gagagcccca gggctgctac    480

caggaaggcc agcgcatccc tccagagaga gaagaattaa tccagagcgt gctggcgcag    540

gttgcagagc agttctcaag agcattcaaa atcaatgaac tgaaagctga agttgcaaat    600

cacttggctg tcctagagaa acgcgtggaa ttggaaggac taaaagtggt ggagattgag    660

aaatgcaaga gtgacattaa gaagatgagg gaggagctgg cggccagaag cagcaggacc    720

aactgcccct gtaagtacag ttttttggat aaccacaaga agttgactcc tcgacgcgat    780

gttcccactt accccaagta cctgctctct ccagagacca tcgaggccct gcggaagccg    840

acctttgacg tctggctttg ggagcccaat gagatgctga gctgcctgga gcacatgtac    900

cacgacctcg ggctggtcag ggacttcagc atcaaccctg tcaccctcag gaggtggctg    960

ttctgcgtcc acgacaacta cagaaacaac cccttccaca acttccggca ctgcttctgc   1020

gtggcccaga tgatgtacag catggtctgg ctctgcagtc tccaggagaa gttctcacaa   1080

acggatatcc tgatcctaat gacagcggcc atctgccacg atctggacca tcccggctac   1140

aacaacacgt accagatcaa tgcccgcaca gagctggcgg tccgctacaa tgacatctca   1200

ccgctggaga accaccactg cgccgtggcc ttccagatcc tcgccgagcc tgagtgcaac   1260

atcttctcca acatcccacc tgatgggttc aagcagatcc gacagggaat gatcacatta   1320

atcttggcca ctgacatggc aagacatgca gaaattatgg attctttcaa agagaaaatg   1380
```

gagaattttg actacagcaa cgaggagcac atgaccctgc tgaagatgat tttgataaaa 1440
tgctgtgata tctctaacga ggtccgtcca atggaagtcg cagagccttg ggtggactgt 1500
ttattagagg aatattttat gcagagcgac cgtgagaagt cagaaggcct tcctgtggca 1560
ccgttcatgg accgagacaa agtgaccaag gccacagccc agattgggtt catcaagttt 1620
gtcctgatcc caatgtttga aacagtgacc aagctcttcc ccatggttga ggagatcatg 1680
ctgcagccac tttgggaatc ccgagatcgc tacgaggagc tgaagcggat agatgacgcc 1740
atgaaagagt tacagaagaa gactgacagc ttgacgtctg gggccaccga gaagtccaga 1800
gagagaagca gagatgtgaa aaacagtgaa ggagactgtg cctgaggaaa gcggggggcg 1860
tggctgcagt tctggacggg ctggccgagc tgcgcgggat ccttgtgcag ggaagagctg 1920
ccctgggcac ctggcaccac aagaccatgt tttctaagaa ccattttgtt cactgataca 1980
aaaaaaaaaa aaggaattca tgatgctgta cagaatttta tttttaaact gtcttttaaa 2040
taatatattc ttatacggaa aaaaaaaaaa aaaaaaaaaa aaaaaaaaaa aaaaaaaaaa 2100
aaa 2103

<210> SEQ ID NO 2
<211> LENGTH: 1923
<212> TYPE: DNA
<213> ORGANISM: Homo sapiens
<300> PUBLICATION INFORMATION:
<308> DATABASE ACCESSION NUMBER: Genbank / NM_001001567.1
<309> DATABASE ENTRY DATE: 2008-10-24
<313> RELEVANT RESIDUES IN SEQ ID NO: (1)..(1923)

<400> SEQUENCE: 2
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga aggtaatctt cagcaagtac tgcaactcca gcgacatcat ggacctgttc 180
tgcatcgcca ccggcctgcc tcggaacacg accatctccc tgctgaccac cgacgacgcc 240
atggtctcca tcgaccccac catgcccgcg aattcagaac gcactccgta caaagtgaga 300
cctgtggcca tcaagcaact ctccgagaga gaagaattaa tccagagcgt gctggcgcag 360
gttgcagagc agttctcaag agcattcaaa atcaatgaac tgaaagctga agttgcaaat 420
cacttggctg tcctagagaa acgcgtggaa ttggaaggac taaaagtggt ggagattgag 480
aaatgcaaga gtgacattaa gaagatgagg gaggagctgg cggccagaag cagcaggacc 540
aactgcccct gtaagtacag ttttttggat aaccacaaga agttgactcc tcgacgcgat 600
gttcccactt accccaagta cctgctctct ccagagacca tcgaggccct gcggaagccg 660
acctttgacg tctggctttg ggagcccaat gagatgctga gctgcctgga gcacatgtac 720
cacgacctcg ggctggtcag ggacttcagc atcaaccctg tcaccctcag gaggtggctg 780
ttctgcgtcc acgacaacta cagaaacaac cccttccaca acttccggca ctgcttctgc 840
gtggcccaga tgatgtacag catggtctgg ctctgcagtc tccaggagaa gttctcacaa 900
acggatatcc tgatcctaat gacagcggcc atctgccacg atctggacca tcccggctac 960
aacaacacgt accagatcaa tgcccgcaca gagctggcgg tccgctacaa tgacatctca 1020
ccgctggaga accaccactg cgccgtggcc ttccagatcc tcgccgagcc tgagtgcaac 1080
atcttctcca acatcccacc tgatgggttc aagcagatcc gacagggaat gatcacatta 1140
atcttggcca ctgacatggc aagacatgca gaaattatgg attctttcaa agagaaaatg 1200

```
gagaatttttg actacagcaa cgaggagcac atgaccctgc tgaagatgat tttgataaaa   1260

tgctgtgata tctctaacga ggtccgtcca atggaagtcg cagagccttg ggtggactgt   1320

ttattagagg aatattttat gcagagcgac cgtgagaagt cagaaggcct tcctgtggca   1380

ccgttcatgg accgagacaa agtgaccaag gccacagccc agattgggtt catcaagttt   1440

gtcctgatcc caatgtttga aacagtgacc aagctcttcc ccatggttga ggagatcatg   1500

ctgcagccac tttgggaatc ccgagatcgc tacgaggagc tgaagcggat agatgacgcc   1560

atgaaagagt tacagaagaa gactgacagc ttgacgtctg gggccaccga gaagtccaga   1620

gagagaagca gagatgtgaa aaacagtgaa ggagactgtg cctgaggaaa gcggggggcg   1680

tggctgcagt tctggacggg ctggccgagc tgcgcgggat ccttgtgcag ggaagagctg   1740

ccctgggcac ctggcaccac aagaccatgt tttctaagaa ccattttgtt cactgataca   1800

aaaaaaaaaa aaggaattca tgatgctgta cagaatttta tttttaaact gtcttttaaa   1860

taatatattc ttatacggaa aaaaaaaaaa aaaaaaaaaa aaaaaaaaaa aaaaaaaaaa   1920

aaa                                                                  1923


<210> SEQ ID NO 3
<211> LENGTH: 1774
<212> TYPE: DNA
<213> ORGANISM: Homo sapiens
<300> PUBLICATION INFORMATION:
<308> DATABASE ACCESSION NUMBER: Genbank / NM_001001568.1
<309> DATABASE ENTRY DATE: 2008-10-24
<313> RELEVANT RESIDUES IN SEQ ID NO: (1)..(1774)

<400> SEQUENCE: 3

tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga agcactccgt acaaagtgag acctgtggcc atcaagcaac tctccgagag    180

agaagaatta atccagagcg tgctggcgca ggttgcagag cagttctcaa gagcattcaa    240

aatcaatgaa ctgaaagctg aagttgcaaa tcacttggct gtcctagaga aacgcgtgga    300

attggaagga ctaaaagtgg tggagattga gaaatgcaag agtgacatta agaagatgag    360

ggaggagctg gcggccagaa gcagcaggac caactgcccc tgtaagtaca gtttttttgga    420

taaccacaag aagttgactc ctcgacgcga tgttcccact taccccaagt acctgctctc    480

tccagagacc atcgaggccc tgcggaagcc gacctttgac gtctggcttt gggagcccaa    540

tgagatgctg agctgcctgg agcacatgta ccacgacctc gggctggtca gggacttcag    600

catcaaccct gtcaccctca ggaggtggct gttctgcgtc cacgacaact acagaaacaa    660

ccccttccac aacttccggc actgcttctg cgtggcccag atgatgtaca gcatggtctg    720

gctctgcagt ctccaggaga agttctcaca aacggatatc ctgatcctaa tgacagcggc    780

catctgccac gatctggacc atcccggcta caacaacacg taccagatca atgcccgcac    840

agagctggcg gtccgctaca atgacatctc accgctggag aaccaccact gcgccgtggc    900

cttccagatc ctcgccgagc ctgagtgcaa catcttctcc aacatcccac ctgatgggtt    960

caagcagatc cgacagggaa tgatcacatt aatcttggcc actgacatgg caagacatgc   1020

agaaattatg gattctttca aagagaaaat ggagaatttt gactacagca acgaggagca   1080

catgaccctg ctgaagatga ttttgataaa atgctgtgat atctctaacg aggtccgtcc   1140

aatggaagtc gcagagcctt gggtggactg tttattagag gaatatttta tgcagagcga   1200

ccgtgagaag tcagaaggcc ttcctgtggc accgttcatg gaccgagaca aagtgaccaa   1260
```

```
ggccacagcc cagattgggt tcatcaagtt tgtcctgatc ccaatgtttg aaacagtgac   1320

caagctcttc cccatggttg aggagatcat gctgcagcca ctttgggaat cccgagatcg   1380

ctacgaggag ctgaagcgga tagatgacgc catgaaagag ttacagaaga agactgacag   1440

cttgacgtct ggggccaccg agaagtccag agagagaagc agagatgtga aaaacagtga   1500

aggagactgt gcctgaggaa agcgggggc gtggctgcag ttctggacgg gctggccgag   1560

ctgcgcggga tccttgtgca gggaagagct gccctgggca cctggcacca caagaccatg   1620

ttttctaaga accattttgt tcactgatac aaaaaaaaaa aaaggaattc atgatgctgt   1680

acagaatttt atttttaaac tgtcttttaa ataatatatt cttatacgga aaaaaaaaaa   1740

aaaaaaaaaa aaaaaaaaaa aaaaaaaaaa aaaa                               1774
```

<210> SEQ ID NO 4
<211> LENGTH: 1719
<212> TYPE: DNA
<213> ORGANISM: Homo sapiens
<300> PUBLICATION INFORMATION:
<308> DATABASE ACCESSION NUMBER: Genbank / NM_001001569.1
<309> DATABASE ENTRY DATE: 2008-10-24
<313> RELEVANT RESIDUES IN SEQ ID NO: (1)..(1719)

<400> SEQUENCE: 4

```
tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga agcactccgt acaaagtgag acctgtggcc atcaagcaac tctccgagca    180

ttcaaaatca atgaactgaa agctgaagtt gcaaatcact tggctgtcct agagaaacgc    240

gtggaattgg aaggactaaa agtggtggag attgagaaat gcaagagtga cattaagaag    300

atgagggagg agctggcggc cagaagcagc aggaccaact gcccctgtaa gtacagtttt    360

ttggataacc acaagaagtt gactcctcga cgcgatgttc ccacttaccc caagtacctg    420

ctctctccag agaccatcga ggccctgcgg aagccgacct ttgacgtctg gctttgggag    480

cccaatgaga tgctgagctg cctggagcac atgtaccacg acctcgggct ggtcagggac    540

ttcagcatca accctgtcac cctcaggagg tggctgttct gcgtccacga caactacaga    600

aacaacccct tccacaactt ccggcactgc ttctgcgtgg cccagatgat gtacagcatg    660

gtctggctct gcagtctcca ggagaagttc tcacaaacgg atatcctgat cctaatgaca    720

gcggccatct gccacgatct ggaccatccc ggctacaaca acacgtacca gatcaatgcc    780

cgcacagagc tggcggtccg ctacaatgac atctcaccgc tggagaacca ccactgcgcc    840

gtggccttcc agatcctcgc cgagcctgag tgcaacatct tctccaacat cccacctgat    900

gggttcaagc agatccgaca gggaatgatc acattaatct tggccactga catggcaaga    960

catgcagaaa ttatggattc tttcaaagag aaaatggaga attttgacta cagcaacgag   1020

gagcacatga ccctgctgaa gatgattttg ataaaatgct gtgatatctc taacgaggtc   1080

cgtccaatgg aagtcgcaga gccttgggtg gactgtttat tagaggaata ttttatgcag   1140

agcgaccgtg agaagtcaga aggccttcct gtggcaccgt tcatggaccg agacaaagtg   1200

accaaggcca cagcccagat tgggttcatc aagtttgtcc tgatcccaat gtttgaaaca   1260

gtgaccaagc tcttccccat ggttgaggag atcatgctgc agccactttg ggaatcccga   1320

gatcgctacg aggagctgaa gcggatagat gacgccatga aagagttaca gaagaagact   1380

gacagcttga cgtctggggc caccgagaag tccagagaga gaagcagaga tgtgaaaaac   1440
```

-continued

```
agtgaaggag actgtgcctg aggaaagcgg ggggcgtggc tgcagttctg gacgggctgg   1500

ccgagctgcg cgggatcctt gtgcagggaa gagctgccct gggcacctgg caccacaaga   1560

ccatgttttc taagaaccat tttgttcact gatacaaaaa aaaaaaaagg aattcatgat   1620

gctgtacaga attttatttt taaactgtct tttaaataat atattcttat acggaaaaaa   1680

aaaaaaaaaa aaaaaaaaaa aaaaaaaaaa aaaaaaaaa                          1719


<210> SEQ ID NO 5
<211> LENGTH: 1944
<212> TYPE: DNA
<213> ORGANISM: Homo sapiens
<300> PUBLICATION INFORMATION:
<308> DATABASE ACCESSION NUMBER: Genbank / NM_001001570.1
<309> DATABASE ENTRY DATE: 2008-10-24
<313> RELEVANT RESIDUES IN SEQ ID NO: (1)..(1944)

<400> SEQUENCE: 5

tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga aggtaatctt cagcaagtac tgcaactcca gcgacatcat ggacctgttc    180

tgcatcgcca ccggcctgcc tcggaacacg accatctccc tgctgaccac cgacgacgcc    240

atggtctcca tcgaccccac catgcccgcg aattcagaac ggaatgagct cattctctat    300

acatcactcc gtaacttgtt gtttttacct agtaaggagt catgggcgtc ccaccagcac    360

tccgtacaaa gtgagacctg tggccatcaa gcaactctcc gagcattcaa aatcaatgaa    420

ctgaaagctg aagttgcaaa tcacttggct gtcctagaga aacgcgtgga attggaagga    480

ctaaaagtgg tggagattga gaaatgcaag agtgacatta agaagatgag ggaggagctg    540

gcggccagaa gcagcaggac caactgcccc tgtaagtaca gtttttttgga taaccacaag    600

aagttgactc ctcgacgcga tgttcccact taccccaagt acctgctctc tccagagacc    660

atcgaggccc tgcggaagcc gacctttgac gtctggcttt gggagcccaa tgagatgctg    720

agctgcctgg agcacatgta ccacgacctc gggctggtca gggacttcag catcaaccct    780

gtcaccctca ggaggtggct gttctgcgtc cacgacaact acagaaacaa ccccttccac    840

aacttccggc actgcttctg cgtggcccag atgatgtaca gcatggtctg gctctgcagt    900

ctccaggaga agttctcaca aacggatatc ctgatcctaa tgacagcggc catctgccac    960

gatctggacc atcccggcta caacaacacg taccagatca atgcccgcac agagctggcg   1020

gtccgctaca atgacatctc accgctggag aaccaccact gcgccgtggc cttccagatc   1080

ctcgccgagc ctgagtgcaa catcttctcc aacatcccac ctgatgggtt caagcagatc   1140

cgacagggaa tgatcacatt aatcttggcc actgacatgg caagacatgc agaaattatg   1200

gattctttca aagagaaaat ggagaatttt gactacagca acgaggagca catgaccctg   1260

ctgaagatga ttttgataaa atgctgtgat atctctaacg aggtccgtcc aatggaagtc   1320

gcagagcctt gggtggactg tttattagag gaatatttta tgcagagcga ccgtgagaag   1380

tcagaaggcc ttcctgtggc accgttcatg gaccgagaca aagtgaccaa ggccacagcc   1440

cagattgggt tcatcaagtt tgtcctgatc ccaatgtttg aaacagtgac caagctcttc   1500

cccatggttg aggagatcat gctgcagcca ctttgggaat cccgagatcg ctacgaggag   1560

ctgaagcgga tagatgacgc catgaaagag ttacagaaga agactgacag cttgacgtct   1620

ggggccaccg agaagtccag agagagaagc agagatgtga aaaacagtga aggagactgt   1680

gcctgaggaa agcgggggc gtggctgcag ttctggacgg gctggccgag ctgcgcggga   1740
```

```
tccttgtgca gggaagagct gccctgggca cctggcacca caagaccatg ttttctaaga   1800

accattttgt tcactgatac aaaaaaaaaa aaaggaattc atgatgctgt acagaatttt   1860

atttttaaac tgtcttttaa ataatatatt cttatacgga aaaaaaaaaa aaaaaaaaaa   1920

aaaaaaaaaa aaaaaaaaaa aaaa                                          1944


<210> SEQ ID NO 6
<211> LENGTH: 1852
<212> TYPE: DNA
<213> ORGANISM: Homo sapiens
<300> PUBLICATION INFORMATION:
<308> DATABASE ACCESSION NUMBER: Genbank / NM_001001571.1
<309> DATABASE ENTRY DATE: 2008-10-24
<313> RELEVANT RESIDUES IN SEQ ID NO: (1)..(1852)

<400> SEQUENCE: 6

tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga aggaacacga ccatctccct gctgaccacc gacgacgcca tggtctccat    180

cgaccccacc atgcccgcga attcagaacg cactccgtac aaagtgagac ctgtggccat    240

caagcaactc tccgagagag aagaattaat ccagagcgtg ctggcgcagg ttgcagagca    300

gttctcaaga gcattcaaaa tcaatgaact gaaagctgaa gttgcaaatc acttggctgt    360

cctagagaaa cgcgtggaat tggaaggact aaaagtggtg gagattgaga aatgcaagag    420

tgacattaag aagatgaggg aggagctggc ggccagaagc agcaggacca actgcccctg    480

taagtacagt tttttggata accacaagaa gttgactcct cgacgcgatg ttcccactta    540

ccccaagtac ctgctctctc cagagaccat cgaggccctg cggaagccga cctttgacgt    600

ctggctttgg gagcccaatg agatgctgag ctgcctggag cacatgtacc acgacctcgg    660

gctggtcagg gacttcagca tcaaccctgt caccctcagg aggtggctgt tctgcgtcca    720

cgacaactac agaaacaacc ccttccacaa cttccggcac tgcttctgcg tggcccagat    780

gatgtacagc atggtctggc tctgcagtct ccaggagaag ttctcacaaa cggatatcct    840

gatcctaatg acagcggcca tctgccacga tctggaccat cccggctaca acaacacgta    900

ccagatcaat gcccgcacag agctggcggt ccgctacaat gacatctcac cgctggagaa    960

ccaccactgc gccgtggcct tccagatcct cgccgagcct gagtgcaaca tcttctccaa   1020

catcccacct gatgggttca agcagatccg acagggaatg atcacattaa tcttggccac   1080

tgacatggca agacatgcag aaattatgga ttctttcaaa gagaaaatgg agaattttga   1140

ctacagcaac gaggagcaca tgaccctgct gaagatgatt ttgataaaat gctgtgatat   1200

ctctaacgag gtccgtccaa tggaagtcgc agagccttgg gtggactgtt tattagagga   1260

atattttatg cagagcgacc gtgagaagtc agaaggcctt cctgtggcac cgttcatgga   1320

ccgagacaaa gtgaccaagg ccacagccca gattgggttc atcaagtttg tcctgatccc   1380

aatgtttgaa acagtgacca agctcttccc catggttgag gagatcatgc tgcagccact   1440

ttgggaatcc cgagatcgct acgaggagct gaagcggata gatgacgcca tgaaagagtt   1500

acagaagaag actgacagct tgacgtctgg ggccaccgag aagtccagag agagaagcag   1560

agatgtgaaa aacagtgaag gagactgtgc ctgaggaaag cgggggcgt ggctgcagtt   1620

ctggacgggc tggccgagct gcgcgggatc cttgtgcagg gaagagctgc cctgggcacc   1680

tggcaccaca agaccatgtt ttctaagaac cattttgttc actgatacaa aaaaaaaaaa   1740
```

-continued

```
aggaattcat gatgctgtac agaattttat ttttaaactg tcttttaaat aatatattct   1800

tatacggaaa aaaaaaaaaa aaaaaaaaaa aaaaaaaaaa aaaaaaaaaa aa           1852


<210> SEQ ID NO 7
<211> LENGTH: 1730
<212> TYPE: DNA
<213> ORGANISM: Homo sapiens
<300> PUBLICATION INFORMATION:
<308> DATABASE ACCESSION NUMBER: Genbank / NM_001001572.1
<309> DATABASE ENTRY DATE: 2008-10-24
<313> RELEVANT RESIDUES IN SEQ ID NO: (1)..(1730)

<400> SEQUENCE: 7

tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga agagagagaa gaattaatcc agagcgtgct ggcgcaggtt gcagagcagt    180

tctcaagagc attcaaaatc aatgaactga aagctgaagt tgcaaatcac ttggctgtcc    240

tagagaaacg cgtggaattg gaaggactaa aagtggtgga gattgagaaa tgcaagagtg    300

acattaagaa gatgagggag gagctggcgg ccagaagcag caggaccaac tgcccctgta    360

agtacagttt tttggataac cacaagaagt tgactcctcg acgcgatgtt cccacttacc    420

ccaagtacct gctctctcca gagaccatcg aggccctgcg gaagccgacc tttgacgtct    480

ggctttggga gcccaatgag atgctgagct gcctggagca catgtaccac gacctcgggc    540

tggtcaggga cttcagcatc aaccctgtca ccctcaggag gtggctgttc tgcgtccacg    600

acaactacag aaacaacccc ttccacaact tccggcactg cttctgcgtg gcccagatga    660

tgtacagcat ggtctggctc tgcagtctcc aggagaagtt ctcacaaacg gatatcctga    720

tcctaatgac agcggccatc tgccacgatc tggaccatcc cggctacaac aacacgtacc    780

agatcaatgc ccgcacagag ctggcggtcc gctacaatga catctcaccg ctggagaacc    840

accactgcgc cgtggccttc cagatcctcg ccgagcctga gtgcaacatc ttctccaaca    900

tcccacctga tgggttcaag cagatccgac agggaatgat cacattaatc ttggccactg    960

acatggcaag acatgcagaa attatggatt ctttcaaaga gaaaatggag aattttgact   1020

acagcaacga ggagcacatg accctgctga agatgatttt gataaaatgc tgtgatatct   1080

ctaacgaggt ccgtccaatg gaagtcgcag agccttgggt ggactgttta ttagaggaat   1140

attttatgca gagcgaccgt gagaagtcag aaggccttcc tgtggcaccg ttcatggacc   1200

gagacaaagt gaccaaggcc acagcccaga ttgggttcat caagtttgtc ctgatcccaa   1260

tgtttgaaac agtgaccaag ctcttcccca tggttgagga gatcatgctg cagccacttt   1320

gggaatcccg agatcgctac gaggagctga agcggataga tgacgccatg aaagagttac   1380

agaagaagac tgacagcttg acgtctgggg ccaccgagaa gtccagagag agaagcagag   1440

atgtgaaaaa cagtgaagga gactgtgcct gaggaaagcg gggggcgtgg ctgcagttct   1500

ggacgggctg gccgagctgc gcgggatcct tgtgcaggga agagctgccc tgggcacctg   1560

gcaccacaag accatgtttt ctaagaacca ttttgttcac tgatacaaaa aaaaaaaaag   1620

gaattcatga tgctgtacag aattttattt ttaaactgtc ttttaaataa tatattctta   1680

tacggaaaaa aaaaaaaaaa aaaaaaaaaa aaaaaaaaaa aaaaaaaaaa              1730


<210> SEQ ID NO 8
<211> LENGTH: 1910
<212> TYPE: DNA
<213> ORGANISM: Homo sapiens
```

-continued

<300> PUBLICATION INFORMATION:
<308> DATABASE ACCESSION NUMBER: Genbank / NM_001001573.1
<309> DATABASE ENTRY DATE: 2008-10-24
<313> RELEVANT RESIDUES IN SEQ ID NO: (1)..(1910)

<400> SEQUENCE: 8

```
tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga agctggtgtc gaggacaaga gaaccacaag ccgtggccag tctgctgaga    180

gaccactgag ggacagacgg gttgtgggcc tggagcagcc ccggagggaa ggagcatttg    240

aaagtggaca ggtagagccc aggcccagag agccccaggg ctgctaccag gaaggccagc    300

gcatccctcc agagagagaa gaattaatcc agagcgtgct ggcgcaggtt gcagagcagt    360

tctcaagagc attcaaaatc aatgaactga aagctgaagt tgcaaatcac ttggctgtcc    420

tagagaaacg cgtggaattg gaaggactaa aagtggtgga gattgagaaa tgcaagagtg    480

acattaagaa gatgagggag gagctggcgg ccagaagcag caggaccaac tgcccctgta    540

agtacagttt tttggataac cacaagaagt tgactcctcg acgcgatgtt cccacttacc    600

ccaagtacct gctctctcca gagaccatcg aggccctgcg gaagccgacc tttgacgtct    660

ggctttggga gcccaatgag atgctgagct gcctggagca catgtaccac gacctcgggc    720

tggtcaggga cttcagcatc aaccctgtca ccctcaggag gtggctgttc tgcgtccacg    780

acaactacag aaacaacccc ttccacaact tccggcactg cttctgcgtg gcccagatga    840

tgtacagcat ggtctggctc tgcagtctcc aggagaagtt ctcacaaacg gatatcctga    900

tcctaatgac agcggccatc tgccacgatc tggaccatcc cggctacaac aacacgtacc    960

agatcaatgc ccgcacagag ctggcggtcc gctacaatga catctcaccg ctggagaacc   1020

accactgcgc cgtggccttc cagatcctcg ccgagcctga gtgcaacatc ttctccaaca   1080

tcccacctga tgggttcaag cagatccgac agggaatgat cacattaatc ttggccactg   1140

acatggcaag acatgcagaa attatggatt ctttcaaaga gaaaatggag aattttgact   1200

acagcaacga ggagcacatg accctgctga agatgatttt gataaaatgc tgtgatatct   1260

ctaacgaggt ccgtccaatg gaagtcgcag agccttgggt ggactgttta ttagaggaat   1320

attttatgca gagcgaccgt gagaagtcag aaggccttcc tgtggcaccg ttcatggacc   1380

gagacaaagt gaccaaggcc acagcccaga ttgggttcat caagtttgtc ctgatcccaa   1440

tgtttgaaac agtgaccaag ctcttcccca tggttgagga gatcatgctg cagccacttt   1500

gggaatcccg agatcgctac gaggagctga agcggataga tgacgccatg aaagagttac   1560

agaagaagac tgacagcttg acgtctgggg ccaccgagaa gtccagagag agaagcagag   1620

atgtgaaaaa cagtgaagga gactgtgcct gaggaaagcg gggggcgtgg ctgcagttct   1680

ggacgggctg gccgagctgc gcgggatcct tgtgcaggga agagctgccc tgggcacctg   1740

gcaccacaag accatgtttt ctaagaacca ttttgttcac tgatacaaaa aaaaaaaaag   1800

gaattcatga tgctgtacag aattttattt ttaaactgtc ttttaaataa tatattctta   1860

tacggaaaaa aaaaaaaaaa aaaaaaaaaa aaaaaaaaaa aaaaaaaaaa              1910
```

<210> SEQ ID NO 9
<211> LENGTH: 1845
<212> TYPE: DNA
<213> ORGANISM: Homo sapiens
<300> PUBLICATION INFORMATION:
<308> DATABASE ACCESSION NUMBER: Genbank / NM_001001574.1
<309> DATABASE ENTRY DATE: 2008-10-24

<313> RELEVANT RESIDUES IN SEQ ID NO: (1)..(1845)

<400> SEQUENCE: 9
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga aggtaatctt cagcaagtac tgcaactcca gcgacatcat ggacctgttc 180
tgcatcgcca ccggcctgcc tcgcactccg tacaaagtga gacctgtggc catcaagcaa 240
ctctccgaga gagaagaatt aatccagagc gtgctggcgc aggttgcaga gcagttctca 300
agagcattca aaatcaatga actgaaagct gaagttgcaa atcacttggc tgtcctagag 360
aaacgcgtgg aattggaagg actaaaagtg gtggagattg agaaatgcaa gagtgacatt 420
aagaagatga gggaggagct ggcggccaga agcagcagga ccaactgccc ctgtaagtac 480 agtttttttgg ataaccacaa gaagttgact cctcgacgcg atgttcccac ttaccccaag 540
tacctgctct ctccagagac catcgaggcc ctgcggaagc cgacctttga cgtctggctt 600
tgggagccca atgagatgct gagctgcctg gagcacatgt accacgacct cgggctggtc 660
agggacttca gcatcaaccc tgtcaccctc aggaggtggc tgttctgcgt ccacgacaac 720
tacagaaaca accccttcca caacttccgg cactgcttct gcgtggccca gatgatgtac 780
agcatggtct ggctctgcag tctccaggag aagttctcac aaacggatat cctgatccta 840
atgacagcgg ccatctgcca cgatctggac catcccggct acaacaacac gtaccagatc 900
aatgcccgca cagagctggc ggtccgctac aatgacatct caccgctgga gaaccaccac 960
tgcgccgtgg ccttccagat cctcgccgag cctgagtgca acatcttctc caacatccca 1020
cctgatgggt tcaagcagat ccgacaggga atgatcacat taatcttggc cactgacatg 1080
gcaagacatg cagaaattat ggattctttc aaagagaaaa tggagaattt tgactacagc 1140
aacgaggagc acatgaccct gctgaagatg attttgataa aatgctgtga tatctctaac 1200
gaggtccgtc caatggaagt cgcagagcct tgggtggact gtttattaga ggaatatttt 1260
atgcagagcg accgtgagaa gtcagaaggc cttcctgtgg caccgttcat ggaccgagac 1320
aaagtgacca aggccacagc ccagattggg ttcatcaagt ttgtcctgat cccaatgttt 1380
gaaacagtga ccaagctctt ccccatggtt gaggagatca tgctgcagcc actttgggaa 1440
tcccgagatc gctacgagga gctgaagcgg atagatgacg ccatgaaaga gttacagaag 1500
aagactgaca gcttgacgtc tggggccacc gagaagtcca gagagagaag cagagatgtg 1560
aaaaacagtg aaggagactg tgcctgagga aagcgggggg cgtggctgca gttctggacg 1620
ggctggccga gctgcgcggg atccttgtgc agggaagagc tgccctgggc acctggcacc 1680
acaagaccat gttttctaag aaccattttg ttcactgata caaaaaaaaa aaaaggaatt 1740
catgatgctg tacagaattt tatttttaaa ctgtctttta aataatatat tcttatacgg 1800
aaaaaaaaaa aaaaaaaaaa aaaaaaaaaa aaaaaaaaaa aaaaa 1845

<210> SEQ ID NO 10
<211> LENGTH: 1675
<212> TYPE: DNA
<213> ORGANISM: Homo sapiens
<300> PUBLICATION INFORMATION:
<308> DATABASE ACCESSION NUMBER: Genbank / NM_001001575.1
<309> DATABASE ENTRY DATE: 2008-10-24
<313> RELEVANT RESIDUES IN SEQ ID NO: (1)..(1675)

<400> SEQUENCE: 10
tcccgcggcg gctggcgtcg ggaaagtaca gtaaaaagtc cgagtgcagc cgccgggcgc 60

```
aggatgggat ccggctcctc cagctaccgg cccaaggcca tctacctgga catcgatgga    120
cgcattcaga agagcattca aaatcaatga actgaaagct gaagttgcaa atcacttggc    180
tgtcctagag aaacgcgtgg aattggaagg actaaaagtg gtggagattg agaaatgcaa    240
gagtgacatt aagaagatga gggaggagct ggcggccaga agcagcagga ccaactgccc    300
ctgtaagtac agtttttttgg ataaccacaa gaagttgact cctcgacgcg atgttcccac    360
ttaccccaag tacctgctct ctccagagac catcgaggcc ctgcggaagc cgacctttga    420
cgtctggctt tgggagccca atgagatgct gagctgcctg gagcacatgt accacgacct    480
cgggctggtc agggacttca gcatcaaccc tgtcaccctc aggaggtggc tgttctgcgt    540
ccacgacaac tacagaaaca accccttcca caacttccgg cactgcttct gcgtggccca    600
gatgatgtac agcatggtct ggctctgcag tctccaggag aagttctcac aaacggatat    660
cctgatccta atgacagcgg ccatctgcca cgatctggac catcccggct acaacaacac    720
gtaccagatc aatgcccgca cagagctggc ggtccgctac aatgacatct caccgctgga    780
gaaccaccac tgcgccgtgg ccttccagat cctcgccgag cctgagtgca acatcttctc    840
caacatccca cctgatgggt tcaagcagat ccgacaggga atgatcacat taatcttggc    900
cactgacatg gcaagacatg cagaaattat ggattctttc aaagagaaaa tggagaattt    960
tgactacagc aacgaggagc acatgaccct gctgaagatg attttgataa aatgctgtga   1020
tatctctaac gaggtccgtc caatggaagt cgcagagcct tgggtggact gtttattaga   1080
ggaatatttt atgcagagcg accgtgagaa gtcagaaggc cttcctgtgg caccgttcat   1140
ggaccgagac aaagtgacca aggccacagc ccagattggg ttcatcaagt ttgtcctgat   1200
cccaatgttt gaaacagtga ccaagctctt ccccatggtt gaggagatca tgctgcagcc   1260
actttgggaa tcccgagatc gctacgagga gctgaagcgg atagatgacg ccatgaaaga   1320
gttacagaag aagactgaca gcttgacgtc tggggccacc gagaagtcca gagagagaag   1380
cagagatgtg aaaaacagtg aaggagactg tgcctgagga aagcgggggg cgtggctgca   1440
gttctggacg ggctggccga gctgcgcggg atccttgtgc agggaagagc tgccctgggc   1500
acctggcacc acaagaccat gttttctaag aaccattttg ttcactgata caaaaaaaaa   1560
aaaaggaatt catgatgctg tacagaattt tatttttaaa ctgtctttta aataatatat   1620
tcttatacgg aaaaaaaaaa aaaaaaaaaa aaaaaaaaaa aaaaaaaaaa aaaaa        1675
```

<210> SEQ ID NO 11
<211> LENGTH: 1634
<212> TYPE: DNA
<213> ORGANISM: Homo sapiens
<300> PUBLICATION INFORMATION:
<308> DATABASE ACCESSION NUMBER: Genbank / NM_001001576.1
<309> DATABASE ENTRY DATE: 2008-10-24
<313> RELEVANT RESIDUES IN SEQ ID NO: (1)..(1634)

<400> SEQUENCE: 11

```
tcccgcggcg gctggcgtcg ggaaagtaca gtaaaaagtc cgagtgcagc cgccgggcgc     60
aggatgggat ccggctcctc cagctaccgg cccaaggcca tctacctgga catcgatgga    120
cgcattcaga agcactccgt acaaagtgag acctgtggcc atcaagcaac tctccgagca    180
ttcaaaatca atgaactgaa agctgaagtt gcaaatcact tggctgtcct agagaaacgc    240
gtggaatgac caactgcccc tgtaagtaca gtttttttgga taaccacaag aagttgactc    300
ctcgacgcga tgttcccact taccccaagt acctgctctc tccagagacc atcgaggccc    360
```

```
tgcggaagcc gacctttgac gtctggcttt gggagcccaa tgagatgctg agctgcctgg    420

agcacatgta ccacgacctc gggctggtca gggacttcag catcaaccct gtcaccctca    480

ggaggtggct gttctgcgtc cacgacaact acagaaacaa cccccttccac aacttccggc    540

actgcttctg cgtggcccag atgatgtaca gcatggtctg gctctgcagt ctccaggaga    600

agttctcaca aacggatatc ctgatcctaa tgacagcggc catctgccac gatctggacc    660

atcccggcta caacaacacg taccagatca atgcccgcac agagctggcg gtccgctaca    720

atgacatctc accgctggag aaccaccact gcgccgtggc cttccagatc ctcgccgagc    780

ctgagtgcaa catcttctcc aacatcccac ctgatgggtt caagcagatc cgacagggaa    840

tgatcacatt aatcttggcc actgacatgg caagacatgc agaaattatg gattctttca    900

aagagaaaat ggagaatttt gactacagca acgaggagca catgaccctg ctgaagatga    960

ttttgataaa atgctgtgat atctctaacg aggtccgtcc aatggaagtc gcagagcctt   1020

gggtggactg tttattagag gaatatttta tgcagagcga ccgtgagaag tcagaaggcc   1080

ttcctgtggc accgttcatg gaccgagaca aagtgaccaa ggccacagcc cagattgggt   1140

tcatcaagtt tgtcctgatc ccaatgtttg aaacagtgac caagctcttc cccatggttg   1200

aggagatcat gctgcagcca ctttgggaat cccgagatcg ctacgaggag ctgaagcgga   1260

tagatgacgc catgaaagag ttacagaaga agactgacag cttgacgtct ggggccaccg   1320

agaagtccag agagagaagc agagatgtga aaaacagtga aggagactgt gcctgaggaa   1380

agcgggggc gtggctgcag ttctggacgg gctggccgag ctgcgcggga tccttgtgca   1440

gggaagagct gccctgggca cctggcacca caagaccatg ttttctaaga accattttgt   1500

tcactgatac aaaaaaaaaa aaaggaattc atgatgctgt acagaatttt atttttaaac   1560

tgtcttttaa ataatatatt cttatacgga aaaaaaaaaa aaaaaaaaaa aaaaaaaaaa   1620

aaaaaaaaaa aaaa                                                     1634
```

<210> SEQ ID NO 12
<211> LENGTH: 1753
<212> TYPE: DNA
<213> ORGANISM: Homo sapiens
<300> PUBLICATION INFORMATION:
<308> DATABASE ACCESSION NUMBER: Genbank / NM_001001577.1
<309> DATABASE ENTRY DATE: 2008-10-24
<313> RELEVANT RESIDUES IN SEQ ID NO: (1)..(1753)

<400> SEQUENCE: 12

```
tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga aggaacacga ccatctccct gctgaccacc gacgacgcca tggtctccat    180

cgaccccacc atgcccgcga attcagaacg agcattcaaa atcaatgaac tgaaagctga    240

agttgcaaat cacttggctg tcctagagaa acgcgtggaa ttggaaggac taaaagtggt    300

ggagattgag aaatgcaaga gtgacattaa gaagatgagg gaggagctgg cggccagaag    360

cagcaggacc aactgcccct gtaagtacag ttttttggat aaccacaaga agttgactcc    420

tcgacgcgat gttcccactt accccaagta cctgctctct ccagagacca tcgaggccct    480

gcggaagccg acctttgacg tctggctttg ggagcccaat gagatgctga gctgcctgga    540

gcacatgtac cacgacctcg ggctggtcag ggacttcagc atcaaccctg tcaccctcag    600

gaggtggctg ttctgcgtcc acgacaacta cagaaacaac cccttccaca acttccggca    660

ctgcttctgc gtggcccaga tgatgtacag catggtctgg ctctgcagtc tccaggagaa    720
```

```
gttctcacaa acggatatcc tgatcctaat gacagcggcc atctgccacg atctggacca    780

tcccggctac aacaacacgt accagatcaa tgcccgcaca gagctggcgg tccgctacaa    840

tgacatctca ccgctggaga accaccactg cgccgtggcc ttccagatcc tcgccgagcc    900

tgagtgcaac atcttctcca acatcccacc tgatgggttc aagcagatcc gacagggaat    960

gatcacatta atcttggcca ctgacatggc aagacatgca gaaattatgg attctttcaa   1020

agagaaaatg gagaattttg actacagcaa cgaggagcac atgaccctgc tgaagatgat   1080

tttgataaaa tgctgtgata tctctaacga ggtccgtcca atggaagtcg cagagccttg   1140

ggtggactgt ttattagagg aatattttat gcagagcgac cgtgagaagt cagaaggcct   1200

tcctgtggca ccgttcatgg accgagacaa agtgaccaag gccacagccc agattgggtt   1260

catcaagttt gtcctgatcc caatgtttga aacagtgacc aagctcttcc ccatggttga   1320

ggagatcatg ctgcagccac tttgggaatc ccgagatcgc tacgaggagc tgaagcggat   1380

agatgacgcc atgaaagagt tacagaagaa gactgacagc ttgacgtctg ggccaccga    1440

gaagtccaga gagagaagca gagatgtgaa aaacagtgaa ggagactgtg cctgaggaaa   1500

gcggggggcg tggctgcagt tctggacggg ctggccgagc tgcgcgggat ccttgtgcag   1560

ggaagagctg ccctgggcac ctggcaccac aagaccatgt tttctaagaa ccattttgtt   1620

cactgataca aaaaaaaaaa aaggaattca tgatgctgta cagaatttta tttttaaact   1680

gtcttttaaa taatatattc ttatacggaa aaaaaaaaaa aaaaaaaaaa aaaaaaaaaa   1740

aaaaaaaaaa aaa                                                      1753
```

<210> SEQ ID NO 13
<211> LENGTH: 1797
<212> TYPE: DNA
<213> ORGANISM: Homo sapiens
<300> PUBLICATION INFORMATION:
<308> DATABASE ACCESSION NUMBER: Genbank / NM_001001578.1
<309> DATABASE ENTRY DATE: 2008-10-24
<313> RELEVANT RESIDUES IN SEQ ID NO: (1)..(1797)

<400> SEQUENCE: 13

```
tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga aggaacacga ccatctccct gctgaccacc gacgacgcca tggtctccat    180

cgaccccacc atgcccgcga attcagaacg cactccgtac aaagtgagac ctgtggccat    240

caagcaactc tccgagcatt caaaatcaat gaactgaaag ctgaagttgc aaatcacttg    300

gctgtcctag agaaacgcgt ggaattggaa ggactaaaag tggtggagat tgagaaatgc    360

aagagtgaca ttaagaagat gagggaggag ctggcggcca gaagcagcag gaccaactgc    420

ccctgtaagt acagtttttt ggataaccac aagaagttga ctcctcgacg cgatgttccc    480

acttacccca agtacctgct ctctccagag accatcgagg ccctgcggaa gccgaccttt    540

gacgtctggc tttgggagcc caatgagatg ctgagctgcc tggagcacat gtaccacgac    600

ctcgggctgg tcagggactt cagcatcaac cctgtcaccc tcaggaggtg gctgttctgc    660

gtccacgaca actacagaaa caacccctto cacaacttcc ggcactgctt ctgcgtggcc    720

cagatgatgt acagcatggt ctggctctgc agtctccagg agaagttctc acaaacggat    780

atcctgatcc taatgacagc ggccatctgc cacgatctgg accatcccgg ctacaacaac    840

acgtaccaga tcaatgcccg cacagagctg gcggtccgct acaatgacat ctcaccgctg    900
```

-continued

```
gagaaccacc actgcgccgt ggccttccag atcctcgccg agcctgagtg caacatcttc    960

tccaacatcc cacctgatgg gttcaagcag atccgacagg gaatgatcac attaatcttg   1020

gccactgaca tggcaagaca tgcagaaatt atggattctt tcaaagagaa aatggagaat   1080

tttgactaca gcaacgagga gcacatgacc ctgctgaaga tgattttgat aaaatgctgt   1140

gatatctcta acgaggtccg tccaatggaa gtcgcagagc cttgggtgga ctgtttatta   1200

gaggaatatt ttatgcagag cgaccgtgag aagtcagaag gccttcctgt ggcaccgttc   1260

atggaccgag acaaagtgac caaggccaca gcccagattg ggttcatcaa gtttgtcctg   1320

atcccaatgt ttgaaacagt gaccaagctc ttccccatgg ttgaggagat catgctgcag   1380

ccactttggg aatcccgaga tcgctacgag gagctgaagc ggatagatga cgccatgaaa   1440

gagttacaga agaagactga cagcttgacg tctggggcca ccgagaagtc cagagagaga   1500

agcagagatg tgaaaaacag tgaaggagac tgtgcctgag gaaagcgggg ggcgtggctg   1560

cagttctgga cgggctggcc gagctgcgcg ggatccttgt gcagggaaga gctgccctgg   1620

gcacctggca ccacaagacc atgttttcta agaaccattt tgttcactga tacaaaaaaa   1680

aaaaaaggaa ttcatgatgc tgtacagaat tttattttta aactgtcttt taaataatat   1740

attcttatac ggaaaaaaaa aaaaaaaaaa aaaaaaaaaa aaaaaaaaaa aaaaaaa      1797
```

<210> SEQ ID NO 14
<211> LENGTH: 1790
<212> TYPE: DNA
<213> ORGANISM: Homo sapiens
<300> PUBLICATION INFORMATION:
<308> DATABASE ACCESSION NUMBER: Genbank / NM_001001579.1
<309> DATABASE ENTRY DATE: 2008-10-24
<313> RELEVANT RESIDUES IN SEQ ID NO: (1)..(1790)

<400> SEQUENCE: 14

```
tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga aggtaatctt cagcaagtac tgcaactcca gcgacatcat ggacctgttc    180

tgcatcgcca ccggcctgcc tcgcactccg tacaaagtga gacctgtggc catcaagcaa    240

ctctccgagc attcaaaatc aatgaactga aagctgaagt tgcaaatcac ttggctgtcc    300

tagagaaacg cgtggaattg gaaggactaa aagtggtgga gattgagaaa tgcaagagtg    360

acattaagaa gatgagggag gagctggcgg ccagaagcag caggaccaac tgcccctgta    420

agtacagttt tttggataac cacaagaagt tgactcctcg acgcgatgtt cccacttacc    480

ccaagtacct gctctctcca gagaccatcg aggccctgcg gaagccgacc tttgacgtct    540

ggctttggga gcccaatgag atgctgagct gcctggagca catgtaccac gacctcgggc    600

tggtcaggga cttcagcatc aaccctgtca ccctcaggag gtggctgttc tgcgtccacg    660

acaactacag aaacaacccc ttccacaact tccggcactg cttctgcgtg gcccagatga    720

tgtacagcat ggtctggctc tgcagtctcc aggagaagtt ctcacaaacg gatatcctga    780

tcctaatgac agcggccatc tgccacgatc tggaccatcc cggctacaac aacacgtacc    840

agatcaatgc ccgcacagag ctggcggtcc gctacaatga catctcaccg ctggagaacc    900

accactgcgc cgtggccttc cagatcctcg ccgagcctga gtgcaacatc ttctccaaca    960

tcccacctga tgggttcaag cagatccgac agggaatgat cacattaatc ttggccactg   1020

acatggcaag acatgcagaa attatggatt ctttcaaaga gaaaatggag aattttgact   1080

acagcaacga ggagcacatg accctgctga agatgatttt gataaaatgc tgtgatatct   1140
```

ctaacgaggt ccgtccaatg gaagtcgcag agccttgggt ggactgttta ttagaggaat 1200
attttatgca gagcgaccgt gagaagtcag aaggccttcc tgtggcaccg ttcatggacc 1260
gagacaaagt gaccaaggcc acagcccaga ttgggttcat caagtttgtc ctgatcccaa 1320
tgtttgaaac agtgaccaag ctcttcccca tggttgagga gatcatgctg cagccacttt 1380
gggaatcccg agatcgctac gaggagctga agcggataga tgacgccatg aaagagttac 1440
agaagaagac tgacagcttg acgtctgggg ccaccgagaa gtccagagag agaagcagag 1500
atgtgaaaaa cagtgaagga gactgtgcct gaggaaagcg gggggcgtgg ctgcagttct 1560
ggacgggctg gccgagctgc gcgggatcct tgtgcaggga agagctgccc tgggcacctg 1620
gcaccacaag accatgtttt ctaagaacca ttttgttcac tgatacaaaa aaaaaaaaag 1680
gaattcatga tgctgtacag aattttattt ttaaactgtc ttttaaataa tatattctta 1740
tacggaaaaa aaaaaaaaaa aaaaaaaaaa aaaaaaaaaa aaaaaaaaaa 1790

<210> SEQ ID NO 15
<211> LENGTH: 1590
<212> TYPE: DNA
<213> ORGANISM: Homo sapiens
<300> PUBLICATION INFORMATION:
<308> DATABASE ACCESSION NUMBER: Genbank / NM_001001580.1
<309> DATABASE ENTRY DATE: 2008-10-24
<313> RELEVANT RESIDUES IN SEQ ID NO: (1)..(1590)

<400> SEQUENCE: 15
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga agagcattca aaatcaatga actgaaagct gaagttgcaa atcacttggc 180
tgtcctagag aaacgcgtgg aatgaccaac tgcccctgta agtacagttt tttggataac 240
cacaagaagt tgactcctcg acgcgatgtt cccacttacc ccaagtacct gctctctcca 300
gagaccatcg aggccctgcg gaagccgacc tttgacgtct ggctttggga gcccaatgag 360
atgctgagct gcctggagca catgtaccac gacctcgggc tggtcaggga cttcagcatc 420
aaccctgtca ccctcaggag gtggctgttc tgcgtccacg acaactacag aaacaacccc 480
ttccacaact tccggcactg cttctgcgtg gcccagatga tgtacagcat ggtctggctc 540
tgcagtctcc aggagaagtt ctcacaaacg gatatcctga tcctaatgac agcggccatc 600
tgccacgatc tggaccatcc cggctacaac aacacgtacc agatcaatgc ccgcacagag 660
ctggcggtcc gctacaatga catctcaccg ctggagaacc accactgcgc cgtggccttc 720
cagatcctcg ccgagcctga gtgcaacatc ttctccaaca tcccacctga tgggttcaag 780
cagatccgac agggaatgat cacattaatc ttggccactg acatggcaag acatgcagaa 840
attatggatt ctttcaaaga gaaaatggag aattttgact acagcaacga ggagcacatg 900
accctgctga agatgatttt gataaaatgc tgtgatatct ctaacgaggt ccgtccaatg 960
gaagtcgcag agccttgggt ggactgttta ttagaggaat attttatgca gagcgaccgt 1020
gagaagtcag aaggccttcc tgtggcaccg ttcatggacc gagacaaagt gaccaaggcc 1080
acagcccaga ttgggttcat caagtttgtc ctgatcccaa tgtttgaaac agtgaccaag 1140
ctcttcccca tggttgagga gatcatgctg cagccacttt gggaatcccg agatcgctac 1200
gaggagctga agcggataga tgacgccatg aaagagttac agaagaagac tgacagcttg 1260
acgtctgggg ccaccgagaa gtccagagag agaagcagag atgtgaaaaa cagtgaagga 1320

```
gactgtgcct gaggaaagcg gggggcgtgg ctgcagttct ggacgggctg gccgagctgc   1380

gcgggatcct tgtgcaggga agagctgccc tgggcacctg gcaccacaag accatgtttt   1440

ctaagaacca ttttgttcac tgatacaaaa aaaaaaaaag gaattcatga tgctgtacag   1500

aattttattt ttaaactgtc ttttaaataa tatattctta tacggaaaaa aaaaaaaaaa   1560

aaaaaaaaaa aaaaaaaaaa aaaaaaaaaa                                    1590
```

<210> SEQ ID NO 16
<211> LENGTH: 1954
<212> TYPE: DNA
<213> ORGANISM: Homo sapiens
<300> PUBLICATION INFORMATION:
<308> DATABASE ACCESSION NUMBER: Genbank / NM_001001581.1
<309> DATABASE ENTRY DATE: 2008-10-24
<313> RELEVANT RESIDUES IN SEQ ID NO: (1)..(1954)

<400> SEQUENCE: 16

```
tcccgcggcg gctggcgtcg ggaaagtaca gtaaaaagtc cgagtgcagc cgccgggcgc     60

aggatgggat ccggctcctc cagctaccgg cccaaggcca tctacctgga catcgatgga    120

cgcattcaga agcactccgt acaaagtgag acctgtggcc atcaagcaac tctccgctgg    180

tgtcgaggac aagagaacca caagccgtgg ccagtctgct gagagaccac tgagggacag    240

acgggttgtg ggcctggagc agccccggag ggaaggagca tttgaaagtg gacaggtaga    300

gcccaggccc agagagcccc agggctgcta ccaggaaggc cagcgcatcc ctccagagag    360

agaagaatta atccagagcg tgctggcgca ggttgcagag cagttctcaa gagcattcaa    420

aatcaatgaa ctgaaagctg aagttgcaaa tcacttggct gtcctagaga aacgcgtgga    480

attggaagga ctaaaagtgg tggagattga gaaatgcaag agtgacatta agaagatgag    540

ggaggagctg gcggccagaa gcagcaggac caactgcccc tgtaagtaca gtttttttgga    600

taaccacaag aagttgactc ctcgacgcga tgttcccact taccccaagt acctgctctc    660

tccagagacc atcgaggccc tgcggaagcc gacctttgac gtctggcttt gggagcccaa    720

tgagatgctg agctgcctgg agcacatgta ccacgacctc gggctggtca gggacttcag    780

catcaaccct gtcaccctca ggaggtggct gttctgcgtc cacgacaact acagaaacaa    840

ccccttccac aacttccggc actgcttctg cgtggcccag atgatgtaca gcatggtctg    900

gctctgcagt ctccaggaga agttctcaca aacggatatc ctgatcctaa tgacagcggc    960

catctgccac gatctggacc atcccggcta caacaacacg taccagatca atgcccgcac   1020

agagctggcg gtccgctaca atgacatctc accgctggag aaccaccact gcgccgtggc   1080

cttccagatc ctcgccgagc ctgagtgcaa catcttctcc aacatcccac ctgatgggtt   1140

caagcagatc cgacagggaa tgatcacatt aatcttggcc actgacatgg caagacatgc   1200

agaaattatg gattctttca aagagaaaat ggagaatttt gactacagca acgaggagca   1260

catgaccctg ctgaagatga ttttgataaa atgctgtgat atctctaacg aggtccgtcc   1320

aatggaagtc gcagagcctt gggtggactg tttattagag gaatatttta tgcagagcga   1380

ccgtgagaag tcagaaggcc ttcctgtggc accgttcatg gaccgagaca aagtgaccaa   1440

ggccacagcc cagattgggt tcatcaagtt tgtcctgatc ccaatgtttg aaacagtgac   1500

caagctcttc cccatggttg aggagatcat gctgcagcca ctttgggaat cccgagatcg   1560

ctacgaggag ctgaagcgga tagatgacgc catgaaagag ttacagaaga agactgacag   1620

cttgacgtct ggggccaccg agaagtccag agagagaagc agagatgtga aaaacagtga   1680

aggagactgt gcctgaggaa agcggggggc gtggctgcag ttctggacgg gctggccgag   1740
```

ctgcgcggga tccttgtgca gggaagagct gccctgggca cctggcacca caagaccatg 1800
ttttctaaga accattttgt tcactgatac aaaaaaaaaa aaaggaattc atgatgctgt 1860
acagaatttt atttttaaac tgtcttttaa ataatatatt cttatacgga aaaaaaaaaa 1920
aaaaaaaaaa aaaaaaaaaa aaaaaaaaaa aaaa 1954

<210> SEQ ID NO 17
<211> LENGTH: 2032
<212> TYPE: DNA
<213> ORGANISM: Homo sapiens
<300> PUBLICATION INFORMATION:
<308> DATABASE ACCESSION NUMBER: Genbank / NM_001001582.1
<309> DATABASE ENTRY DATE: 2008-10-24
<313> RELEVANT RESIDUES IN SEQ ID NO: (1)..(2032)

<400> SEQUENCE: 17
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga aggaacacga ccatctccct gctgaccacc gacgacgcca tggtctccat 180
cgaccccacc atgcccgcga attcagaacg cactccgtac aaagtgagac ctgtggccat 240
caagcaactc tccgctggtg tcgaggacaa gagaaccaca agccgtggcc agtctgctga 300
gagaccactg agggacagac gggttgtggg cctggagcag ccccggaggg aaggagcatt 360
tgaaagtgga caggtagagc ccaggcccag agagccccag ggctgctacc aggaaggcca 420
gcgcatccct ccagagagag aagaattaat ccagagcgtg ctggcgcagg ttgcagagca 480
gttctcaaga gcattcaaaa tcaatgaact gaaagctgaa gttgcaaatc acttggctgt 540
cctagagaaa cgcgtggaat tggaaggact aaaagtggtg gagattgaga aatgcaagag 600
tgacattaag aagatgaggg aggagctggc ggccagaagc agcaggacca actgcccctg 660
taagtacagt tttttggata accacaagaa gttgactcct cgacgcgatg ttcccactta 720
ccccaagtac ctgctctctc cagagaccat cgaggccctg cggaagccga cctttgacgt 780
ctggctttgg gagcccaatg agatgctgag ctgcctggag cacatgtacc acgacctcgg 840
gctggtcagg gacttcagca tcaaccctgt caccctcagg aggtggctgt tctgcgtcca 900
cgacaactac agaaacaacc ccttccacaa cttccggcac tgcttctgcg tggcccagat 960
gatgtacagc atggtctggc tctgcagtct ccaggagaag ttctcacaaa cggatatcct 1020
gatcctaatg acagcggcca tctgccacga tctggaccat cccggctaca acaacacgta 1080
ccagatcaat gcccgcacag agctggcggt ccgctacaat gacatctcac cgctggagaa 1140
ccaccactgc gccgtggcct tccagatcct cgccgagcct gagtgcaaca tcttctccaa 1200
catcccacct gatgggttca agcagatccg acagggaatg atcacattaa tcttggccac 1260
tgacatggca agacatgcag aaattatgga ttctttcaaa gagaaaatgg agaattttga 1320
ctacagcaac gaggagcaca tgaccctgct gaagatgatt ttgataaaat gctgtgatat 1380
ctctaacgag gtccgtccaa tggaagtcgc agagccttgg gtggactgtt tattagagga 1440
atattttatg cagagcgacc gtgagaagtc agaaggcctt cctgtggcac cgttcatgga 1500
ccgagacaaa gtgaccaagg ccacagccca gattgggttc atcaagtttg tcctgatccc 1560
aatgtttgaa acagtgacca agctcttccc catggttgag gagatcatgc tgcagccact 1620
ttgggaatcc cgagatcgct acgaggagct gaagcggata gatgacgcca tgaaagagtt 1680
acagaagaag actgacagct tgacgtctgg ggccaccgag aagtccagag agagaagcag 1740
agatgtgaaa aacagtgaag gagactgtgc ctgaggaaag cggggggcgt ggctgcagtt 1800
ctggacgggc tggccgagct gcgcgggatc cttgtgcagg gaagagctgc cctgggcacc 1860
tggcaccaca agaccatgtt ttctaagaac cattttgttc actgatacaa aaaaaaaaaa 1920
aggaattcat gatgctgtac agaattttat ttttaaactg tcttttaaat aatatattct 1980
tatacggaaa aaaaaaaaaa aaaaaaaaaa aaaaaaaaaa aaaaaaaaaa aa 2032

<210> SEQ ID NO 18
<211> LENGTH: 2025
<212> TYPE: DNA
<213> ORGANISM: Homo sapiens
<300> PUBLICATION INFORMATION:
<308> DATABASE ACCESSION NUMBER: Genbank / NM_001001583.1
<309> DATABASE ENTRY DATE: 2008-10-24
<313> RELEVANT RESIDUES IN SEQ ID NO: (1)..(2025)

<400> SEQUENCE: 18
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga aggtaatctt cagcaagtac tgcaactcca gcgacatcat ggacctgttc 180
tgcatcgcca ccggcctgcc tcgcactccg tacaaagtga gacctgtggc catcaagcaa 240
ctctccgctg gtgtcgagga caagagaacc acaagccgtg gccagtctgc tgagagacca 300
ctgagggaca gacgggttgt gggcctggag cagccccgga gggaaggagc atttgaaagt 360
ggacaggtag agcccaggcc cagagagccc cagggctgct accaggaagg ccagcgcatc 420
cctccagaga gagaagaatt aatccagagc gtgctggcgc aggttgcaga gcagttctca 480
agagcattca aaatcaatga actgaaagct gaagttgcaa atcacttggc tgtcctagag 540
aaacgcgtgg aattggaagg actaaaagtg gtggagattg agaaatgcaa gagtgacatt 600
aagaagatga gggaggagct ggcggccaga agcagcagga ccaactgccc ctgtaagtac 660 agtttttttgg ataaccacaa gaagttgact cctcgacgcg atgttcccac ttaccccaag 720
tacctgctct ctccagagac catcgaggcc ctgcggaagc cgacctttga cgtctggctt 780
tgggagccca atgagatgct gagctgcctg gagcacatgt accacgacct cgggctggtc 840
agggacttca gcatcaaccc tgtcaccctc aggaggtggc tgttctgcgt ccacgacaac 900
tacagaaaca accccttcca caacttccgg cactgcttct gcgtggccca gatgatgtac 960
agcatggtct ggctctgcag tctccaggag aagttctcac aaacggatat cctgatccta 1020
atgacagcgg ccatctgcca cgatctggac catcccggct acaacaacac gtaccagatc 1080
aatgcccgca cagagctggc ggtccgctac aatgacatct caccgctgga gaaccaccac 1140
tgcgccgtgg ccttccagat cctcgccgag cctgagtgca acatcttctc caacatccca 1200
cctgatgggt tcaagcagat ccgacaggga atgatcacat taatcttggc cactgacatg 1260
gcaagacatg cagaaattat ggattctttc aaagagaaaa tggagaattt tgactacagc 1320
aacgaggagc acatgaccct gctgaagatg attttgataa aatgctgtga tatctctaac 1380
gaggtccgtc caatggaagt cgcagagcct tgggtggact gtttattaga ggaatatttt 1440
atgcagagcg accgtgagaa gtcagaaggc cttcctgtgg caccgttcat ggaccgagac 1500
aaagtgacca aggccacagc ccagattggg ttcatcaagt ttgtcctgat cccaatgttt 1560
gaaacagtga ccaagctctt ccccatggtt gaggagatca tgctgcagcc actttgggaa 1620
tcccgagatc gctacgagga gctgaagcgg atagatgacg ccatgaaaga gttacagaag 1680
aagactgaca gcttgacgtc tggggccacc gagaagtcca gagagagaag cagagatgtg 1740
aaaaacagtg aaggagactg tgcctgagga aagcgggggg cgtggctgca gttctggacg 1800
ggctggccga gctgcgcggg atccttgtgc agggaagagc tgccctgggc acctggcacc 1860
acaagaccat gttttctaag aaccattttg ttcactgata caaaaaaaaa aaaaggaatt 1920
catgatgctg tacagaattt tatttttaaa ctgtctttta aataatatat tcttatacgg 1980
aaaaaaaaaa aaaaaaaaaa aaaaaaaaaa aaaaaaaaaa aaaaa 2025

<210> SEQ ID NO 19
<211> LENGTH: 1853
<212> TYPE: DNA
<213> ORGANISM: Homo sapiens
<300> PUBLICATION INFORMATION:
<308> DATABASE ACCESSION NUMBER: Genbank / NM_001001584.2
<309> DATABASE ENTRY DATE: 2008-10-24
<313> RELEVANT RESIDUES IN SEQ ID NO: (1)..(1853)

<400> SEQUENCE: 19
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga agcactccgt acaaagtgag acctgtggcc atcaagcaac tctccgcaaa 180
agaatgcaga ttttgcatta tctaaagagg cggttccgtg agcccactgt gctgagtcac 240
atatattcca tcggtagaga gaagaattaa tccagagcgt gctggcgcag gttgcagagc 300
agttctcaag agcattcaaa atcaatgaac tgaaagctga agttgcaaat cacttggctg 360
tcctagagaa acgcgtggaa ttggaaggac taaaagtggt ggagattgag aaatgcaaga 420
gtgacattaa gaagatgagg gaggagctgg cggccagaag cagcaggacc aactgcccct 480
gtaagtacag tttttggat aaccacaaga agttgactcc tcgacgcgat gttcccactt 540
accccaagta cctgctctct ccagagacca tcgaggccct gcggaagccg acctttgacg 600
tctggctttg ggagcccaat gagatgctga gctgcctgga gcacatgtac cacgacctcg 660
ggctggtcag ggacttcagc atcaaccctg tcaccctcag gaggtggctg ttctgcgtcc 720
acgacaacta cagaaacaac cccttccaca acttccggca ctgcttctgc gtggcccaga 780
tgatgtacag catggtctgg ctctgcagtc tccaggagaa gttctcacaa acggatatcc 840
tgatcctaat gacagcggcc atctgccacg atctggacca tcccggctac aacaacacgt 900
accagatcaa tgcccgcaca gagctggcgg tccgctacaa tgacatctca ccgctggaga 960
accaccactg cgccgtggcc ttccagatcc tcgccgagcc tgagtgcaac atcttctcca 1020
acatccccac tgatgggttc aagcagatcc gacagggaat gatcacatta atcttggcca 1080
ctgacatggc aagacatgca gaaattatgg attctttcaa agagaaaatg gagaattttg 1140
actacagcaa cgaggagcac atgaccctgc tgaagatgat tttgataaaa tgctgtgata 1200
tctctaacga ggtccgtcca atggaagtcg cagagccttg ggtggactgt ttattagagg 1260
aatattttat gcagagcgac cgtgagaagt cagaaggcct tcctgtggca ccgttcatgg 1320
accgagacaa agtgaccaag gccacagccc agattgggtt catcaagttt gtcctgatcc 1380
caatgtttga aacagtgacc aagctcttcc ccatggttga ggagatcatg ctgcagccac 1440
tttgggaatc ccgagatcgc tacgaggagc tgaagcggat agatgacgcc atgaaagagt 1500
tacagaagaa gactgacagc ttgacgtctg gggccaccga gaagtccaga gagagaagca 1560
gagatgtgaa aaacagtgaa ggagactgtg cctgaggaaa gcggggggcg tggctgcagt 1620
tctggacggg ctggccgagc tgcgcgggat ccttgtgcag ggaagagctg ccctgggcac 1680
ctggcaccac aagaccatgt tttctaagaa ccattttgtt cactgataca aaaaaaaaaa 1740
aaggaattca tgatgctgta cagaatttta tttttaaact gtcttttaaa taatatattc 1800
ttatacggaa aaaaaaaaaa aaaaaaaaaa aaaaaaaaaa aaaaaaaaaa aaa 1853

<210> SEQ ID NO 20
<211> LENGTH: 1977
<212> TYPE: DNA
<213> ORGANISM: Homo sapiens
<300> PUBLICATION INFORMATION:
<308> DATABASE ACCESSION NUMBER: Genbank / NM_001001585.1
<309> DATABASE ENTRY DATE: 2008-10-24
<313> RELEVANT RESIDUES IN SEQ ID NO: (1)..(1977)

<400> SEQUENCE: 20
tcccgcggcg gctggcgtcg ggaaagtaca gtaaaaagtc cgagtgcagc cgccgggcgc 60
aggatgggat ccggctcctc cagctaccgg cccaaggcca tctacctgga catcgatgga 120
cgcattcaga aggaacacga ccatctccct gctgaccacc gacgacgcca tggtctccat 180
cgaccccacc atgcccgcga attcagaacg cactccgtac aaagtgagac ctgtggccat 240
caagcaactc tccgctggtg tcgaggacaa gagaaccaca agccgtggcc agtctgctga 300
gagaccactg agggacagac gggttgtggg cctggagcag ccccggaggg aaggagcatt 360
tgaaagtgga caggtagagc ccaggcccag agagccccag ggctgctacc aggaaggcca 420
gcgcatccct ccagagcatt caaaatcaat gaactgaaag ctgaagttgc aaatcacttg 480
gctgtcctag agaaacgcgt ggaattggaa ggactaaaag tggtggagat tgagaaatgc 540
aagagtgaca ttaagaagat gagggaggag ctggcggcca gaagcagcag gaccaactgc 600
ccctgtaagt acagtttttt ggataaccac aagaagttga ctcctcgacg cgatgttccc 660
acttacccca agtacctgct ctctccagag accatcgagg ccctgcggaa gccgaccttt 720
gacgtctggc tttgggagcc caatgagatg ctgagctgcc tggagcacat gtaccacgac 780
ctcgggctgg tcagggactt cagcatcaac cctgtcaccc tcaggaggtg gctgttctgc 840
gtccacgaca actacagaaa caacccctte cacaacttcc ggcactgctt ctgcgtggcc 900
cagatgatgt acagcatggt ctggctctgc agtctccagg agaagttctc acaaacggat 960
atcctgatcc taatgacagc ggccatctgc cacgatctgg accatcccgg ctacaacaac 1020
acgtaccaga tcaatgcccg cacagagctg gcggtccgct acaatgacat ctcaccgctg 1080
gagaaccacc actgcgccgt ggccttccag atcctcgccg agcctgagtg caacatcttc 1140
tccaacatcc cacctgatgg gttcaagcag atccgacagg gaatgatcac attaatcttg 1200
gccactgaca tggcaagaca tgcagaaatt atggattctt tcaaagagaa aatggagaat 1260
tttgactaca gcaacgagga gcacatgacc ctgctgaaga tgattttgat aaaatgctgt 1320
gatatctcta acgaggtccg tccaatggaa gtcgcagagc cttgggtgga ctgtttatta 1380
gaggaatatt ttatgcagag cgaccgtgag aagtcagaag gccttcctgt ggcaccgttc 1440
atggaccgag acaaagtgac caaggccaca gcccagattg ggttcatcaa gtttgtcctg 1500
atcccaatgt ttgaaacagt gaccaagctc ttccccatgg ttgaggagat catgctgcag 1560
ccactttggg aatcccgaga tcgctacgag gagctgaagc ggatagatga cgccatgaaa 1620
gagttacaga agaagactga cagcttgacg tctggggcca ccgagaagtc cagagagaga 1680
agcagagatg tgaaaaacag tgaaggagac tgtgcctgag gaaagcgggg ggcgtggctg 1740
cagttctgga cgggctggcc gagctgcgcg ggatccttgt gcagggaaga gctgccctgg 1800
gcacctggca ccacaagacc atgttttcta agaaccattt tgttcactga tacaaaaaaa 1860

```
aaaaaaggaa ttcatgatgc tgtacagaat tttattttta aactgtcttt taaataatat   1920

attcttatac ggaaaaaaaa aaaaaaaaaa aaaaaaaaaa aaaaaaaaaa aaaaaaa      1977


<210> SEQ ID NO 21
<211> LENGTH: 593
<212> TYPE: PRT
<213> ORGANISM: Homo sapiens
<300> PUBLICATION INFORMATION:
<308> DATABASE ACCESSION NUMBER: Genbank / NM_002606.2
<309> DATABASE ENTRY DATE: 2008-10-24
<313> RELEVANT RESIDUES IN SEQ ID NO: (1)..(593)

<400> SEQUENCE: 21

Met Gly Ser Gly Ser Ser Ser Tyr Arg Pro Lys Ala Ile Tyr Leu Asp
1               5                   10                  15

Ile Asp Gly Arg Ile Gln Lys Val Ile Phe Ser Lys Tyr Cys Asn Ser
            20                  25                  30

Ser Asp Ile Met Asp Leu Phe Cys Ile Ala Thr Gly Leu Pro Arg Asn
        35                  40                  45

Thr Thr Ile Ser Leu Leu Thr Thr Asp Asp Ala Met Val Ser Ile Asp
    50                  55                  60

Pro Thr Met Pro Ala Asn Ser Glu Arg Thr Pro Tyr Lys Val Arg Pro
65                  70                  75                  80

Val Ala Ile Lys Gln Leu Ser Ala Gly Val Glu Asp Lys Arg Thr Thr
                85                  90                  95

Ser Arg Gly Gln Ser Ala Glu Arg Pro Leu Arg Asp Arg Arg Val Val
            100                 105                 110

Gly Leu Glu Gln Pro Arg Arg Glu Gly Ala Phe Glu Ser Gly Gln Val
        115                 120                 125

Glu Pro Arg Pro Arg Glu Pro Gln Gly Cys Tyr Gln Glu Gly Gln Arg
    130                 135                 140

Ile Pro Pro Glu Arg Glu Glu Leu Ile Gln Ser Val Leu Ala Gln Val
145                 150                 155                 160

Ala Glu Gln Phe Ser Arg Ala Phe Lys Ile Asn Glu Leu Lys Ala Glu
                165                 170                 175

Val Ala Asn His Leu Ala Val Leu Glu Lys Arg Val Glu Leu Glu Gly
            180                 185                 190

Leu Lys Val Val Glu Ile Glu Lys Cys Lys Ser Asp Ile Lys Lys Met
        195                 200                 205

Arg Glu Glu Leu Ala Ala Arg Ser Ser Arg Thr Asn Cys Pro Cys Lys
    210                 215                 220

Tyr Ser Phe Leu Asp Asn His Lys Lys Leu Thr Pro Arg Arg Asp Val
225                 230                 235                 240

Pro Thr Tyr Pro Lys Tyr Leu Leu Ser Pro Glu Thr Ile Glu Ala Leu
                245                 250                 255

Arg Lys Pro Thr Phe Asp Val Trp Leu Trp Glu Pro Asn Glu Met Leu
            260                 265                 270

Ser Cys Leu Glu His Met Tyr His Asp Leu Gly Leu Val Arg Asp Phe
        275                 280                 285

Ser Ile Asn Pro Val Thr Leu Arg Arg Trp Leu Phe Cys Val His Asp
    290                 295                 300

Asn Tyr Arg Asn Asn Pro Phe His Asn Phe Arg His Cys Phe Cys Val
305                 310                 315                 320

Ala Gln Met Met Tyr Ser Met Val Trp Leu Cys Ser Leu Gln Glu Lys
                325                 330                 335
```

Phe Ser Gln Thr Asp Ile Leu Ile Leu Met Thr Ala Ala Ile Cys His
340 345 350

Asp Leu Asp His Pro Gly Tyr Asn Asn Thr Tyr Gln Ile Asn Ala Arg
355 360 365

Thr Glu Leu Ala Val Arg Tyr Asn Asp Ile Ser Pro Leu Glu Asn His
370 375 380

His Cys Ala Val Ala Phe Gln Ile Leu Ala Glu Pro Glu Cys Asn Ile
385 390 395 400

Phe Ser Asn Ile Pro Pro Asp Gly Phe Lys Gln Ile Arg Gln Gly Met
405 410 415

Ile Thr Leu Ile Leu Ala Thr Asp Met Ala Arg His Ala Glu Ile Met
420 425 430

Asp Ser Phe Lys Glu Lys Met Glu Asn Phe Asp Tyr Ser Asn Glu Glu
435 440 445

His Met Thr Leu Leu Lys Met Ile Leu Ile Lys Cys Cys Asp Ile Ser
450 455 460

Asn Glu Val Arg Pro Met Glu Val Ala Glu Pro Trp Val Asp Cys Leu
465 470 475 480

Leu Glu Glu Tyr Phe Met Gln Ser Asp Arg Glu Lys Ser Glu Gly Leu
485 490 495

Pro Val Ala Pro Phe Met Asp Arg Asp Lys Val Thr Lys Ala Thr Ala
500 505 510

Gln Ile Gly Phe Ile Lys Phe Val Leu Ile Pro Met Phe Glu Thr Val
515 520 525

Thr Lys Leu Phe Pro Met Val Glu Glu Ile Met Leu Gln Pro Leu Trp
530 535 540

Glu Ser Arg Asp Arg Tyr Glu Glu Leu Lys Arg Ile Asp Asp Ala Met
545 550 555 560

Lys Glu Leu Gln Lys Lys Thr Asp Ser Leu Thr Ser Gly Ala Thr Glu
565 570 575

Lys Ser Arg Glu Arg Ser Arg Asp Val Lys Asn Ser Glu Gly Asp Cys
580 585 590

Ala

<210> SEQ ID NO 22
<211> LENGTH: 533
<212> TYPE: PRT
<213> ORGANISM: Homo sapiens
<300> PUBLICATION INFORMATION:
<308> DATABASE ACCESSION NUMBER: Genbank / NM_001001567.1
<309> DATABASE ENTRY DATE: 2008-10-24
<313> RELEVANT RESIDUES IN SEQ ID NO: (1)..(533)

<400> SEQUENCE: 22

Met Gly Ser Gly Ser Ser Ser Tyr Arg Pro Lys Ala Ile Tyr Leu Asp
1 5 10 15

Ile Asp Gly Arg Ile Gln Lys Val Ile Phe Ser Lys Tyr Cys Asn Ser
20 25 30

Ser Asp Ile Met Asp Leu Phe Cys Ile Ala Thr Gly Leu Pro Arg Asn
35 40 45

Thr Thr Ile Ser Leu Leu Thr Thr Asp Asp Ala Met Val Ser Ile Asp
50 55 60

Pro Thr Met Pro Ala Asn Ser Glu Arg Thr Pro Tyr Lys Val Arg Pro
65 70 75 80

Val Ala Ile Lys Gln Leu Ser Glu Arg Glu Glu Leu Ile Gln Ser Val

```
                85                  90                  95

Leu Ala Gln Val Ala Glu Gln Phe Ser Arg Ala Phe Lys Ile Asn Glu
            100                 105                 110

Leu Lys Ala Glu Val Ala Asn His Leu Ala Val Leu Glu Lys Arg Val
        115                 120                 125

Glu Leu Glu Gly Leu Lys Val Val Glu Ile Glu Lys Cys Lys Ser Asp
    130                 135                 140

Ile Lys Lys Met Arg Glu Glu Leu Ala Ala Arg Ser Ser Arg Thr Asn
145                 150                 155                 160

Cys Pro Cys Lys Tyr Ser Phe Leu Asp Asn His Lys Lys Leu Thr Pro
                165                 170                 175

Arg Arg Asp Val Pro Thr Tyr Pro Lys Tyr Leu Leu Ser Pro Glu Thr
            180                 185                 190

Ile Glu Ala Leu Arg Lys Pro Thr Phe Asp Val Trp Leu Trp Glu Pro
        195                 200                 205

Asn Glu Met Leu Ser Cys Leu Glu His Met Tyr His Asp Leu Gly Leu
    210                 215                 220

Val Arg Asp Phe Ser Ile Asn Pro Val Thr Leu Arg Arg Trp Leu Phe
225                 230                 235                 240

Cys Val His Asp Asn Tyr Arg Asn Asn Pro Phe His Asn Phe Arg His
                245                 250                 255

Cys Phe Cys Val Ala Gln Met Met Tyr Ser Met Val Trp Leu Cys Ser
            260                 265                 270

Leu Gln Glu Lys Phe Ser Gln Thr Asp Ile Leu Ile Leu Met Thr Ala
        275                 280                 285

Ala Ile Cys His Asp Leu Asp His Pro Gly Tyr Asn Asn Thr Tyr Gln
    290                 295                 300

Ile Asn Ala Arg Thr Glu Leu Ala Val Arg Tyr Asn Asp Ile Ser Pro
305                 310                 315                 320

Leu Glu Asn His His Cys Ala Val Ala Phe Gln Ile Leu Ala Glu Pro
                325                 330                 335

Glu Cys Asn Ile Phe Ser Asn Ile Pro Pro Asp Gly Phe Lys Gln Ile
            340                 345                 350

Arg Gln Gly Met Ile Thr Leu Ile Leu Ala Thr Asp Met Ala Arg His
        355                 360                 365

Ala Glu Ile Met Asp Ser Phe Lys Glu Lys Met Glu Asn Phe Asp Tyr
    370                 375                 380

Ser Asn Glu Glu His Met Thr Leu Leu Lys Met Ile Leu Ile Lys Cys
385                 390                 395                 400

Cys Asp Ile Ser Asn Glu Val Arg Pro Met Glu Val Ala Glu Pro Trp
                405                 410                 415

Val Asp Cys Leu Leu Glu Glu Tyr Phe Met Gln Ser Asp Arg Glu Lys
            420                 425                 430

Ser Glu Gly Leu Pro Val Ala Pro Phe Met Asp Arg Asp Lys Val Thr
        435                 440                 445

Lys Ala Thr Ala Gln Ile Gly Phe Ile Lys Phe Val Leu Ile Pro Met
    450                 455                 460

Phe Glu Thr Val Thr Lys Leu Phe Pro Met Val Glu Glu Ile Met Leu
465                 470                 475                 480

Gln Pro Leu Trp Glu Ser Arg Asp Arg Tyr Glu Glu Leu Lys Arg Ile
                485                 490                 495

Asp Asp Ala Met Lys Glu Leu Gln Lys Lys Thr Asp Ser Leu Thr Ser
            500                 505                 510
```

```
Gly Ala Thr Glu Lys Ser Arg Glu Arg Ser Arg Asp Val Lys Asn Ser
        515                 520                 525

Glu Gly Asp Cys Ala
    530


<210> SEQ ID NO 23
<211> LENGTH: 466
<212> TYPE: PRT
<213> ORGANISM: Homo sapiens
<300> PUBLICATION INFORMATION:
<308> DATABASE ACCESSION NUMBER: Genbank / NM_001001568.1
<309> DATABASE ENTRY DATE: 2008-10-24
<313> RELEVANT RESIDUES IN SEQ ID NO: (1)..(466)

<400> SEQUENCE: 23

Met Asp Ala Phe Arg Ser Thr Pro Tyr Lys Val Arg Pro Val Ala Ile
1               5                   10                  15

Lys Gln Leu Ser Glu Arg Glu Glu Leu Ile Gln Ser Val Leu Ala Gln
            20                  25                  30

Val Ala Glu Gln Phe Ser Arg Ala Phe Lys Ile Asn Glu Leu Lys Ala
        35                  40                  45

Glu Val Ala Asn His Leu Ala Val Leu Glu Lys Arg Val Glu Leu Glu
    50                  55                  60

Gly Leu Lys Val Val Glu Ile Glu Lys Cys Lys Ser Asp Ile Lys Lys
65                  70                  75                  80

Met Arg Glu Glu Leu Ala Ala Arg Ser Ser Arg Thr Asn Cys Pro Cys
                85                  90                  95

Lys Tyr Ser Phe Leu Asp Asn His Lys Lys Leu Thr Pro Arg Arg Asp
            100                 105                 110

Val Pro Thr Tyr Pro Lys Tyr Leu Leu Ser Pro Glu Thr Ile Glu Ala
        115                 120                 125

Leu Arg Lys Pro Thr Phe Asp Val Trp Leu Trp Glu Pro Asn Glu Met
    130                 135                 140

Leu Ser Cys Leu Glu His Met Tyr His Asp Leu Gly Leu Val Arg Asp
145                 150                 155                 160

Phe Ser Ile Asn Pro Val Thr Leu Arg Arg Trp Leu Phe Cys Val His
                165                 170                 175

Asp Asn Tyr Arg Asn Asn Pro Phe His Asn Phe Arg His Cys Phe Cys
            180                 185                 190

Val Ala Gln Met Met Tyr Ser Met Val Trp Leu Cys Ser Leu Gln Glu
        195                 200                 205

Lys Phe Ser Gln Thr Asp Ile Leu Ile Leu Met Thr Ala Ala Ile Cys
    210                 215                 220

His Asp Leu Asp His Pro Gly Tyr Asn Asn Thr Tyr Gln Ile Asn Ala
225                 230                 235                 240

Arg Thr Glu Leu Ala Val Arg Tyr Asn Asp Ile Ser Pro Leu Glu Asn
                245                 250                 255

His His Cys Ala Val Ala Phe Gln Ile Leu Ala Glu Pro Glu Cys Asn
            260                 265                 270

Ile Phe Ser Asn Ile Pro Pro Asp Gly Phe Lys Gln Ile Arg Gln Gly
        275                 280                 285

Met Ile Thr Leu Ile Leu Ala Thr Asp Met Ala Arg His Ala Glu Ile
    290                 295                 300

Met Asp Ser Phe Lys Glu Lys Met Glu Asn Phe Asp Tyr Ser Asn Glu
305                 310                 315                 320
```

```
Glu His Met Thr Leu Leu Lys Met Ile Leu Ile Lys Cys Cys Asp Ile
                325                 330                 335

Ser Asn Glu Val Arg Pro Met Glu Val Ala Glu Pro Trp Val Asp Cys
            340                 345                 350

Leu Leu Glu Glu Tyr Phe Met Gln Ser Asp Arg Glu Lys Ser Glu Gly
        355                 360                 365

Leu Pro Val Ala Pro Phe Met Asp Arg Asp Lys Val Thr Lys Ala Thr
    370                 375                 380

Ala Gln Ile Gly Phe Ile Lys Phe Val Leu Ile Pro Met Phe Glu Thr
385                 390                 395                 400

Val Thr Lys Leu Phe Pro Met Val Glu Glu Ile Met Leu Gln Pro Leu
                405                 410                 415

Trp Glu Ser Arg Asp Arg Tyr Glu Glu Leu Lys Arg Ile Asp Asp Ala
            420                 425                 430

Met Lys Glu Leu Gln Lys Lys Thr Asp Ser Leu Thr Ser Gly Ala Thr
        435                 440                 445

Glu Lys Ser Arg Glu Arg Ser Arg Asp Val Lys Asn Ser Glu Gly Asp
    450                 455                 460

Cys Ala
465


<210> SEQ ID NO 24
<211> LENGTH: 465
<212> TYPE: PRT
<213> ORGANISM: Homo sapiens
<300> PUBLICATION INFORMATION:
<308> DATABASE ACCESSION NUMBER: Genbank / NM_001001569.1
<309> DATABASE ENTRY DATE: 2008-10-24
<313> RELEVANT RESIDUES IN SEQ ID NO: (1)..(465)

<400> SEQUENCE: 24

Met Gly Ser Gly Ser Ser Ser Tyr Arg Pro Lys Ala Ile Tyr Leu Asp
1               5                   10                  15

Ile Asp Gly Arg Ile Gln Lys His Ser Val Gln Ser Glu Thr Cys Gly
            20                  25                  30

His Gln Ala Thr Leu Arg Ala Phe Lys Ile Asn Glu Leu Lys Ala Glu
        35                  40                  45

Val Ala Asn His Leu Ala Val Leu Glu Lys Arg Val Glu Leu Glu Gly
    50                  55                  60

Leu Lys Val Val Glu Ile Glu Lys Cys Lys Ser Asp Ile Lys Lys Met
65                  70                  75                  80

Arg Glu Glu Leu Ala Ala Arg Ser Ser Arg Thr Asn Cys Pro Cys Lys
                85                  90                  95

Tyr Ser Phe Leu Asp Asn His Lys Lys Leu Thr Pro Arg Arg Asp Val
            100                 105                 110

Pro Thr Tyr Pro Lys Tyr Leu Leu Ser Pro Glu Thr Ile Glu Ala Leu
        115                 120                 125

Arg Lys Pro Thr Phe Asp Val Trp Leu Trp Glu Pro Asn Glu Met Leu
    130                 135                 140

Ser Cys Leu Glu His Met Tyr His Asp Leu Gly Leu Val Arg Asp Phe
145                 150                 155                 160

Ser Ile Asn Pro Val Thr Leu Arg Arg Trp Leu Phe Cys Val His Asp
                165                 170                 175

Asn Tyr Arg Asn Asn Pro Phe His Asn Phe Arg His Cys Phe Cys Val
            180                 185                 190

Ala Gln Met Met Tyr Ser Met Val Trp Leu Cys Ser Leu Gln Glu Lys
```

```
        195                 200                 205

Phe Ser Gln Thr Asp Ile Leu Ile Leu Met Thr Ala Ala Ile Cys His
    210                 215                 220

Asp Leu Asp His Pro Gly Tyr Asn Asn Thr Tyr Gln Ile Asn Ala Arg
225                 230                 235                 240

Thr Glu Leu Ala Val Arg Tyr Asn Asp Ile Ser Pro Leu Glu Asn His
                245                 250                 255

His Cys Ala Val Ala Phe Gln Ile Leu Ala Glu Pro Glu Cys Asn Ile
            260                 265                 270

Phe Ser Asn Ile Pro Pro Asp Gly Phe Lys Gln Ile Arg Gln Gly Met
        275                 280                 285

Ile Thr Leu Ile Leu Ala Thr Asp Met Ala Arg His Ala Glu Ile Met
    290                 295                 300

Asp Ser Phe Lys Glu Lys Met Glu Asn Phe Asp Tyr Ser Asn Glu Glu
305                 310                 315                 320

His Met Thr Leu Leu Lys Met Ile Leu Ile Lys Cys Cys Asp Ile Ser
                325                 330                 335

Asn Glu Val Arg Pro Met Glu Val Ala Glu Pro Trp Val Asp Cys Leu
            340                 345                 350

Leu Glu Glu Tyr Phe Met Gln Ser Asp Arg Glu Lys Ser Glu Gly Leu
        355                 360                 365

Pro Val Ala Pro Phe Met Asp Arg Asp Lys Val Thr Lys Ala Thr Ala
    370                 375                 380

Gln Ile Gly Phe Ile Lys Phe Val Leu Ile Pro Met Phe Glu Thr Val
385                 390                 395                 400

Thr Lys Leu Phe Pro Met Val Glu Glu Ile Met Leu Gln Pro Leu Trp
                405                 410                 415

Glu Ser Arg Asp Arg Tyr Glu Glu Leu Lys Arg Ile Asp Asp Ala Met
            420                 425                 430

Lys Glu Leu Gln Lys Lys Thr Asp Ser Leu Thr Ser Gly Ala Thr Glu
        435                 440                 445

Lys Ser Arg Glu Arg Ser Arg Asp Val Lys Asn Ser Glu Gly Asp Cys
    450                 455                 460

Ala
465
```

<210> SEQ ID NO 25
<211> LENGTH: 540
<212> TYPE: PRT
<213> ORGANISM: Homo sapiens
<300> PUBLICATION INFORMATION:
<308> DATABASE ACCESSION NUMBER: Genbank / NM_001001570.1
<309> DATABASE ENTRY DATE: 2008-10-24
<313> RELEVANT RESIDUES IN SEQ ID NO: (1)..(540)

<400> SEQUENCE: 25

```
Met Gly Ser Gly Ser Ser Ser Tyr Arg Pro Lys Ala Ile Tyr Leu Asp
1               5                   10                  15

Ile Asp Gly Arg Ile Gln Lys Val Ile Phe Ser Lys Tyr Cys Asn Ser
            20                  25                  30

Ser Asp Ile Met Asp Leu Phe Cys Ile Ala Thr Gly Leu Pro Arg Asn
        35                  40                  45

Thr Thr Ile Ser Leu Leu Thr Thr Asp Asp Ala Met Val Ser Ile Asp
    50                  55                  60

Pro Thr Met Pro Ala Asn Ser Glu Arg Asn Glu Leu Ile Leu Tyr Thr
65                  70                  75                  80
```

-continued

```
Ser Leu Arg Asn Leu Leu Phe Leu Pro Ser Lys Glu Ser Trp Ala Ser
                85                  90                  95

His Gln His Ser Val Gln Ser Glu Thr Cys Gly His Gln Ala Thr Leu
            100                 105                 110

Arg Ala Phe Lys Ile Asn Glu Leu Lys Ala Glu Val Ala Asn His Leu
        115                 120                 125

Ala Val Leu Glu Lys Arg Val Glu Leu Glu Gly Leu Lys Val Val Glu
    130                 135                 140

Ile Glu Lys Cys Lys Ser Asp Ile Lys Lys Met Arg Glu Glu Leu Ala
145                 150                 155                 160

Ala Arg Ser Ser Arg Thr Asn Cys Pro Cys Lys Tyr Ser Phe Leu Asp
                165                 170                 175

Asn His Lys Lys Leu Thr Pro Arg Arg Asp Val Pro Thr Tyr Pro Lys
            180                 185                 190

Tyr Leu Leu Ser Pro Glu Thr Ile Glu Ala Leu Arg Lys Pro Thr Phe
        195                 200                 205

Asp Val Trp Leu Trp Glu Pro Asn Glu Met Leu Ser Cys Leu Glu His
    210                 215                 220

Met Tyr His Asp Leu Gly Leu Val Arg Asp Phe Ser Ile Asn Pro Val
225                 230                 235                 240

Thr Leu Arg Arg Trp Leu Phe Cys Val His Asp Asn Tyr Arg Asn Asn
                245                 250                 255

Pro Phe His Asn Phe Arg His Cys Phe Cys Val Ala Gln Met Met Tyr
            260                 265                 270

Ser Met Val Trp Leu Cys Ser Leu Gln Glu Lys Phe Ser Gln Thr Asp
        275                 280                 285

Ile Leu Ile Leu Met Thr Ala Ala Ile Cys His Asp Leu Asp His Pro
    290                 295                 300

Gly Tyr Asn Asn Thr Tyr Gln Ile Asn Ala Arg Thr Glu Leu Ala Val
305                 310                 315                 320

Arg Tyr Asn Asp Ile Ser Pro Leu Glu Asn His His Cys Ala Val Ala
                325                 330                 335

Phe Gln Ile Leu Ala Glu Pro Glu Cys Asn Ile Phe Ser Asn Ile Pro
            340                 345                 350

Pro Asp Gly Phe Lys Gln Ile Arg Gln Gly Met Ile Thr Leu Ile Leu
        355                 360                 365

Ala Thr Asp Met Ala Arg His Ala Glu Ile Met Asp Ser Phe Lys Glu
    370                 375                 380

Lys Met Glu Asn Phe Asp Tyr Ser Asn Glu Glu His Met Thr Leu Leu
385                 390                 395                 400

Lys Met Ile Leu Ile Lys Cys Cys Asp Ile Ser Asn Glu Val Arg Pro
                405                 410                 415

Met Glu Val Ala Glu Pro Trp Val Asp Cys Leu Leu Glu Glu Tyr Phe
            420                 425                 430

Met Gln Ser Asp Arg Glu Lys Ser Glu Gly Leu Pro Val Ala Pro Phe
        435                 440                 445

Met Asp Arg Asp Lys Val Thr Lys Ala Thr Ala Gln Ile Gly Phe Ile
    450                 455                 460

Lys Phe Val Leu Ile Pro Met Phe Glu Thr Val Thr Lys Leu Phe Pro
465                 470                 475                 480

Met Val Glu Glu Ile Met Leu Gln Pro Leu Trp Glu Ser Arg Asp Arg
                485                 490                 495
```

```
Tyr Glu Glu Leu Lys Arg Ile Asp Asp Ala Met Lys Glu Leu Gln Lys
            500                 505                 510

Lys Thr Asp Ser Leu Thr Ser Gly Ala Thr Glu Lys Ser Arg Glu Arg
        515                 520                 525

Ser Arg Asp Val Lys Asn Ser Glu Gly Asp Cys Ala
    530                 535                 540


<210> SEQ ID NO 26
<211> LENGTH: 492
<212> TYPE: PRT
<213> ORGANISM: Homo sapiens
<300> PUBLICATION INFORMATION:
<308> DATABASE ACCESSION NUMBER: Genbank / NM_001001571.1
<309> DATABASE ENTRY DATE: 2008-10-24
<313> RELEVANT RESIDUES IN SEQ ID NO: (1)..(492)

<400> SEQUENCE: 26

Met Asp Ala Phe Arg Arg Asn Thr Thr Ile Ser Leu Leu Thr Thr Asp
1               5                   10                  15

Asp Ala Met Val Ser Ile Asp Pro Thr Met Pro Ala Asn Ser Glu Arg
            20                  25                  30

Thr Pro Tyr Lys Val Arg Pro Val Ala Ile Lys Gln Leu Ser Glu Arg
        35                  40                  45

Glu Glu Leu Ile Gln Ser Val Leu Ala Gln Val Ala Glu Gln Phe Ser
    50                  55                  60

Arg Ala Phe Lys Ile Asn Glu Leu Lys Ala Glu Val Ala Asn His Leu
65                  70                  75                  80

Ala Val Leu Glu Lys Arg Val Glu Leu Glu Gly Leu Lys Val Val Glu
                85                  90                  95

Ile Glu Lys Cys Lys Ser Asp Ile Lys Lys Met Arg Glu Glu Leu Ala
            100                 105                 110

Ala Arg Ser Ser Arg Thr Asn Cys Pro Cys Lys Tyr Ser Phe Leu Asp
        115                 120                 125

Asn His Lys Lys Leu Thr Pro Arg Arg Asp Val Pro Thr Tyr Pro Lys
    130                 135                 140

Tyr Leu Leu Ser Pro Glu Thr Ile Glu Ala Leu Arg Lys Pro Thr Phe
145                 150                 155                 160

Asp Val Trp Leu Trp Glu Pro Asn Glu Met Leu Ser Cys Leu Glu His
                165                 170                 175

Met Tyr His Asp Leu Gly Leu Val Arg Asp Phe Ser Ile Asn Pro Val
            180                 185                 190

Thr Leu Arg Arg Trp Leu Phe Cys Val His Asp Asn Tyr Arg Asn Asn
        195                 200                 205

Pro Phe His Asn Phe Arg His Cys Phe Cys Val Ala Gln Met Met Tyr
    210                 215                 220

Ser Met Val Trp Leu Cys Ser Leu Gln Glu Lys Phe Ser Gln Thr Asp
225                 230                 235                 240

Ile Leu Ile Leu Met Thr Ala Ala Ile Cys His Asp Leu Asp His Pro
                245                 250                 255

Gly Tyr Asn Asn Thr Tyr Gln Ile Asn Ala Arg Thr Glu Leu Ala Val
            260                 265                 270

Arg Tyr Asn Asp Ile Ser Pro Leu Glu Asn His His Cys Ala Val Ala
        275                 280                 285

Phe Gln Ile Leu Ala Glu Pro Glu Cys Asn Ile Phe Ser Asn Ile Pro
    290                 295                 300

Pro Asp Gly Phe Lys Gln Ile Arg Gln Gly Met Ile Thr Leu Ile Leu
```

```
305                 310                 315                 320

Ala Thr Asp Met Ala Arg His Ala Glu Ile Met Asp Ser Phe Lys Glu
                325                 330                 335

Lys Met Glu Asn Phe Asp Tyr Ser Asn Glu Glu His Met Thr Leu Leu
            340                 345                 350

Lys Met Ile Leu Ile Lys Cys Cys Asp Ile Ser Asn Glu Val Arg Pro
        355                 360                 365

Met Glu Val Ala Glu Pro Trp Val Asp Cys Leu Leu Glu Glu Tyr Phe
    370                 375                 380

Met Gln Ser Asp Arg Glu Lys Ser Glu Gly Leu Pro Val Ala Pro Phe
385                 390                 395                 400

Met Asp Arg Asp Lys Val Thr Lys Ala Thr Ala Gln Ile Gly Phe Ile
                405                 410                 415

Lys Phe Val Leu Ile Pro Met Phe Glu Thr Val Thr Lys Leu Phe Pro
            420                 425                 430

Met Val Glu Glu Ile Met Leu Gln Pro Leu Trp Glu Ser Arg Asp Arg
        435                 440                 445

Tyr Glu Glu Leu Lys Arg Ile Asp Asp Ala Met Lys Glu Leu Gln Lys
    450                 455                 460

Lys Thr Asp Ser Leu Thr Ser Gly Ala Thr Glu Lys Ser Arg Glu Arg
465                 470                 475                 480

Ser Arg Asp Val Lys Asn Ser Glu Gly Asp Cys Ala
                485                 490


<210> SEQ ID NO 27
<211> LENGTH: 386
<212> TYPE: PRT
<213> ORGANISM: Homo sapiens
<300> PUBLICATION INFORMATION:
<308> DATABASE ACCESSION NUMBER: Genbank / NM_001001572.1
<309> DATABASE ENTRY DATE: 2008-10-24
<313> RELEVANT RESIDUES IN SEQ ID NO: (1)..(386)

<400> SEQUENCE: 27

Met Arg Glu Glu Leu Ala Ala Arg Ser Ser Arg Thr Asn Cys Pro Cys
1               5                   10                  15

Lys Tyr Ser Phe Leu Asp Asn His Lys Lys Leu Thr Pro Arg Arg Asp
            20                  25                  30

Val Pro Thr Tyr Pro Lys Tyr Leu Leu Ser Pro Glu Thr Ile Glu Ala
        35                  40                  45

Leu Arg Lys Pro Thr Phe Asp Val Trp Leu Trp Glu Pro Asn Glu Met
    50                  55                  60

Leu Ser Cys Leu Glu His Met Tyr His Asp Leu Gly Leu Val Arg Asp
65                  70                  75                  80

Phe Ser Ile Asn Pro Val Thr Leu Arg Arg Trp Leu Phe Cys Val His
                85                  90                  95

Asp Asn Tyr Arg Asn Asn Pro Phe His Asn Phe Arg His Cys Phe Cys
            100                 105                 110

Val Ala Gln Met Met Tyr Ser Met Val Trp Leu Cys Ser Leu Gln Glu
        115                 120                 125

Lys Phe Ser Gln Thr Asp Ile Leu Ile Leu Met Thr Ala Ala Ile Cys
    130                 135                 140

His Asp Leu Asp His Pro Gly Tyr Asn Asn Thr Tyr Gln Ile Asn Ala
145                 150                 155                 160

Arg Thr Glu Leu Ala Val Arg Tyr Asn Asp Ile Ser Pro Leu Glu Asn
                165                 170                 175
```

```
His His Cys Ala Val Ala Phe Gln Ile Leu Ala Glu Pro Glu Cys Asn
            180                 185                 190

Ile Phe Ser Asn Ile Pro Pro Asp Gly Phe Lys Gln Ile Arg Gln Gly
        195                 200                 205

Met Ile Thr Leu Ile Leu Ala Thr Asp Met Ala Arg His Ala Glu Ile
    210                 215                 220

Met Asp Ser Phe Lys Glu Lys Met Glu Asn Phe Asp Tyr Ser Asn Glu
225                 230                 235                 240

Glu His Met Thr Leu Leu Lys Met Ile Leu Ile Lys Cys Cys Asp Ile
                245                 250                 255

Ser Asn Glu Val Arg Pro Met Glu Val Ala Glu Pro Trp Val Asp Cys
            260                 265                 270

Leu Leu Glu Glu Tyr Phe Met Gln Ser Asp Arg Glu Lys Ser Glu Gly
        275                 280                 285

Leu Pro Val Ala Pro Phe Met Asp Arg Asp Lys Val Thr Lys Ala Thr
    290                 295                 300

Ala Gln Ile Gly Phe Ile Lys Phe Val Leu Ile Pro Met Phe Glu Thr
305                 310                 315                 320

Val Thr Lys Leu Phe Pro Met Val Glu Glu Ile Met Leu Gln Pro Leu
                325                 330                 335

Trp Glu Ser Arg Asp Arg Tyr Glu Glu Leu Lys Arg Ile Asp Asp Ala
            340                 345                 350

Met Lys Glu Leu Gln Lys Lys Thr Asp Ser Leu Thr Ser Gly Ala Thr
        355                 360                 365

Glu Lys Ser Arg Glu Arg Ser Arg Asp Val Lys Asn Ser Glu Gly Asp
    370                 375                 380

Cys Ala
385


<210> SEQ ID NO 28
<211> LENGTH: 386
<212> TYPE: PRT
<213> ORGANISM: Homo sapiens
<300> PUBLICATION INFORMATION:
<308> DATABASE ACCESSION NUMBER: Genbank / NM_001001573.1
<309> DATABASE ENTRY DATE: 2008-10-24
<313> RELEVANT RESIDUES IN SEQ ID NO: (1)..(386)

<400> SEQUENCE: 28

Met Arg Glu Glu Leu Ala Ala Arg Ser Ser Arg Thr Asn Cys Pro Cys
1               5                   10                  15

Lys Tyr Ser Phe Leu Asp Asn His Lys Lys Leu Thr Pro Arg Arg Asp
            20                  25                  30

Val Pro Thr Tyr Pro Lys Tyr Leu Leu Ser Pro Glu Thr Ile Glu Ala
        35                  40                  45

Leu Arg Lys Pro Thr Phe Asp Val Trp Leu Trp Glu Pro Asn Glu Met
    50                  55                  60

Leu Ser Cys Leu Glu His Met Tyr His Asp Leu Gly Leu Val Arg Asp
65                  70                  75                  80

Phe Ser Ile Asn Pro Val Thr Leu Arg Arg Trp Leu Phe Cys Val His
                85                  90                  95

Asp Asn Tyr Arg Asn Asn Pro Phe His Asn Phe Arg His Cys Phe Cys
            100                 105                 110

Val Ala Gln Met Met Tyr Ser Met Val Trp Leu Cys Ser Leu Gln Glu
        115                 120                 125
```

```
Lys Phe Ser Gln Thr Asp Ile Leu Ile Leu Met Thr Ala Ala Ile Cys
    130                 135                 140

His Asp Leu Asp His Pro Gly Tyr Asn Asn Thr Tyr Gln Ile Asn Ala
145                 150                 155                 160

Arg Thr Glu Leu Ala Val Arg Tyr Asn Asp Ile Ser Pro Leu Glu Asn
                165                 170                 175

His His Cys Ala Val Ala Phe Gln Ile Leu Ala Glu Pro Glu Cys Asn
            180                 185                 190

Ile Phe Ser Asn Ile Pro Pro Asp Gly Phe Lys Gln Ile Arg Gln Gly
        195                 200                 205

Met Ile Thr Leu Ile Leu Ala Thr Asp Met Ala Arg His Ala Glu Ile
    210                 215                 220

Met Asp Ser Phe Lys Glu Lys Met Glu Asn Phe Asp Tyr Ser Asn Glu
225                 230                 235                 240

Glu His Met Thr Leu Leu Lys Met Ile Leu Ile Lys Cys Cys Asp Ile
                245                 250                 255

Ser Asn Glu Val Arg Pro Met Glu Val Ala Glu Pro Trp Val Asp Cys
            260                 265                 270

Leu Leu Glu Glu Tyr Phe Met Gln Ser Asp Arg Glu Lys Ser Glu Gly
        275                 280                 285

Leu Pro Val Ala Pro Phe Met Asp Arg Asp Lys Val Thr Lys Ala Thr
    290                 295                 300

Ala Gln Ile Gly Phe Ile Lys Phe Val Leu Ile Pro Met Phe Glu Thr
305                 310                 315                 320

Val Thr Lys Leu Phe Pro Met Val Glu Glu Ile Met Leu Gln Pro Leu
                325                 330                 335

Trp Glu Ser Arg Asp Arg Tyr Glu Glu Leu Lys Arg Ile Asp Asp Ala
            340                 345                 350

Met Lys Glu Leu Gln Lys Lys Thr Asp Ser Leu Thr Ser Gly Ala Thr
        355                 360                 365

Glu Lys Ser Arg Glu Arg Ser Arg Asp Val Lys Asn Ser Glu Gly Asp
    370                 375                 380

Cys Ala
385
```

```
<210> SEQ ID NO 29
<211> LENGTH: 507
<212> TYPE: PRT
<213> ORGANISM: Homo sapiens
<300> PUBLICATION INFORMATION:
<308> DATABASE ACCESSION NUMBER: Genbank / NM_001001574.1
<309> DATABASE ENTRY DATE: 2008-10-24
<313> RELEVANT RESIDUES IN SEQ ID NO: (1)..(507)

<400> SEQUENCE: 29

Met Gly Ser Gly Ser Ser Ser Tyr Arg Pro Lys Ala Ile Tyr Leu Asp
1               5                   10                  15

Ile Asp Gly Arg Ile Gln Lys Val Ile Phe Ser Lys Tyr Cys Asn Ser
            20                  25                  30

Ser Asp Ile Met Asp Leu Phe Cys Ile Ala Thr Gly Leu Pro Arg Thr
        35                  40                  45

Pro Tyr Lys Val Arg Pro Val Ala Ile Lys Gln Leu Ser Glu Arg Glu
    50                  55                  60

Glu Leu Ile Gln Ser Val Leu Ala Gln Val Ala Glu Gln Phe Ser Arg
65                  70                  75                  80

Ala Phe Lys Ile Asn Glu Leu Lys Ala Glu Val Ala Asn His Leu Ala
```

-continued

```
                85                  90                  95

Val Leu Glu Lys Arg Val Glu Leu Glu Gly Leu Lys Val Val Glu Ile
            100                 105                 110

Glu Lys Cys Lys Ser Asp Ile Lys Lys Met Arg Glu Glu Leu Ala Ala
        115                 120                 125

Arg Ser Ser Arg Thr Asn Cys Pro Cys Lys Tyr Ser Phe Leu Asp Asn
    130                 135                 140

His Lys Lys Leu Thr Pro Arg Arg Asp Val Pro Thr Tyr Pro Lys Tyr
145                 150                 155                 160

Leu Leu Ser Pro Glu Thr Ile Glu Ala Leu Arg Lys Pro Thr Phe Asp
                165                 170                 175

Val Trp Leu Trp Glu Pro Asn Glu Met Leu Ser Cys Leu Glu His Met
            180                 185                 190

Tyr His Asp Leu Gly Leu Val Arg Asp Phe Ser Ile Asn Pro Val Thr
        195                 200                 205

Leu Arg Arg Trp Leu Phe Cys Val His Asp Asn Tyr Arg Asn Asn Pro
    210                 215                 220

Phe His Asn Phe Arg His Cys Phe Cys Val Ala Gln Met Met Tyr Ser
225                 230                 235                 240

Met Val Trp Leu Cys Ser Leu Gln Glu Lys Phe Ser Gln Thr Asp Ile
                245                 250                 255

Leu Ile Leu Met Thr Ala Ala Ile Cys His Asp Leu Asp His Pro Gly
            260                 265                 270

Tyr Asn Asn Thr Tyr Gln Ile Asn Ala Arg Thr Glu Leu Ala Val Arg
        275                 280                 285

Tyr Asn Asp Ile Ser Pro Leu Glu Asn His His Cys Ala Val Ala Phe
    290                 295                 300

Gln Ile Leu Ala Glu Pro Glu Cys Asn Ile Phe Ser Asn Ile Pro Pro
305                 310                 315                 320

Asp Gly Phe Lys Gln Ile Arg Gln Gly Met Ile Thr Leu Ile Leu Ala
                325                 330                 335

Thr Asp Met Ala Arg His Ala Glu Ile Met Asp Ser Phe Lys Glu Lys
            340                 345                 350

Met Glu Asn Phe Asp Tyr Ser Asn Glu Glu His Met Thr Leu Leu Lys
        355                 360                 365

Met Ile Leu Ile Lys Cys Cys Asp Ile Ser Asn Glu Val Arg Pro Met
    370                 375                 380

Glu Val Ala Glu Pro Trp Val Asp Cys Leu Leu Glu Glu Tyr Phe Met
385                 390                 395                 400

Gln Ser Asp Arg Glu Lys Ser Glu Gly Leu Pro Val Ala Pro Phe Met
                405                 410                 415

Asp Arg Asp Lys Val Thr Lys Ala Thr Ala Gln Ile Gly Phe Ile Lys
            420                 425                 430

Phe Val Leu Ile Pro Met Phe Glu Thr Val Thr Lys Leu Phe Pro Met
        435                 440                 445

Val Glu Glu Ile Met Leu Gln Pro Leu Trp Glu Ser Arg Asp Arg Tyr
    450                 455                 460

Glu Glu Leu Lys Arg Ile Asp Asp Ala Met Lys Glu Leu Gln Lys Lys
465                 470                 475                 480

Thr Asp Ser Leu Thr Ser Gly Ala Thr Glu Lys Ser Arg Glu Arg Ser
                485                 490                 495

Arg Asp Val Lys Asn Ser Glu Gly Asp Cys Ala
            500                 505
```

<210> SEQ ID NO 30
<211> LENGTH: 433
<212> TYPE: PRT
<213> ORGANISM: Homo sapiens
<300> PUBLICATION INFORMATION:
<308> DATABASE ACCESSION NUMBER: Genbank / NM_001001575.1
<309> DATABASE ENTRY DATE: 2008-10-24
<313> RELEVANT RESIDUES IN SEQ ID NO: (1)..(433)

<400> SEQUENCE: 30

```
Met Asp Ala Phe Arg Arg Ala Phe Lys Ile Asn Glu Leu Lys Ala Glu
1               5                   10                  15

Val Ala Asn His Leu Ala Val Leu Glu Lys Arg Val Glu Leu Glu Gly
            20                  25                  30

Leu Lys Val Val Glu Ile Glu Lys Cys Lys Ser Asp Ile Lys Lys Met
        35                  40                  45

Arg Glu Glu Leu Ala Ala Arg Ser Ser Arg Thr Asn Cys Pro Cys Lys
    50                  55                  60

Tyr Ser Phe Leu Asp Asn His Lys Lys Leu Thr Pro Arg Arg Asp Val
65                  70                  75                  80

Pro Thr Tyr Pro Lys Tyr Leu Leu Ser Pro Glu Thr Ile Glu Ala Leu
                85                  90                  95

Arg Lys Pro Thr Phe Asp Val Trp Leu Trp Glu Pro Asn Glu Met Leu
            100                 105                 110

Ser Cys Leu Glu His Met Tyr His Asp Leu Gly Leu Val Arg Asp Phe
        115                 120                 125

Ser Ile Asn Pro Val Thr Leu Arg Arg Trp Leu Phe Cys Val His Asp
    130                 135                 140

Asn Tyr Arg Asn Asn Pro Phe His Asn Phe Arg His Cys Phe Cys Val
145                 150                 155                 160

Ala Gln Met Met Tyr Ser Met Val Trp Leu Cys Ser Leu Gln Glu Lys
                165                 170                 175

Phe Ser Gln Thr Asp Ile Leu Ile Leu Met Thr Ala Ala Ile Cys His
            180                 185                 190

Asp Leu Asp His Pro Gly Tyr Asn Asn Thr Tyr Gln Ile Asn Ala Arg
        195                 200                 205

Thr Glu Leu Ala Val Arg Tyr Asn Asp Ile Ser Pro Leu Glu Asn His
    210                 215                 220

His Cys Ala Val Ala Phe Gln Ile Leu Ala Glu Pro Glu Cys Asn Ile
225                 230                 235                 240

Phe Ser Asn Ile Pro Pro Asp Gly Phe Lys Gln Ile Arg Gln Gly Met
                245                 250                 255

Ile Thr Leu Ile Leu Ala Thr Asp Met Ala Arg His Ala Glu Ile Met
            260                 265                 270

Asp Ser Phe Lys Glu Lys Met Glu Asn Phe Asp Tyr Ser Asn Glu Glu
        275                 280                 285

His Met Thr Leu Leu Lys Met Ile Leu Ile Lys Cys Cys Asp Ile Ser
    290                 295                 300

Asn Glu Val Arg Pro Met Glu Val Ala Glu Pro Trp Val Asp Cys Leu
305                 310                 315                 320

Leu Glu Glu Tyr Phe Met Gln Ser Asp Arg Glu Lys Ser Glu Gly Leu
                325                 330                 335

Pro Val Ala Pro Phe Met Asp Arg Asp Lys Val Thr Lys Ala Thr Ala
            340                 345                 350
```

```
Gln Ile Gly Phe Ile Lys Phe Val Leu Ile Pro Met Phe Glu Thr Val
        355                 360                 365

Thr Lys Leu Phe Pro Met Val Glu Glu Ile Met Leu Gln Pro Leu Trp
    370                 375                 380

Glu Ser Arg Asp Arg Tyr Glu Glu Leu Lys Arg Ile Asp Asp Ala Met
385                 390                 395                 400

Lys Glu Leu Gln Lys Lys Thr Asp Ser Leu Thr Ser Gly Ala Thr Glu
                405                 410                 415

Lys Ser Arg Glu Arg Ser Arg Asp Val Lys Asn Ser Glu Gly Asp Cys
            420                 425                 430

Ala


<210> SEQ ID NO 31
<211> LENGTH: 376
<212> TYPE: PRT
<213> ORGANISM: Homo sapiens
<300> PUBLICATION INFORMATION:
<308> DATABASE ACCESSION NUMBER: Genbank / NM_001001576.1
<309> DATABASE ENTRY DATE: 2008-10-24
<313> RELEVANT RESIDUES IN SEQ ID NO: (1)..(376)

<400> SEQUENCE: 31

Met Thr Asn Cys Pro Cys Lys Tyr Ser Phe Leu Asp Asn His Lys Lys
1               5                   10                  15

Leu Thr Pro Arg Arg Asp Val Pro Thr Tyr Pro Lys Tyr Leu Leu Ser
            20                  25                  30

Pro Glu Thr Ile Glu Ala Leu Arg Lys Pro Thr Phe Asp Val Trp Leu
        35                  40                  45

Trp Glu Pro Asn Glu Met Leu Ser Cys Leu Glu His Met Tyr His Asp
    50                  55                  60

Leu Gly Leu Val Arg Asp Phe Ser Ile Asn Pro Val Thr Leu Arg Arg
65                  70                  75                  80

Trp Leu Phe Cys Val His Asp Asn Tyr Arg Asn Asn Pro Phe His Asn
                85                  90                  95

Phe Arg His Cys Phe Cys Val Ala Gln Met Met Tyr Ser Met Val Trp
            100                 105                 110

Leu Cys Ser Leu Gln Glu Lys Phe Ser Gln Thr Asp Ile Leu Ile Leu
        115                 120                 125

Met Thr Ala Ala Ile Cys His Asp Leu Asp His Pro Gly Tyr Asn Asn
    130                 135                 140

Thr Tyr Gln Ile Asn Ala Arg Thr Glu Leu Ala Val Arg Tyr Asn Asp
145                 150                 155                 160

Ile Ser Pro Leu Glu Asn His His Cys Ala Val Ala Phe Gln Ile Leu
                165                 170                 175

Ala Glu Pro Glu Cys Asn Ile Phe Ser Asn Ile Pro Pro Asp Gly Phe
            180                 185                 190

Lys Gln Ile Arg Gln Gly Met Ile Thr Leu Ile Leu Ala Thr Asp Met
        195                 200                 205

Ala Arg His Ala Glu Ile Met Asp Ser Phe Lys Glu Lys Met Glu Asn
    210                 215                 220

Phe Asp Tyr Ser Asn Glu Glu His Met Thr Leu Leu Lys Met Ile Leu
225                 230                 235                 240

Ile Lys Cys Cys Asp Ile Ser Asn Glu Val Arg Pro Met Glu Val Ala
                245                 250                 255

Glu Pro Trp Val Asp Cys Leu Leu Glu Glu Tyr Phe Met Gln Ser Asp
            260                 265                 270
```

```
Arg Glu Lys Ser Glu Gly Leu Pro Val Ala Pro Phe Met Asp Arg Asp
        275                 280                 285

Lys Val Thr Lys Ala Thr Ala Gln Ile Gly Phe Ile Lys Phe Val Leu
    290                 295                 300

Ile Pro Met Phe Glu Thr Val Thr Lys Leu Phe Pro Met Val Glu Glu
305                 310                 315                 320

Ile Met Leu Gln Pro Leu Trp Glu Ser Arg Asp Arg Tyr Glu Glu Leu
                325                 330                 335

Lys Arg Ile Asp Asp Ala Met Lys Glu Leu Gln Lys Lys Thr Asp Ser
            340                 345                 350

Leu Thr Ser Gly Ala Thr Glu Lys Ser Arg Glu Arg Ser Arg Asp Val
        355                 360                 365

Lys Asn Ser Glu Gly Asp Cys Ala
    370                 375


<210> SEQ ID NO 32
<211> LENGTH: 459
<212> TYPE: PRT
<213> ORGANISM: Homo sapiens
<300> PUBLICATION INFORMATION:
<308> DATABASE ACCESSION NUMBER: Genbank / NM_001001577.1
<309> DATABASE ENTRY DATE: 2008-10-24
<313> RELEVANT RESIDUES IN SEQ ID NO: (1)..(459)

<400> SEQUENCE: 32

Met Asp Ala Phe Arg Arg Asn Thr Thr Ile Ser Leu Leu Thr Thr Asp
1               5                   10                  15

Asp Ala Met Val Ser Ile Asp Pro Thr Met Pro Ala Asn Ser Glu Arg
            20                  25                  30

Ala Phe Lys Ile Asn Glu Leu Lys Ala Glu Val Ala Asn His Leu Ala
        35                  40                  45

Val Leu Glu Lys Arg Val Glu Leu Glu Gly Leu Lys Val Val Glu Ile
    50                  55                  60

Glu Lys Cys Lys Ser Asp Ile Lys Lys Met Arg Glu Glu Leu Ala Ala
65                  70                  75                  80

Arg Ser Ser Arg Thr Asn Cys Pro Cys Lys Tyr Ser Phe Leu Asp Asn
                85                  90                  95

His Lys Lys Leu Thr Pro Arg Arg Asp Val Pro Thr Tyr Pro Lys Tyr
            100                 105                 110

Leu Leu Ser Pro Glu Thr Ile Glu Ala Leu Arg Lys Pro Thr Phe Asp
        115                 120                 125

Val Trp Leu Trp Glu Pro Asn Glu Met Leu Ser Cys Leu Glu His Met
    130                 135                 140

Tyr His Asp Leu Gly Leu Val Arg Asp Phe Ser Ile Asn Pro Val Thr
145                 150                 155                 160

Leu Arg Arg Trp Leu Phe Cys Val His Asp Asn Tyr Arg Asn Asn Pro
                165                 170                 175

Phe His Asn Phe Arg His Cys Phe Cys Val Ala Gln Met Met Tyr Ser
            180                 185                 190

Met Val Trp Leu Cys Ser Leu Gln Glu Lys Phe Ser Gln Thr Asp Ile
        195                 200                 205

Leu Ile Leu Met Thr Ala Ala Ile Cys His Asp Leu Asp His Pro Gly
    210                 215                 220

Tyr Asn Asn Thr Tyr Gln Ile Asn Ala Arg Thr Glu Leu Ala Val Arg
225                 230                 235                 240
```

-continued

```
Tyr Asn Asp Ile Ser Pro Leu Glu Asn His His Cys Ala Val Ala Phe
            245                 250                 255

Gln Ile Leu Ala Glu Pro Glu Cys Asn Ile Phe Ser Asn Ile Pro Pro
            260                 265                 270

Asp Gly Phe Lys Gln Ile Arg Gln Gly Met Ile Thr Leu Ile Leu Ala
        275                 280                 285

Thr Asp Met Ala Arg His Ala Glu Ile Met Asp Ser Phe Lys Glu Lys
    290                 295                 300

Met Glu Asn Phe Asp Tyr Ser Asn Glu Glu His Met Thr Leu Leu Lys
305                 310                 315                 320

Met Ile Leu Ile Lys Cys Cys Asp Ile Ser Asn Glu Val Arg Pro Met
                325                 330                 335

Glu Val Ala Glu Pro Trp Val Asp Cys Leu Leu Glu Glu Tyr Phe Met
            340                 345                 350

Gln Ser Asp Arg Glu Lys Ser Glu Gly Leu Pro Val Ala Pro Phe Met
        355                 360                 365

Asp Arg Asp Lys Val Thr Lys Ala Thr Ala Gln Ile Gly Phe Ile Lys
    370                 375                 380

Phe Val Leu Ile Pro Met Phe Glu Thr Val Thr Lys Leu Phe Pro Met
385                 390                 395                 400

Val Glu Glu Ile Met Leu Gln Pro Leu Trp Glu Ser Arg Asp Arg Tyr
                405                 410                 415

Glu Glu Leu Lys Arg Ile Asp Asp Ala Met Lys Glu Leu Gln Lys Lys
            420                 425                 430

Thr Asp Ser Leu Thr Ser Gly Ala Thr Glu Lys Ser Arg Glu Arg Ser
        435                 440                 445

Arg Asp Val Lys Asn Ser Glu Gly Asp Cys Ala
    450                 455
```

<210> SEQ ID NO 33
<211> LENGTH: 491
<212> TYPE: PRT
<213> ORGANISM: Homo sapiens
<300> PUBLICATION INFORMATION:
<308> DATABASE ACCESSION NUMBER: Genbank / NM_001001578.1
<309> DATABASE ENTRY DATE: 2008-10-24
<313> RELEVANT RESIDUES IN SEQ ID NO: (1)..(491)

<400> SEQUENCE: 33

```
Met Gly Ser Gly Ser Ser Ser Tyr Arg Pro Lys Ala Ile Tyr Leu Asp
1               5                   10                  15

Ile Asp Gly Arg Ile Gln Lys Glu His Asp His Leu Pro Ala Asp His
            20                  25                  30

Arg Arg Arg His Gly Leu His Arg Pro His His Ala Arg Glu Phe Arg
        35                  40                  45

Thr His Ser Val Gln Ser Glu Thr Cys Gly His Gln Ala Thr Leu Arg
    50                  55                  60

Ala Phe Lys Ile Asn Glu Leu Lys Ala Glu Val Ala Asn His Leu Ala
65                  70                  75                  80

Val Leu Glu Lys Arg Val Glu Leu Glu Gly Leu Lys Val Val Glu Ile
                85                  90                  95

Glu Lys Cys Lys Ser Asp Ile Lys Lys Met Arg Glu Glu Leu Ala Ala
            100                 105                 110

Arg Ser Ser Arg Thr Asn Cys Pro Cys Lys Tyr Ser Phe Leu Asp Asn
        115                 120                 125

His Lys Lys Leu Thr Pro Arg Arg Asp Val Pro Thr Tyr Pro Lys Tyr
```

```
    130                 135                 140

Leu Leu Ser Pro Glu Thr Ile Glu Ala Leu Arg Lys Pro Thr Phe Asp
145                 150                 155                 160

Val Trp Leu Trp Glu Pro Asn Glu Met Leu Ser Cys Leu Glu His Met
                165                 170                 175

Tyr His Asp Leu Gly Leu Val Arg Asp Phe Ser Ile Asn Pro Val Thr
            180                 185                 190

Leu Arg Arg Trp Leu Phe Cys Val His Asp Asn Tyr Arg Asn Asn Pro
        195                 200                 205

Phe His Asn Phe Arg His Cys Phe Cys Val Ala Gln Met Met Tyr Ser
    210                 215                 220

Met Val Trp Leu Cys Ser Leu Gln Glu Lys Phe Ser Gln Thr Asp Ile
225                 230                 235                 240

Leu Ile Leu Met Thr Ala Ala Ile Cys His Asp Leu Asp His Pro Gly
                245                 250                 255

Tyr Asn Asn Thr Tyr Gln Ile Asn Ala Arg Thr Glu Leu Ala Val Arg
            260                 265                 270

Tyr Asn Asp Ile Ser Pro Leu Glu Asn His His Cys Ala Val Ala Phe
        275                 280                 285

Gln Ile Leu Ala Glu Pro Glu Cys Asn Ile Phe Ser Asn Ile Pro Pro
    290                 295                 300

Asp Gly Phe Lys Gln Ile Arg Gln Gly Met Ile Thr Leu Ile Leu Ala
305                 310                 315                 320

Thr Asp Met Ala Arg His Ala Glu Ile Met Asp Ser Phe Lys Glu Lys
                325                 330                 335

Met Glu Asn Phe Asp Tyr Ser Asn Glu Glu His Met Thr Leu Leu Lys
            340                 345                 350

Met Ile Leu Ile Lys Cys Cys Asp Ile Ser Asn Glu Val Arg Pro Met
        355                 360                 365

Glu Val Ala Glu Pro Trp Val Asp Cys Leu Leu Glu Glu Tyr Phe Met
    370                 375                 380

Gln Ser Asp Arg Glu Lys Ser Glu Gly Leu Pro Val Ala Pro Phe Met
385                 390                 395                 400

Asp Arg Asp Lys Val Thr Lys Ala Thr Ala Gln Ile Gly Phe Ile Lys
                405                 410                 415

Phe Val Leu Ile Pro Met Phe Glu Thr Val Thr Lys Leu Phe Pro Met
            420                 425                 430

Val Glu Glu Ile Met Leu Gln Pro Leu Trp Glu Ser Arg Asp Arg Tyr
        435                 440                 445

Glu Glu Leu Lys Arg Ile Asp Asp Ala Met Lys Glu Leu Gln Lys Lys
    450                 455                 460

Thr Asp Ser Leu Thr Ser Gly Ala Thr Glu Lys Ser Arg Glu Arg Ser
465                 470                 475                 480

Arg Asp Val Lys Asn Ser Glu Gly Asp Cys Ala
                485                 490


<210> SEQ ID NO 34
<211> LENGTH: 386
<212> TYPE: PRT
<213> ORGANISM: Homo sapiens
<300> PUBLICATION INFORMATION:
<308> DATABASE ACCESSION NUMBER: Genbank / NM_001001579.1
<309> DATABASE ENTRY DATE: 2008-10-24
<313> RELEVANT RESIDUES IN SEQ ID NO: (1)..(386)

<400> SEQUENCE: 34
```

```
Met Arg Glu Glu Leu Ala Ala Arg Ser Ser Arg Thr Asn Cys Pro Cys
1               5                   10                  15

Lys Tyr Ser Phe Leu Asp Asn His Lys Lys Leu Thr Pro Arg Arg Asp
            20                  25                  30

Val Pro Thr Tyr Pro Lys Tyr Leu Leu Ser Pro Glu Thr Ile Glu Ala
        35                  40                  45

Leu Arg Lys Pro Thr Phe Asp Val Trp Leu Trp Glu Pro Asn Glu Met
    50                  55                  60

Leu Ser Cys Leu Glu His Met Tyr His Asp Leu Gly Leu Val Arg Asp
65                  70                  75                  80

Phe Ser Ile Asn Pro Val Thr Leu Arg Arg Trp Leu Phe Cys Val His
                85                  90                  95

Asp Asn Tyr Arg Asn Asn Pro Phe His Asn Phe Arg His Cys Phe Cys
            100                 105                 110

Val Ala Gln Met Met Tyr Ser Met Val Trp Leu Cys Ser Leu Gln Glu
        115                 120                 125

Lys Phe Ser Gln Thr Asp Ile Leu Ile Leu Met Thr Ala Ala Ile Cys
    130                 135                 140

His Asp Leu Asp His Pro Gly Tyr Asn Asn Thr Tyr Gln Ile Asn Ala
145                 150                 155                 160

Arg Thr Glu Leu Ala Val Arg Tyr Asn Asp Ile Ser Pro Leu Glu Asn
                165                 170                 175

His His Cys Ala Val Ala Phe Gln Ile Leu Ala Glu Pro Glu Cys Asn
            180                 185                 190

Ile Phe Ser Asn Ile Pro Pro Asp Gly Phe Lys Gln Ile Arg Gln Gly
        195                 200                 205

Met Ile Thr Leu Ile Leu Ala Thr Asp Met Ala Arg His Ala Glu Ile
    210                 215                 220

Met Asp Ser Phe Lys Glu Lys Met Glu Asn Phe Asp Tyr Ser Asn Glu
225                 230                 235                 240

Glu His Met Thr Leu Leu Lys Met Ile Leu Ile Lys Cys Cys Asp Ile
                245                 250                 255

Ser Asn Glu Val Arg Pro Met Glu Val Ala Glu Pro Trp Val Asp Cys
            260                 265                 270

Leu Leu Glu Glu Tyr Phe Met Gln Ser Asp Arg Glu Lys Ser Glu Gly
        275                 280                 285

Leu Pro Val Ala Pro Phe Met Asp Arg Asp Lys Val Thr Lys Ala Thr
    290                 295                 300

Ala Gln Ile Gly Phe Ile Lys Phe Val Leu Ile Pro Met Phe Glu Thr
305                 310                 315                 320

Val Thr Lys Leu Phe Pro Met Val Glu Glu Ile Met Leu Gln Pro Leu
                325                 330                 335

Trp Glu Ser Arg Asp Arg Tyr Glu Glu Leu Lys Arg Ile Asp Asp Ala
            340                 345                 350

Met Lys Glu Leu Gln Lys Lys Thr Asp Ser Leu Thr Ser Gly Ala Thr
        355                 360                 365

Glu Lys Ser Arg Glu Arg Ser Arg Asp Val Lys Asn Ser Glu Gly Asp
    370                 375                 380

Cys Ala
385
```

<210> SEQ ID NO 35
<211> LENGTH: 376

```
<212> TYPE: PRT
<213> ORGANISM: Homo sapiens
<300> PUBLICATION INFORMATION:
<308> DATABASE ACCESSION NUMBER: Genbank / NM_001001580.1
<309> DATABASE ENTRY DATE: 2008-10-24
<313> RELEVANT RESIDUES IN SEQ ID NO: (1)..(376)

<400> SEQUENCE: 35

Met Thr Asn Cys Pro Cys Lys Tyr Ser Phe Leu Asp Asn His Lys Lys
1               5                   10                  15

Leu Thr Pro Arg Arg Asp Val Pro Thr Tyr Pro Lys Tyr Leu Leu Ser
            20                  25                  30

Pro Glu Thr Ile Glu Ala Leu Arg Lys Pro Thr Phe Asp Val Trp Leu
        35                  40                  45

Trp Glu Pro Asn Glu Met Leu Ser Cys Leu Glu His Met Tyr His Asp
    50                  55                  60

Leu Gly Leu Val Arg Asp Phe Ser Ile Asn Pro Val Thr Leu Arg Arg
65                  70                  75                  80

Trp Leu Phe Cys Val His Asp Asn Tyr Arg Asn Asn Pro Phe His Asn
                85                  90                  95

Phe Arg His Cys Phe Cys Val Ala Gln Met Met Tyr Ser Met Val Trp
            100                 105                 110

Leu Cys Ser Leu Gln Glu Lys Phe Ser Gln Thr Asp Ile Leu Ile Leu
        115                 120                 125

Met Thr Ala Ala Ile Cys His Asp Leu Asp His Pro Gly Tyr Asn Asn
    130                 135                 140

Thr Tyr Gln Ile Asn Ala Arg Thr Glu Leu Ala Val Arg Tyr Asn Asp
145                 150                 155                 160

Ile Ser Pro Leu Glu Asn His His Cys Ala Val Ala Phe Gln Ile Leu
                165                 170                 175

Ala Glu Pro Glu Cys Asn Ile Phe Ser Asn Ile Pro Pro Asp Gly Phe
            180                 185                 190

Lys Gln Ile Arg Gln Gly Met Ile Thr Leu Ile Leu Ala Thr Asp Met
        195                 200                 205

Ala Arg His Ala Glu Ile Met Asp Ser Phe Lys Glu Lys Met Glu Asn
    210                 215                 220

Phe Asp Tyr Ser Asn Glu Glu His Met Thr Leu Leu Lys Met Ile Leu
225                 230                 235                 240

Ile Lys Cys Cys Asp Ile Ser Asn Glu Val Arg Pro Met Glu Val Ala
                245                 250                 255

Glu Pro Trp Val Asp Cys Leu Leu Glu Glu Tyr Phe Met Gln Ser Asp
            260                 265                 270

Arg Glu Lys Ser Glu Gly Leu Pro Val Ala Pro Phe Met Asp Arg Asp
        275                 280                 285

Lys Val Thr Lys Ala Thr Ala Gln Ile Gly Phe Ile Lys Phe Val Leu
    290                 295                 300

Ile Pro Met Phe Glu Thr Val Thr Lys Leu Phe Pro Met Val Glu Glu
305                 310                 315                 320

Ile Met Leu Gln Pro Leu Trp Glu Ser Arg Asp Arg Tyr Glu Glu Leu
                325                 330                 335

Lys Arg Ile Asp Asp Ala Met Lys Glu Leu Gln Lys Lys Thr Asp Ser
            340                 345                 350

Leu Thr Ser Gly Ala Thr Glu Lys Ser Arg Glu Arg Ser Arg Asp Val
        355                 360                 365

Lys Asn Ser Glu Gly Asp Cys Ala
```

```
    370                 375


<210> SEQ ID NO 36
<211> LENGTH: 526
<212> TYPE: PRT
<213> ORGANISM: Homo sapiens
<300> PUBLICATION INFORMATION:
<308> DATABASE ACCESSION NUMBER: Genbank / NM_001001581.1
<309> DATABASE ENTRY DATE: 2008-10-24
<313> RELEVANT RESIDUES IN SEQ ID NO: (1)..(526)

<400> SEQUENCE: 36

Met Asp Ala Phe Arg Ser Thr Pro Tyr Lys Val Arg Pro Val Ala Ile
1               5                   10                  15

Lys Gln Leu Ser Ala Gly Val Glu Asp Lys Arg Thr Thr Ser Arg Gly
            20                  25                  30

Gln Ser Ala Glu Arg Pro Leu Arg Asp Arg Arg Val Val Gly Leu Glu
        35                  40                  45

Gln Pro Arg Arg Glu Gly Ala Phe Glu Ser Gly Gln Val Glu Pro Arg
    50                  55                  60

Pro Arg Glu Pro Gln Gly Cys Tyr Gln Glu Gly Gln Arg Ile Pro Pro
65                  70                  75                  80

Glu Arg Glu Glu Leu Ile Gln Ser Val Leu Ala Gln Val Ala Glu Gln
                85                  90                  95

Phe Ser Arg Ala Phe Lys Ile Asn Glu Leu Lys Ala Glu Val Ala Asn
            100                 105                 110

His Leu Ala Val Leu Glu Lys Arg Val Glu Leu Glu Gly Leu Lys Val
        115                 120                 125

Val Glu Ile Glu Lys Cys Lys Ser Asp Ile Lys Lys Met Arg Glu Glu
    130                 135                 140

Leu Ala Ala Arg Ser Ser Arg Thr Asn Cys Pro Cys Lys Tyr Ser Phe
145                 150                 155                 160

Leu Asp Asn His Lys Lys Leu Thr Pro Arg Arg Asp Val Pro Thr Tyr
                165                 170                 175

Pro Lys Tyr Leu Leu Ser Pro Glu Thr Ile Glu Ala Leu Arg Lys Pro
            180                 185                 190

Thr Phe Asp Val Trp Leu Trp Glu Pro Asn Glu Met Leu Ser Cys Leu
        195                 200                 205

Glu His Met Tyr His Asp Leu Gly Leu Val Arg Asp Phe Ser Ile Asn
    210                 215                 220

Pro Val Thr Leu Arg Arg Trp Leu Phe Cys Val His Asp Asn Tyr Arg
225                 230                 235                 240

Asn Asn Pro Phe His Asn Phe Arg His Cys Phe Cys Val Ala Gln Met
                245                 250                 255

Met Tyr Ser Met Val Trp Leu Cys Ser Leu Gln Glu Lys Phe Ser Gln
            260                 265                 270

Thr Asp Ile Leu Ile Leu Met Thr Ala Ala Ile Cys His Asp Leu Asp
        275                 280                 285

His Pro Gly Tyr Asn Asn Thr Tyr Gln Ile Asn Ala Arg Thr Glu Leu
    290                 295                 300

Ala Val Arg Tyr Asn Asp Ile Ser Pro Leu Glu Asn His His Cys Ala
305                 310                 315                 320

Val Ala Phe Gln Ile Leu Ala Glu Pro Glu Cys Asn Ile Phe Ser Asn
                325                 330                 335

Ile Pro Pro Asp Gly Phe Lys Gln Ile Arg Gln Gly Met Ile Thr Leu
            340                 345                 350
```

```
Ile Leu Ala Thr Asp Met Ala Arg His Ala Glu Ile Met Asp Ser Phe
        355                 360                 365

Lys Glu Lys Met Glu Asn Phe Asp Tyr Ser Asn Glu Glu His Met Thr
    370                 375                 380

Leu Leu Lys Met Ile Leu Ile Lys Cys Cys Asp Ile Ser Asn Glu Val
385                 390                 395                 400

Arg Pro Met Glu Val Ala Glu Pro Trp Val Asp Cys Leu Leu Glu Glu
                405                 410                 415

Tyr Phe Met Gln Ser Asp Arg Glu Lys Ser Glu Gly Leu Pro Val Ala
            420                 425                 430

Pro Phe Met Asp Arg Asp Lys Val Thr Lys Ala Thr Ala Gln Ile Gly
        435                 440                 445

Phe Ile Lys Phe Val Leu Ile Pro Met Phe Glu Thr Val Thr Lys Leu
    450                 455                 460

Phe Pro Met Val Glu Glu Ile Met Leu Gln Pro Leu Trp Glu Ser Arg
465                 470                 475                 480

Asp Arg Tyr Glu Glu Leu Lys Arg Ile Asp Asp Ala Met Lys Glu Leu
                485                 490                 495

Gln Lys Lys Thr Asp Ser Leu Thr Ser Gly Ala Thr Glu Lys Ser Arg
            500                 505                 510

Glu Arg Ser Arg Asp Val Lys Asn Ser Glu Gly Asp Cys Ala
        515                 520                 525


<210> SEQ ID NO 37
<211> LENGTH: 552
<212> TYPE: PRT
<213> ORGANISM: Homo sapiens
<300> PUBLICATION INFORMATION:
<308> DATABASE ACCESSION NUMBER: Genbank / NM_001001582.1
<309> DATABASE ENTRY DATE: 2008-10-24
<313> RELEVANT RESIDUES IN SEQ ID NO: (1)..(552)

<400> SEQUENCE: 37

Met Asp Ala Phe Arg Arg Asn Thr Thr Ile Ser Leu Leu Thr Thr Asp
1               5                   10                  15

Asp Ala Met Val Ser Ile Asp Pro Thr Met Pro Ala Asn Ser Glu Arg
            20                  25                  30

Thr Pro Tyr Lys Val Arg Pro Val Ala Ile Lys Gln Leu Ser Ala Gly
        35                  40                  45

Val Glu Asp Lys Arg Thr Thr Ser Arg Gly Gln Ser Ala Glu Arg Pro
    50                  55                  60

Leu Arg Asp Arg Arg Val Val Gly Leu Glu Gln Pro Arg Arg Glu Gly
65                  70                  75                  80

Ala Phe Glu Ser Gly Gln Val Glu Pro Arg Pro Arg Glu Pro Gln Gly
                85                  90                  95

Cys Tyr Gln Glu Gly Gln Arg Ile Pro Pro Glu Arg Glu Glu Leu Ile
            100                 105                 110

Gln Ser Val Leu Ala Gln Val Ala Glu Gln Phe Ser Arg Ala Phe Lys
        115                 120                 125

Ile Asn Glu Leu Lys Ala Glu Val Ala Asn His Leu Ala Val Leu Glu
    130                 135                 140

Lys Arg Val Glu Leu Glu Gly Leu Lys Val Val Glu Ile Glu Lys Cys
145                 150                 155                 160

Lys Ser Asp Ile Lys Lys Met Arg Glu Glu Leu Ala Ala Arg Ser Ser
                165                 170                 175
```

-continued

```
Arg Thr Asn Cys Pro Cys Lys Tyr Ser Phe Leu Asp Asn His Lys Lys
            180                 185                 190

Leu Thr Pro Arg Arg Asp Val Pro Thr Tyr Pro Lys Tyr Leu Leu Ser
        195                 200                 205

Pro Glu Thr Ile Glu Ala Leu Arg Lys Pro Thr Phe Asp Val Trp Leu
    210                 215                 220

Trp Glu Pro Asn Glu Met Leu Ser Cys Leu Glu His Met Tyr His Asp
225                 230                 235                 240

Leu Gly Leu Val Arg Asp Phe Ser Ile Asn Pro Val Thr Leu Arg Arg
                245                 250                 255

Trp Leu Phe Cys Val His Asp Asn Tyr Arg Asn Asn Pro Phe His Asn
            260                 265                 270

Phe Arg His Cys Phe Cys Val Ala Gln Met Met Tyr Ser Met Val Trp
        275                 280                 285

Leu Cys Ser Leu Gln Glu Lys Phe Ser Gln Thr Asp Ile Leu Ile Leu
    290                 295                 300

Met Thr Ala Ala Ile Cys His Asp Leu Asp His Pro Gly Tyr Asn Asn
305                 310                 315                 320

Thr Tyr Gln Ile Asn Ala Arg Thr Glu Leu Ala Val Arg Tyr Asn Asp
                325                 330                 335

Ile Ser Pro Leu Glu Asn His His Cys Ala Val Ala Phe Gln Ile Leu
            340                 345                 350

Ala Glu Pro Glu Cys Asn Ile Phe Ser Asn Ile Pro Pro Asp Gly Phe
        355                 360                 365

Lys Gln Ile Arg Gln Gly Met Ile Thr Leu Ile Leu Ala Thr Asp Met
    370                 375                 380

Ala Arg His Ala Glu Ile Met Asp Ser Phe Lys Glu Lys Met Glu Asn
385                 390                 395                 400

Phe Asp Tyr Ser Asn Glu Glu His Met Thr Leu Leu Lys Met Ile Leu
                405                 410                 415

Ile Lys Cys Cys Asp Ile Ser Asn Glu Val Arg Pro Met Glu Val Ala
            420                 425                 430

Glu Pro Trp Val Asp Cys Leu Leu Glu Glu Tyr Phe Met Gln Ser Asp
        435                 440                 445

Arg Glu Lys Ser Glu Gly Leu Pro Val Ala Pro Phe Met Asp Arg Asp
    450                 455                 460

Lys Val Thr Lys Ala Thr Ala Gln Ile Gly Phe Ile Lys Phe Val Leu
465                 470                 475                 480

Ile Pro Met Phe Glu Thr Val Thr Lys Leu Phe Pro Met Val Glu Glu
                485                 490                 495

Ile Met Leu Gln Pro Leu Trp Glu Ser Arg Asp Arg Tyr Glu Glu Leu
            500                 505                 510

Lys Arg Ile Asp Asp Ala Met Lys Glu Leu Gln Lys Lys Thr Asp Ser
        515                 520                 525

Leu Thr Ser Gly Ala Thr Glu Lys Ser Arg Glu Arg Ser Arg Asp Val
    530                 535                 540

Lys Asn Ser Glu Gly Asp Cys Ala
545                 550
```

```
<210> SEQ ID NO 38
<211> LENGTH: 566
<212> TYPE: PRT
<213> ORGANISM: Homo sapiens
<300> PUBLICATION INFORMATION:
<308> DATABASE ACCESSION NUMBER: Genbank / NM_001001583.1
```

```
<309> DATABASE ENTRY DATE: 2008-10-24
<313> RELEVANT RESIDUES IN SEQ ID NO: (1)..(566)

<400> SEQUENCE: 38

Met Gly Ser Gly Ser Ser Ser Tyr Arg Pro Lys Ala Ile Tyr Leu Asp
1               5                   10                  15

Ile Asp Gly Arg Ile Gln Lys Val Ile Phe Ser Lys Tyr Cys Asn Ser
            20                  25                  30

Ser Asp Ile Met Asp Leu Phe Cys Ile Ala Thr Gly Leu Pro Arg Thr
        35                  40                  45

Pro Tyr Lys Val Arg Pro Val Ala Ile Lys Gln Leu Ser Ala Gly Val
    50                  55                  60

Glu Asp Lys Arg Thr Thr Ser Arg Gly Gln Ser Ala Glu Arg Pro Leu
65                  70                  75                  80

Arg Asp Arg Arg Val Val Gly Leu Glu Gln Pro Arg Arg Glu Gly Ala
                85                  90                  95

Phe Glu Ser Gly Gln Val Glu Pro Arg Pro Arg Glu Pro Gln Gly Cys
            100                 105                 110

Tyr Gln Glu Gly Gln Arg Ile Pro Pro Glu Arg Glu Glu Leu Ile Gln
        115                 120                 125

Ser Val Leu Ala Gln Val Ala Glu Gln Phe Ser Arg Ala Phe Lys Ile
    130                 135                 140

Asn Glu Leu Lys Ala Glu Val Ala Asn His Leu Ala Val Leu Glu Lys
145                 150                 155                 160

Arg Val Glu Leu Glu Gly Leu Lys Val Val Glu Ile Glu Lys Cys Lys
                165                 170                 175

Ser Asp Ile Lys Lys Met Arg Glu Glu Leu Ala Ala Arg Ser Ser Arg
            180                 185                 190

Thr Asn Cys Pro Cys Lys Tyr Ser Phe Leu Asp Asn His Lys Lys Leu
        195                 200                 205

Thr Pro Arg Arg Asp Val Pro Thr Tyr Pro Lys Tyr Leu Leu Ser Pro
    210                 215                 220

Glu Thr Ile Glu Ala Leu Arg Lys Pro Thr Phe Asp Val Trp Leu Trp
225                 230                 235                 240

Glu Pro Asn Glu Met Leu Ser Cys Leu Glu His Met Tyr His Asp Leu
                245                 250                 255

Gly Leu Val Arg Asp Phe Ser Ile Asn Pro Val Thr Leu Arg Arg Trp
            260                 265                 270

Leu Phe Cys Val His Asp Asn Tyr Arg Asn Asn Pro Phe His Asn Phe
        275                 280                 285

Arg His Cys Phe Cys Val Ala Gln Met Met Tyr Ser Met Val Trp Leu
    290                 295                 300

Cys Ser Leu Gln Glu Lys Phe Ser Gln Thr Asp Ile Leu Ile Leu Met
305                 310                 315                 320

Thr Ala Ala Ile Cys His Asp Leu Asp His Pro Gly Tyr Asn Asn Thr
                325                 330                 335

Tyr Gln Ile Asn Ala Arg Thr Glu Leu Ala Val Arg Tyr Asn Asp Ile
            340                 345                 350

Ser Pro Leu Glu Asn His His Cys Ala Val Ala Phe Gln Ile Leu Ala
        355                 360                 365

Glu Pro Glu Cys Asn Ile Phe Ser Asn Ile Pro Pro Asp Gly Phe Lys
    370                 375                 380

Gln Ile Arg Gln Gly Met Ile Thr Leu Ile Leu Ala Thr Asp Met Ala
385                 390                 395                 400
```

```
Arg His Ala Glu Ile Met Asp Ser Phe Lys Glu Lys Met Glu Asn Phe
                405                 410                 415

Asp Tyr Ser Asn Glu Glu His Met Thr Leu Leu Lys Met Ile Leu Ile
            420                 425                 430

Lys Cys Cys Asp Ile Ser Asn Glu Val Arg Pro Met Glu Val Ala Glu
        435                 440                 445

Pro Trp Val Asp Cys Leu Leu Glu Glu Tyr Phe Met Gln Ser Asp Arg
    450                 455                 460

Glu Lys Ser Glu Gly Leu Pro Val Ala Pro Phe Met Asp Arg Asp Lys
465                 470                 475                 480

Val Thr Lys Ala Thr Ala Gln Ile Gly Phe Ile Lys Phe Val Leu Ile
                485                 490                 495

Pro Met Phe Glu Thr Val Thr Lys Leu Phe Pro Met Val Glu Glu Ile
            500                 505                 510

Met Leu Gln Pro Leu Trp Glu Ser Arg Asp Arg Tyr Glu Glu Leu Lys
        515                 520                 525

Arg Ile Asp Asp Ala Met Lys Glu Leu Gln Lys Lys Thr Asp Ser Leu
    530                 535                 540

Thr Ser Gly Ala Thr Glu Lys Ser Arg Glu Arg Ser Arg Asp Val Lys
545                 550                 555                 560

Asn Ser Glu Gly Asp Cys
                565


<210> SEQ ID NO 39
<211> LENGTH: 386
<212> TYPE: PRT
<213> ORGANISM: Homo sapiens
<300> PUBLICATION INFORMATION:
<308> DATABASE ACCESSION NUMBER: Genbank / NM_001001584.2
<309> DATABASE ENTRY DATE: 2008-10-24
<313> RELEVANT RESIDUES IN SEQ ID NO: (1)..(386)

<400> SEQUENCE: 39

Met Arg Glu Glu Leu Ala Ala Arg Ser Ser Arg Thr Asn Cys Pro Cys
1               5                   10                  15

Lys Tyr Ser Phe Leu Asp Asn His Lys Lys Leu Thr Pro Arg Arg Asp
            20                  25                  30

Val Pro Thr Tyr Pro Lys Tyr Leu Leu Ser Pro Glu Thr Ile Glu Ala
        35                  40                  45

Leu Arg Lys Pro Thr Phe Asp Val Trp Leu Trp Glu Pro Asn Glu Met
    50                  55                  60

Leu Ser Cys Leu Glu His Met Tyr His Asp Leu Gly Leu Val Arg Asp
65                  70                  75                  80

Phe Ser Ile Asn Pro Val Thr Leu Arg Arg Trp Leu Phe Cys Val His
                85                  90                  95

Asp Asn Tyr Arg Asn Asn Pro Phe His Asn Phe Arg His Cys Phe Cys
            100                 105                 110

Val Ala Gln Met Met Tyr Ser Met Val Trp Leu Cys Ser Leu Gln Glu
        115                 120                 125

Lys Phe Ser Gln Thr Asp Ile Leu Ile Leu Met Thr Ala Ala Ile Cys
    130                 135                 140

His Asp Leu Asp His Pro Gly Tyr Asn Asn Thr Tyr Gln Ile Asn Ala
145                 150                 155                 160

Arg Thr Glu Leu Ala Val Arg Tyr Asn Asp Ile Ser Pro Leu Glu Asn
                165                 170                 175
```

```
His His Cys Ala Val Ala Phe Gln Ile Leu Ala Glu Pro Glu Cys Asn
            180                 185                 190

Ile Phe Ser Asn Ile Pro Pro Asp Gly Phe Lys Gln Ile Arg Gln Gly
        195                 200                 205

Met Ile Thr Leu Ile Leu Ala Thr Asp Met Ala Arg His Ala Glu Ile
    210                 215                 220

Met Asp Ser Phe Lys Glu Lys Met Glu Asn Phe Asp Tyr Ser Asn Glu
225                 230                 235                 240

Glu His Met Thr Leu Leu Lys Met Ile Leu Ile Lys Cys Cys Asp Ile
                245                 250                 255

Ser Asn Glu Val Arg Pro Met Glu Val Ala Glu Pro Trp Val Asp Cys
            260                 265                 270

Leu Leu Glu Glu Tyr Phe Met Gln Ser Asp Arg Glu Lys Ser Glu Gly
        275                 280                 285

Leu Pro Val Ala Pro Phe Met Asp Arg Asp Lys Val Thr Lys Ala Thr
    290                 295                 300

Ala Gln Ile Gly Phe Ile Lys Phe Val Leu Ile Pro Met Phe Glu Thr
305                 310                 315                 320

Val Thr Lys Leu Phe Pro Met Val Glu Glu Ile Met Leu Gln Pro Leu
                325                 330                 335

Trp Glu Ser Arg Asp Arg Tyr Glu Glu Leu Lys Arg Ile Asp Asp Ala
            340                 345                 350

Met Lys Glu Leu Gln Lys Lys Thr Asp Ser Leu Thr Ser Gly Ala Thr
        355                 360                 365

Glu Lys Ser Arg Glu Arg Ser Arg Asp Val Lys Asn Ser Glu Gly Asp
    370                 375                 380

Cys Ala
385


<210> SEQ ID NO 40
<211> LENGTH: 386
<212> TYPE: PRT
<213> ORGANISM: Homo sapiens
<300> PUBLICATION INFORMATION:
<308> DATABASE ACCESSION NUMBER: Genbank / NM_001001585.1
<309> DATABASE ENTRY DATE: 2008-10-24
<313> RELEVANT RESIDUES IN SEQ ID NO: (1)..(386)

<400> SEQUENCE: 40

Met Arg Glu Glu Leu Ala Ala Arg Ser Ser Arg Thr Asn Cys Pro Cys
1               5                   10                  15

Lys Tyr Ser Phe Leu Asp Asn His Lys Lys Leu Thr Pro Arg Arg Asp
            20                  25                  30

Val Pro Thr Tyr Pro Lys Tyr Leu Leu Ser Pro Glu Thr Ile Glu Ala
        35                  40                  45

Leu Arg Lys Pro Thr Phe Asp Val Trp Leu Trp Glu Pro Asn Glu Met
    50                  55                  60

Leu Ser Cys Leu Glu His Met Tyr His Asp Leu Gly Leu Val Arg Asp
65                  70                  75                  80

Phe Ser Ile Asn Pro Val Thr Leu Arg Arg Trp Leu Phe Cys Val His
                85                  90                  95

Asp Asn Tyr Arg Asn Asn Pro Phe His Asn Phe Arg His Cys Phe Cys
            100                 105                 110

Val Ala Gln Met Met Tyr Ser Met Val Trp Leu Cys Ser Leu Gln Glu
        115                 120                 125

Lys Phe Ser Gln Thr Asp Ile Leu Ile Leu Met Thr Ala Ala Ile Cys
```

```
    130                 135                 140

His Asp Leu Asp His Pro Gly Tyr Asn Asn Thr Tyr Gln Ile Asn Ala
145                 150                 155                 160

Arg Thr Glu Leu Ala Val Arg Tyr Asn Asp Ile Ser Pro Leu Glu Asn
                165                 170                 175

His His Cys Ala Val Ala Phe Gln Ile Leu Ala Glu Pro Glu Cys Asn
            180                 185                 190

Ile Phe Ser Asn Ile Pro Pro Asp Gly Phe Lys Gln Ile Arg Gln Gly
        195                 200                 205

Met Ile Thr Leu Ile Leu Ala Thr Asp Met Ala Arg His Ala Glu Ile
    210                 215                 220

Met Asp Ser Phe Lys Glu Lys Met Glu Asn Phe Asp Tyr Ser Asn Glu
225                 230                 235                 240

Glu His Met Thr Leu Leu Lys Met Ile Leu Ile Lys Cys Cys Asp Ile
                245                 250                 255

Ser Asn Glu Val Arg Pro Met Glu Val Ala Glu Pro Trp Val Asp Cys
            260                 265                 270

Leu Leu Glu Glu Tyr Phe Met Gln Ser Asp Arg Glu Lys Ser Glu Gly
        275                 280                 285

Leu Pro Val Ala Pro Phe Met Asp Arg Asp Lys Val Thr Lys Ala Thr
    290                 295                 300

Ala Gln Ile Gly Phe Ile Lys Phe Val Leu Ile Pro Met Phe Glu Thr
305                 310                 315                 320

Val Thr Lys Leu Phe Pro Met Val Glu Glu Ile Met Leu Gln Pro Leu
                325                 330                 335

Trp Glu Ser Arg Asp Arg Tyr Glu Glu Leu Lys Arg Ile Asp Asp Ala
            340                 345                 350

Met Lys Glu Leu Gln Lys Lys Thr Asp Ser Leu Thr Ser Gly Ala Thr
        355                 360                 365

Glu Lys Ser Arg Glu Arg Ser Arg Asp Val Lys Asn Ser Glu Gly Asp
    370                 375                 380

Cys Ala
385
```

<210> SEQ ID NO 41
<211> LENGTH: 19
<212> TYPE: DNA
<213> ORGANISM: Artificial sequence
<220> FEATURE:
<223> OTHER INFORMATION: Primer sequence

<400> SEQUENCE: 41
cgaggagctg aagcggata 19

<210> SEQ ID NO 42
<211> LENGTH: 19
<212> TYPE: DNA
<213> ORGANISM: Artificial sequence
<220> FEATURE:
<223> OTHER INFORMATION: Primer sequence

<400> SEQUENCE: 42
ccccagacgt caagctgtc 19

<210> SEQ ID NO 43
<211> LENGTH: 21
<212> TYPE: DNA
<213> ORGANISM: Artificial sequence
<220> FEATURE:
<223> OTHER INFORMATION: Probe oligonucleotide
<400> SEQUENCE: 43
tgacgccatg aaagagttac a 21

<210> SEQ ID NO 44
<211> LENGTH: 125000
<212> TYPE: DNA
<213> ORGANISM: Homo sapiens
<300> PUBLICATION INFORMATION:
<308> DATABASE ACCESSION NUMBER: GenBank / AB017602.1
<309> DATABASE ENTRY DATE: 2000-06-06
<313> RELEVANT RESIDUES IN SEQ ID NO: (1)..(125000)

<400> SEQUENCE: 44
tgtgcatggg atcatgcaac cccttgaagg gctgaagaga acaagaaggc agaggaagga 60
ggaacttgcc tctttcctcc cacctgcctg cttgggctgg gacactggcc ttctcctgcc 120
ctgggactgg gtccccacca tcagctcccg ggtgctgccc tcaggcttgc actggagcca 180
caccaccagc tttcccgggg ctccggcttg caggcggtag ctggcaggac ttctcagcct 240
ccgtcctcat gtgagccaac tcctcactat tggtctgctt ctctgaagga ccccaactca 300
tgggtccacc tgaccgtggt ccaagtccca tcacactttg caaagctgac tgcagctgct 360
gctcactggc ctccctgcct ggccccttcc atgcaccctc ctccagcatc caagaggatc 420
ctgtgaaaac ccacgtcaga ccatggccct ctgcaccgcc tcctgcaagg catgcagtgg 480
aggaagagtg acctcaagtc actcgtgtga ccacgcgggg ttgcccccgt cacctctctg 540
acctcacagc ccactacggt cccccacagc ccactccctc cctccgctct ggccacgtgg 600
cctcctgcat aaggctgctt ctgtgccaga acgtccttcc ctctgacaca cacaggctcc 660
ttgctcctaa cacctgtaag atccctcctc ctatgtgacc ttttgcctgg ccactttctc 720
taaaattcca actccctcac actgcacatt ccctcacact gcacattcta tatccccttc 780
cccgcaggat ttttcttttt tagagatggg gtctcactat ggatttttct tctttgcctt 840
aatttttatc caacacccta cacattctat ttatttatac catcgtgtct gtcttcccca 900
gagaatgcca gcttcttcag gccagggatc tctgcttatt ctgttcacta ctgaattccc 960
agtgcccaga acagcaccca acacgcagta atgagattgt tgacgaatgg aagaccgcac 1020
tgctccatgg ggatctggga gaggaaaggg ttcctctcta ggcagctgct gaggcctcat 1080
cgatccagta tctacacagg ggtccagtcc agctcctaaa agtgcaaagt aattatagat 1140
gcgattattc tcctgagcac agaatcagcc aggcagtgtg aggggccagc ctgcactggt 1200
gctggacgca cacagagtct cagagccaca ccctccaccc tcctggggaa ctgccctgca 1260
gaaccacccc ccatgggcgg gcactcgtcc ttctggggct cttggaggaa atggttacag 1320
aagactaggc cagatgacaa taagggatgg agaataacta agtgccaagc caatgagcca 1380
tctgctggta agaactccat gccaggcagc acaggcggtc ccaacagcac gatctctgga 1440
ttagcccaaa tagcatcgga acatttgaca acaaattgaa ctactagtaa tagtgctcac 1500
ttcaatgagc cggggacaca gtatccccat ggcgagtcag ctggcccgct gtaaccaccc 1560
agctgggtct ccccacccca aaggcctcca ggctgtcccc ttctcatcct gtcacttgaa 1620
aagcacaact catggtgcca aagctctgac acggactcca ctggagctgt gggcaggggg 1680
tgccaaggta ccgagttcca agccgttgtt atttgagagc gtgccccccg ccatgagagc 1740
aggtgggggg acataaagtg acacaggatg gactggccaa aggctgagga cgatcactta 1800

-continued

```
cctcacagga tgatgccacc cccacggaca ggcaaggagc tctcaccttc cccaggaccc   1860
cagctgccac cagagctcca gatggccctg ggggtgtctg taaagcctgt gaccgtccac   1920
caggtggaga ccaggctggc caggggaggg agaggaagtg accactggcc ctggcactgg   1980
ctggccggct ccagcaggcc cgaaggggag ggaggagcct gggtgcacca gactctctca   2040
ataagcagca cccagacact taacagatgg aaagcggtgg cttggaactc acttccaacg   2100
aaacaatagc acatgctccg gctggctttg acacttgctt ccaaaggcga cctgcaccca   2160
gggccaggac cacggcatct gagcctcctc ccccagccgc caaccccatt cccaatggag   2220
gagcccagga gaactggggg cggccaaggc agcccttccc tgctccgcag atccagagga   2280
tgcccacagc cccccttcccc tcccgccttt cccacactcc ctgtagcaat tcacacaagc   2340
ggggagggga cgaaactgct gaatccagca gatagcttgt ggcggggtaa tcctcggtcc   2400
ggccccatac aggacagaaa taaaatcgcc atttcagctc cgggcgcagc tggaggaggc   2460
tgacgccccc tagttagggg aaggctgtgg gtgaccgaga aggaactttt cccgttttct   2520
attcaaatga aatgagggtg gcggtcgcag cagggagaga ggagcgaggg gagttttccc   2580
ggcggggctg gggggtccac agcggcgcgg ccacgctcag cccagcgctg gcttaggagg   2640
gacgggctgc gtggggaggc gacggctccg ggccgaaggg gtcgctcagg gctctgcaca   2700
gctgtccagg gggcatcggg agataggcag ccgaccgggg gctggagtca agggaagaag   2760
aaagaggggg aagggaggtg cagggagtga agaggagggg agagaggaga gacgggggag   2820
ggagggggga gggggggaggg ggaggggcgg gcgggcggcc gggaggagga gcgcgcgagc   2880
cggagtcgga gcccgagccc gagcgcgagc cgagcggagg agaccctgcg gcgcgcggcg   2940
gcggctcccg ggcgtcccgg gcccggtggc ggcgcggctg tggttggctg agcgccgcgg   3000
gccgcccccc gcccgccccc tcccctgctc ccctccccg cctcccgcgg cggctggcgt   3060
cgggaaagta cagtaaaaag tccgagtgca gccgccgggc gcaggatggg atccggctcc   3120
tccagctacc ggcccaaggc catctacctg gacatcgatg gacgcattca gaaggtagcc   3180
cctcccccac ccagacaccc cctcctcccc ccgggtgaca gcgccggggc cgggcgcggc   3240
ggggcgggac tgtccgtgcg tctgccggtc caggctgcgg cctccgtgcg ctccgccagc   3300
tctggtcggg ggcgggggtc cccacgcgcc ggctccccgg ggaaaggggc gactcgccct   3360
gggggtggg gggtgggggg gcgggctagt gtttccgttt cacaggcaga gcttttcttt   3420
ttgaaaatct gattaggctg agtttttaca ttcaagggct ggcacatgaa gcctttaatt   3480
tccggtggat cggcccgccg ggcagccccg gggtcgtggt ccgcggaggg ggcgagcagc   3540
cgccgcttcc tgtcgcgcgg gggcaggtgc ggggggcgcc ggcggggaca ctgctccccc   3600
gcaggtgagt agctccgact gcagaggggg actcgggccg ctgcacctcc ggggccccgc   3660
ggagagcctg gggggcagcg ggtccggctc tcccctgctg tgcggagata ggaagtccct   3720
cgaatgtcca gcgttcctag cggacttgag ttacacggga gaggggttca gaatagaccc   3780
cctttgttcg tggccccctc tgacgggcag ggagggacaa tgagcgcgcc ggcttggaag   3840
gggctctcat gagctccccc taaagtcccc agggaaaagc cattgtgagg aaatccctca   3900
aacctcagct gggcgtttca ggaagccctt gcagctgctt ctcacctttc tgcccacgga   3960
gtactccact gaaggaggcc agggagagat gccccagcca ggcacagagc aggtgccggc   4020
caggcttgag tctttcctgt tcccagaggt gcatttggcc agtttaatca gtagatttaa   4080
gccaacaagc ctccctcacc ctgtgcccgg cttgatcccc gtgaaatgga aagtacagcc   4140
ctctcccacc gtagcccgct ttgagagact cagataaccg ggaggaggaa gcatcttcaa   4200
```

-continued

```
ggacaggtgg tcacccccttt atttaatcag tgctgggcag ctgggcagct gggcagcggc   4260
agacgcacaa ctagacccag gtccctgact ccaggactag gcgtctgcaa ttgcatggga   4320
ctgtaacagc ctcctttctc cccaaaggaa ggagtggccc tcccttgaat atgtcactgc   4380
accagcatgc acactcacac acacacacac atgctccaat gctcacacat ccactcacaa   4440
acacacacac gcacacacgt gcatacacac acgtgcacat gagcacacag acatgcacac   4500
cacataggca catgcacaca cactttttct gcccgataga tgagaatgta tcaaagacct   4560
gcctttaaaa gcaaaagtct ttttaaagtg agttgtcacc agatcaacag tagcaggtcc   4620
gtcctaagaa cttcctaaag atgtcccggg agcagctctc ttggaagcag gtgaaaagtg   4680
gaggagagct tcaggagggg tgggaggagg acgctgggca tggcaggcca ggctgttatt   4740
gtgggcaggg tagcttttca cagtggacac gctgaggttg gggtgatctc cagaaaagca   4800
gcctgcaggt gggccctggg gaagacatgg catgtggcac ctttgcgggg gagaggcgga   4860
ttgactgcca gctctaccac ttcctgtacc acgagcaagc ccctgggctc cccaagctgg   4920
catccccgtc cataaagaag ggataataaa atctgcttta tagactggaa tgagaaggga   4980
atgagtgaat gtaaacactg cctggaacac tgcagaacac gatgagcatt attcttccct   5040
cagttccttc cataaacgtc cttttgtggt gcaaacaggg aggcgccaga cgggtctcca   5100
acccccaccc cgccccccat ctccacgagg tctgttgctt gctcctgagc tgccccccgcc   5160
ctctgcccct tgctgtgaac cccgttggaa gctcctagct ggactgtgag tcctggttga   5220
agctgaatcg tttgcccaag ccatgtgccg ggcaaagcat gataacttct cgctcacctc   5280
ccaggctgca cacccagcag tgctgtcacg gatgggttgc accgggctca gctgagagca   5340
ctttcagtgc cgctgccatc agccgccatt ccttctctta aagtaccagg cactgggtaa   5400
atcctggaat ttccagcgtg aatctgtctc cctgccatcc gccccatctc ctctccatca   5460
aaggtcatgg aaacaaaccc atgttgcttc ctaggaggga gccctggggg tcactgggtg   5520
caggagataa gggatgtgtt gctttccgtc actgtgttcg tcggcaccac ctggccatga   5580
gtcctggcga tgggcacacc cgccccttcg ttatctctgc tctttgtccc tctggttacc   5640
tgacccctgg ccatctcagt ttccccctga gaccgcagag acggggagga aggagggaac   5700
attagaaact gggggttctg ccgagttctg tgctccggca aagctccagg ttgacaatct   5760
gaagttgtct gagggaggcc ccgggcagca agtgccggtg tctcctggct tggccttacc   5820
tgtgcaggta accctgcaga catgcccagt gattcagagg agccgctgca gccacttggc   5880
gccaggccaa tgctttattt atatgaagaa aactccagac acgcacaggt gtcacatcac   5940
cagagtgaca cagtgggagt cagcaacagg aatttggggg attgtcttcc ctcctcagga   6000
gcttttcctt cagaggttgt gcagaggaag ctgggcgtgt gaagtgagtc ggaggttgcc   6060
tcctgagccc tacacgaagg caggactctg tgccctggag tccaactgag gctccgtttt   6120
cagtgctccc ctctcatctc gagaaccttg ggtcagttac ttcactctgt gcccctgtgc   6180
tgctgtgcta ataattaaat gggataaggc agattgcctg gtcaatgagc ccgccgtgtt   6240
tattgagcat ctactatgtg ctgagtgctg gggtccatgg gaagctgagt gctggcggaa   6300
tgggaaggca actacaaatg ataaacagca gcagacgttg caggctgggt gggccagccc   6360
cgtgtggggc ctgatgaaca ggttttttttc cctgacgatc ggctttgcag gctttgtggg   6420
ctttgtgggg aaggagccct ttgtgcagaa ctggtagcca tgaggatggc ctggtgagaa   6480
gctgctgaag ggctggggac agcctccacc cagccagcag catctgcacc ggcctgttcc   6540
```

-continued

```
cgtcatctgt tccttggctt gccagggtgc acagatcagg acttggcact tccccagcac   6600
caggtgaagc cctcctgtca cccccaaccc cgtgtctaga ccctcaggtg ggctgttaaa   6660
gaaggggaga ggtggaagcc aggtccccaa acctagggtg ctgaggtcct tgcttcagag   6720
agactgtgtc ctctaggagc tgaagcgctt cgtctttccc cagaggattc gtttttttcct   6780
ttcctcagct gcccctaccc tggggggccc tggctgcagc acctgctcct ttctcttgcc   6840
tatggagaaa gggtttgctc agctgagctg cccatggagt gacagggacg acgcactcag   6900
cactggggag ctggaggggg tcccacctgg tggcacatcc aggcttgggt ttgccaatct   6960
tccgaatcgg ggaagagaga ggcctttggg acccctgggc caggctgtgg gctcgggtgt   7020
ggtgaggagc cacatctggg caagactgaa tgctccgggg cctctgtggt gccactgccc   7080
tgacctggcg gccccctcgg gacactcgca ctgtgcgcgg cctccctggc gcctctgggc   7140
tgtggtgttc tggtcttggc cttgctctgc agctggaacc caggtctgaa cacatcggtg   7200
gccgcttgag tttgcggggc tgtttctact gtaaaccaga gcagtgaatg cgcacagccc   7260
aaagggagga gccgcgctag aaagtgttca agcgtccgca gaagtcggct cccagttctt   7320
aatagtttgc cacccaccgt ggctacgcca cacctacgct tgcctccacc cgacctatgc   7380
ctgcccccctt cacatgcggg agcccagggc tccgtgccct gggcagctgg tggggtctgc   7440
ccaggccttc tcgtgatgct tccacccagc ctggtcctgg cacccaaggc caacctctgc   7500
gggccccaga gctgtgcctt tttggctcag gtcctccccg cagtgcttgg agtccaggcc   7560
tctgcaccct gctggggtgg tctgtggtcc tggcccaagg gaatgtcgct ccctgctgcc   7620
tggttctact gatctgtcct gttcaggccc ctctgccttc atttcttgct ttggcacaag   7680
catgagctgc tgtttccccc agctcctcag gggagaggag tgcactgccc caaccttgtc   7740
tggtgtggtt agcatggtgg ggccttaagc cctacccggc tcctgcgtgc ctttcccctc   7800
tcctgcccac gacatggtca aatgcaaacc tcctttcatt ttagaaggca tgggctgctc   7860
agcccacacg cgcagtgccc tttcctgtgg ctgcaggcat ctctgctcaa ttgtgcaggg   7920
ctgcgtcccc cggccacact gactcctctc caggtttctc ggctccagca ccactgtctg   7980
cgccctcctt cccaggtgga cggcggctct cctcgccatc ctctccactt ccagcctatc   8040
atctgtctgc ctgttacatg tttgtaactt ttgaccttta aattggtata aaaatggtac   8100
tgtaagttca ctgaaccaag aaaatctgct gaaggaaggg ggtcagtcac accctttttgg   8160
ggtttccagt gtatgaatgg agggggtggc ggtggtggag ggacagggag caatgagagt   8220
tgccagcctt attgctgtcc tgacccctgg ctggggacga ctcccctgtc tccacctgaa   8280
ttgaagctgg gctgtgaaaa gtagtaagaa ccctcggttt ttggttcctt tttcaaccag   8340
caatcagcca tgaagtgcct gaccacttga gagctacagc aggtgctgtc tcggagaggg   8400
cacaggaaac tgggcccttc ccaattttag cccaagggtg ccgaaaagtc agggagctgc   8460
tggcctccac actccttccc attggtgtgg tccgaattcc cctttagcca gacatttcca   8520
atgtccagag gcccaggagg ggacagctgg aagccagaag cccacctgac gccatcagga   8580
atttccatga atgacctgga aacctctcag actaaaccaa tgccgcccaa tctgggaatc   8640
caggagggct ggtcccatag agtggtgggg acatggtgct gagacggaca gcctcgcctc   8700
atccgccttt cccacttgcc agccgggagg cctgggcaaa atcactttct ccccagggaa   8760
gtggaggctc actgtgcagt ccacgcggag caatggggtg aagtttccag agcagggcag   8820
ggcatgtggg gaggctcagg aatgccaccc ttgccctcag gcctgggcac agcatagccc   8880
ccatgacgct tctctcatcc tggacccatc agcccggaag actctggaag cagcagtggc   8940
```

```
agcaccttcc tgtcacttgt cttgtcactc cccgagtcca ctgtgagcta gaaccacagg   9000
ctcccatgaa gaaggagcca gaaccacagg ccccatgagc ccaggtccca cagcccgcac   9060
cttcgtcttc cagccagcct ctccggagct cagtgtgggt ggaggggctg tctggcctca   9120
gaaatgggca aaagacagct ctcgttgtca gcgaggtaaa tctagcgcag aggaagggca   9180
cactgtcccc gtcagacgcc tcagatgaac tgacatgcaa atgagagatg aaacggggac   9240
gagccgggca gctgatctca gtgcagcaac tgggacacct cggggcataa gccgggcagg   9300
gaggcggcag gaactgggcc ccagggggcc aagacttcct gagaggctgg gcccggtagc   9360
ccagtcctgg gcttgcttcc caggggtgg tgggcaaccc tgaaccctct ctcacccaat   9420
cacctgctcc cctgggtgca ggtgacccag caagccgcac tcctgggaaa tttcagaagg   9480
ttttgggcaa gaagggccca gagagccccc agagaccaga cggcacagcc cgatagctgg   9540
gcctgcccca gacaaagcgt gtctgcactc cttggctttc tccccagaca aacccaccct   9600
gagctcagga tccctccagc ttccaggagc aggtgcgggg cctgcaggga cggctcgcag   9660
agaaggcagt ttgcgagtca gtgcctggct tgtggaggtt gagaccaagg ccagttgggt   9720
gcttgcattt ccaggggtcc aaatattttt gagaagaaaa tgttctaaga aagtgcacag   9780
ggtggtggat gaaagaccac gctctgggta ccgtgtacac cgctcgggtg acagtgcacc   9840
agaatctcag aaatcaccac taaagaactt acccatgtaa ccaaacacca cccctccccc   9900
aaacactatt ggaattaaaa aaaaaaaaaa agattaaaat ggttaaaaat agaaagtgca   9960
caagcaaggg tccatctgca ggagttggag gagcgcatgc ctgtattcct ggcactgcgg  10020
gcacagtcat gccatgggca ccagggacgc ccagtgcact cagccaccca ggggtggctc  10080
ccaacatttt caagctcaaa aagaaatatt ttcacttgag ggtgcaactt atttgtcttg  10140
aacccatccc tgactgcctg tctccccccct caccctgacc acatctcccc aaatcccgaa  10200
gctggtcacg caacgggagc attggccctg aacagaaacc cgcagtaccc ctgaaaactc  10260
ggtctagaaa caactaaaag aagaaccaca gcattttatt ccgtttgctt tagattctct  10320
gccaattttt tttttttttt gagatggagt ctcgctctgt cgcccaggct agagtgcagt  10380
ggcgtgatct cggctcactg caacctccgc ctcccaggtt caaggaattc tcctgcctca  10440
gcctccggag tagctgggac tacaggcgcc tgccaccagg cccggctaat tttttatttt  10500
tagtagagac ggggtttcag caccttgacc aggctggtct cgaactcctg accatgtgat  10560
ccgcccgcct cagcctccca aagtgctggg attataggcg tgagccacca cgcccagcct  10620
tttttttttt tttaatttta aattgtggta aaatatatga acaataaacc ctccctcccc  10680
atccccctcc cccagcccct gacccccact gtacattccg ctttctatct ccatgaaact  10740
gctgagtgcg gggacctcac agaagtggaa tcacacagga tcgccctgct gtgcctggcc  10800
tccttcactc ggatcatgcc ctcaggtgca tccatgttgt agcacgtgtc cgaatttcct  10860
gcctttttaa ggccgagcgg tattccattg tgtgcgtgga ccacattttg tgtttccatt  10920
caaaacggat gaatcgatga aactgcctga tatttttaaa gcctcagtca ttttcattct  10980
tagttcttca gtttgcaaag ggccggcctg ttgtgatggg tttattgttg catcttctga  11040
aaaactttgt gagttcccga aggcctctcc acgtcttgag tcatggctgt gctgctttgc  11100
gaagctgtgt gcatgtctgt ggtgtagcct gtgtacagcc tgtgatgcgt cgcagcggaa  11160
gggtaggggg ctgcccaggg aagacagatg cgccaggttc cgctccacgg agctcagcta  11220
ccagccctgg tggagagcgc agatggggcc gatttgtcat ttgtctgcgc ttgagcccag  11280
```

-continued

```
cagctgtgtg gcctccctgg ggcaagtcat tcaccctctc tgtgcctcag tgtctctgtg  11340
aagtgggggg aagtttttgg aagattaagt gggctaatac gcgtcaaatg ctagaacaca  11400
ctggcacttg gtaaatgcta tataagtgtt atcatttttg tttgtttatt atttatttat  11460
ccatgtcatg gatttaaggc agtctaatct cagtgcctgg tggagacccg ggcgccaccc  11520
ccccaggttg tcaagtggtc cctgtgcctc ccactatcgt ccccagcacg gtgccgtgtc  11580
cgggcgtgcg tgaagggcca gctcacctca cagctctgct tcccaggtta gctcccatcc  11640
accctccccc tacctgtttc ctcaccgaag gaaggggcag aaagatgccc tccatgcccc  11700
ttccgactgt tgcagaggga tggaggacta tggtacatac acacatatac acgcacacac  11760
ccaccacaca cacacaccat gcacatgcac atcacacaca cgcacacacc atgcacacac  11820
accacacacg tacacaccat gcacatcaca cacaagcaca ccacacacac caagcacacg  11880
cacatcatac acatgcacac acaccacaca caccacacac cacacacacg cacatcccac  11940
accatgcaca cacacaccac gcacacgcac tgcacacaca tgcacacacc atgcacacgc  12000
acatcacaca cttgtacaca ccaggcacat cacacacaag aacgcacacc acacacaagg  12060
acacacacca cacacacaca ccaagcacac acacaccaca cacacgcaca cacacgcaca  12120
cacccaccac acaccacaca catgcacatc acacacgtac acaccacaca cagcacacac  12180
aaaaacacac cacacacacc atgcacatgc acatcacaca catgcacacc acgcacacgc  12240
acatcacatg cacacgccac gcgcctcaca cacaagaaca cacaccacac acacgcacac  12300
cacacacacg cacatatcac acacatgcac atcacataca tgcacacacc acacttacac  12360
acatgcacat cacacacaag aatgcacacc acatacacgc acatcacaca catgcacaca  12420
ccacacatgc acatcacaca cctgcatata catcacacac acatcacaca catccacatg  12480
caccacaccc accacacaca tgcacgcacc taccacacat gcatatcaca cacatgcaca  12540
cacaccacac acaagcacat cacaaacacc acacaggcac atcacacaca tacatacaca  12600
ccgcgcacac atcacacaca tgcacacaca ccacacacgc acagtatgaa gatgacagag  12660
aagtcagcag agcccctggg ggtttcagga gttgagtggg gacgaggcag gtggccacac  12720
agctcggagg gagggcagaa ggcacccgtc ttcgcagagt cacagtgggg cttgcctcct  12780
atacgtgccg gaagggtgaa gccccttatc tcattgcccg atgtgatgag gtttgaagtg  12840
gttgagcttg gagggtatgg gctgagccca cagcagacag gcctggcagt gcccccccgtc  12900
ttcccaccct gcggtcatgc agcccgactc ttgggggcgg ggtgccaccg tgatgtgccg  12960
tcacttgcag cagtatgtcc tcatgccagg ctgagaccag cactgtgtga ccagcctgcc  13020
ccatgtccct cagcgctgtg tcacactcca cactgaggcc ccactgaagc atgccaggcc  13080
ccatcctatt tcttccaggt agtcgtctgc ccagcacctc ccctcccagg ccttgcccta  13140
aagcccaggc ctctcagcat ccaggactct ggaatctccc aggtgttgat ggctgaggtc  13200
atcagctgga tgccaggaca cccaggatgc tccaggtcct tgctggggtc tggagtttgt  13260
gattcagcct cagtccctgt ggtgagtcca ccatgtgtcc tcagacaatg gatcagagag  13320
cccccagagg acggcccggg gccgagtcgg gtccagatgc caaaggggct tctcgaggca  13380
tctccagctc ccacctgccc ctcggagtgc caggcttggc ttctggaaga gaaagctggg  13440
ggtttagtga ctccagccaa ctgctgtgag cccaaggcat caaactaaaa atagcgaggc  13500
caagagggag tctttgtgtt cggctcagtg ggcaatggtg cctcacctcg cagcatgaca  13560
cagggctgat gacacggggc acgttggtca caaagtgcca gtctcagcct ggcacaggga  13620
cgtgccacct gcaggtgatg acacatcaca gtggcagccg ctcctgatgg tgctgctgca  13680
```

ttgagtagga gcccagatcc agggagacag ttgcagcaga tgaggcagga ggccagcgag 13740
gggttctacc tgctttccgg gctggcctct gcatggacac aaagcagaaa gggcataaag 13800
gtgaccctgg ccaccaaagc agacctggag caaactggac cagcgcaagg ccccggtgcc 13860
agcactcaga gacatttctt ttctggcagg aaatttgtgc ttcattttct aatgaaattc 13920
caaggcaatc aaaaggcaag gaaagaggag ggaaaggaag ggagggaggg agggggttcc 13980
attcccatcc gaatggaagc ccccaaggct tctgtagctc cccccatcac caacttcact 14040
caccactctt atctgatgcc tcctatttgg gtacacacgg ccgggtcggc cttgcgagag 14100
actcagtttc ctctcgactt ccgcccgcct gcactgtcac cacgtcctgc cattgacctc 14160
tgttcatcca ctcatggtca ctgctgtgag ttgaattgtg tctcccaaaa aagtggattt 14220
ctgtgctaac ctgtgaatgt cccgttagtt ggaaataggg tatttgcaga cataatcaca 14280
tcaagatgag gtcatactgc attgggatgg gcctcaagcc catatgcccg ccatccttct 14340
aaggagaggg aaaggcagac acacatttgt ccatggaaat gagaacggaa gacgtagaga 14400
cagaatcagg ccatgtaaag acagactcag agaccagagt gatgcatgta caagccaggc 14460
tctgcgggca gcccctagaa gctggaagag gcaagcctcc tccctggagt cctgggaagg 14520
agccagcccc gcccatgcct cgagctcagg cttcaggcct ccggagccaa gagagataaa 14580
cctctgtggt ttcatgtcac ccagtttgtg gtctttgtta tagcagcccc aggacactca 14640
gggggttgcc ttgtccaccc ccatcctggc cctctgaggg actggttggc tcttagaaga 14700
ccgttcaacc tgccctctgg tcctcctccc ccacccagag acccctggct acaccctgcc 14760
caagggagct caccaaagcc cacagggtcc ctgtgatctt gtcacctggg ctcccacagg 14820
ccagcagtgt tggaacctgg acatctggct ccagccttgg tggccacccc cgaccttgct 14880
ctgctcctac agctcccggc cttccctgcc ctggccggcc cttgctgaat gtccccgctc 14940
ctaggaagcc ggatgtgtcg cgtgcaggtg cctctctgca ctgtaataac tcctcaccag 15000
gcacccttgg agcccaggat caagtcactc accttccaac cctgcccctg cccagagact 15060
ggcacgagaa ccagtaacag ttgttgaata atgaacaatg gatgcatgca gctcacccgt 15120
gagagggcgt tgctcggctg ggccagggat gaagcttctc ccgcgtggct ccaccgtcta 15180
tccctcaagc tcctgatgct cccctgggca cctctgcgcc atgaggcccc gttgaagtca 15240
gttggggagg cagtgtggac cgtgagaagg gagtcctaag cacaggaaac gctgccttcc 15300
tggggcccta aagaacaggc tcaccttccc caagggcctt caggccctga catctaaaaa 15360
gatgttcttt atcaaagggg aaagcagccc tggggtgggg gcgtggccac cagtgcagtg 15420
ggcgtggcca caaccgagag ggcgtggtca ttcgtgcagt gggcgtggtc atcaagaaag 15480
ggcgtggctg cagccggaag ggcgtggcta tcagctccag aaggcccttc ttgctgtcct 15540
tggacttggg ttctccttgt cgacgaggat ctcagctgga gctgccaggg gcagggctgg 15600
caccaaagca cttctgaagt ctccccgcct cccaagtgtg aggctgtggg gaaggaggga 15660
gggcagctgg cttgtttctg gatgagccca tctgactcag cagctgggac ccagcaggag 15720
cgcagagcag gtcctgaagg tgccgaggcc ccacccgcag ctccgtctca gctttgtgag 15780
ggctgcactc ccccgtgtgc atccggcgtc acaaaggacc acaggcccgg cggcctccac 15840
agcagacacc aaggccctcg cggtctgaag gccgaattcc caggtcaggc tgcagcaggg 15900
ctggttcctg aggcctctcc tgggctggca cctcctcccc gtgtccatgc agggccgagc 15960
ctctgcatgt ctgtgtcctc ggcgcctcgt tttacaagga catctcattt taaaggcccg 16020
gtctccaaat aaggtcatat cgtgaagtgc tggggtcaga actacagcat gaattttgac 16080
gggacacagt tcagtccata gcacccgctt tgggaagtgg gaatgacctc tcccttcccc 16140
atcttctggc ctttgtaacc ctaatgtggg aaagcaggag ggatccagaa cgacattggg 16200
tcaccaaaga gagcatcgca gcccaaaagg ttgaaaggcg gcaccaaggt cccgcgcctg 16260
gtgaccgccg actcgccctc ccgggctcca ggctgtcccc actccccccc gccccaaccc 16320
cagcatgttg aggcgcctgg tcccaactgc ccattcactc cctgtacaca gactgcttct 16380
ttgtcctcca gccaggggtg aagggccatg ctggcgaaac agcaaacaac cccaacatgc 16440
tttgcagcct ggccaaccac atgaccagtt tgaggaggtt ggctggagat cacaatgagg 16500
aagttggatg agggggtcca acttctagca gcccataagc ctatccattc agacaccaaa 16560
tccatggaaa acagagagac aatatactga ttttcaaaag ggagacatac cccagcaagt 16620
acagaccagg gaacagggtg ctgacgtggc cacagttctt aaactactcg acttcatgga 16680
tggggcacag tttttttaa aggaggattt agaattctat ttggcaggtg gcatgaaaaa 16740
gagttttgaa tagaaacaca cccctccctc ccagttgcct gcccagtatg tttgttttgt 16800
tctcttgaaa caaaggaaga gagtggtgag gagggaggga agatgaacca ggaagaatga 16860
aagcacttgg cctgcttctc agatggtctt ggactgtctc cgctcacagg agttgcaggt 16920
ttttgggttt tatgcaagtt cggatcacaa caggcctctt gcaagaacca ggcattacct 16980
ttattccaaa agccttgctg ggccttcttg aaaggactgg cagccaccac ttccctagaa 17040
acccgtggca agttccctcc tcccgacccc ctgctgtttg gtccaggacc ccctgcagtc 17100
ctgactggga cccacttggc ccttctcaag ggacccagca caggacgtgt gtttctgctt 17160
tgatgaaccg ccctttcccc cctgcagttc tagtggaatc tcccctccct tatcccattc 17220
ccacttggaa atgatgatga tggaatgggc gatgccggct taccaagaca tccaagctct 17280
ctgggtcgaa gttggagaga ggggtgcaca aaaaggattc cactcctgtc tgccttcccc 17340
tgcctccccg ctggggtgtc cctttcccat ggtttcctct aaatcttttc acccatgtcc 17400
agccacacca ttctcacata ctgccttgaa actgggctcg aaggggctgc gtgctgagag 17460
aaggtcctct cccccagtga tcctccagag gggctgccgc ctgggtcccc cgagcacctc 17520
ctaccccacc ctccccattc ctgccatccc cagggtccag ggagcccaga ttccagggaa 17580
gggttgcatt agctcccact cggagtcctg atgcagcaga gacagacaga ggccctggga 17640
gaagtgagca tgaattatta agacaagaca agggtgaggc cccagagagg gggtggcgga 17700
agggtcatgt tcatgcagcg agagttgctt cgagcttgaa ccgcgtatcc aggagtcaag 17760
cagattgcaa ctggcgagag gccttcagaa atgccccgtg agagtcctgt gtgcagagct 17820
ccatctcagc acacttcctg ttcttttggt tcgtcgattt ttgcattttc agtcccctgt 17880
gatccattat ttataacagt ggagattggc ctcagacact agcagtgagg aaaacaaaag 17940
cgaagctacg cagaaaaatg acaagagtga tgagcacagc agtcatgaca aatgagccct 18000
gtgcggaggc ccgggatccg cgcagatgcc ggcgcggggg aaatgggccc tgaaatccca 18060
ccgtcaggcc aggcagctct gagcgtgacc tggagggctg ttcagacggt ctgggtagcc 18120
gtgtcctgcg catgaacatc ctccgtcggg agaggaattc cccacggatt atcagagctg 18180
ctccctccac cccccgccac gtcccacgcg ggccacatca actccctctg cagcctctgg 18240
ccagcggctg agccctccgt gtctcccctc gttaatgcct ccttcaccat cccctcctga 18300
agtttccccc attgcataca cgcgctgagg cccacccggt atcaaggact cccattgctt 18360
gcgaaaaaga ttccacccct cttagaacag agaccagggc cgctgtagca aatggccata 18420
aatgccacag cttaaaacaa cagaaacgga ttatctcgca gctctggagg atggagtcca 18480
aaatctgaat cgctgggctg aaatccaggt gtgggcaggg ccgcgctccc tctagaggct 18540
cccccggaga ttcccttcct tgcctcttcc agctgctggt ggctgccagc agtttgggaa 18600
ttgcggccgc atcacaccac ctttctgttt gttgttgaca tccccgcctc ccctgcctgc 18660
ggggtcttag atgtctctct ccttcccact gagtttcact ccacatttga attggattaa 18720
ctcatgccat gttaggcaaa cgtgcccctc aaatccttcc acttaacaga catttattga 18780
aggttcctgt gtgcggggcc caagagaagg gacattaaat taggagatga accttgggag 18840
gccatggcat gcttcggagc ctcggcgtca aaatgacaac ccacacccca cttggcggtt 18900
catctggggc cctggaatca gcagactgag gctggaaccc agcaatggca catgctggct 18960
gtatgttctc gggcctcagt ttcaacatca gtgacatggg gatagaatct gcccagcgga 19020
gttaagtcac cgcatcccgg agagccgagt gtctcataga ggctcctggt gtggtctcca 19080
tgctgctgct cagcacggaa tgaagaggtt caggaacttg cccacagcca cggataatga 19140
gggacagagc tggaattgag cccgggaacc tgcacacaca gcccagtgtg accgtgcctt 19200
ctagagagag gccagccctg gcaccaggtg ggcatgccag catcaccttc aaggtgtgct 19260
ttaaggatcc aagataatgt gggtgcttca acagatgcat ggcaataaaa ggaaagcacc 19320
atgtttcacc ttcacacaca cacacttaca cattcacaca ctcacatact tacacacatt 19380
ctcatacact cacacatatg cttacacaca ttcacaggct cacacatgct tacacacaca 19440
ttcacacgca cacacattca cacgcacaca tacacttaca cacattcaca cacatacact 19500
tacattcaca cacatacact tacattcaca ctcatacaca tacatacatt cacacacata 19560
ttcacacatt cacacataca cattcacaca catacactta gacaccacac tcacattcac 19620
acacattcac atacatttac acacacatcc acacacacat tcacacacat tcacatttac 19680
attcacaaac attcacacat acattcacac gcacttacag tcacacatac acttatacac 19740
agtcacacag acttgcacat agacttacac acatacactt acacacgcac tcacaccttc 19800
acacacacag gcaatcacac attcacactc acgtacactt acccacacat tcacacatac 19860
acacaccaca tacacgcata cacttacaca tgcactcaca cactatcaca ttcacacaca 19920
catacactta caaactatca ttcacacaca tacacacata cacatgcatt cacacacatg 19980
ctcacacact cacacataca cttacactca cagtcacata cacccacatt cacacacata 20040
cactcacatt cacacgcaca tacactctga cacacatata catacattca ctcacacata 20100
cattcacaca cacacggatg cattagtttt caagtcagga tcctagcaca gcccacaccc 20160
tgcatttgct tggtgtctcc tgaggtctct agttatactt cccatccctt ttcttgccat 20220
gtatttcctg aacacatgtt atctttgatc cttaaaccat gacttagaga tacagatgta 20280
tgacaagctg agagatgatg tgagactgtt gttaattttt tctccatgta ctaattacat 20340
tgtggttatc ttaaccacaa aggaagcgtt ctactccaga gaaccgcgtg gaaacagtgc 20400
agatggacta gcacgatacc tgagaggagc tttaggataa ctccggtgct ggggaggttg 20460
gggcccagtt caagcaggag gggaggcgtg gggacaggtg ttgaagctgt gggtgtgcag 20520
cggaggcttc atgacgcttt cctcctgctc ttgtgtacgt ctgagcattt ccataacagg 20580
gaagtgtttt gttttgtttt ttaaataaca ttttaaatgc ctctggcaca tgggaatcca 20640
tggtaatttc tgtcgttgtt gtatattctt tttcaaatgc aaggacctga aaaatatctc 20700
ctaaactgga aaaggaaatg aggctgaata cagattttat tttagcaaat agagaagcag 20760
tgattgtctg gcggttaact gtaatccatt ctgagtgtga ctttactgtt aagtattcta 20820
aaaacaagag accaaacaaa atgaacaata tgtccaaatg tgtatatata taatttgtaa 20880
ctagaggtaa attgcagatg aattgcagat gtacacagac agatggatgg acagatgatt 20940
gatatagatt gattgacaga tgattcatag ataacttgca atgtttcttc agtgaacgca 21000
tatttatttc ttgggtaata agaaaaaaca atagaatgtg gaatttgggg cttggcctct 21060
tttagctcat ttaaaaaaat attaaacact tggaattatc gagcgctgaa aaaggcaata 21120
gaaaattcac cttttaactc cctcaaagat agaaatgtgt gaatctgcta gtgggttgcg 21180
tttggctggt cctgcaggct gatttggtct gttctctctc ccagagagat ccccaagccc 21240
ggctgagatg tgcctgtttg tcttgagggc agacaaagcc tagcaaaatc ttatggaagc 21300
tgatataaaa gcttaatagc ttataaaagc tctaaaaatg attcacagtc taggatagag 21360
aaaataaaag gaatttgaat tggtttattt tcctttagag gagcctaaat caatatttat 21420
tctgagtatg caatcagaaa tatcagtaat ttgagaacaa ggcaaacaga gctgcacatc 21480
ccgttatggc cacgagccca cctcgccttc gttcagacca cagctgaagg tctgacttag 21540
gtgcagcacg cacccctgga gctgagggcc tggagcaggg ccaggccggg ctcttctctc 21600
tcttgtctgt cctcgtctgt gggggaatga agatgacaca gcactcagga ggtccttttc 21660
aggacccaga gtcactgggc ttttagggcg tttggctctg gttctagccc gagtgtggtc 21720
tcagtcccca ttggtggttg tggttgtggc atgggcatca ttagtcacac aacataaaac 21780
cacagaacgc agaatttgct caccctggtt cacacaggag caagcttggg caccagcacc 21840
ccctgaacgc atgccaaagg gcaggtccag ctcagtgctg gggtgtggag gaacccacct 21900
ggggcctgcc tgcaaagaca gatgccctgc cgtgtttaga aaaagagaaa actggcctaa 21960
accacagtga ggtcaaatgg atcatttaac ccgtcgagtt tggtttcttg ttcatccgac 22020
gcggttgatc ttattaacgc atatgtgttt gtgttgatgt ggcctccagc ttctgtcgca 22080
ctgtggacac agttggatgt ggctgctaat caatgcgggg ctccgtaggt cagtgagagc 22140
aatcagagcc tgctgtgcgg tggcatcccc gagttaagac aggcttttgt cccatactct 22200
attgaaacac ccagaaatgc tgacatgttg aagttaaggc catgtgcctt ggtgctactt 22260
gcttgcgaaa cagcctttga aggaaaaagg aggaggagga tccatgagtt tcaagggtcc 22320
cctcctgtaa tcacggctgc cactcaacgg agtaagtaat gtgtagcggg ccctctatct 22380
gcatgacgaa tcctcctaac attcctgtgg gcgaggtagg atttgtctcg ctttgcagcc 22440
gaagaatcag agcctcagaa aagttaagaa atcttccctg ggtcaagctg gtaggaggag 22500
ggactggaac tgaactcaca tctccacctc ctctcttcct actcctctgc ctttcttgca 22560
cctagagcag tgtacaacat caacaactga ccagggcgat cctagaggta agagacagcc 22620
gaatggcacg gacccagcca agcccaggcc tgcccaggtg gaacagagcc agctaggagc 22680
attcggtagc agaggtcagt ccgctgattg actgttctca cttccaggcc cacagcctcc 22740
tccaccctga tggtctatga gtctagtgcg gccctttgca caattttagc aactgaaccc 22800
ttttcctcac agaattgtga taccgtccta acatatgaag catatataaa cagttgggca 22860
aatcataata gtttccatta tttcataaat ttgcatttgt ggcaccaagg agagaattaa 22920
tgggaacaag agggttcttg tgtgagttcc gcatttggat ttgggggttc gaggtggcag 22980
ctataggctc acattagtgt ctgcatcact ttgcttcagt ttgtcacggt ggccccccaa 23040
atccagaacc gccctcctcg ctgtgtgagg agggtcctgc ctgcaccgct ttgcagacat 23100
gggccagcct ggatgcctgg gcgacgctgc cctgcgactc gctggcctgc aggacatctg 23160
caaaacattc aggtctcacg gcagtggcca tgaacggcct cacagacact gagtggacct 23220
gaccccaaag agaatgcgtc gtccttgaac gtgtcgatat ttaggttatt acacaatgag 23280
tgtgttgctt tgcaattagt gtctgaaaga gttagagcag atgtacatat agaaacgaag 23340
aaacgaaatc tgaatccatg ctgacagatt cccccteccc aaaccttgct caaggtaaca 23400
caggcgacca ggagcaagtc ccggccggcc ccctgctagc gtggtctgag tggcccaagc 23460
aggacccctg cccaggctca ctggactctc ctggagcccc cagacacgac acccttcctc 23520
atcactgaaa atccacttcc acagtgtagg agatgcatgg atctgagggc cagtaggaag 23580
tgctggagct ttaggcttta gacattcttt tttttttttt ttttgagaca gggtctccat 23640
ttgtggccca ggctggggta cagtggcgtg agaaattctt taacactctg ccgagtcctg 23700
gcccttgggg agtgaggcct ggctatgagg cttcttgtca gaactccgtg tgactctcag 23760
gatggaagaa cagggtgggg gctgctcctc ccctccctcc ctccagcccc tggcctttgt 23820
aaaacggctc cgcctacgcg cctgtagcca gtgcagaacc agggaggcct ctccccttcc 23880
cttcccagga ggggccccgc cttgtcctcc atgccggatt ctgttcgtcc tcccccaggt 23940
cctctctgct gcctccccact gccccatttc ctccaggaac cttcctctct cctaccacca 24000
gcctctctcc tacccccaga cacacactct ttacatgccg atttctgtcc tctggttaac 24060
tggcgtttaa ttttctcagc tgcttggctt aatgccaaag agtgttcttc caaataaaaa 24120
tggtaaagac ctttttctc ccatgagaat tttatgtaaa cgcagtgcag catgctcgta 24180
ggctggttct gttatcaatt tctaagctca gcttccagag ctagagaact tttttattgg 24240
ttataaaaac cctacatatt cagtgcagaa attctgaaaa atgcagaaca gtatcaggga 24300
gaaaataact catcccccac tacccagaga aaaccgctgt taacaccgaa gtgccacagt 24360
tgctggcgtt ctcacacagg tgtgcgttta ggagtgtgta agtgcgtgta agtgtgtgtc 24420
tggctttctt tcacataatt ttgtgtcctg atcattttca ctcagcatta catcagcagc 24480
ggtttccaat atagcattaa attgtcttca aaaacatgat tttaatgcct ctataaagtt 24540
ccatcatgga ggctcactaa aatgtaatca cttcattgtt tatgagatac tcagcttaat 24600
tccatttctc tgcagtgaat aatccagagg aacacgctca gtgtgcatct ttgcttgcag 24660
cagggcagcg cagggcattg gttggggtat aaatccgggg gtgcagtgga gattagatta 24720
gatcgtccgt ggaaagcacc agaatggtgc ctggcactta ataaatgctc ttattagtat 24780
gtttatcttc attatgtccc taagagccat tcctggaaat gagactgtga gtcaaagggc 24840
acaaataccg ccaacctgct ttccgacagc gctgtgtgga tacacgggcc cgaacggcgc 24900
cagcctcact gcctctgcgt tagtgccgcc acttcatctc agatactctc ctgaagataa 24960
gaggagagtc ccatgcagcc ataagaaaga caacggagag atctgtgtac cctccaccca 25020
gtctccccta ctgggactgt cgtgcaaaat tatggcccag tcttacaacc agggtattga 25080
cagcgagaca agcccccatc tgatccagat tctccagttg tacttgctga tgtcgtttag 25140
atatttgtcc ccgccaaatc tcatgttgaa ttggtatcct cagtgttgga gtggggcctg 25200
gtgggaggtg actggatcgt ggggtgggtt tctcacaaat ggtttagtgc catccccttg 25260
gtgctatcct tgagatagtg aattcttgca agatctggtt gtttatgtgt gaaggtagaa 25320
ggcatctcct ctctctccct cacgggtgtg cacgcctccc ttcatcatgt gatatgcctg 25380
ctcctgtttc accttccatc ctgagtgaaa gctccctgag gcctccccag aagcccagtg 25440
atgtcggtgc catgcttata cagcctgcag aactgtgagc caattagaaa ttggctttat 25500
aaatgaccca gtctcagata tttctttata gcaatgcaag aacagcctca tgcacttgta 25560
ctcacttgag catgtgcact tacttctgca cgatgttctt gcctgtgtag actcttacat 25620
ccacaaccac agtcacagtc tagaacattc catcgccgca aggctgcctc ttataaccaa 25680
ccacatcccc tacctgcacc catttccaac accccatgcc taactcgatt tccagcaccc 25740
cgtcctggtg aacatgaatc tgttctctat ctcttcaatt ccgtcatttc aagaatatta 25800
tataaatggg attacacagt atgtaacctc ttgagactgg ctttttccaa ctggcatcat 25860
tcccttgaga tccatccaag tggttgtgtg caccttttcc ttgctgagcc gtgttccatg 25920
ttgtgggccg accccagttt agcactcgcc cattggaggg ttggagggca tccgactcat 25980
ctctagtgtg gggcagtgcg tcaccttctc acaattgtca acgggattgt cactagtatt 26040
tgccttccat gtcttggagg ccaatgtggc tgctcttaga aatcagtcct ccttattttg 26100
gttggggaga tttctgatgt cagtttgacg tttataatta ataagcatca tcatcaagtt 26160
acaagagtaa ataaaaatat gaggcagggt gaaatgtaag atgctcgaga ggctgagatc 26220
agtagctgtg tgaatacagc agggcgggca ccagcagtga gctccacggg gcccagcgtc 26280
cggcctcatt aaccagctgc ccttggggag gagcagagcc cgctcttccc tcctggggaa 26340
gggtagtgtg atggaaagac aggctgccct tctctcctgc aggagctcag catcatgctg 26400
tgtacatgcc tgggctctct tcttcagccc tagccactta aaaccacttg gagggaaaga 26460
ttgtagaata attataatga ggaaaatttc gctccagatt cgttactcca agttcagaga 26520
agctctgtaa aaattgttgc taaggcaatt gaataaagaa tgtcagccga tgtaagcgat 26580
aacagcaaga caatgaacat aattgcatgt tttacaacaa ccaacctcaa agcatgactt 26640
ccctgacata gatatgtttt ttaatgattt tgaaaggtaa cacagacatt ttcagggatt 26700
tggagaggaa actaatgcca tcctggttta ccagctttat ggggtcatct ctccggtgaa 26760
aaagactgca gccagccttg cagagagggc gctgtcttag ggaggcacct ccaactgtcc 26820
ccgcgaccca gcccctaagt gcttcacatc aacactgttc ttttgtgacg gtgctgctgt 26880
ctttcattcg ccagcctgtc atgctcaact caaacctcag ttgccatcca gttatctttt 26940
tttttttct tgagatggag tcttgctctg ttgcccaggc tggaatgcag tggcacaatc 27000
ttggctcacc gcagtctcca catcccgggt tcaagtgatt ctcctgcctc ggcctcctga 27060
ggagctggga ctacaggcac atgcccccac gcccagctaa tttttgtatt tttagtagag 27120
atgggatttc gccacactgg ccaggctggg ctcaaactcc taaccttggg tgatccaccc 27180
acctcagtct cccaaagagc taggatcaca ggcgtgagcc actgagccca gcctagttat 27240
cttgtttgtc caggaattgg agcatttcta ggtagcacca caaatgtctg tgcaagaaac 27300
ccacaatttc cagtggtcat tggctttgtg ccaatccaaa ctagagtctg acaaacccag 27360
caagaaatat tcgcggcagc tgcaaggaag ctcctcaaat agaaatagaa aaatgaacca 27420
gggtctgctc ttcccttccg ggtgtggaat caacggaagc cgactcaaca cagagccctg 27480
ggggcgtgag gggtttggcg ggatctctgc cggctgcaga tctctgctct gttattacca 27540
gcccttctgc ccagctccta attgctctga agagggaata attttctcag cagccattgc 27600
cagccacatt tggactgaat agatgctgaa atggcaaggg taaatggggc agagacagtg 27660
aaaagccatt ttctatctgg agcccaaata aaatcttcct cccacactcc tgcctggctc 27720
ctccgcagcc tcaatgccct tctgagagct gcctgcccca gtaggaggcc aggctgggac 27780
caaggacacc cagttctggg taaccatctt cccatggctc cttggacaac caccttaaag 27840
aagggaaagg caagaagcag aaggaaagca gaggctggac attggaatca gcctttcttt 27900

-continued aaactaaaaa aaagttttca catatgtgaa tgcgtgtgtg aatttgaagt cgtatgtgga 27960
aggggccata tatccgtcaa tgcatgctcc aaaaatcaga actgatggac ggcaaacagc 28020
atcggatgtg cagccagcat tcttccggcg gccacctccc gggggaaata ggtgcagcag 28080
acaggaccgt ctgtgggacg gggacaggca agcatgacag caggtaccac agatcagggt 28140
gcacagacag ggctggggga ggcagcgtgg cacggcaccc acttcccctc ggcgtgtctg 28200
ggctgaagcc cagtggactc ccgctgatca gaaggatcct ccactagaag gatctcactg 28260
gacgagtccc ctccaaactg gaacatgcag gtgccttggg cttcatgctg cacctttcag 28320
ataaaaacac acaggtgagc tgggagagct ggagtcccat ggaccccaga gatccaggtc 28380
acgaggaggg gatcgcgctg caccaggaca cattcaccaa ggtgagccct ggttcctccc 28440
cacaggctgt gggcaaggaa gtgtcgatgc caggctggct cagtaggtgg aagaaccttc 28500
cggaatgcct gcccgcaggc tgctgctggc atcgagtctg tgtcctattt tccattcact 28560
gcatgcatcc tccaagtatg atttccactc ggaaccctga gctgcctcat ccctcgctcc 28620
gtctcccctc cctcccgccc agctcacact gaaatcacgc ctcgcgttca gcggctggag 28680
tcctggtgga ttgctgcttc ggggctctca gaaatccctt tacttgagtc ttggttttac 28740
aggaagacca tgaagcaccc cccaggagct ggagctcctc cttctggacc cagtgtctct 28800
tctcagcctc acgacgagga gacctgctca tggagctgct gcgccggcct gagctctgat 28860
ccctcctccg acccagcctc accctgcaag cagcaccatg tggggctcag aatggggatc 28920
ttaagggacc cttcccacaa cctcccgata agcctttcca cggagggccc aagcggagac 28980
aggagaacac tgtatttgat aaaatagagt caaatccagg aaaatgcctc tggacccgga 29040
aaggaaacga ctcacccccc acccatgaga gacccttctg tcctgtccct taacccagag 29100
gccctgggca tgggtttcgc agccccctgg aggccagacc ctcaaactcc agccttgttt 29160
cttctaagtg tgccagtcaa gatgcttctc actgcaagaa acagactctt tctcaagcca 29220
gttcaagaag atctgcgttg ctgcagaggc cgatgggtgt ggggagcagg ctcagtgaga 29280
gactgtcgta aggaggctga gaggtcttca gaaaaatccc caggacctgg ggtgccagga 29340
gcctgggcgg gcctgggctc tcgcagcctg cagcccctcc cctccctctc acagcctccg 29400
ctgcccccgg gctcagggcc cctgcctgtg ccttctcctg aggcttctcc tttttacctc 29460
tcagggtccc agtgtggcca gcccggcact aaacccatgc gaccctggct cactgacagt 29520
cgccaccagc tccacatctc tcagtaaaag ttcccccaaa agagtgtgat tgggagctag 29580
ccagcggggc ttaaggcagc cccctgctcc agtccccttg gccatggaga cagggcaggg 29640
ttagcaggag gcaaggcatg cgcaggacag ctggccggca gaggtcccgt gtgctgtcat 29700
gggtgcaggg tggacactgt gaccctgggt cccccacttg gaaggggtga tctagaggga 29760
cttttgtcag aaagaccccc acccagccaa tctgactgat ggggccatca ccttgacaac 29820
aggcttggtg gcaaagcaag agggtacaac cgaccagagc cccgggtccc ctgtgccctc 29880
ctgcactgcc tgacagggct gggccatggc ccgtaccaac cgtgagctga gccaggaatc 29940
cagtcaaacc gtgtgcctga gtgacacgta gctctcttcc ttctctggat tcactgctga 30000
tcaaccccaa caagcagcag gactgtcttg ctgtgaaccc accgcttgcg gacccctccc 30060
caggcctcca ttcccgcctt tctgaaggtc aaggcagcgc cctccccaag aaacggtggg 30120
aacagaggag ccaggtgttc gttcttccca gctccggaaa cgctgcagat tgcgcactcg 30180
agttcctgct gacataacag tggctgccag acaaaatgtg gcgaaaagtt tttctaggtg 30240
cctttgttca ctcagagact tcctagagac ttgtgtgaaa atcacaggat ttgcaaccag 30300
tggggacgtt gagattcgtg gcaactgaaa tgatacaaac ttgaactttg tgtcaaacca 30360
gtagtgtttt gtgtaattct tttcaaacct gtcatttcac ttactgcttc tcacagcccc 30420
aaggggcagg tggagttgat gccatcaacc ctatttacag aatggtaaac tgaggctccc 30480
actggttatg cgcttgccca cagggttgaa agagaagcca tggacaaaag gagtcactgg 30540
ttacccaaag ggcttcctgt tctcaaatcc actgctcctt ccattacgtg gtgtctagaa 30600
ggaggctctt ttggatatag acattaaata atctgggagt cagtgtatgc tgtgatcaag 30660
catgtgcggt ccgcagccga tggcccagga tgcagtcctg atgtacactt ctggctgggt 30720
gcgtgggagc cacacacatc tctgtgtgcc ttggtttccg tgtgtaaaca tcttagacta 30780
gtgcttgcct gtggttggca cctggtaagt gtcagccttc tctaatgtag gcagcttgag 30840
ggctcccaga cagtgatgtt cccgctgaca ttcccaggtc tcagctgatt atgaagaggc 30900
atcaatttcc agtgggggag ccgccctctg tctcatcatt tgtttctctc atcttgcttt 30960
aatatcacag cactgccagt caaaccacac aaaagggttt gtgatgacct gccgtgcatt 31020
ctcgtaagct ccagccctga ctcgcctgca agccagaagc caacataaaa ctttcgtttt 31080
tcccttaatc ttgctgcctc tgcatctcat tttcaaattt cattttatca actttttttg 31140
cactatttgt ttctggataa aggatttgca aaattcttca gcatgtggtc aggaagccct 31200
atggcctcct gacgaggcag cctaggggtc ctcccgtggt ctgaagctgc agccgggctg 31260
gcctcccaca gtcaggagca gcatcaggct gggtgcttct gacaccagcg aagagcgcgg 31320
ctgtccaagc cccatccct agggctcacg cctcatgccc aaactcgcac ccactttggc 31380
gccgctggag actaatgaac agcaaaagct gaagtcatga ctctcatcca gatctaaaat 31440
gaccgtgtgt caaacatttt tactgaactg atgaatcgaa tgggaactgg taagaaggta 31500
cgaccagttc aaaagagaaa tccaagaacc ctaaatgtat aaggagtgaa gcaatgttga 31560
aatggactta caaacggatg cagctatatt ctccagtgga gacagccagt gccaactttt 31620
gtgcttattc caaatttcct gacagcctcc ccaccttttt tccaacataa tctcaaagag 31680
agattattct ggatggcaga ataaggctgg tccccctagg tgtggcatcc ttgcttgcat 31740
agaggtggca agagtgccac cataccaaac aggccttttt cagtttgttt tgctggaaga 31800
cctcagaaga tatcagaagc aaaagcctct gttgtttgct atcctaaggt taggaagcca 31860
agcataaaaa gctctcctcc agatttcacc ggcagtactt ataaatttga tgaacccctc 31920
tcttctcaag gcccccacga tattccaaaa ccctggcctg ccagagtaga gccttttttc 31980
ccatcttgga ggctgtgacc ctgagagccc ctaccctccc ccaggggact ttgtgggcat 32040
ggacgttgca cagtcaccct cggcccctca agagcggtca cagcccagca aatgagcgtc 32100
gttctcacgc acgtctctca ggcttaggct cggttgcata aaccttcccc aattttatcc 32160
tggcaaggag gaggacagat ccttccggaa cctttgcaga tattgccacc aaaagtaaag 32220
ccttcataaa agtttgcatt tggggaggaa ggagagcaga tggtgaaaat cagatatcac 32280
ttaagaatta ctcatttcag tttacaaaaa atctaggtcg ttaaaggtga ctgatagctt 32340
aagaagacag ggaaagggct tcataacaga gccggaaagt ccaacagtac aacgacacgc 32400
atgatgccaa aaagtaaagc gttcctcact cattccactc agtgctccgt aactgattct 32460
ccactggctc ctgggctgca gcctcatgaa gccagctgtt cctcaactga aaagagccct 32520
ggaagccctg ggcagcccac tggcagggtc tgaatatcat ctgagcgagg ccatcagaag 32580
ctgtccccag gagtctgtgc ttgggggtca gtcatcggag gtgcttactg cggtcctttt 32640
ccatggggct cgaagcttct gcattgaatc acgagctctg gcctccagcc tggtgcagaa 32700
ccttccaggg ggcattggag taaaagcttc tgtagatgac agctacccct tttttggtcc 32760
attttatagc agaggaaatt taggttcaaa gaagttgagt tgagagtccc aggagtaaga 32820
agcagtcaag gatcccccca ggcctccggg gccgcctggg ctgcctggcc tcacgacctg 32880
gccccatgct cctgagatgg agaagcccca ggcccatgag cctgttgccc ttggcaaagc 32940
cacttccctt ctgagtaaag tcagacgagc ctgcccagtc ccaagagact gcgattccgt 33000
aatcgccctc ccctcgcctt ttgaggtctt gctggtaggt gcacccccctt caagccagcc 33060 caaggagcca tgatttgagt cggtcttgcc agatgtgtct ggagagaatt taactccaag 33120
atcatccccc gtgcactctg aggggctggg acaggatgtg gtgccctttg tgcccaggag 33180
gagaagcacc cagtggggcg gggtggggcg aggactttat aaaggcgtca tttgctgcgg 33240
ccacccaggt tggaacacag ggaccacagg gccccccgcc ttctgcagga ccacccccgct 33300 catctgaggg agacactgta gaaacacatc tttgagcagt ggcttctaat ccaagaaacc 33360
caatagaagt caaacgcaga ttcctagggc ccaacccgga cccactgcgt gggaatccct 33420
cagccggggc cagaagcacg ctttgaagac accaacctcc tcagcaagcc tcttgcaaac 33480
cacatcctgc ttctccagaa gctgcagatc cagaatgttc aaagaaagag ccctccttgc 33540
cttcctcttc ttccacccct gccctctgca gactggggtt ctgtagaccc ccaaagtaag 33600
tccgccacac cggaaggaag tgagttacac aggggcccac atgggaaccg ctttttgtcc 33660
tgtcttggtg ggaaaatggc cacgacccca gcccaggctc tgccacgcca caactccacg 33720
ggcatagcct gggaggccgc agcgtgaact gtgactaggg ctgaggatgg tgccatggta 33780
gaagtgaggg cctggcaccc ggccaagtgc aggactcctc ggcagtgggg ttgggagaag 33840
cagcctctgc aggcgaggcc aggaaccagg acacaggagg agaagcacat ctcagaggag 33900
ggagctctgg gaggagccag cagagtcctg caaaggagga tgtgggggaa atggggtgag 33960
gccaaagtgg gggctgctga aggggctact gcacccgtgc gagcagggcc aggaccaagc 34020
tgcataggca gccagggaca cagccgatgc cacagacgtc aggaaccacg caatgacaca 34080
ggccaccttt gaccgaccgt tacccctggg gcaaatacca gtggggataa cgggcaagga 34140
gaggtgctgt ttactgtctt attgttgcca gttcagcagc ccacaggaaa tggtgttagt 34200
cacagaaaaa aaaaatctgt tttctatatt tcactgtttc caagtaaaga aaaaagaaaa 34260
ctaatcttag cttaaaaaaa aaaaaaatgg tgcgctgggc accgaaaaat aaccatcttc 34320
ctaggcctgc gtttccccca caccggggac ttgtgctgga aagaaaagct gcgttggcag 34380
ccaggagccg gggaaactgt ccagggaggc atcctctgcg atgaaggcgg ggcctcggcg 34440
tggcccgttc cgcgctctgt ccagccctgg agaagcccca ccctcaccga gctcgaaata 34500
ccccctccct gagagccgag actcatggcc gggacccctt ggacagaaga tgcggatgct 34560
aacccggcgc ttccaccaca gccccggcgg cactggggag cgagcgcggc catcccgcgc 34620
gtaggtggtg tttctctgca ggcgccagtt tcaccgcggg cgcccaggat cctcaacggt 34680
tctgttgtga tgtgattccc ctcttcgact tcgtcattca gcctcagtcc ctcagtcccc 34740
aaataccgaa aggcagtctt tttttttttt ttttgagacg gagtttcact cttgttgccc 34800
aggctggagt gcaatggtgc gatctcggtt cactgcaacc tccgtctccc tggctcaagc 34860
gattctcccg gctcagcctc ccgagtagct gggattacag gcacctgcca ccacgcccgg 34920
ctaatttttt gtatttttag tagagacggg gtttcaccat gttggccagg atggtctgga 34980

-continued

```
actcctgatc tcaggtgatc cacccgcctc tgcctcccaa agtgctggga ttacaggcgt  35040
gagccaccgc gcccggcctt tttttctttt ttcttttgaa gttaatgaac ttgaatttta  35100
ttttatttac agaatagccc ccatgagata cttgaagacc cggtgccaag cgacagtgtt  35160
gaccccaggt ggtcagtcct gcctggcccc ttccgaggga tgcgccttca ccataaccat  35220
gtcacggaca ggcgtgtggg caagggggca tcgctgtatt tttcacaact ctttccactg  35280
aacacgacaa tgacattttt caccacccgt atgcatcaac caaatgaaaa gatgagcctg  35340
tgacattccc gtgcgtagag ttacagcttt tcttttcaaa acgaaccttc agtttggagc  35400
cgaagcggaa gcacgtggcg tctgacgtct ccagggagac ccgccgccct cgctgccgcc  35460
tcaccgcgct tctgttttgc aggtaatctt cagcaagtac tgcaactcca gcgacatcat  35520
ggacctgttc tgcatcgcca ccggcctgcc tcggtgagtg cgcgctgcgg gctctgcccg  35580
gtgacgccac gcggcctcct cgccttttcg ggatggctgg gaggggcggg aagaggcgct  35640
gaagggcccg aggcaccggc cttctacaag gggctcttcg aaatcaatca atgcgcagaa  35700
tcccgaggga ggctcagccg ccctccgggc ctctctgcct ccacaggtga tggctgtgtc  35760
cacaaggagg aaaccgtcgg gctgaattaa acagaaccgc cctcctaaga gtgtgggttt  35820
ttctgccggg cgtggtgtct cacacctgta atcccaacac tttgagaggc cgaggtgggc  35880
agatcacctg aggtcaggag ttcgagacca gcctggccaa catggtgaaa tcttgtctct  35940
actaaaaata caaaaattag ccgggcgtgg tggcgagcac ctgtcatccc agctgcttgg  36000
gaggctgagg caggagaatg gcttgaaccc tggaggcaga ggttgtagtg agctgagatc  36060
atgccattgc actccagcct gggcaacaga gcgagactcc gcctcaaaat aaataaataa  36120
ataaaaaaga gtgtgggttt tttcctctca cttcttcatt cacttttgga gaaagcgggg  36180
tggttgtgtg tgtttggtcc ccagccccac atcaccccat aggtgccttt tctacccagg  36240
gggcttgacc cagatcaaca ctgggtgaaa ggctgacttc agaaatgggt tgaaaagacc  36300
agtgatctgc cttatcgagt cctcagagtc ccacaggagt taatgtccta aatcaacagt  36360
gtgttcgagc cagtgaattt tctaattatc agcaaacttt ccaaatgtaa agggtgagca  36420
ggagtagctt tggctcaagg attaacttta aagttaggac ggaggtggag aagggcaatt  36480
gaagtttctc acagacaggt gagaaaaggg agatgaaagt acacgtctga aagtgcagca  36540
aatggcagtt ttagccgcaa aaatagccca tggtctgggg catctttggg caccatatat  36600
gaagcaatgt gccaataaat aaatatatat acacagtatt ccgtatagca gccctgggat  36660
ttgagtatca cctctatttc acagatttta acaatttaca actgaagatc agagattaac  36720
ttggtcgagg taacacatct tgcaagaggc cccaaaacat gtgaggttgg aggaagactc  36780
atcctaagca tttaaaacta ttttgtagga gagacttgcg cagttcagac ggactcccaa  36840
aggcactgga agcggaaaga caaactatga gttcgtcatc tgctgatata aatgttagtt  36900
cctattttac cacagttttt taaaaaaaat ctcccaactc aataaagtag acttgctcca  36960
attcccattt taaagtattt cagcatctac acgcacttag gattatacgc agctgtttaa  37020
tttcatttac aatcggagtc tcaatgccct ggggacggcc tcccaccctt cccatcccac  37080
cacaccttgg tcaggctggt cctgggactg tcctggttgt ctcagggctc tggccccatg  37140
tgtacattca agtgtacatc ccagagcaca ctatgggcga aaacacgggc ttgggtgtgt  37200
tttccaggaa cacgaccatc tccctgctga ccaccgacga cgccatggtc tccatcgacc  37260
ccaccatgcc cgcgaattca gaacggtaag aggctccggc cgcgctcctc ggggtgtgcc  37320
tggcacttct ctccatgaca tgggaggctt tctgtgattt tgtaaatgtg ctactgcaga  37380
```

aaggtgtgaa ttgacagcag agatggagag cgagggtagg agccagtgtg aaggaagctt 37440
gactcgtcgt gttcccctgc agaggagctg ggcacgttcc aagataacaa ttgcagccgt 37500
ggctctgcac ctgcttctca acgggaggag gcattgtaca gaggggaaac tgaggcccag 37560
gagggtgagc caagagctgc agagccaggc cccgggatcc ccacattaac cccaggaagg 37620
acctcgggag attccctaca gagcccctgg ggacatttcg tgtttaccca cttagggccg 37680
gtctctgtgt tcataaagtg atgcctgtgg gagattctaa gcacagaagg gccagggaca 37740
agggaggccc aggaagtcaa gaggagaggc cggtgaaagc ctccgtgaat gtctgtgaac 37800
taggtcaagc cagcggtgta tggcccagga aggacgcgga gcaggggccc tcaggtcagt 37860
gacctgcccc tgttcctggt gacctgggga gaccccagca gcctccactg ctctttgtgg 37920
ttgggcaaag tggaacttag atttcctcat gaggcgaggg agcaggtgag ctgggggcgg 37980
ggcgtgcgac ctcaggaccc ctctctggcg tcctctgttc ctcccagagt ggggctcact 38040
gtgcctccaa gggactcagt agatgcgatg gtacacttgt caatctggtc atcagggtgt 38100
cctgcccaac tgacccatgg ccagctctga gcccacagga gaaagtgcat gtcaggcaga 38160
cccttgtgtc agtgaggtcc cagtgggcgt ggccagcacc gtccccctca gtgaggcccc 38220
ccagtggacg tggccagtgc tgcctccctc agtgaggtct cagtggacat ggccagagcc 38280
gtccccctca gtgagcgctc agtagacatg gccagtgccg tcctcagcga ggtccccgtg 38340
ggtgtggcca gcgccatccc cctcagcgag gtcctcgtgg gtgtggccag caccatccca 38400
ctcagcgagg tcccagtgga catggccagc gccgccccc tcagtgaggc ttcagtgggc 38460
atggccagtg ccgtccccct cagcgaggtc ccagtggacg tgtccagagc tgtcctggtc 38520
agccgtcctc cctgtcacct tgaggcctca gccgagctcc tctcatctgg ctgtgcccgt 38580
cagtctcccc tcctgcccta gccaggatgc ccgtctcctg ccccacacag tctggctctg 38640
actcttggct tccagactcc ccggaaggtg cagtgctaat tggctcccca gagactccag 38700
taagcatctt gtcagcctca gcaccagctc cagcctgggg ggtctcgctc agaagcaaag 38760
tcactgagtg acctgtcctc ctgacaccca caagactaaa atgatctctc agaggggacc 38820
tcacagaaac cagcaccttg tccatgccag ctgggtatct gagagaaact gctttgtttt 38880
cctgaagtca tttgaaacag cgtgcagaga catttaaact cggcgggaaa taggagaagc 38940
ccaccttgac ccttctaatt ctctggcccc aggtgcctta ttaacaagag acagtatcag 39000
acacaccaga caaaagccct cctgagccca aagagcccaa atgtctggaa gctctctgct 39060
gagatgccaa aatgcatgcc tttctgataa agagacagag acagatgagg taccatgata 39120
tggacatggc agtggacgtg gacaggggag cagtggagat ggagaagatg gagacacacg 39180
cagttgagga tacaggcgaa gaagatggag acacacgcgg atgaggatac aggcgaagaa 39240
gatggagaca cacgcggatg aggatacagg tgaagaagat ggagacacac gcggatgagg 39300
atacaggtga agaaggtgga gacagacgcg gatgaggata cagatggaga agatggaggt 39360
agacgcgggt gaggatacag gtggagaaga tggaggtaga cgcgggtgag gatacaggtg 39420
gagaagatgg aggtagacgc ggatgaggat acaggtggag aagatggagg tagacgcgga 39480
tgaggacaca ggtggagaag atggaggtag acgcggatga ggatacaggt ggagaagatg 39540
gggttagacg cggatgagga cacaggtgga gaagaggaag ttagacgcgg atgaggatat 39600
agatagatgc atagggtgtg gatctaaccg ggtacaggtg atgcggaaac ggatctagac 39660
agcgatgtgg aaatggatct agacagcgat gtggatgtga tctagataat gtggctctgg 39720

-continued

```
acgtagaaag agcttcagat gctctatcta tgatcgtggg tgtggatata ggcatagaca  39780
tggtgaagag gagagaatag actctcctct ctcatgacaa actgatcgtg gctgggggcg  39840
gcacgtgctg agatgtggct gtatttgtcc cccaggctgg tgcctgcgcc tcctgcaccc  39900
ccgtctcctt tgtgccttct tccattccct ctgccactgt taggtccagg cctcactgag  39960
ctctgacctc cctgcctcca gcctgcctct cccacacggc tgccaggttc aacctggtaa  40020
gacaccttct tctccatggt ggcctcccaa tctgggccct gccaacttat gcctcaccaa  40080
cttctccaac ttacccctgt acccacgccc gcaccatgcc cagcccacag gatcctgcct  40140
tcccagctct gcagaaccag cttctgctta tccgctaggt gccagcccag ccacctgcct  40200
taagcaccat ccacagtcac ccagcccatc accatcacta gcaaagtcac ccagacccat  40260
caccatcacc atccagagtc acccagccct tcactatcac catccaaagt caccagcccc  40320
atcaccatca ctatccagag tcaccagccc catcaccatc accattcaaa gtcacccacc  40380
ccgataccat caccatccaa agtcacccag acctatcacc atcatcatcc agagtcacca  40440
gccccttcac catcaccatc caaagtcacc agccccttta ccatcaccat ccagagtcac  40500
ccagtcccat cgccatcacc atccagattc acccagaccc atcaccatct ccatctaaag  40560
tcacccagac ccatcaccat cactatccaa agtcacgcat cctgtcacta tcaccatcca  40620
aagtcaccaa gccccttcac catcaccatc caaagtcacc cagtcctatc accatcacca  40680
tcctaagtta ccagcctttc accatcacca tcaaagtcac cagccccatc atcgtcacca  40740
tcctatccaa agtcatccag taccaccacc atccaaaatc acccagacac atcaccatca  40800
ccatccaaag ccacctagcc catcaccatc actatccaaa gtcatctagc accatcacca  40860
tccaaagtca cccagacaca tcaccatcac catccaaagt taccagcccc atcaccatca  40920
tcatccagag tcacccagat ccatcaccat caccatccaa agtcactcag cccatcacca  40980
tcactatcca aagtcaccag cctcttcacc atcactatca ccaggccctt caccatcatc  41040
cgaagtcacc cagacccatg accatcacca tccaaagtct tccagaccca tcatcatcac  41100
catttgaggt cacccagacc catcaccatc accatccaaa gtcacccagc ccatcaccat  41160
cactatccaa agtgaccagc ccctttacca tcactatcca aagtcaccca gacccatcac  41220
catcaccacc caaagtcacc cagccccttc accatctcca tccaaagtca cccaacctgt  41280
caccatcagc acatcactgg cttcctcccc tcagtgtgcg cctcagtctg aagtgatctc  41340
acttacttgt ttgaggttct cactgctgct ggccccgctg gacggtcttc tctcatagga  41400
aggaaatttc accttgctct ctgctggatt tccagcccct aaacgaggcg gggcatgctg  41460
ggtgcaggat ggaatgagtt ggggacggag tgaaccagtc cagctcgtgc gtgcctcccc  41520
ctctgcactg cccagagcag ttttttcttc tggggacgca gggcaacgtc tggagacatt  41580
tctggatgtc accaggggta agggcctgct acttgtatct gatgggtgga gacccgggat  41640
gccaatggca tcctacagcg cacaggacag gcccacaaca atgacacacg tggccggaga  41700
catcagcggt gctgaggcgg agcacctggt gtctgaggtc tcccctgtgc tctgtcgctg  41760
tcctctcacc ctcccccaat cttccaacct agtagttctc agacaactgc gtcagaatcc  41820
gcagggggct tggtggagca cagagctccc ctcagtctct ggtttgtgac ggaggtgggc  41880
cccgagaatc tttctgcagc agaaagccag gctttctgca ggttcccagt gaggaggacg  41940
aggctggccc gggacacgcc actgatgctc ttctgaccca ggggcttttc tctcccgctt  42000
ccgtccctct tccctcgccg gcaggtgacg ttactggcct tttctttttt ggccctgcct  42060
cccccttggc ttctcccctc ttcctctcct ccactcggtg cctggtgaca tgcggccatc  42120
```

ctcagagatg tgcttcgggg cccgcacgcc ttgctcctcg cactcttcct gcaccggagc 42180
cgcggtgcga ggcctcggga atgctcaccg tttctctccc gccccccggc cgcatgctgc 42240
agccattccc tcaccacatg tccaggaggg agccggcatc ctttgctgac tttcttgctg 42300
tgactatggt gctgcgtgga aaaggggccg tgggaaggct gggcaggtgg ctgctcagag 42360
ccccacctga cacggtgacc cacggggcct ggaaattcac tgccccgatt tccacacagg 42420
tgcctgagct cctgcagaga atgcctgaga gcgagacgca tgcccgtcaa tttgtgcttt 42480
caggcgtcct aagcacacac gcctgctctt atttgaacca ctccctgtaa gctagttcca 42540
ctaaagagtg gctttccacc ctggctgcag attgcaacca cccaggaatc ttttttttt 42600
tttttttgag acggagtctg gctctgtcgc ccaggctgga gtgcagtggc gcgatctcgg 42660
ctcactgcaa gctctgcctt ccgggttcac gccattctcc tgcctcagcc tcccgagtag 42720
ctgggactac aggcgcccgc caccacgccc agctaatttt ttgtgttttt agtagagacg 42780
ggatgttagc caggatgatc acgatctcct gacctcgtga tccacctgcc tcggcccccc 42840
agagtgctgc gattacaggc gtgagccacc gcgtcctact ttttttttt ttttttttt 42900
gagacagagt ttcactctta ttgcccaggc tgcagtgcaa tggtgtgatc tcagctcact 42960
gcaacctctg cctcccaggt tccagggatt ctcctgcctc agcctcccaa gtagctggga 43020
tcacaggcat gcacgaccac acctggctaa ttttgtattt ttagtaaaga tggggtttct 43080
ccatgttggt caggctggtc tcaaactcct gacctcaggt gatccgccca cctcagcctc 43140
ccaaagtgct gagattacag gcgtgagcca ccatgcccag cccacccagg aatcttttaa 43200
aaggtaccag ttgatgccca gacccctcaa ttaagtccag atttttaaga gatttttttt 43260
ttttaaagct ctgcaagtga ttccagcaca cagtctgggg actaaccgct gatataaggt 43320
ctggaaaatc taagaaacca ctctacccca ccctctggtg accagaagct tatgtctacc 43380
agacccaggg ccttcccttg ctgaaacatg ctgggtaaac tctttgtttc ttcctagcag 43440
acagcagccc tctccctcta gctcagaagc tacgtcagca gttggttggt tggttggttg 43500
gtgggttggt tgggttgtgt ctctctttaa cttcctccac ttctgaagtc acctgcagtg 43560
acttggtgtg gacttggtca cctcactgtc cccccagcct caggcccagg aaccatgtct 43620
ttggaggagg ctctcctgct ggcagctggt tgcatctggc atgcttggat tcctgcaggt 43680
ggctggttgc acctagcttg cttggattct tcccagattc acagccatag ggtgggcgtt 43740
tcatgaaatc tccaaattcc aagggctctt gacagaccac ctccatcctg atcagaaggg 43800
gtgatgccgg ttgcacggtc tcttagagct taaaactcta gcttcttctc tgctcctcat 43860
tccaaactaa acaaattgtt gcattggatt attctttcaa aatactcctt gccttaatgc 43920
catcctttag attttggtgg ctggctcctg ttgtggaccg catctcacag gtggacttcc 43980
tggtttctgc ctcctgttac ccctcacagt tatctctccc ttgagtcctg ctaccttcca 44040
gaaaaatagg ctccaaacac actttcatcc catcactccc agcatggagt tctccagtgg 44100
cctgttggct acaggacact ctccagcccc ccgcattggg atgtctggcc ccaatccacc 44160
ataatgtact tgtctccaat ctgctgagct gcatgaatgc ccaccccagc ccagcgggca 44220
ctccccttct gcaaacctcc aagcacattc cccctctgca cactgccaat cttcctgtcc 44280
ccgccccaaa tccaaaggcc cctcctatgg ctggggatcc actggcagct gcctaaccct 44340
tcctatgctc ctggacgttt ggtgcaatct ggagcacgct caagccggca tttgaaataa 44400
cctggaacac gtttacatca tggaaaatat ggaaaatagg ctgattggct tccactccct 44460
tttagagctg gcaagaaaaa taattgatga ctaaacaacc taacgaccaa caaatataaa 44520
aagtcatagc ccaaccatga tcaaataagg ctccagcatt cctccttgga gggactctga 44580
gccatctggt gtcattttcc tttccaatcc gggaacattc tggagatcct gacatccagc 44640
taacatgggc gttgcttcct gacaacccta ccccttccat tccccagtca ctactgcttc 44700
aagatgcagt ggaaggagat aaatcagaca cctcagtagc gtgagtgaaa gtggggtgtg 44760
tggtgagaca catacagagg ggagagggcc agaggacggc gccgtgcgac acacaccatt 44820
gctccttttg ttcccggttt cggccaagtt gtgccgcagg tgactctcca ccggctgagc 44880
tctgtgcatg cagggccagt attctcggcc attctggctt agagaaaagc tttctatatt 44940
ccagaatggc tccaggcctc ctcctcctcc tattaaatgt gttttaaaag aggtcttaga 45000
gcccaggcag ttagatctta gaaaaagaca aatacagtag aagctggagg caagcttatc 45060
ctttccaaag agggagtgct tcctgtgtta atttgttatt gagcatgatg aagattcagc 45120
tccattgaga ctgagccaag agttgactca ttcatgggag caacataacg ggttgtgaga 45180
agccaaagga ttaagcatct gggagccaag actgatcttg agtggcccag aaatgcaacc 45240
caaggatctt gggcccaagg gccaggaagg tttctgcagc ctcctggagc attcacagag 45300
gctccctgtc cgtccacttt tccctctgtt gctgatgtga tggctcctgc cctcagctta 45360
ccagactcct cggagaggct ggcctctgaa ttggttgaat gggcttgaag ggggctggac 45420
tccatttggg tggatgagca ggcccagtgc ccctgtatga ggggaagttg tcttggtaag 45480
cctgtttttg tgtcaggtcc ccaggacacc ttcctctgag tctcttgcgt gggagaagtt 45540
gctggacacg cctctctggc tctgtccccg ccggcactgt gtgggatcca tgctgttctc 45600
cctccagccc ttgccccacc tcctggagcc cttctctgcg cctggtcact acccgccccc 45660
cacctccagc attaattttc tagggacaag gggcagggga aggaggagaa gaaagagtcc 45720
ttgctgctcc tcagagaaga cacaggagaa gaaagtcgga gaggagtggg gagccagggt 45780
ggcaaagccc cttcctgctg cccacgcagg tcctggcttt ctctccaccc actgcaccat 45840
ttccagggct gctctcatgg tgggagccgg agagacactg agaagaggaa ggaaggagga 45900
tccaagagga gcccagcaca cccggcttct ctgctgccca ccctccactc tgtcctccca 45960
gcccaggccc ttcctaggca accctggcac gggtcctcac tggccacact gaggccatca 46020
gcaaagcacc tggcctcttc acgccttggg ctctgggtct gtaaggcagt gaggctgagg 46080
ttcctgggac agctgggcac tgtggacttg cccagctgag cacaggcatc aggggctaga 46140
ggggccctag tcccgatgac gaccgagtgc cctctccacc tggggagctt ggaggacttt 46200
gctctgcact tagggccacg cttcaagccc agtgcctctt atgaccaagt ctctggggag 46260
aaatgagccc tccagtgcca aatgacccac cactaaaagg ccttttgagg cagggcctct 46320
cctgagccca cgcaggcacg tggtgggaga tgagagggtg tgggctcact tcttgacatt 46380
ctgtgtgagt gaggtcattc atagggtgag gggagaatca aggggacaga gggccctcta 46440
gtccccagca cttgggctca gctggcaagt ccacagtgcc cggctctccc gagaacctca 46500
gcctcaccgc cctacagaca aagggcccaa agtgcaggga ggtcagtgcc acacaggttt 46560
tattttttca cattattggt gtttaaaatt gtaaagattt tccacgttac ctgtaaccat 46620
caaaccacat gtattgcccc cagttaatca ccatgaacag cttggtgtgt atacccctcc 46680
atattcactg tgtttcttct tccaggaatg agctcattct ctatacatca ctccgtaact 46740
tgttgttttt acctagtaag gagtcatggg cgtcccacca ggtgaatact tgcatgtttg 46800
tcttcatctt cttaacaact acctgacact gcagtgtctc agtctgtctg aacttaaaca 46860

```
gctagacatt gagttctcag agtctggagg ctgaaatcca agatgagggt gtgggcaggt  46920
tctgttcctg gggaggcctc tcttcctggc ttgcatacag ctgccttctg gctgtgccct  46980
catgaggcag agcaagagac agctctggtg tctttggccc ttgtaaggac accaacccca  47040
tcccatgggc cccaccctca ggaactcctc caaacccaat cacctcccaa ggccctacct  47100
cctaatctta cccactgggg atgagggctt cattatatga atttggggtg ggggtgcctc  47160
aacattcaga ccccagcacc atgggaccac taatgtggca tcctgcctgt ggagagatgc  47220
acagactgac ccatccagac agcacagtgg agcacgctct ttcaacccac ctgcacctga  47280
ccacagtggg cactcaggaa gaaatgggta gagcgagtga atgaatgaat gagcaagtca  47340
aagacatgaa cacatgacat ctgactgtct ccctgtgtgc ttgtgtttca ttctgataca  47400
tccctcccta aattcatctg ctgagacaaa ggattttaac tggtgtttct acactgcttt  47460
ccccaagatg tggcaaccca caccccacca gcaacacctg tgatgtctgc cgccctgtgt  47520
ccttgtagca cctctcttac caggtttcca aatgttgcta aactgctggg tcaaggaata  47580
gcatctgcct ggggttagcc tcacttgtgt ggatttttc ttactcctct tggccactga  47640
ctgctcctgg tctatgcctg ttccattggc tgcactgtcc ttccctgcct cttggccaga  47700
ggctgtcgtg tgtcagcgac agaaacgttt tggctgtcgt ctgcacagcc agtattctct  47760
ccccatcacg ctgggcctcg tgatgatggg gggagggggg ttgacatcac agagatccca  47820
gtgcattttc gacttcatca ctgtcaccat cctctcttgt tcatttgggg gatacagccg  47880
ccatcagctc aacagagcaa aagagaggga ggccacctgc atccgccagg tgctgaaatg  47940
ggtccaggca gctgccagag tctgacattt ccaacttgat acagcacctg tgatcggcag  48000
tagtacccat gacaacattt atttaattga ccaaacacga acattataga ggaaggtgat  48060
catttaaatg atatacttga aattcatctg agtaaggaag ctgagaacag tcaaagaagc  48120
taatttaaaa aataaaaata aataaaaaga accacctaat ccgctgattt ctaatcatgc  48180
cgagtgctta tctctcctgc caggcataca gcgagcgcct tgcagagtct cacagcggca  48240
ctgtcttctc ttttgcagca ctccgtacaa agtgagacct gtggccatca agcaactctc  48300
cggtaaggcc ctgctgtcgt tttttaaact aaaagaagga aaaagaaatc ttgagcttgc  48360
ccctgtgata aaatatatac tagttaagca tttgaatcta agcatttgaa atatatatga  48420
gttacctttg aagcatttaa ctatatgtta gttaagcatt tgaatctgca tttgaagccg  48480
atacaactgc agaatctgaa accttgtact actgtaaggg ctctgccttt ctaaccccag  48540
ggagaatagc atctgcctgg ggttagcctc ccttgtgtgg attttttctt actccttttg  48600
gccactgcct gttcctggtc tatggccgtt ccattggctg cactgtctgt ccctgcccct  48660
cggccagagg ccatcccaag gactttgcag ttgcagggcg gcatccactc tggtcttcct  48720
ggcccagcac ctgtcctccc cgctccactg tgagttgcca aggcaggcat ttgtggcccc  48780
tgggatgcct tggggtgcct catacagtta cttgggccgc tgtgttacaa tccttttct  48840
ttttcttttt tttttttaa aaaaaaacgg agtctggtcc tgtcacccag ggctggaatg  48900
cagtggcacg atctcggctc actgcaacct ctgcctccca agttcaagtg attctcctgc  48960
ctcaccctcc caggtagctg ggattacagg cgtgcaccac caagcctggg taattttttt  49020
tgtatttttg gtagagacgg gattttgcca tgttagccag gctggtctcg aactcctgac  49080
ctcaggtgat ccacctgtct tagcctccca aagtgctagg attacaggcg tgagccacag  49140
cacccagcct agaatgcctt ttccatttga tttttatcac ttttatttat gtgtgattta  49200
```

tacatcataa aatgccattt aagtgcctat tttgatgact tttgaaaaat gtgtacaccc 49260
ttgtaaccat caccaaaatc aagacatttg caccacctag aaaagctctc tcttgccccc 49320
tccagtgtgt ctcagtccac aacggacctg ctttctgaca tcatccatga gatttctttt 49380
tgagagtttc atatataaga aattacatgg tatatgtact ctttttgact caacataatg 49440
tttttgagat ccatccatgt gctgtgtgta gagacagttc atgctttgta ttgctaagtg 49500
gtatcccatg gtgtaggttg taccacaggg cgtcttccat tcactgtgga tggacatttg 49560
ggttgttacc agtctggggg cttttaagaa taaggctgct gtgagcatta aagtacaagt 49620
attggtggaa acgtatattt ttatatattt catttcactt ggctaaatac ctatgatacc 49680
tataaccttg ccaacttttt tatacagtta aacatatact taaccgtctt ccctaagagt 49740
ggatataaga gtctgtagag tgttccccag tctgggtttg tctgacgttt ctctcacgac 49800
cagcctgggt gtggtgggtt ttggaaggaa tacgtggggc gcatgacagc caggtaggac 49860
cacgagcttc tccactgcag agttactgtt gatctccttc cctgctcttc tttgaaagca 49920
agtcacgaag tccagcccac ccaaacacag gagagaaaaa ccgaggttcg ttttctctac 49980
acagatattc atttctccag caccatttgt tgaaaagatg atcttttctc ccactgaatt 50040
accatgacac ctttgtggaa aatcgatggg ccatgtatgt gtgagtcttt ttctggactc 50100
cagatcctgt cgtgtgaatt tacatgtctt aaaacaacag cacaccatct tgactaccgt 50160
agataaatag taggtcttga aatcaggtac tctaagttat ctctggtttc tttttttcttt 50220
ttcaaaaatg ttattgcttt tattttcaaa taaattttag aatcagtcta tgaattgctt 50280
ccaaaaaaac agtctgctag gattttgact gaagttgcat taaatataca gaccaatgtg 50340
ggaagaatta atatcttaag aatgttgagt cttctggttc ataaatatgg tctatctccc 50400
cattcatttg ggtttccttt aatgtttctc aataatgtgt taccattgtt aatatgaagt 50460
acttaataaa tactgataaa tacatcacta tttcatgtat ttaatggtac tgcaaatgga 50520
cttttttttc atttcaattt ccggtagttt ttagtttata ggaattggct tctgtatggg 50580
accttgctaa actcatttat taggtctagt accttttttgc agatttcctg tgattctata 50640
gatgattttc ttatagtgct ggtcttctga caacaaattc cttctgcttt tgtctgaaaa 50700
agcttttctt tgctgttttg cttttttttt tttcaaagag agagagagat aaagtctttg 50760
tctgttgccc aggctggagt gcagtgatgc ggtcatagct cacgacagcc ttgacctcct 50820
aggctgaagc aatcctccct cctcagcctc ccaagtagct gggactatag gcacacacca 50880
ccatgcccgg cgaatttttt aagtttttat agggacaagg tcttacagta ttgcccaggc 50940
tggtctcaaa ctcctaaact caagtaatcc tccctccctg agattacaga cgtgagccac 51000
catgcccgac tgacagtgtt tttatttcat cttcatttttg aaagggtatt ttcttgccat 51060
agagaatttt agtttcacag ttttccagca ctgtgaatat gtcttctcat tgtgttttag 51120
ctagtacagc ttctaatgag aagtctgtga tgtcttatct ttgttcctct gtgtgcaatg 51180
tgtctttttc cctctggcaa cttaagatgt tttctttatc actggtttgc aggaatttga 51240
ttatgatggc cttggtgtgg ttttcttttg gtttaacctg cttggtgttc attgatcttc 51300
ttggaacttt gggatcatat ttttcatgaa atttggaatt ttttctgctc tcctctgtct 51360
ctctcctttc ccctgggacc ctaactacct gaatgataga cagcctgaga gcgtcccctg 51420
actcactcac actgtttctt tctttccaga cctttttttc tgtttgcttt atttttctta 51480
gacttttccg tgacgtcttc cattgcactg gtcttccctc ctgcagtatc tagtctgctg 51540
ttaatctcgt tcagtgaaat tttcatttca gatattgcat tcttcatccc taggaattat 51600
gtttccctcc tttttcgtat ctcccatttt tacatctccc atttatgcct cattatgttt 51660
atatttcctg taaatgctta tacctcatta taattctgtt tcatgccatt gtctgctggt 51720
ttcctcctct ctgccatatc cgagtctgtc tctgttgatt gatttatctc ctgggtatgg 51780
gtcatatttt tctgattctc gtgaatctag tagatcttga tggaatgctg atcacaggaa 51840
tgcacgctgg ttcatcatct ggttttgttt ctcccagtta agagtgttgg gctttgcctt 51900
ggcaagcagt taagttactt gcacatcagt ttgatgcctt tgagccccac ctttaagctt 51960
tgtgagaatg gctctagagg gcccttaccc cagggatagc tcagtcctac taagacttga 52020
tccctttggg gtctccccca aactcctggc tgatcaccaa attccactct ggctgtttag 52080
agtgcaaatg tttggagatg agaatgaaag cgccagggcc ttgaaggtcg ttgcaaggat 52140
gctggctttt atgctgagtg gcgtgggcag ctattagaag gctttcagga gaggagtgac 52200
atcatcacat ttgtgtttta aatcttgctc agggcgctgg gtcgagatca cgaaagggaa 52260
gtggcagcaa aggtggaggc agagaaatcc aagaggaagc tattttttttg ggaggaggcg 52320
gaggcctagg ccggggtggg ggccatggag gtgatgagga gcgcaggttc cagcaggttc 52380
taaaggaaga gacaagcttt ttcctaagtg gaagcgggat atagagaccc atccggggct 52440
tctttgacct gagcactgag cgccacggcc cagggagggg gttgctgcgg gtgggcttgg 52500
tctgctcatc agacatcagg tgcatgagga gcaggcagag tcagggcagg cggcctctcg 52560
gctgtcggct cccaatggat ggtgttgaag tctgggactt ggtgaggcca gcagggagtg 52620
agtgagcacc agcaggaggg gccaggcctg agccggacgg agaccgaacc catccgtggg 52680
agaaggacgc tggtgacagg acaccatcgg gagcagaggg gaagccataa agccctggag 52740
gcaggaagag gcaaaggctg gccgggtgtg ggtgaggtgc tgcagggctc tcgcaggcca 52800
gcgaagacag gcgagatggc tgtgctcaga gttagaagag catcgctggg agcagaggaa 52860
agagggattt ctgtgtcacc tggggaccca tccaggacca gtgggagatg gagttgggct 52920
cattgaggga aagaggtgaa tggaaggaag ttggaaccag ctgtcctaag gccggagctg 52980
ctcctccctg gaggactccg gcaaaggctg ctggccttgg gctgtgcggg cacccagtgg 53040
ctgagagatc gttgccctct gcagccctcc tgcaacttgg atcctaggag ccacaaagag 53100
gcttgaaaaa taatccatcc tgagaaacac aaaggctcac attaaacttc gcatcgtaaa 53160
gttttgagta aaagaacaat aaggggcatt tctgctaaag gtgccaggat gagaaaaagc 53220
aggaaacagt gctgcaccgc caggctctgc accgtctcta cagagggctg gggttggttc 53280
aggagcattc ggcccaggct gtgatctcga gaaggtggtc agggcccagg ctcccgccag 53340
ccctcacggc agcacgaggc tggtacgaga caggtgcttc aggtgtttgt tgagagctgc 53400
acacacttct gctgggctgg gcaagacttc cctcttcaga gaggatgagc ggccacacgg 53460
aaggccaggc tgggtgtccc tccgggccag ccgaggagcg ctgcgcttat tccgcagtga 53520
ggagtcgctg gctgtccagg ggagctgcat tttcctagca gcgacaaccc ctcccacatc 53580
tccatagtca catcctggct gggctaacac cacctttccc cgcctctggg tgcgtgggga 53640
ccccgctctc caaataggcc agtgttccag gcttttcttt aggagacaaa gtcggtgtca 53700
ggtagacccc ccccacccca ccaaacacac acacacacac acacacacac acacacacac 53760
agctttcctg agaaatgtgt ttacagaaca ttttttccat ttggggtttg tccttaggaa 53820
ttcttcactc tctctatggc aacaaccttc cctctcccgt ccatcggcct tgggtcccag 53880
agccactgag ccgtggccca aggtcaggag ttagctctag cgacgccgcc ctgagttctg 53940
gcctgtaagc aaccccaggt gcccttgtga atcaacagac cacatttcca gtggcagaaa 54000
aggaaatggg agctgtttct agactagcac aaggctcagg gggtgggggg tgggggcagg 54060
gtgcagggag gccaacgcca cacagcccca cacccagcct ttcccaaggc cctgggttcc 54120
tcactgattc tcagcaggtt tcagtaaatg cctctaacgg gcccggtgga actgtgcaat 54180
gcagaaacac cccagggttt tgctgttttg ctacttaaat attcaggaaa tagtaaagag 54240
aagagtatta tcaaaaacgt gacttttcat agaaaaggga gaataggcca gccctggcct 54300
gggtccacaa ccccagtgtg agctgcagag acttctctgg agcggtgaac agctcctgcc 54360
aggaaagagc atggcacagc ctcgttctcc agcgtagagt agaaggaatg gccccgtcca 54420
cgcgaaggtc tgtgttcacc aagcatcttc tgtagaaaaa tgctctcttc gcctgatcat 54480
gggagggaat caaatggata gagcatttat cccttttgtg actaaaataa aggtaatagc 54540
aactacaaaa accacgacac aggcttctca gcatcttttt ataacgatag tgctgatttt 54600
ttggaaaatc cttgagcctc aatcactttt atttgatgta agccgctcaa actcaaagag 54660
tgttgttttc cagattataa aacacagatc tcagctgatg gcggttgacg ggtgtccccc 54720
gagtgccctc ggctgccagg agctggcagg ggagatgcct gtgatgagga ttgggtgctg 54780
tgatcacagc acgcgggaaa aggacagggc ctccctcagc gtggcagatc gcgtgggtcc 54840
atgggtccgt gtgatctcat gaccgtatca aggggattgt gtctttttga ccagagcgtt 54900
agggaaagcg tgctgcagtc acacgccagg acggcccccc acggcccaag tcctatagga 54960
gagccagggg ccatcacgat tttcttaggc acagcagcag ttgaaccgtg ctgtcacact 55020
taacccaagt gatgacagcc tcttcaacta ggacagtgct gtaggggtct ggttctgctt 55080
gttctccccc acattcctgc ctgccctagg acccaggacc tgtctctagt cacacacacc 55140
ctgttcagcc tctgcatctg gcccccgcgg agacccacac cacattctac tcccctggcc 55200
agagaccgag ggtgactcgg aggcttccag ttcccagcag ctttattggc gttgctgttt 55260
ccatagaagg acaataaaag ggggccataa ggaggcgcat ccgcagagtg cgtgcttgag 55320
cttctgcaag ccagaggagg ccggcggccg gcagggtggg caggctggct ggctgtgccc 55380
cacaacatgc atgtggagag gttttggggg cagccatgga accccggagc tgcccccaca 55440
tgagagttcc cccaggtggt gaccaaatgc atttacagtc cagccgcagt ccagatgcag 55500
atgcgctgta actgtagaac acacagcaaa ttctgaaggc ttagtatgaa aaagaatata 55560
aaaatctcag tcatttttat attgatttca tgtttcctgg ttgagatgtc attgatataa 55620
cataaagccc accattttaa agtgtacaac ctcagccagg catggtggct cacgcctgta 55680
atcccagcac tctgggaggc tgaggcgggc agatcacctg aggtcaggag tttgagacca 55740
gactggccaa catggtgaaa ccctgtctct actaaaaata caaaaattag ccgggtgtgg 55800
tggtgcacat ctgtaatcct agctacttgg aaggctgagg caggagaatc gcttgaacct 55860
gggggtagag gttgcagcaa gccgagatca caccactgca ctctagcctg ggtgacacag 55920
tgagactcta tctcaaaaaa aaaaaaattg tacaacctca gtctttttta gtgtcttcat 55980
tttgttgtgc aaccatcacc actatttaat tccagaacat ttccatcaac ccaaaaagaa 56040
tccctgtacc tgtgagcagt ccccccctcca tccccttcac cccccagccc ctggcaggcc 56100
ctgttctctg tcctgtgcat tctgaccttt cacataacag aatccgtggc ctttccagcc 56160
tggcttcttc cactttgcac acggtgttgc aggctccccg cgttgtggca tatgacagct 56220
ctttgttcct ttatggctgg atgacgttcc gttgcgtggc tgcgtcctgt ggctgcattg 56280
tgtggctgtg tcacgtggct acgtcacgtt tggttgatcc gttcatcagc tgatggacat 56340
ttgggctgtt tccacaaagg ctcttgtgaa tgatgctgct gcaaacgttt gtgtgcaaat 56400
ttttgtatga aagatacatg gtgaaatgag gtattttgag gtacattgga ttaaatgaga 56460
tattaaaaat ttttttaaag tctagccgtc ttgaagggga gggcctgaga gaagtgctga 56520
aagttcacag cagaggatac cggatgctgc gggtgtgcca ggctggcctg tccaggaggt 56580
ccctgcagcc tgggtgggag gtcccttacc cactaatggg tgcctcctcc aacccctgag 56640
tccccctacc tgaggacttc ctctgtgtgt ggcatacgcg gctgccccga ggtcagtcct 56700
ccccagtgaa agggagctga aggacaggtg cccagcttct ttgctccaca gtgggaccaa 56760
tctctgacat catcaatgca gttgctcaaa gggagctcag agcgaggagt cacctgtaca 56820
tcaactcacc ctctgggagc tctcttccct tccatgcctc aatcccccac tccctcccag 56880
ggcttcctgg gctggcctcc aaatgcacca ctagccccca gctccttgtc tccggtgggc 56940
ttttgaggat ttccaactaa gaaccttaga ctccaagaca ggtcaagccc cctggcatac 57000
tcatttgtca tttggatgaa atagccttag gagagctact taaccccact gaacttccat 57060
ttccctgaca aaataggaat tctaatgcat accttgcatg gttcttggag gataaatgaa 57120
gtaatttatg caaaatgctg agcacagtgc ctgccacttg gtaagcgccc agtaaatggt 57180
tgttatcatt gaaaatgact tagggggcat ttttgaatgg ctaaagttat gtctctctgg 57240
aattgctgaa ttttaataga acaggaatgc ttcctaaggt ctaaaacaaa aggcggagga 57300
ctggctgtgt ctgccctgga agccaagtta atgctggatg tctgcgcata gacatgttgc 57360
tcatgagaaa taataatgct ccttaataat attgtctatt tcagtgcaat ttcagtctag 57420
aaggctttat aagcaaagcc acagtcatcc ttacttgcat tttttgaaa caaaaagact 57480
gcagtgtata aatgaaaaat aaccatttct ggaatggtgt gttcagacgg attcccctta 57540
gagtagccta gccaacaaag acagcagcag cccttagcgt gccactgtca gagatattga 57600
tggcaaacag taatacggaa gcctgcggaa tggaagtgtc ctgacggcag atttgagtaa 57660
aatggagatg atgacagctg aacattgctg cacggacctc aagactgcaa acgttaggac 57720
tgccctccct gctcctaggc atttgtgaga accaggccaa cccataccca cccactgctg 57780
tgtcctgcct gactgcactg aaatgcacag atcctgtggg tgcagtttga tgagttttgt 57840
tttgtttttt gttgtttttg tttttgagga gtttcgctct tgttgccgag gctggagtgc 57900
agtggcgcga tctcggctca ctgcaacttc tgcctcctgg gttcaagcaa ttatcctgcc 57960
tcagcctccc gtgtagctga gattacaggc gcatgccacc atgcccagct aatttttgt 58020
atttttagta gagacaaggt ttcaccatgt tggccaggct gatctcgaac tcctgacctc 58080
aggtgatcca cctgcctcag cctcccaaag tgctgggatt acaggcatga gccactgtgc 58140
ccagccacag tttgatgagt tttgatagaa gtgcatgtgt tagatctttc aggaatcacc 58200
acccaaacca gaaataccat ttgacccagc aatgacgttt atatatatac ccaaaggaat 58260
ataaatcatt ctattataaa gatatatcta catgtatgtt cattgtagca ctattcacaa 58320
tagcaaagag atagtatcaa tccaaatgcc catcaatgat agattggata aagaaaatgt 58380
ggtacatata caccatggaa tactatgcag ccataaaaag gaacaagatc atgtcctttg 58440
cagtgacata gacagagctg gaagccatta tcctcagcaa attaatgcag gaacagaaaa 58500
ccaaacacca catgttctca cttataagtg ggagctggac aatgagaaca catggacaca 58560
gggaggggaa taacacacac tggggcctgt tgggagggtt gggggaggga gagcatcagg 58620
ataaatagct aatgcatgct gggcttaata cctaggtgat gggttgacag gtgcagcaaa 58680
ccaccatgac acacgtttac ctgtgtaaca tccctgcatg tcctgcacat gtatcccaga 58740
acttaaaatt aaattaaatt ttttaaaagt gcacgtgcat gtaaccgcca ccacaatcaa 58800
gacagaggac atttccatca ccctagaaaa atgtccccgt acccccttca aggcagtcct 58860
cactgtggag tgctctgcct atttttgagt ttcacggagt tgaaatcata cagcacgagc 58920
tctttgtgtc tggactcttt cactcaacat catttttgtt tgtttgtttg tgtgtgtgtg 58980
cgtttgtttt ttgagacagg gtctcacgcc tgttgcccag gctggggtgt gaggcacaat 59040
catggctcac tgcagcctcg acctcctggg ctcaggtgat cctcccacct cagcctccga 59100
gtagagacat gttgcccacg ctggtgtcga actcctgggc taaagcaatc cgcatcatga 59160
tgtttgtaag atccattcgt gcagttattt ccttttgcac tgctgagcac tgcatgcctc 59220
gctcattcat tcttctgtgg agggacattt gggtcatttc cagtttaggg ttcggctact 59280
agaattattg tacaagtctt attgtgggca tccttgtcca tgatcttggg tccacctagg 59340
agttaaatgg ctggctcata tgctgtgttt gtttaactta agacttactt gttaagtgta 59400
agaaactgcc aagctgggcc gggcacagtg gctcacgcct gtaatcccag cactttggga 59460
ggccgaggcg ggcggatcac ttgaggtcag gagttcgaga ccagcctggc caacatggca 59520
aaaccccatc tctacaaaaa gtgcaaaaaa ttagcagggt gtggtggtgt gtgcctgtag 59580
tcccagctac tcaggaggct gaggcaggag aatctcttga acctgggagg aggaggttgc 59640
agtgagcaga ggttgcgcca ctgcactcca gtctgggcga cagagcgaga ctccatctca 59700
aaaaaaaaaa aaaaagaaag aaaaaaagaa actgccaagc tgttctacca agaggttgta 59760
ccattccaca ttcccaccag cagcatctga gtgatccagc tgttccacat ccctgcaaca 59820
ctaagcattc tctgcttaca ttttagacat tcgagtaggt gtaagagcaa tcctatcttc 59880
ttatagtttt aatttgcatt tccaagtaac ttaatgatgt tgaacatgtt gctatgtctt 59940
attgactatt tgaatgtcat attttgtgta gtgtctgttc aacaatactt tgctcaggcc 60000
aggtccggtg gctcacgcct gtaatcctag ctctttggaa ggccaaggtg ggtggattac 60060
ctgcggtcaa gagttcgaga ccagcctgac caacatggtg aaacctcctc tctactaaaa 60120
atacaaaaat tagctgggtg tggtggcagg tgcctgtaat cccaggtact cgagaggctg 60180
aggcaggaga atcgcttgaa cccaggaggt ggatgttgca gtaagctgag atcgcgcctt 60240
gcactccagc ctgggtgaca gagcaaaagc tgcatctcaa aaaaaatatg taaaaaggat 60300
tttgctcatt ttttaagctg gcttgtatta tttttgtcac tggtttgtag gaaactctac 60360
ataagctagg atataattca tttgtcagat atatgtggca aacatttttc ccaatttgtg 60420
atttgccttt ttcgttttct taatgaggtc atttgatgag cagaggtttt taatttggtg 60480
aattccatcc aatgtaacaa gtttttctgt tgtggtcagt acttcttgtg tcttctctaa 60540
taagttttgt tttttttttt ttttgagaca aggtttcttg ttgcccaggc tggggtgcag 60600
ctgtgcgata agctcactgc aacctccgcc tcccgggttc aagtgattct cctgcctcag 60660
gctcccgagt aactaggatt acaggcgttt gccaccacgc ctggctaatt tttttgtatt 60720
tttagtagag atggggtttc accatgttgg ccaggctggt cttgaactcc tgacctcatg 60780
atccacccac ctcggcctcc caaagtgctg agccaccgca ccaggccccc caaattgcta 60840
ggattacagg agtgagccac catgcctggc cctaataatt ttttttatcc caaggtcatg 60900
gagatacatt ttagaagatt tagagttata gctgttatgt tttttcttaa tttaaagaaa 60960
atttttaaca acccaatctg ttgagatgtt atgttttaat ctgtcattca tttcaagtta 61020
atgttgtgtg tgttgtgaag tagagactgc cattcatttt cttccccacg ctgacaccca 61080

```
gctgttactg caccacttgt taaaaagact ccttttcccg ctgaatccat ggctcctttg  61140
ttgaaagtta atggtatctc tgtgtttggg cctctcgctg aactctgttc tgcttcattg  61200
atctatttgt ctatcctcac accaacacca cactggctac gttactgtgc cctggaatca  61260
ggtactctaa gttctccatg tgttcttcct ctgcatttgt tttgactgta taggttcttt  61320
tcttttccct acaaatttta ggatcaactt gtcaatttca aaaaaaaaag ccatctatga  61380
ctttgattac tattttattt actatataat ttggggaggg tagtgtctta accatactga  61440
gtcttccaac ccatgaacat gatacatccc tccacttatt taggtctcat ttaacttctc  61500
aaaaggttat ggctttcaag ataaaggtcc ttcatgtctt cggttaactt tactccaaag  61560
tgttttctgt tttctggttt tattgtgaat aagatttcat taattttcca attgtttgct  61620
gctagtttat aaaaatataa tagatttttg gatgttggcg ttggatcctg tgaatttgct  61680
taattcattg gttagttcta gttgttgttt tataggttcc tataattgtc cacagagaca  61740
atcatgacat ctaagaataa tgacagtttt aattattgca ttccaatttt tggcttttat  61800
ttcttttact tgtcttgttg tactagttga aactgcaata cagttaaata aaagtgagag  61860
cagacgtcct cgccttgttc ccaatcttag aggagatgcc ttcggtctct caccattaca  61920
tacgatgtta gccacagatt tttttgtgga tgcctttcat aaggttggaa gtccccgtct  61980
aatgttagtt ttctgagagt tttttgtctc atgttctttg acaaaattct ttgttaactt  62040
ttatcaaatg ttctctctac agctactgag gtgggttgag gaggtgtcct ctttttcctt  62100
gttttctaat ggttttgtcc cataaagagg tattggattt tgttccagta cctttctgca  62160
tctatgggat gagcatacat atggtttttc tgctttattc tattaagata atgaataata  62220
ctgattgatt ttcaaatgtt aaaaccactt tgctttccta gggtaaatgc acttatattt  62280
ccaggaaatg ttcctaggaa atttcctggg gtaaactcac ttgtatttcc aggaaatatt  62340
tccaggaaaa tacttgggaa taaatgtaac aaagtatatg taggccctct ccctggtgtg  62400
tttgcttttt atgtattgac ttgtttttgt ttttgttttt gttttgagac agtgtcgctc  62460
tgtcacccag gctggagtgc agtgctgcca tctcggctca ctgcaacctc cgcctccagg  62520
cttcaagtga ttctcctgcc tcagcctccc gggtagctgg gattacaggt gtgcaccacc  62580
acaccagata atttttgtat ttttagtaga gacagggttt caccatgttg gtcagggtgg  62640
tctcgaactc ctgacctcag gtgatccacc cgcctcagcc tcccaaagtg ctgggattac  62700
aggcgtgagc cacagcacct ggccgctttt catgtattgc tagatttgat ttcctaacaa  62760
ttcgttaaga atgtggctgt ctatgcttaa atgggatatt gatttgtaat ttttttttctt  62820
gcagtgtctt tgtcatgttt tgatattggc cctatagtgg cctcataaaa cacattggga  62880
agtttacttt cttctgtatt ttctgaaaga ttttatgtaa ttttggtatt attttgtcct  62940
atgtcccttt acacttaatg tatttgggtt ttttgtgtgt gtctttttaa tagttaataa  63000
caatgtattt tattcttgaa aatcactgag agtacatttt gcattctcac cacaaaaaaa  63060
aactatgtgg cataatgtgt atgttaattc acttgattta gccattctac aatgtatata  63120
tttcaaaaca tcatcttgac catgggaaat gtatctaatt tttgtcaatt tgttaaaact  63180
ttttttttaa ttccaatttt tttttttttg aggtggagtc tcgctttgtt gcccaggctg  63240
gagtgcatga ccatgggaaa tgtatctaat ttttgtcaat ttgttaaaac tttttttttc  63300
attccaattt tttttttttt ttttttgag atggagtctc actttgtcgc ccaggctgga  63360
gtgcagtggt gcaatcttgg ctcactgcaa gctccacctc ccgggttcac gccattctcc  63420
```

```
tgcctcagcc tcccaagtag ctgggactac aggcgcccac caccgtgcct ggctaacgtt  63480
tgtattttta gtagagatgg ggtttcactg cattagccag gatggtctcg ctctcctgac  63540
ctcatgatcc acctgccttg acctcccaaa gtgctgggat tacaggtgtg agccaccacg  63600
cccagcccca acttttattt tacgtacaga tctaaacgta tcacatgcag gtttgttatg  63660
tggtgtgtcg cacccagatg gtgagcagag cccccaagtc tttgttgata tggttggggt  63720
tagctctccc agtctttgtt catatggttg gggttggctc taccagtctt tgttcatatg  63780
gttggggtta gctctaccag tctttattga tatggttgag gttagctcta ccagtctttg  63840
tcgatatggt tggggttagc tctaccagtc tttgttgata tggttggggt tagctctacc  63900
agtctttgtt gatatggttg gggttagctc taccagtctt tgttgattag ctctcccagt  63960
ctttgttgat atggttgggg ttagctctac cagtctttgt tcatatggtt ggggttagct  64020
ctaccagtct ttgttgatat ggttgaggtt agctctacca gtctttgttg atatggttgg  64080
ggttagctct cccagtcttt gttgatatgg ttggggttag ctctaccagt ctttgttcat  64140
atggttgggg ttagctctac cagtctttgt tgatatggtt gaggttagct ctaccagtct  64200
ttgttgatat ggttggggtt agctctacct gtctttgttc atatggttgg ggttagctct  64260
accagccttt gttcatatgg ttggggttag ctctaccacg ttgctatttg ctgtttcttg  64320
atcttgggtt ttgtttttct gttcctcctt ttctgccttc tcctgtgtta attgaataaa  64380
tttttgtttt ccattttatt ccttctgctg actctttagc tgtctctttt tgcattattt  64440
ttcctcggct gttgtaagtg ttacaatatg catctttact tttttttttt ttttttttta  64500
caattgatag actttgtttt ttagattcac ggcaaaattg agtgaaaagt gtggagctcc  64560
cacatgttcc ccccacacac agacattcag cctctgccac cgtcaacgtc ctgcatcaga  64620
ttgtatattg gttacagccg ggcgcactgg ctcacgcctg taatcacagc actttgagag  64680
gccaaggcag gcagatcact ggaggtcagg agttcaagac cagactggcc aacatggtga  64740
aaccctgtct ctactaaaaa tataaaaatt agccaggcgt catggcgcac acctgtaatg  64800
ccaactactt ggcaggggaa tcgcttgaat ccggaaggcg gaggttgcag tgagctgaga  64860
ttgcatcact gcactccagc ctgggcgaca gagagagact ctgtctccag acaaaagaaa  64920
aaaaaaagac tgtacattgg ttacaatcag tgaaccaaca ttgacatatc cttatcagcc  64980
aaagtctata ttccacctca gaattcactc tcagggctgt acattccctg ggtttggaca  65040
aatatatgat gacctgtgtg tcccatccca gtctcagaca gaatcggttc tctcagggct  65100
gtacattccc tgggtttgga caaatatatg atgacctgtg tgtcccatcc cagtctcaga  65160
cagaatcggt tcactgcctt caaaaccccc tgtgcgccac ctattcatcc ctcccgcccc  65220
aagccccaga tctttttact gtctccatag tttggccttt tccagaatgt cacatagttg  65280
gagtcataca gaataaagcc tcttcaggtt ttctttcact tactaatatg tctttaagat  65340
tcttttatgc cttttcccgg catcttagca ttgaagcata ttccatggtc tgtatgtatc  65400
acagtttatt tgcccactca cctattgaag agcatcttgg ttgcttccag gtttgggcag  65460
ttatgaataa agctgccata aatatttgtg cacaagtttt tgtgtgcaca taagatttta  65520
acacatttgg ataaatacca agaagcacaa ttgctggatc ttttggtaac agcatgttta  65580
gttttgtaag aagctgccaa acggtcttcc aaagtgactg ggccattttg cattcccagc  65640
agcaatgaac gagcattcct gccgctccac atcctcccca gcttttgtgt ttcagtgtct  65700
tggattttca ccactctgat aggtgtattg cagtatcttc ttcttgtttt attttgcaat  65760
tccctagtga catatcatga taagcatctt ctcatatgcc tgcttgccat ctgcatgtct  65820
```

tctttgaggt gtctgttcat atcttttggc cacttttaat catcctgaac ttttcacaat 65880
ctatttagaa ttaatactgt accgcctcac ataaaaaata aggacactgc agctatataa 65940
gtctacttac tcccctctcc caccaccttt gagttattgt gtcatatgtt ttatatctgc 66000
atacatttta agccccataa tacaatatta taatttcctt tttttttttt tttttttttg 66060
agacggagtc tcactctctt gcccaggctg gagtgcagta gtgagatctc agctcactgc 66120
aacctccacc tcctaggttc aagcgattct cctgcctcag cctcccgagt agctgggatt 66180
acagatgtgt gccgccacgc ccggctaatt ttttgtattt ttagtagaga cggggtttca 66240
tcatcttggt cagactggtc tcgaactcct gacctcaagt gatccacccg cctcagcctc 66300
ccaaagtgct gggattatag gcgtgattat aggccactgt gcctggccta taatttctta 66360
tttaaacagc tagttgtttt ctgaagaaat tatgaaaata aacttccaga tagtttttta 66420
atagttgcct atatatttgc catttctgat gtttttattt cttctcaact tccaacttat 66480
attatatccc ttcactctaa agcatttctt ttttctttta atgtttcttg cagtgcatat 66540
ctgctagtaa ctaattctct cagcttttgc tgattggaac atgccttttt tttttttttt 66600
tttttttgaa atgatgtctt gctctgtcgc ccaggttgga gtgtacaatc agttcactgc 66660
aacctccgcc tcctaggttc aagcaattct cctgcctcag cctcccaagt acctgggatt 66720
acaggcgccc accaccatgc ccacccaggc actccaccca ggaggtggag gttgcagtga 66780
actgagatct cactactgca ctccagcctg ggcaagagag tgagactcca tctcaaaaaa 66840
aaaaaaattt ttttgtattt ttagtagaga cgaggtttca ccatgttggc caggttggtc 66900
tcgaactcct gacctcaggt gatccaccca cctcggcctc ccaaagtgct gggattacag 66960
gcgtgaacca ccgtgcccag gcaaggaaca tgcctttatt ttgccttcat tgtgaaggat 67020
gagttttcat ggtgtggaat tctgcattca cagtttgttt tcttcaagaa gcttaaagat 67080
gttgactcac tttctttctg gcctccattg tttctgatga gaagtcagct taatttgatc 67140
attattcctc tgtatgaagt gtgtctttct tctctggctg ctttctttgg ggtttgtttg 67200
tttgtttgtt tgttttgttt tgtttttgag atgaagtttt tgctctgttg cccaggctag 67260
agtgcagtgg tgcgatctcg gctcactgca acctccgcct cctgattctc ctgcctcagc 67320
ctccaagtag ctgggattgc aggtgcccgc caccacgccc aactaatttt tagtagagac 67380
aggatttcac catgttggcc aggctggtct cgaactcttg acctcaggtg atccacccac 67440
ctcgggctcc caaagtgcta ggattacagg cgtgagccac tgtgcccagg cctctggctg 67500
ttttcaagct gttgatttct ttcctttatc tttaggtttc agcagttgga ctatgatgtg 67560
cttcagtctc attttcttct tatttatcct tcttcatgtt cattgagctt ccatggacta 67620
tgaatttacc ttttcagcaa atttgcaaaa ttgtcagcca ttacgtgtta tatgtgccat 67680
tctttctcac taatgacctg tatgttagaa agtttgctgt tgtctttcaa gtgactgcag 67740
ctttgcggtt ttttataatc tttttttttct ttgcccttca aattgggtaa tttctgttga 67800
cctgtccttg atttccctga ctcttccact gactccagac ttctgtaagt tgatccatga 67860
agtttttttt tgtttaggat attatatttt aaaattctaa aatttgcact tgactcttgt 67920
tcatagattt gtctctcgag actcccctct gtttacgatt tactgacgcc gcttttgttt 67980
cggtgtttgc acgtacctgc aattgctgca ttaaagtctc gtttgctcat tttggcatct 68040
gagccggcaa gcgtccaggg tgtctgaggg atgattttct cttggccatg ggtcacattt 68100
tcctatttct ttgcatgtct attttttatt gtagactaag attatgaata acacctagga 68160

```
gagacattgg attttgttat catcctctga agagtgttaa ttttgctcca gcagtcagtt  68220
ccgttactca ctgatcatct gaacttcgtg cagcctggtt ttatgctttg ttggggtaga  68280
tctctagact gacccttctg tggttttagt aggaagcctg aggtatttat caagcctctc  68340
taactcgact acatttaaac tccaaacttt gtctcctcca cagcaggagc tgaaacctct  68400
gccacactag gcccacaaac atgcgtcatt cagggatcca ccaaggaaca gggtagttta  68460
tacagaattt gggtcccact gccatggctt cctcctttgg gaactctcct ttccatttcc  68520
atcctctctg acaacctaaa actgtgtcat ctgacgcttc aacctggaac tttctgctta  68580
agttttagcc atctacatta taagggcact ttatagcaag aaatagaata ttattccatt  68640
ctaggccaag tacagtggct cacacctgac atctcagcac tttgggaggc cgaggtgggt  68700
ggatcaactg aggtcaggag tttgaaacca gcctggccaa catggtgaaa tcctgtctct  68760
tctaaaaaaa attttgaaaa aattagccgg gtgtggtggt gcatacctgt aatcccagct  68820
actcaggagc tgaggcagga gaatcccttg aacctgggag ccagaggttg cagtgagccg  68880
agatggcgcc actgccctcc agcctgggtg acagagtgag agtctgtctc aaaaaaaaaa  68940
aaaaaaaaaa aagaaatatt ccttcgttct tttataggag catagtactt cattttgtag  69000
atgtactatt gtgtatccta ctgatagata cttgtgttgc ttccagtctt gtttttacag  69060
cgatcagatg gttcttctta atttctcttg ctacaaatgt tgctgctgtg tacaacctgt  69120
taaagtccac agatggaata aaagctttgg tttgcaaaaa tgactcaatc tttacaaaca  69180
ttctgtcatt tgtaccataa tcaattagtt tattggatca ccgaattgcc tgacagaatc  69240
cttcctggaa ctagtctatg ggtcatttg gcatagagtc aaagcctcag acacgatgag  69300
ccagagttga tttcctttgg cttcacataa ttaaactttc ccagaggatt atcaggttac  69360
agtgacacac acacaggctg tcagataatg gacaaagtcc cagcagcgtg tacaaccagc  69420
tggtggctcc caaattcaaa ttcccccagc ggcatccgtt cggttattcg tacccacacc  69480
ctcccttaga agtttacccc tccgccaggc gcagtgactc acgcctgtaa tcccagcact  69540
ttgggaggcc aaggcgggcg gatcacctga ggttgggagt tcgagaccag cctgaccaac  69600
atggagaaac cccgtctcta ctaaaaatac aaaaattagc cgggcatggt cacgcatgcc  69660
tgtaatccca gctactcggg aggctgaggc aggagaatcg cttgaacctg ggaggcggag  69720
gttgcggtga gccgagatca tgccattgca ctccagcctg ggcaacaaga gcaaaactcc  69780
atctcaataa ataaataaat aagttcaccc cactacgggc aagaagccac acagaaagaa  69840
aaataaaata ggtatctctg gggttttctg aagggaaagt aagtgcagct ctgtcccgtc  69900
tttgcagctc taaataggaa catggtggag tagggcaggt cgggcttgac gatgtcatga  69960
cttggcctct ctcagtgtca cgcagcccct gcaggttata aggaggattg agctggccag  70020
gcacagtggc tcatacctgt aatcccagca ctttgggagg ccgaggtggg cggatcacct  70080
gaggtcggga gttcgagacc agcctggcca acgtggagaa accccatgtc tactaaaaat  70140
acaaaattag cccggcgtgg tggtgcatgt ctgttaaccc agctgctcgg gaggctgagg  70200
caggagaatt gcttgaaccc gggaggcgga ggttgcagtg agctgagatt tcgccattgc  70260
attccagcct gggtaacaag agcgaaactc cgtctcaaaa aaaaaaagaa ggatagagct  70320
aacatgcatg aaccacctag aacagcaccc agagcatagt aacagctcct tgcagatgtt  70380
acagtacctt gatctataca acagtaaagg gaaatgcatg ctagctgccc cagatgctgc  70440
cagcttcaca ggcatttttc tgcctgcaaa ctaatcctaa ggaagagagg agggcagggg  70500
gagaaattgc acccagtcaa atgtaaacga tacaaaatgt gaaattcccc tctctgaaaa  70560
```

-continued

```
tgaaagggaa aaaactcgat tcaatgcctg cccctgaggt gaacctgaaa tgacaaggca  70620
gacactctct agaacttcac gtttggccac cagggtcttc ggttgatttt cctttcttcg  70680
tcatatctga gtggctgaaa cgccagtgat ctgggatagt cctttggctg ctgatagact  70740
tatgcaatcc cttggcaggc aggacaggcc agaggaaggg ctcctgtgcc tttaaggtca  70800
ctgttaatca tgtaacttta ttgtgttcct gggctataaa ggaaatgtcg tccttgatct  70860
gaatgtctgt tttatgatgt ccataaacag tgaattgcca gtgactgtac cctgagtgag  70920
aacatcctca gccagttgaa tagttcaagg gcagttgcag gggtcaggag agagcaaaag  70980
tgggacagaa gatgagtttg cttcccagga agagagacag tgccacccca cccctcgctg  71040
acagggaagc cttccagccc ttcctccaaa gagccttggc tctcaggggt tggaggttgg  71100
acaagagcag aaataaaggc accctgctcc caccccccac aatcttccgg acgtctagag  71160
tgcttatctc tttgggggca agtaatgtga attattttcc ctaatgcaaa aataaaaaat  71220
aagagacccc ttttaccctt ttctgaaagg atagcagagg tatttttctt ttcttttttt  71280
tttttgagat ggaatcttgc tctgtcacca ggctggagtg cagtggcaca atctcagctc  71340
actgcaacct ccgactccct ggttcaagtg attctcctgc ctcagcctcc cgagtagctg  71400
ggattacagg cacgtaccac catgcccagc taattttttt gtatttttag tagagacgga  71460
gtttcaccat gttggccagg atggtcttga acttctgacc tcatgatccg cccacctcag  71520
cctccagaag tgctgagatt acaggcgtga gccaccatgc ccgtccagca gaggtatttt  71580
ttctaatact tgagaagtgt ctgctaagta tgtattcacc ggagggtgct cagcacctcg  71640
ccctgttgct ctgggttggg actaacaagg tgaaacatgg ctcattgcat catattaata  71700
gcatgcaaat ctaagcccag tgatgccgtg caatggctac gatcaagggc aatagaatgg  71760
atcgtgcatg agctcccagg ccacacacac acgcccttgt gatgtattat tccctctact  71820
cttgcaggtc ggtgcttggg atgctagtgc ccaagctgat gttcctaggt cacctccctc  71880
aatgcatggg tctaggggcc agcatgttct attgctaggg ccatgtgtgc attcgtttgc  71940
ctaggggaga aaagtacaca ttcccatcag ctcaggtgcg tggaggacgg aagaactgct  72000
gttgctgcta gtattctctt cagcacaaga taaaaaggag ataggcaaat cagctggctg  72060
gccaatcaaa ttaacttatt gttacactaa tttttagaat cagaattatg ggtcaggctg  72120
tgctagcaat cagtgaaatc aaatttcatg tcattctgca ctgggtagac tcaggatttg  72180
cctgaaacaa gtaaacaatt cctggaagaa gtgggcgagg cagaggcttg aactatccac  72240
tcagaccaag gaggagtcag gcaatggctt ctgggcatcg tgtggggtgg gggcagcccc  72300
tgccctggac acccgtgaac acggaggcag ccgtgtgaac accatgaggc agggtgtcca  72360
tcctgccacc cacacagctg cgtcctgccc aggaatgagg ctggcagccc ataggcccct  72420
ccttggtccc tctagaggtt tgcttcattc cagtaccctt ggttctgtca agtgggcagg  72480
gcctgggccc ctctgctgca aacccatggc ccaaagcgga cctgatccgg cagcatctaa  72540
aaacaggacc cggagaatct gctggactcc aggattgccc tggaacaaac ctaaagtctc  72600
ctatgacatg caaacaattc tgccagcccc ggccagcatt ccctgcatgt gcttatcaag  72660
tgaggaggcc agcaggactt agcacccagg tgagcacact tcattgagtc caggtgtgtg  72720
cagatgagaa gcagccagga gttgaggctg aagaggagcc tacctaaacc tgtcattaca  72780
actgattgat ccttggtgta gtcaaatctt ctgcctttat gaaagtcatg gtatctagag  72840
gtaaatcccc atcagcttgg agcagcacca tgaaatccac tctagcatgc agactcgggg  72900
```

gcacttttag atattctatt ggttgttctt gggggacagc ttcctttgga gaacatgtga 72960
gttgtctgtg aatatcagct tgctctccct aggtttccat cacatggatc agcgagagtt 73020
aatgctgact ccccctccct cgggggctta tttgcaatct cccgatttgc tcaaaaactt 73080
ccaggtccag agggacccta aagaccctgt catgtccccc tgtgaattac cagcatccca 73140
ggccattgct gggttttctt aaaactatta agacactatc aacgtgaaat gacttgaata 73200
ggctttaatt tttaaaattc attatacgtc ctgcagcatt taggaaaaag agggaggtgt 73260
cacacataat atcaaatttg gctgacacaa ggtgattttg ccacgaaggt tgggaaggat 73320
gaacatttgc aattgaaaac tgtttgttgc ccccagaatc cagcggtttc aggctctctg 73380
aggattccag aggtgctaga gggggtaagg ccacattcag gtggtgcagg tgggattcac 73440
cccttcacag cctggaggtg gtgcccggag cgcaccctgt caccccaagg atgatgacac 73500
cccagggaag gtggtggaag caggaagggg aggtcagagg aaaactgggg ccctcagtgg 73560
gcatccgtga tgcggaaaca ctaataatgc caacagcaat agcagaggca ggcagggctt 73620
acgtggccag ggctgggctg gtgctgtcct gagcacttga catgcatgaa atcacagttg 73680
ttttaagttc tgaactcccc tgggaggaaa ctgtggccac agcaggaatt ccaatgattc 73740
tagggtcagg agaggaggca cccacttcct gatcagggct ctgtttgtgg atgcgtgggt 73800
gtggttggcc tttgtgcaca ctggtggttt tgcttctttc ccccagcaaa agaatgcaga 73860
ttttgcatta tctaaagagg cggttccgtg agcccactgt gctgagtcac atatattcca 73920
tcggtgtaag taccaccacc tgggcagtgc ccctggagtg ttctcactgg gagcgcagct 73980
ttgtgtctgt acccttcctg agaatagctg acatgctggc ctgggtggcg cattggccga 74040
ggtgtggcta tgacagacca ggataccagc atctgcccca gcactgaact gagcacacca 74100
cagaaggtgt ggacagagtg gcatgaaaca tgacagctgc ttgtgctcga aattagatgt 74160
agccacacaa atcctgtcgt gctcaaaggg ttccatctcc aaagtccaaa ggaaaactct 74220
tccttaactg ttattccatt ctgtctatac atttcttatt ttgaagcaag gataggttca 74280
cacgctgctg taatgatgca tgcagagaaa gcccactcat ggcccggttt ctcccagtgg 74340
tgacatcttg caaaactcta gcacaatgtc acagcctggc attgaccgtg acacggtcca 74400
gatccggaac atggcgtccc ccacaaggat cccacctgcc gctctttaat agccacgctg 74460
cttcccttcc attccccact ggatccctgt cccctggcaa ccaagaggtc tctctctttt 74520
ttgtttttgt ttttgttttt tttttgagac agagtttcgc tcttgttgcc caggctggag 74580
tgcaatggca caatctcggc tcaccccaca acctccgcct ccagggttca agcgattctc 74640
ctgcctcagt ctcctgagta ggtgtgatta caggcatgca ccatcatgcc tggctaattt 74700
tgtattttca gtacagacgg ggtttctcca tgttggtcag gctggtctcg aactcctgac 74760
ctctggtgat ccacccacct cagcctccca tagtgctggg attacaggca tgatccacca 74820
tgcccggcct ctggtctcta tttgtatgat gttgtcaatt ctgtaacgtt ctacacatgt 74880
aatcatgcag taggtgactt tgggattggc gccttccacc cagcacaacc ccctggcatc 74940
catccgggtt gtcgcctata tccgtggttc attcccttct ttctgagtca tactccgcgg 75000
tatggatgga ccacggttgg ttcaaccatt ctcccttgaa aggcatctgc atcgtttgca 75060
tttgggacta ctacaaatac atccgccagg aacatgtgga caggcctttg tgtgaacatc 75120
agttctccgc gtacatcatc tctctgccct ggtgcttgca tctttagttg gttttttctg 75180
tcttttgaag aacctaccag actgttttca gaatgactgt accatttttc attcccacca 75240
gccacgagtg agtgagccgt gtttccacgg gggttggcat tattttgtat cccagccatt 75300
ttgataggtg tgcagtggtg tctcactgtg gttgtaactg gcatttccta atggccgagt 75360
ggctctcagc atctcttcat gggcttcttt ccatctgtga ctttctccag tacccatctg 75420
ctcatctctt gcccgctttc aagttggctg gttttgtttt ctaccattga gttttgacca 75480
ttctttatac atgctatctg caagtctttg tcagatacgt gtcttgcaaa tattttctgc 75540
cacaccgtag cttgtcttgt catcctctta ccaggatctt tctctgagcg aaaattttca 75600
ttttgatgaa gtccagtcta tccatttttc tttttctggt ttgtgttttt gctgtcaagt 75660
ctaagaactc cccaccttac cgaagaccct gaagatttct cctatcttct ctctgtgttt 75720
tatagtttca tgttttacat ctgtggtcca ctttgcattg atttttatat aaactgaatt 75780
ctaggtcaag gctctttttc ttgttggcct gcggatatct aatttttcca acactactga 75840
aacactattt ccaacactat tactgaatgc caccacgcct ggccatatat atatatatat 75900
atatatatat atatattttt tttttttttt ttgtagagat ggagatctct ctttgttccc 75960
cggctggtct caaactcctg ggctcaagca atcctccaac ctcgacctcc caaagtgctg 76020
ggattacagg catgcgccac tgtgtgtggc tggtatttta tttataattt cagtgtctac 76080
atggtcattg ctaagctttc ttttctctgt tgaattgctt ttacatctgg gtcaaaaatc 76140
agttgggcgt atttgtatgg acatggtcat aggccctctg tttctttcca ttgctctacc 76200
tgtctgtctt tctgccagta cctcacagtc ttgattaccg aaattatgtc ataagtctca 76260
aaaataagat aggctgattc ctctcatttt gtctgttgtt tttcaaaatt gtttttattc 76320
ttgtgaatcc tttccctatc taaatgttag aataatctct atttctacaa aaaaaaaaaa 76380
aaaaaaaaaa agtcttgcta ggctttcaat gggaattgtg taaaacttgt ttacctatgt 76440
ggggagaatt tactatgttg agtcttccaa cccattaaca tggtcagtct tgccatttgt 76500
ttatatcttc tttgatttct ttcatgaatg ttttgtagtt ttcaacatac aacttctgca 76560
tatgttttgt cagtttgaca cctaggggca tttttgagtg actgtaaatg gtactggtgt 76620
ttgtttgttt gtttttgaga cagggtcttt gtccctgagg ctggagtgca gtggcatgat 76680
cgtggctcac tacagcctca acctcccaag ctcaagcaat cctcccacct cagcctcctg 76740
agtagctgga accacaggca catgccacca cgcctggcta tttttttttt tttttttttt 76800
ttttgtagag atggagatct ctctttgttc cccaggctgg tctcaaactc ctgggctcaa 76860
gcaaccctcc aacctcgacc tcccaaagtg ctgggattac aggcatgtgc cactatgtgt 76920
ggctggtatt ttatttataa tttcagtgtc tacatgatca ttgctagtat atacaattgt 76980
agtaaataca attgaatttt gtatgctttc caccctgcaa acttgctaaa ctcgcttctt 77040
agttctagga gggttgtgtt tttttgttgt tgttgtttgt agattcattg gggttttcta 77100
tgtagacaac atgtcattgg caaacaagga cagttttctt tcttcctttc taatctgttt 77160
gccttttatt tccttctctt gcctattgca ctggctagga ctcccagcac tatgttaatt 77220
agcagcagtg agagcagaca gctttgcctt gtgacagtct tagacaccaa gcactgagtt 77280
tttcaccatt aagtacagtt ggctcttctg tatctgtgtg ttccatatcc atatatccaa 77340
ccaaccgctg atcagaaatg ttttaaaaac aagaaaaaca atacaaatta gtaaacagta 77400
cagtatagca actctttaca taacatttac attgtattag gtattctaag taatctagag 77460
atgatgtagc gtgtacggga ggatgtgcat aggttatatg caaatactat accatcttat 77520
ataaggaatt tgagcatcct tggattttgg catccttgtg gggagtcctg gaaccaatcc 77580
ctcagagaca ccaaggaaca actgtataat attggctgta aggttatggt tgatgctttt 77640
aatcaacttg aagaagttct cctccattcc taattttatg agagttttct catgaacatg 77700
tgttgaattt tgtcagatgt tttttatgaa ttagttaata tgatcatgta atttttcttc 77760
tttagcctgt tgattggaga ctacattgat tggttcccaa atattgagcc aaccttatat 77820
ccccagaata aaccccacta aatcttgata tgcaattatt tttatctatt actgaattct 77880
acttgctatt tcattagtga tttttgtatc tatattcatg agggatgttg gcatgtagtt 77940
ttctttttgt tgtttttcct tgtctgcatt tggtatcagg gtaataccaa cttcataaaa 78000
tgaatggggc ccaggtgcag tggctcacac ctgtaatccc agcactttgg gaggccaagg 78060
caggcagatc acttgaggcc aggagttcaa gaccagcctg gctaacatgc taaaaccccg 78120
gctctactaa aaatacaaaa aattagcctg gcttagtggc gggcacctat aatcccagct 78180
actcaggagg ctgaggcaga gaatcacttg agcccaggag gcggaggctg cagagagctg 78240
ggatcatacc actgcactcc agcttggggg acagagtgag actcagtctc aaaaaaaaaa 78300
aaaaaaaaga atggtagtgt tccctcctct tctgttttct tgaagatatt gttagaatca 78360
tgttgacttt ttaaacattt ggtagaattc tctataaatg tttagaacca tcttggcctg 78420
gacatttcgt tttggggagt ttttaaatta caaattgact tttgctatag gttgtttaaa 78480
ttacctgttt gatattgaat gagttgtagt acctcatgct tctctaggag ttggtccatt 78540
ttattgaaga tgtcagagtt atgtgtgtag aggcatttgt agtgttcccg tattatcctt 78600
ttgatgtctg cagggtctgt agtgatgttc cctctttcat tcctgatatt gacagtctgt 78660
gtcttccctc taattgtttc tttgtcagtc ttgctagaag tttgacaatt tcttattttc 78720
aaatacctag ctctgttttg ttgattttct gcattgtttt tctgttttct gttaccggga 78780
tttctattcc cctatctttg tgatttccct ccttccttcc tttgctatca ttgtgggttt 78840
actttgctct tcttttcctg ggtgctcatg gtgggatctt ggcttattga gttgagattt 78900
ttcctctctt caaatgaaag cccatagtgc tataaatttc cctctcagca ttgctttagt 78960
catgtcccac agctaagttt tgtgttgtat tttcattttt attgagttca atgtcttttt 79020
aattttccct tgagacttcc tctttgaccc ttaagttatt tagaagtgtg ttgttaagtt 79080
tccacgtgtt tggagatttg tctgctatct ttctgttatt gatttctact ttgatcctcg 79140
tgtggtcaga ggacatgctc tgtatagcct cagttccttt agattgggtg agatttcctg 79200
tatagcccag gatatggtca atcttggtac atgctctgta ggtgcctgaa atgaacatag 79260
cactctgctg ctgttgggtg aagtggtctg taaatattca tcatttgatg gacttctaaa 79320
tttatctcaa gactctgaga tcatttactc tcaaaggtta tgtgatacgc taccttttcc 79380
agacaattcc taagtgatct aaacccctgc tgagttcacc aagtggcctg taaaacccta 79440
tgatgattct tgttgatggg agccatcttc ccccactagt aggtgtgggc ctttcttaag 79500
gtgagggcct tgagctcgca ccagttcaac ctatggctgt atgaaaattt tctggctgac 79560
atttttacgc ttgtaccttc aagaaatata acaaaacatc atttttcttc ttcttatcaa 79620
gtcatagaat gctaaaggca gcgggaatct agggtgatct ggtctaccct ctcgtttgac 79680
aggtgaagca atgaggtgtt gcgaagttaa actgattagt tttttttaat tttttaaatg 79740
aaattaatat acgttaatta tagaaaatgc ataagaaaaa ggggaaatgc ataagataga 79800
gggaagcaaa catttttaaa taaaatttat ataaaactta taaccaaaga tgactactat 79860
ttttattttg gagtatactc tcccaatatg ttttcaaaag caggatcact ctctatgact 79920
gctttaaaat cttttttttg tactttaaca acagacatga acatttttca aaatattatt 79980
tctaatagca aaatatcatt ccagatatat gtctgatgat acagttttct catcatttat 80040

```
ttaatgagtc tccattgggt gggcgtgcag gttgtgacag ttttctctgt gttaaataac  80100
actgtgatga atatcttttg tgtacatgca tgatgatttc ctagaaatgg gaccctgggt  80160
cagtgcttgt gaacattttt agcttctgag ccccattgcc aagttggatt cttgaaattt  80220
tttgtttgtt tgggcagctt tggttttgtt tttttgtttt cttttgagat ggagtttcgc  80280
tcttgttccc caggctggag tgcaatggca cgatctcagc tcaccgcaac ctctgcctcc  80340
caggttcaag tgattctcct gcctcagcct cccgagtacc tgggattaca ggcatgcacc  80400
accatgcctg gctaattttg tattttttag tagagacggg gtttctccat gttggtcagg  80460
ctggtctcga actcccgacc tcaggtgatc tgcctgcctc ggcctcccaa agtgctggga  80520
ttacaggcgt gagccactgc gcccagcgca gctttggttt tatttgtttt gtttatagtg  80580
gagggttaga catgaaatca acatagaaga tgacgtaaac ttatgactaa gcctggtgtg  80640
ggctctcggt gttctggggc atgagctaga ggatggctgg agccaggtag agaccgctcc  80700
cttccttaga atgtcacctt gctgacaagg acagcgctgt gagcatccac accttcctgt  80760
gaggtatctg gcattgagcc tggtcaggaa acaggaagac aagcaggttc cattgagcct  80820
gggacctgga ccttgtaaag ccagccaccc agcccagttt tacaggccag gcaacaaagg  80880
gagcaaccgg ctggacccag gcctgcctcc cccgtgcaga cccgccgtga gaacaccgtg  80940
ttctgaattg agacgtgcct tgcactcact ttgtcccagt aattgccccc ataaaataga  81000
cctggacact aagaggaaac ttcccatatt tggaaaccca gtcctgcctg ctttttatag  81060
ctggtgtcga ggacaagaga accacaagcc gtggccagtc tgctgagaga ccactgaggg  81120
acagacgggt tgtgggcctg gagcagcccc ggagggaagg agcatttgaa agtggacagg  81180
tagagcccag gcccagagag ccccagggct gctaccagga aggccagcgc atccctccag  81240
gtaacgggca gctcctcggc cacagcctcc accccccaac acgtgggatt cgggctgcaa  81300
tggcctacac atcttttcct cttgtccgtg ttccatctgt ctttcttctt tggtttgtag  81360
agagagaaga attaatccag agcgtgctgg cgcaggttgc agagcagttc tcaaggtaca  81420
gagtcttcta aacttacaac cagccagaga tgggcacatc tttctctaag agcgagggca  81480
ggccccaggc tctgaggctg gccttggccg gcaagcgtgg ctgtctcacc tgcctggagg  81540
agctgcccgc acggtggaag ccttctgtgg cttctgtaac taagccagct tggatggggc  81600
ccaggaaacg ctcaccttag accaaagacc atgttgagtg ggtgcattag aatgtgagct  81660
cgtgaggtcg agaatgttct ccaccggctc ttctgggatg ggagaacaag ctataagaat  81720
tggctccact ggaaaataag cttcctcgct gagcttctgt gtagttagga gacttccttt  81780
tcatcggagt catcccaaca atcctgacct ggataccgta ttttccattt ctcaaactga  81840
cttctctgtg gcgtcttact gcccaggtta attaaaatag tgaaaagcac agacgggtgg  81900
gattttttaa aaacctttga attggccggg tgcggtggct cacgcctgta atcccagcac  81960
tttgggaggc ggaggcgggc agatcacctg aggtcgggag ttcaagacca gcctgaccaa  82020
catggagaaa ccccgtctct acgaaaaata caaaattagc cgggcgtggt ggcacatgcc  82080
tgtaatccca gctacccggg aggctgaggc aggagaatca cttgaacccg ggaggtggag  82140
gttgccgtga gccgagatca cgccactgca ctccagcctg ggcaagagtg acactctgtc  82200
tcaaaaaaca aaacaaaaca aaaaaacctt tgaattgttt aactgactgg gttggagcct  82260
ccagagagca caacaggtcc tccgaaggtg tctgtgccca tcaggggaag gtgcggggac  82320
tggaccatct caactgcatg agcagagaga gggccatgtg tccaccccag agagcttggg  82380
```

-continued

```
tccactgctc aggcccgaag aagtaaatat gcccaaccag cccagaaaat acacctcatg  82440
atactttggt gattctttcc tccccatggg acatgatgat ttctgaaaag caagtcctag  82500
catgttggca cctcagaccc tcaccagccc acctagaggc cttgcccatg cccacagcag  82560
ggactcagta ggtgtttgct taaccggttt tggctctgag aattttaagg gtcatattta  82620
ctctctcttt tctttttcat tcctagagca ttcaaaatca atgaactgaa agctgaagtt  82680
gcaaatcact tggctgtcct agagaaacgc gtggaatgtg agtgacgttt ctgtttcctt  82740
tttgcttctc tgtcctttaa cctctattca aattaaccac ttggaacggg gaggagttca  82800
gtgccgaagg taaatacaaa taaatgtctt ttctttgtga aatacttgaa aattaccttt  82860
gatgttaaca aaggctagca cagtgactaa ctaagcattt tatttctatt ttaaaagaag  82920
cacagctcat ggtataaagc attctttcag ccccaaagaa taaaaatgaa cacacgaagc  82980
cttccgcact tagcccctct gagaacctct gctgagtgtc ttgtctgtgt ctttttgtgt  83040
gtaaatgaag acattctctg cacactgatc ggcaccctgt gggtcataat tttttggaat  83100
atgtctacta agttgttatc tcttggtttc tgatacagtc tggatgtccc ctccacatct  83160
cacgttgaaa tgtcattcgc aatgttggag gtggggctgg tgggaggtgt ttgggtcacc  83220
aggcagatgc ctcctaaatg gcttggtgct ctccttgaga tagtgagttc tcgcaagatc  83280
tggttgttta aaagcacgtg gcatctctct accctcctgc ttctccgttg ccttccacca  83340
tgattggagg cttctcgagg cctccccaag agccaagcag atgccggcac caggcttcct  83400
gtaaagccca cagaactggg agccaatcaa acctcttttg cttataaatt gcccagcctc  83460
aggtatctct ttatagcaac agaagaacag cctactacag cctccaatca ccaccaaagg  83520
aaaagcagaa aaaggactag ggagccaagg agtgtcgatt caagtcctga ttcaatgatc  83580
acaaagctca aattctggga agaaaacagc ttcaagtcac ccaccctttt tgtcctcatc  83640
cataatatca agatcaatgc ttgaattcca taggcctcac aattctgtgt tccactcaca  83700
gcttgacaag tgaactcttt gtcaatgaca aggcaaaggt taatgattaa caggcactgt  83760
atttaccaac ttaggaacta aataaacaga atccagacag gataccatta agagttgcag  83820
catcaccaaa aatatctggc tgattgactg aatgtcgtcg cttttctttt tcttttttg  83880
agagacagag tcttgctctg ttgtccaggc tggagtgcaa tagcacaatc ttggctcaat  83940
gcaaccttcg cctcctgggt tcaagtgatt ctcctgaaac atgatttaca tagtcagatt  84000
tatacttttc aaagtgtgtt gacatttcta aaaatgtatg tggtcactgg atcttcaaga  84060
cagtttcatt ttccccattg tcaacgagga agccacagag aggttaggta acctcaagtt  84120
cactcagcaa attagaaaaa taaataaagc tgggactggc acccagggtc ctggccgggc  84180
tgctgtcacg gcctgctacc tgcccttctg gaacgagtca cttccctgca cacctggctg  84240
aagaggacca ggcactccat gaggattcct tgataacgca ggttagaaag ctaaagctgc  84300
aagcaacaga aactgatcgt ggctgctttc aacagaaaag gagtttttcc ctaaaggatt  84360
ttgggaagct tccccagatc cccaggaagg cttgggaaca gggctcagag gttgtgcagc  84420
agcaacaatt ccccaaatcc cgtgcagagc tgatgctgtg cggatgcctg tgctgccgtc  84480
tctgagcccc agatgcggca ccagctcccc tgtactcctc actctggacc taggtccccc  84540
ggaggctcca caaccactta tgcagatatc aggctgcttc tccatgtcac tggctacagg  84600
ttcaaaatct agacagagcc aggccgcgca cccaaggtct agctgcaagg caggccccac  84660
gaagggaggc tgtgagtatc ctgaagctgc ctcacaaagc accacagact gggaggctta  84720
agcatcaaaa actgactctt tcacagctct gcaggccaga agtcagaaat caaggcatga  84780
```

gcatgactgg ctatttctgg aggctctgag gggccctggt tccatgcctg tctcctagaa 84840
ccttgtggtt cccagcaatc cttaccgttc ctgagcttgg aaggctacat tgctataatc 84900
tctgcctgtg tctacacgtg atgacattct cccaggatgt ctccatgtca acagtctctc 84960
tcagctaggt cttataaaga tgcctctctt tgaatttagg gcccaaccta aatccaggat 85020
gggcccatct ccagatccct aatggattat atctgccaag gacctttttc tacataaggt 85080
cccattcaca agttccaggg agtaggttgt gaacagatct ttctggagga cacaattcaa 85140
cccaccacag cgagtgtttg catttccata ttctgcactg ggaggctggc tcagctctcc 85200
accaagcccc atgtcgcagg gaattctcca aacttgggta ggggtttgag ccaaagcatg 85260
caaaaaaggc ttgctgcaga gtccccaccc ctctttacgg acacaaaaag ccacgcagtc 85320
actacggggc gagtgtgcag atgcccgcgg gcagcaggtg cctcccacct ctcctcctct 85380
ctccagcacc tgggtttttc ctcagccttc cccatctcct acgccccacc tggaagccag 85440
tgccagctcc ccccatgctc ttcccggaaa gtgcaaacag gcaagttgaa gaggccatgt 85500
cgtaactctc aaaactctta cagagaatta tgtcgcccac aacaagatga atagtaaccc 85560
tgtgtgtctt tgaataactg accctggaaa ataaccatca agccagaaga aaagtgttcc 85620
tattttacct gcaagtggca ggtgagtcga agaccactga aggaaatggc ccataggacc 85680
ttccccccta gcctgttctg gctgcggaat tctccaaaat ttctcacttc tcagagggaa 85740
gcatcttccc ataaaaccct cagtaaatgc acatagatgg cctggaaaag gacaccgctc 85800
ttgacccacc gagctcaggc tcactgcact gaccaaaatt cctggcgctt ctatgggtaa 85860
aaccggttgt gactagttgt actgatttct agcaccagag acctaggact gcagaaatgg 85920
gattgaggga gctcacctct ctaaggagta gagaaggagg aacagtctag gagttgtgga 85980
gggtaaggga ggggcttggg tgaggtcagg ggggactctc ctcagtcctc ctggctgccc 86040
tcctcccctg gcatgcaact cacaccccca ccccaggagg cagccatgtc cagacaggct 86100
gtcctcctcc tgaactccac ctggctttgg gctcatcctc cccgggcact tctggctgat 86160
ggctccccac tctccagcgg atgtgcttta gcgggaggtg gccaggatgc tgcacctgtg 86220
ctgagcccca gagattctga gttccagaga cactacaagg gcagcagagc cttaacccaa 86280
agatgcaaga gcccagacat tttaggaagc ttggagggca gaaacggaaa gtcctttga 86340
ggagagggcc tgcagctgaa cctctcacgc aggccactgg gtaggtgcgc gcccagcttc 86400
tcagaaggtc agtcccaacc ctgcacggct gccagaagct agccagatgg ggaaggcggc 86460
caggagcctg gtccgacacc ccgatgcaca gggcctgggc cagaggcaga tgctcccatc 86520
tacatatgca cacacacata taaacacaaa cagagaaagg tgcacatgca ctcacatata 86580
cacatgtgaa atcacacagg catgtcagga tgtcacatat acatgcacac gtgtaagcac 86640
ccaggcacgt gcagatacat tcatatatat gatcacatac ccacacatgc gcacacacag 86700
ctgcttctgc tatacatgag ctgctgtgag ctgttttgtt ttgtcttgtc ttgtttttgt 86760
tgttgtttga gacggagttt tgctctttgg cccaggctag agagaagtgg cgtgatcttg 86820
gctcactgca acctctgccc cccgaagaca ggacacttct gtctcagcct cccaagtagc 86880
tgggattata gctgcccgcc accatgtccg gctaattttt gtatttttag tagagatggg 86940
gttccgccat gttggccagg ctggtctcga actcctgacc tcaggtgatc gacccgcctc 87000
ggcctcccaa agtgctgaga ttacaggcgt gagccattgt gcccggccaa gctgttttct 87060
gcctcttgag ttaaaggatt catccactag aactggccac cttaaggcca tattatattg 87120

-continued

```
tggtggactt gtcttaaatg gaatttcctg cttcttctta aatgtataat tcctctgaat  87180
tgaatataaa tttcttcatt tctcctcatt gactttcaaa gctcttcttc cttttgatat  87240
acaaagttta gccttgttcg agagatctgg gatttccctt acgttacgga ttattttgta  87300
aacagaacac ccaggctcct cccctcatgt cctggctgga ggtgaaacat taaaaagaga  87360
ttttaaagca gggcccttta ctcccttcct tcctggtttg tggccagggc acagggcagc  87420
tctgctccat ccaccctttg tccctgtgct ctgggcttgg accaaaacct aaacacagcg  87480
tgggccgtgg caggagctga ccggctgggg caaagtttaa cacaggccat acaaacagcc  87540
cagagcctgg atgctagaac caagccttgc ttttctctgt cactccggaa gtgtgctcta  87600
cgcgggctct ttagtgaggc tcctggagga agtgttgaaa cacaactcta ttcatacatg  87660
tctttaaaca gctttcacta gctctgtagc caaaggactg ggcctgccag gttcccggcc  87720
tcttgctgga gcacagtgag gctggggaag gagcacagca cagagcctcc tgagcctcgg  87780
ctcagctctc cccgaccccc agctcggctc tccccaccct ccggctcggc tctctctgac  87840
ccccagctca gctcttcccc acctgccagg acgatttccc caaagccagc gtctgtcaga  87900
aaatcaccct tagtttttcc tgcaggtggc ctgtgacttg tagaagctca caaaaatctc  87960
tttcaaagcc ctttttttgtt gctgttttgt tttgttttga gacagagtct cactttaatg  88020
cagtggagtg cagtggtgtg atcttggccc actgcaacct ccacctcccg ggttcaagtg  88080
attctcccgc ctcagccccc agagtagctg gaattacagg cagcctgtga ccacgcctgg  88140
ctaatttttg tatttttagt ggagacgggg tttcattatg ttggctggac aagctggtct  88200
caaactcctg acctcaggtg atccacctgc cttggcctcc caaagtgctg ggattatagg  88260
catgagccac tgcgcccggc ctacagtcct tttaagagga cagcccgggg tttccagata  88320
atactagccc cacacacagg catgtcctag ggtccacacc tggtcagcgg gaataacagg  88380
cagccgtggg ctgggctccc agccccctag cagggtccag tgggccaggg agcctctgct  88440
ttggtttgtg gtgcgtggtc tgtgcccgcc tgtgttcagc gtttgaaggc agaggagcgg  88500
gccatgatgg gcagagccga cgtccaggct ccacggtagg gccgtcctgc tgctgtctgc  88560
agacctctca ggcttgaggc cccccgcccc acaggactgg cccgctcctc cctctggatt  88620
gaggtggagc agggctggca gtgggtcgaa gaggggagct gtggaatctt ccccaaagca  88680
gccgggtgtc ctggaaaggc cagggagtga ggaggcagga cccccgggga cacaggcaca  88740
cacatccacc acatgctcac ctctgcctcc tcctgcagac ctccccgcca gccccgtcat  88800
ttcatggcat cttgctttct cttcattgag gaatgcactt ttgcaatgtt gttactcact  88860
atccatctac ttggccaaca gcctcttcat aaacttaatt gccacaaatt ctgcatctct  88920
gggatgcaaa ctagtgaagc tgtgctgtgt cacccaggag gcttaatttt aacatcacct  88980
caataggtag ccagggaagc ggatctcggt ggactctgca ctgtcaatac aaacgctatg  89040
cacccatcaa aaaccatgag ctggcttaaa acagagcctt gtatggacat gggaaaaaaa  89100
ttataggttt gttgcaaact catttagcag caaaaatgtg atctgaactg acatgaagcc  89160
cttggtattt atttatcctg ctcagtatga taaatagcat tttcctcggg ggataaaaag  89220
aaaaacgtga gctgcgacag cagccactaa catggggaag ggccgtgacc tcctgatgag  89280
tgaaaatagc aagttagaaa acaacaaatt ttatctttta aaattaataa tagatatata  89340
gatacataga cacacacagg atggatagaa gctagataga tacatacata catagataca  89400
tacatagata gatactatat agatatgtaa atagaaagat aggtagaggc tgggtgcagt  89460
ggctcatgcc taaagtggtt ccccagcact ttgggaggtg aaggcaggag gattgcttta  89520
```

gcccaggagt tcaagaccat cctgggcaac atggcaaaac cccatctcta caaaaaatac 89580
aaaaattagc caggtgtggc ggtgcacccc tttagaccct gttattcagg aggctgaagt 89640
ggcaggatca cttgaaccta ggaggtaaag gttgcagtga gctgtgattg ttccactgca 89700
ctccagcctg ggtgacaggg caagcccctg tctcaaaaaa aaaaaaagaa aagaaaagaa 89760
agataggtag atacatagaa tgggtggata gagagataga acggatagaa aaataggatg 89820
gataaataga acataggtag atacataaat atgatgaatg catagatgga tgggtggatg 89880
gatggatgga tggatggatg gatggatgga tggatgaatg gatacataga tgaatggatg 89940
gatagatagt atataaatgg atggatggat agatacacag taggtaggta ggtagtagat 90000
agatagatag atagatagat agatagatag atagatagat aaacaggata gatagataga 90060
tagatagata gatagataga tagatagata aacaggatga atatttagaa ggctgggagt 90120
gggcagaaag cctggaagga cacacattaa tacaaataat attaactgag ttgttttctg 90180
ggcccatagg atcctagaca agtttttaaa tattattctt tgaagtgcta tttcctacac 90240
ttcctacaat gataatagga tattttatat tcagaaaaat gacatttaag acatagtcaa 90300
tggtccatgg accttggaca gagggcccag ctgccctgtt tgcagtctac accgcatgcc 90360
caacccttcc ccagatctac tcactttcag aatgtgctgc cttccacgtg tgaaccagac 90420
tgagctcctt tctgccactg atgttgaatt gtccatttgc tcacgtcagt gtccacgtgg 90480
caaatccaca gggcatgggt gggatcctgc agtctagaca aagccaagga gcaccgctgg 90540
aggccacgtt gggcttccca atccacatgc aaacccaaaa tgtgttcttg ggtacctttt 90600
ctgagaagac agcctgtggc atgcatcagc ttccttgagg ggcccatgat gctggagaaa 90660
acggagaccc ggctccaaag gagaatgtgg actcttagtg gttggacaaa gacgtcccga 90720
cctcagacct caggtaccct gtgtttcccc agcggcagct catctggact cggccatcac 90780
gacagcgacc acactggctc cagccacatg cacttccgga ccccatgtcc tctagctgtt 90840
gggtagaaga ggggtggaga aggtttctgt agcacagaaa cacatcagca ggaccagatc 90900
caaatattgc actctccaga ttcttcgtcc ttctggcaga aagaagcagt gtcccgggaa 90960
catgcccccta cttgacccct gaccctggaa acgcctcgaa acccacccgg gaggctgatt 91020
ccagctagtc tgccctgggc cactgtactg ggagagtttc tttccggagc tgcagtactt 91080
cctttggggt gggaaggagt tgttacaaac tagccaaagg ctctgagttg cttggttttt 91140
cctttagaaa acatttgctt tttattttta gcagttattc agagccaaac ttcatgaaaa 91200
ggggaataga gtggtatcgt gggagtatcc ttttgcataa aaactaaggt gtgattacaa 91260
agtaacaaag ctaatctttt ttatttcaat tggtttatga accaactcta attgaaaagc 91320
cgtgcaaagc tgcttgcttc atggcagctt ttctggggta aacgtgcagt cagccaaggg 91380
taaatatctt gaagtttaac gctcgctcgg aggcataagc tccagtttgt ttttggttga 91440
aaaatagtat cctaactgtt gaggtacacc tttgcagtgg gactctgtaa ctgcccaagg 91500
ggttcaccct gcctgctacc taaacagagc tcattcatca agacagggga actgcaatgg 91560
agaaagagcc attcacccag tgccggctgt gcgggagacc agagttttat tattcctcaa 91620
atcagtctcc ccgagcattc ggggcgcaga gtttttaagg ataacttagt gggtggtggg 91680
aagccagtga gccaggaatg ctgattgatt ggtcagggag gaaatcatag ggagttgaag 91740
ctgtctgctt tttttttttt tttttttttt ttttgagaca gagtctcact ctgtccccca 91800
ggccagagta cagtggcgtg atctcggctc actgcaacct ccgcctcccg ggttcaagct 91860
attctcctgc ctcagcctcc cgagtagctg ggactacagg cactggcaca ccatgcccgg 91920
ctaatttttg tatttttagt agagacaggg tttcactata ttggccaggc tggtcttgaa 91980
ctcctgacct cgtgatctgc ccacctcagc ctcccaaagt gctgggatta caggcgtgag 92040
ccactgtgcc tggctgcagc tgtcttcttg cactgagtca gttcctgact ggggccagaa 92100
gaccagacga gccagtttat ctatctgggt ggtgccagct gatccatcaa ctgcagggtc 92160
tccaaaatat ctcaagcgct gatcttagga gcaatttagg gagggtcaga atctcgtagt 92220
ctccagctgc gtgactctta aactgtaatt tctaatcctg tggctgttag tctcgtcccc 92280
aggcaagaag caggtctgct ttgggaaagg gctgttacag tctttgtcta aactataaac 92340
tacaaatgaa gtttctccca aagttagttc agccaaggaa tgaacacaga cagcttggag 92400
gttcgaagca agatggagcc cgctaagtta gatctctttc actgtctcag tcataatttg 92460
gccaaggcag tttcaactcc aggaatgtga tcaagtccaa gttctgctga tcctcaactt 92520
tgcctattta tttctcttct gttttaagtc aacactttct cctggtgaaa ctgctctgga 92580
aggacgttcc aatgaaaagc ttttcccata atgagatcgt aatccttgct gaaaacgctt 92640
tgccgttcac tgcattttaa tgctctggca ccacatgtgc cccctttct ttttgggata 92700
aaagacgcct ttgtcccatg tcctcagctg gtgcttaggg gtatggagca aaaagtgggt 92760
gccagagttg agattcaggg agtggagagt ggggaggagc ttctgccttc tgaaaactgc 92820
ccggatggat gcggtagtgc agcggtggcc acggcacatg cctgcgagga tagagtcagt 92880
tgtggctgag ctaagcgcgg aagtgcaggc aaaacctgag tatcggcagc cagggcaggt 92940
gtggggacct ctgcactgag gtatattcct ccctgggagc cacagggagc ccttagttac 93000
cagccttgag agatcctcca cattcgtccg tggtaacccc cttgctgtct ctctctctgt 93060
caccagtgga aggactaaaa gtggtggaga ttgagaaatg caagagtgac attaagaaga 93120
tgagggagga gctggcggcc agaagcagca ggtagggtct gcgctggggc cacgggcggc 93180
cgggcctggg gagggctccc cgtaccagtt gggctggggc tgtgggcttt gtttgcctaa 93240
aagaaaggct ggtgcagttc ggtacagttc aggcttggga gagtgcagtc tggaggcagc 93300
caccctgctt gcgacctgct tgtcagtggt gtgactttct tctaacaaaa gagcacgcat 93360
gggccgggtg tggtggctca cgcctgtaat cccagcactt tgggaggccg aggtgggagg 93420
atcacctgag gacaggagtt caataccggc ttggccaaca tggtgaaacc ccgtctctac 93480
taaaaataca aacggtagcc aggcatggtg gcacatgcct gtaaccccag ctacttggga 93540
agctgaggcg ggagaatcgc ttgaacccag gaggtggagg ttgcagtgag ccgagatcgc 93600
gccactgcac tccagcctgg gctcgacaga gcaagactct gtctcaagaa aaaaagagca 93660
catattggag ataggggctg ggaagacgat ttcacagaag aagagtcctc ctcctgcaga 93720
tccaagcctt aggagcaatg tgtccagctt ggaataagtt gatatccact tttaaagaca 93780
gaacaagaag aggaaaagca ttaggggagg agcctcctgt tgccccccagg gacccggttc 93840
cttgtgtgat gttcccactg ggttgcattc cagcgagggc ttcagcactg gggacacaga 93900
agtcattctc ctgggaacag gcatccttca caggcgcttc ggggggccca gtgagctgtg 93960
actcgtgggg aaaatgcccc agtctccacg atgccacctc caaagtcagt tttgtgtaca 94020
gcaggactct ttactggagc cagggtcagg acacgtgtgg atgaaccacg accaaactgg 94080
ggatggaaat gccggtagta gcaaagagac ggcggtgatg atgagcagag cgcatgcatt 94140
gaggcactta ctgtgtgcgg gcgctgtgct tagtgagggg cacacaggac ctgctcacac 94200
ctccgggctt tgcctccatg cccgctggtg ccagcccaga caccacaggc atatgatgtg 94260
gctcatggtt ccccagagtg ccactgcccg gcctcagtgg gatttaatgg ggactaatgg 94320
actgagaaac agccctgtgc aattgcactg agttgtctca gagccacctg gcatgctgac 94380
gatcattccc tgattttgaa attgagggca atctgcttat tgaggaagcg tggcaagtga 94440
aagggtctca gaggcagaag gtgaagggaa agccgacggg cctcatctgg tcccctcaaa 94500
gccccggggg cctggcctcg gggtgggcgc agggaggaag gccgagcgga aggaagcagg 94560
ccttgtctga gccacgtgag agcctgtcct acagggaccg tgccacgtgt ctgtcccatg 94620
cactcatggg ctcatttgga gttagggatg tctcagccca attgacttag gggaagtcag 94680
gccatagttt gtggccatgg aaagttgtga gtgaacaatc catcttcgtc atccctgtgc 94740
tggaggctct ttaaaggacg ggagacagag tctctcattt gtgagccaag gaagagctcc 94800
caagttgcac agggacggcc acacagctgg ggtcccaagg ctgggacctg gcaaggctgg 94860
gacccggctt ggcagcctca gacacacagc accttcacct gtggcaccgc ccttggccgt 94920
gggctctacg tggcttggtt cagccctctg gctgtccctt gcgccccagg tgccatggct 94980
gctttggcag gagggtggtg ttccagggtg gtgctgcctg gcagggttcc cctctgccca 95040
gagccaggcg gagatgggtg gcctcaagct ggggctgcgg gtgtagcagg gccagccttt 95100
ccagccccac cagcagcacg aggggaagag gacaaaaact gagttctagt cttcagcctg 95160
aaaccagact ccctgaacag cggcctctgg gccccatatg ggttggggaa ctccaccgcc 95220
ccaaggggtg tgtctggagc caggccatgc ctcccgaagc tgcccccagc tcctcaccca 95280
caactgtgtg tccctgagca ctttctggag gtgtttgtag gatgcagcct cttatccctt 95340
aaacgactgc atttaccgcc cacctacagc agcaggagtg agtggtgaga cagcctccgg 95400
cctcacaggt cttgcctctg ccgtgcctga tgggcacccg ctctgtagaa agcaaggcga 95460
gtgctcggat cacacgccgc tcctggcgtg gtttctggtg tgcactagtc ctgcaggtca 95520
ggttgaggtt gcaggggggga agattatttt tatcgaagtt gtagtcattt cctggggctg 95580
cgtaacgaat tctcataaac tgggcagctt aaaacaatag aaatgtattc ccacatagtt 95640
ctggaggcca caagtccaaa atcaaggtgc cagcaggccc tgccacctct gaaggcccca 95700
ggggagggac cttcccggtc tctcttggcc tctggtggct gccggcggca ttctctgcct 95760
gcttcttcac ctggtgctcc catccgttct gtccaaattc cccctttttg taaggacacc 95820
catcctattg gagtaggggt caccctcctc caggatgaca tccccttaac tacatctgca 95880
acagtcatgt ccccaaatga ggtcaccctc agaggcagca gggttaggac ttcaacatac 95940
aacttttggg gggagatgta cttcagccca taacacacca cgtgggagga taacaccgat 96000
ttcagagctt gcagaggaag ccgccaggaa ctccagtgag acatcagccc ccaggtgcct 96060
gtcaggcacg ccgggctgtg gggggcacct gggcccatct gagtaacgga ggcgcatccg 96120
cacttccccc aggagtacat ttttagaacc cacagcgcca taaaccaaag acaaggagac 96180
ttcctggtgc cccgtcagct tctggaggcg acgttctcgg ctgacagctc tggcagcctc 96240
ccctgtaggt gagagacagg taaatgggac tcttgcttcc aaaacggaac agggtaaaaa 96300
ttctcaagcg ttgtcgacac attgagaaaa aacaaatcca gcctcctggg ctctggtctc 96360
atccccagcc gcgtcatgtg ccccaggccg gcgttgccac acatgaaacc ccttcctgtt 96420
tttctatgta gaaaggaact cagaatagag acactgagat attcgtgttg tccctttttgt 96480
ctttgtcaac agcagagtta catcttactc atgagagccc tgtagcaatg tggggaccct 96540
gggaccagtc tcagttaagc tggaacttcc ccggatgact ggggagagga gctgcaaaag 96600

-continued gcagggtggg ggtggggggc cttcccgaga tggcagccca gccagaggcc agcgttcttg 96660
cctctgggaa gagaataaag gccccagaca gggtggagct agctcagccc cgtgccacac 96720
aaatggccag tgtgagcctg aaatgtggag ctacattcag cccacatagc acaccctggt 96780
ggggcctcgg agccaggggt atggatccac cagaagctgc cccttgggaa cagcagtggc 96840
atcggggtcc ggcacacagc acccgggagc aggtggccgt cccctgacac tcacgggcta 96900
ggtttctcct gcttttccct caaagaggac agaggtccaa ctgccagctt acatttaggg 96960
caggggcagg ggcaggtcta ccccaggggc cacggccact ctggccccca gcactgtgcc 97020
aggcagagag cagagcatgg aatatggggt tcacccagag ctggggagtc tgcaggagcc 97080
tggggtggca actgagggct cagcgttcat cccaaacaaa tggccttgcc cactggccta 97140
agccccagag aagggggatg gggaccccag gaaatgaaag caaagataag ctccaaatag 97200
gatgaaaaga aagagctcca tgccagctgc tctgtttgct gaagacgctg gttcccgtgg 97260
cagcggagcg cagagagagg ggctgcctgg ccaggcaggg tcagcgggcc ccagcagacc 97320
ctcctctgct cccagctctg gtatctgcaa ggaaacagcg ggattcgaac agtcaaactg 97380
tcttgctcgg tgaagatttc cataaccctc ctggggaatg caggagactt acagagacag 97440
cacatgtgcg aatgtttaca caaaacaggt taaaagcagc gaagaaatca tcatcatgcc 97500
atctattttt tttaactacg cagaaaacgt tcgttacttc tcagaaatgt gtaaatggaa 97560
tttctcgttt aatggatgac aatggaaatc atttgattgg tgcattttgt tggttggttt 97620
tgttaatact ttgctgaatc tgttagcgtt ccccccttaca catcaaactg tggtagcaac 97680
tctgatgggt tttgcaagca tgaaacagag ggaagggcta ccaaatggat ctccgtggag 97740
cggtggttat cacggggaag agacggcagc atgccgagaa aataacaccg aagcctcttt 97800
ttccagaaag gaaatagatt gattattcta gttttgaaaa tagcacaggc tcattggaaa 97860
acctccaaac tacactgatg ggagctgaag ggtgcacacc gatcatgaca acagccggca 97920
atgtcccccc agtttaaacc tggacacgag gccttctaga tgtttttctg tgcatagata 97980
ccttgttttg aaaaacaact aaaacatgcg ttgtgtagtc ttttttttta ctagtggcat 98040
tgtgagcaat aaatagatta aattttaacc agcgtacagc tcatagattt tcccagaagg 98100
ccacaatcaa gcactctttt taaacctacc gaatgtgctc tttcttcctc gtagcgtggc 98160
attttttggc acttgctttc agtacatact gtgcatagca ttcttatttt ccctttttcat 98220
gtcaagtttc ctcacttggc ataatatccg tgatgatcct cctaatggca taatagtcca 98280
tcatgcggag gcactgtgct ggtttaaacc gcttcccgtc ttgggacatt caggtggctt 98340
ctagtcggtt ttgtgttttt gttacagcag atcacaccac ggtgaatatc tgtgtgcata 98400
gagctgtttg ttcctgttta attcttggct taagataaat tccccaggat agatatgtgg 98460
gcttaaagga tacgaatttc tatatggctc ttactgggca gtattaactt gctctcccag 98520
aagaaggggc tttatttaca aatcgcagga gcttctgctg catttagctc cctgagtgcc 98580
cccatagcct ggtgaatgtc acacaagcca ggcgtgaccc ccacccacca tcgtccaagt 98640
acacagggag cctgttcact tccaagcaag ttcacaccca tagggtgtga acccagatcg 98700
gcccagcccc ctggtgcact ctgctgcagg ggcccaagag cagccagacc tcctggggca 98760
gctgctcctc attcagcctc tggggaccac cctgaagcca gcacactgcc caaccggaag 98820
gtggctttcc tctgaaacat gcctggctca ctttgccctg ctcctatgtg ggatacctcg 98880
ataccaagtg ctaaacaaaa acagagtcag acagaaaact catctgctaa cattacatgt 98940
aacagggaaa gttggaaaca ttctaaaagt ccatcactgg ggactggatt gctaacgtgt 99000
gctatggcca caccctggag aaacttggaa aatgaagcta agctctgtgg agcaacttgg 99060
gatgagttca tgatatgtta gatgacaaag caggttgcag cagactgact ttggtgcaat 99120
tccatctttg tttaaaagta caaaggggct gggcgcagtg gctcacgcct gtaatcccaa 99180
cactttggga ggccaaggca ggtggatcgc ttgaagtcag gagttcacga ccagcctggc 99240
caacatggtg aaaccccgtc tctactaaaa gtacaaaaat tagtcaggtg tggcagcatg 99300
cacctgtaat cccagctact caggaggctg aagcacgaga attgcttaaa cccaggaggc 99360
agaggttgcg gtgagcaaag attgcgccac tgcactccag cctgggcaac agagtgagac 99420
tctgtctcaa aaataaataa ataaataaaa attttaaaaa gtacaaaggg gcggggtgca 99480
gtgactcaca cctgtcatcc caatactttg ggaggctgag gcagaaggat cgtttgaacc 99540
taggagttca agaccagcct gggtaacata gcaagaccct atctctacaa aaaataaaaa 99600
ttaaaatatt gttaaaaggt aaaagcggcc acccatgtgt gtccacactt caaaacattc 99660
tggaaagata caccaaacta ttagaagtga tttccagagt atgggattta gggaaataaa 99720
tgggtaaagt gaggacttcg gttttcatat tttggtgttt tttttttac tttactcttg 99780
tgttgtttag atttttaga atgtttttct tttgaaaaca gcttctaaaa gagaagatag 99840
ccctcaacat ctgacttttt tttcttttt ttttgagatg gagtttcgct cttgttgccc 99900
agactggcca ggctggcgtg cagtggcaca atctctgctc actgcaacct ccgcctcctg 99960
ggttcaagcg attctcctgc cttagcctcc cgagtagctg ggactacagg cacacgccac 100020
cacgcccagc taatttttgt attattatta ttttttaat agagatgagg tttcaccatg 100080
ttggccagga tggtctcgat ctcctgacct catgatcatc ccgcctcgac ttcccaaagt 100140
gctgggattg caggcatgag ccaccacgcc cagccccaac atctgacttt ctgtgtgttt 100200
tccaagagtc tagtgtgagg tcagaggtca gacaggtcat cagggatttt gcttcgagtg 100260
agttgctgct gccctgactc ctctcccaca gcaaataaga ccacacgggg cttgggggtt 100320
gggtttgtcg cttgcttttg ctgtgctgag ggcttcacca gactgaaaca gcaggaccac 100380
agctcatctc tgctccttct ctctaggacc aactgcccct gtaagtacag ttttttggat 100440
aaccacaaga agttgactcc tcgacgcgat gttcccactt accccaaggt aagatgagat 100500
tccggcccag aagaagctgc agctgtgtcc ccagccccac gcccagccct gtggccctgc 100560
ggccagaccc tgctgtgtgt acgttcacat caaccgcccc tcccagccct gggccgctga 100620
cggtgcgggt tactttaagg caaagtattt tttctctttg acatttgttt agcaaaagtg 100680
atcccagacc ataccttccc ctgcaaggac ataacagctc cgtgctgctg tctgcccggc 100740
cccgggagct gacctgggta gacagttttt acactcaaac gttactggaa agaactttaa 100800
cgtttaactg aatttttaaa aatccattcc attggccctt gtctctgagc aattcttagt 100860
tgtcctggca agttttgctc ttttgcacaa aagtgttctt agttctaaga gaagctgtga 100920
cgttggtgaa gtagcaatgg catttttgaa ataacgacaa aaggagggtc tcgagttgcc 100980
ggtcacccgc tcaacgcctt cagctgggaa gcaggcaaaa tcccggccca cctgcttttt 101040
tttttttttt ttttgagaca gtgtttcact cttgttgccc aggctggagt gcaatggcac 101100
aatcttggct cactgcaacc tctgcctcct gggttcaagc aattctccta cctcagcctc 101160
ccaagtaggg ggcattacag gtgcccgtca ccatgcccag ttaatttttt tgtatttttt 101220
tagtagagac agggtttcac catgttggcc aggctggtct tgaacttgtg acctcaggtg 101280
atccgcctgc ctcggcctcc caaagtgctg agccaccgca cccggcccgg cccacctgat 101340
ttgtaatgtg ctctcatgct aagattcagg gggcacagct tccagagaca gcagaggcct 101400
gggctaaaca caggtgggct ctgccactgc ctgcggttca agtgatggca gagccttcca 101460
cagcctccat gtaggccact ggtgtccatt agtccgtgat tctatccacg cagttccaaa 101520
caatgtcctg gatattgtca ggttctgggt ggatttgggg ggtttttgtt tttttctttt 101580
gatactgagt ctcactctgt cacccaggct ggagtgcaat ggcatgatct cagctcactg 101640
caacctctgc ctcttgggtt caagtgattc tcctgcctca gcctgagtag gtgggattac 101700
aggcacccac cgccatgccc ggctaattac tgtattttta gtagagacgg tgtttcaccg 101760
tgttggccag gttggtcttg aactcctgac ctcaggtgat ccacccacct cagcatccca 101820
aagtgctggg attacaggcg taagccagcc cagcctcatc tgagattttt gaatggagac 101880
tagtgccttt ttccattgga aaatatgccc cgcgcttctc aggatcctgt cccagggagc 101940
cgtgaagcac agcctagatc caaaataaaa ggtgtcagcc ctccagatct gtccccttac 102000
aaaaaacaga aaaacaaata tccagtaaga cctaggagaa gacagtgtgc aataccaaag 102060
cagtgttctt gtcttctgta tagaaccaca gccttctgtc cttgtgacag cttaacctaa 102120
agcctgatgt cctcagaagc aacccagggg caccggcccc atcagcaggc ctgctcttct 102180
agctctcggc agaaaccagg aatgggttcc agacaggagc atctcagaat aacttcttag 102240
gtggtatctg aatttatgcc aagtgaattt tacccccaca cttcacttta ttgccctttt 102300
tttattatta tttttgagat ggagtctcac tctgtcgccc aggctggtgt gcagtggcac 102360
gatcttggct cactgcaacc tcccccctcct gggttcaagc aattctccca cctcaggctc 102420
ccaagtagct gggattacag gcacctgcca tcatgcctgg ctaatttttg tatttttgta 102480
gagtcgggat tccaccatgt ttgccaggtt ggtcttgaac tcctgacctc aggtgatccg 102540
ctcgcctcgg cttcccaaag cactgggatt acaagcatga gccaccatgc ccagctattg 102600
tccattttat catcgggctt gttgaggtct aatttacatg cagtaaagtt atttaggctt 102660
ggagtacagt gaattttgac aaacttgttt agtcctgtga cctccaccac aagcgagata 102720
tggaacattt ctgtcacccc aaaccctccc ctctgctccc tcaccctgcc tctggcatcc 102780
accgatggga tctccacccg tagcattggc cctttccaga agtatgtggc ctgtgagtct 102840
gacgcaggtg ccttagaaag agaacgggag aagctgggtg cggtggctca cacctgtaat 102900
cccaacactt ggggaggcca aggcgggtgg atcacctgag gtcaggagtt cgagaccagc 102960
ctggccaaca tcgtgaactc cccatctcta ctaaaattac aaaaattagc caggcatggt 103020
ggcgggcgcc tgcagtccca gctactcagg aggctgaggc acgagaatca cttgaaccca 103080
ggaggcagag gttgccgtga gccaagatcg caccactgca ctccagcgtg ggcaagagtg 103140
agactctatc tcaaaaaaaa aaaaaaaaag aaagaaagaa aaagaaagag aacgggagaa 103200
agaggagaaa tatctcagca tgcacatcac tgtcacaggc ccacggcgcc tggttaacac 103260
ggaactcctg tcctttctag tacctgctct ctccagagac catcgaggcc ctgcggaagc 103320
cgacctttga cgtctggctt tgggagccca atgaggtaag tgcggggctt gcaggcacca 103380
cgtcccaggg ggaggcagct caggatcttg gacgccagtg ggaccacccc catcgctctt 103440
cctccttctt gctttttcct cttcttttta aagactgaaa aaaaaaaaca aaacttgttt 103500
tgccaggttt tagttgaaac taactaacac tttatagcag ggcccaggag acttcacagc 103560
aaggggattc tgtgagtggg ggagacggct gtcaggggca gggaggctcc acccagggct 103620
cctgatggcg ctgggccccc cgagccatct gctcatcctg cagaccctca tgcacgccgg 103680
tggcagcccc gtgctgcaga acacccctgc caggagcaaa tctctcctca aggaaggggc 103740
tgcggtcaga gtgctctgct ctgagagcag tgtctgcaaa ggcaaggcac aggcaaccgg 103800
ctgccccaga taagtggaca tgtgggattc cgggaactgt gtcaccttct gcagcaaggc 103860
ttgaggccag gaattccaca ctagcctgag tgatatgatt tggctgtgtc cccacccaaa 103920
tctcaccctg aattgtcata atccccacgt gtcaagggca gggccaggtg gagatcttga 103980
atcatggggg cagttttccc catactgttc tcgtgatagt gagtaagtct cacgagatct 104040
gatggtttta taaatggggg attgtctttt gcctgccgcc atttaagtga ctttctcctt 104100
ctctgccatt ctccatgatt gtgaggcctc cgcagccatg tggaactgtg agtcccttaa 104160
gactcttttt ctttataagt tacccagtct caggtatgtc tttattaaca gtgtgagaac 104220
agactaataa gctgggcaac atagcaagac ctcgtcgcta caaaaaaaag gtgttaaaat 104280
tcctatttgc tgaaaaatac aagaatgggg aattttttgt ttcatctcat tggctaatag 104340
accccctctt ttcacacccc aaaaaatgaa aaagttccct cattgcagac ctcggcctca 104400
gctgttttca acgcaccaaa atctaaggac gttttcctgc ttgtcagcaa cacagaaaat 104460
gcacaaggct cctcagcaag ctcacctgtg ctctttgaca agctcggccg cagcgatgtc 104520
tctgcaaagg gcagaaagtg ggctcttgcc tcttggcacc cctgaggcca ggctgctgac 104580
acctggggca ctgccctctc ctaagtgaac ctcttttcat gtgcatggtc tcccagcagg 104640
agaaaaactg cagcaccagc cagaaaagca aagctccagc ctccactccc cagctcagtt 104700
cacccaagag cagcaggcgg ccagtcccag gggctgcact gctgcaaacc tgctcaaaac 104760
ctccagccgc cacgtggcaa cttgctcccc agctctgaga gtgcaggacc ggggcgcaga 104820
gacgacagaa gaggctttaa atatgcagaa tgactgtcta ggtcaacgca caaaaggaaa 104880
gggccccagg tgtgggagat gcaaggggtg agagggaaag ctcagaagag acgtgttgga 104940
gctgctggcc tgcagcagct cccagggtcc ctgcacagct gctgagattg ggcagagcaa 105000
gtacacagca agtagacacc gcagacagtt agagcacact gactcctgct cccagcctgt 105060
gggcaaccgc cgcacctcag catcatgtag aaaaatcacc atccccaaag tcattttgac 105120
ctcagcctgc tgggaggaag agccaagcca ggggccactg atggcaaagc acctgcgtgg 105180
aaactggcac tcgctgtctt ttctgccacc ttctaccagg gaaccctttg agcacgggcc 105240
actgtgactg gggaggtggg gcttgcccca cgaagctggg ggatctgtgt ctccataata 105300
gaaaggccac ctctctgtcc tctgatcaca gagtggattc acagctgctc tcggggctgg 105360
caggtgggca aggcagacag ctcccggcag ctggactcag cctctgggtg gcatctccca 105420
cggcccgtgg ctcctgccca gcagatctca agggcactcc aggagaccga tgagggttcc 105480
agtgcttcca agaagtatct agctgcctgt gtgtgagaat gcagagatgc ccaagacagg 105540
agccttggcc tctggcagat ctagggatgc caggaatttt ggagtgtgag tggcaaagag 105600
ggacaactaa agggacacac atgaaaacag cccactcggc cccacaaaac tgcatctggc 105660
cacgcatgag gcacctggca ctcagagaac gtcagggcgc ctaaaagtga tcacctccct 105720
cccttccagc aggggcgccc ccacttttct ccgagtggtt tggcccagtg tcctgcccat 105780
cacaaaccag acagaggaca tgacttcagg ctgctgtgtc ctcccatgtg ttagggcctc 105840
cgagggccca gggctgtggc ccgtgagcgt ggcctgcctc tatcctccga gggcccaggg 105900
ctgtggcccg tgagcgtggc ctgcctctat cctccgaggg cccagggctg tggcccgtga 105960
gcatggcccg cctctatcaa gtgcagagct ggaaggctgc aggagcctcc cccgtcatct 106020
catgagtccc ccactcacga ccatgcagcc cactcagacc acgacctgcc gccacatgcg 106080

-continued ggaactgctg gctccctcgt gcccgcccgg ggctgaggac tgcacgtgca gccacagatg 106140
catccggccc tcctgcccca cagcctctat gaaggccaca taaatggcac caagtgtctc 106200
tgtctgccga tcagcatccc ctcttggctt cacagcagac gcatctgcct ttcaggactg 106260
ccttgaacaa catctgggct ggtcaggtgg agagcgagga gtttccaggt tgcagcccct 106320
atggtcctga gggctggcgt ccaggatggt gggggtccag cagctctggg cagcgaggcc 106380
cctggctggg tgatccaggt ggcagctgac cagtggcctg ggagccagcc ctcctgtcct 106440
cacgtggggc cccatctcca aaagccagtg cagtgccctg cacattatcc aacctacatc 106500
tgtactgtct ccccaaggaa aacgagtgtg tggttcacgt gctttaagga cgtttcccag 106560
gtgacattcc aagctcccat ctgtggccgc aagtggggga gtttccagtt ttccagatag 106620
attttctgcc atgccagaga accctccgcc tccttcagag ccatctcatc aatgcagtga 106680
tcgcaagctt cgatttacaa aaactcgcct cccttgcagc atttccaggt ttcacacaca 106740
gcgtaacaag taaaaatgga tttttgggca gcacgcctgt cctagtttgc tgaggctgcc 106800
ataacaaagt accagagact ggggtggcgt cagcagcaaa agttgattcc tcagttctgg 106860
agctggaagt ccaggatcaa ggtgctgcca ggttcggctt ctccggaggc ctcggtccct 106920
ggtctgggac cttcttgctg gggcctcggt ccctggtgtg ggaccttctt gctgggacct 106980
cggtccctgg tgtgggacct tcttcctggc cagcaagatg gccgccttct tgctgggtcc 107040
tcatgtggcc tgttctctcg gcacatgcat cccaggtgct cttcctcctc taatgaagac 107100
actagtccca tgggaccaag gcctcaccct gactagatgg aaacttcatt acctccgtaa 107160
aggccccgtc tccaaatagc cccactgggg tcggggcttt accatgttga cctggggaag 107220
ggggcagttc agttcgtaac atgccctttt gggaggagaa agtcaggcaa tgagcagaca 107280
caggcaggaa gccacgccgg gctccagcag ggatggccca gtgccctgta caggcagcag 107340
gcagctgggc tggaggtggg ccctgggtgg aggacaccta ccaggtgtgt ctaaactgcc 107400
cctttcctac acatcttcct tcgcactggg ctcgccaccc aagacctgct ttttccagaa 107460
agcaaagcct actttggtca aactctcatt tttaaaaatc acttcatctt ttcctcccta 107520
acttaattag ctccaaagca ctgagctgta ttgaaataga tcaccacaat gacaatcctc 107580
tttgggactg aaaacaaaat ctatttcaac ttgaacaggg atattgatag aagacagggc 107640
tccatgaaaa agggttagga ggagccgctt gctggggcag gggccgcatc tgggcactgc 107700
agttaagatg ttaaagtgtc ttcggtccca gggggccgca gatgaacaca gttcagcgtt 107760
tctggatgta aatcgtcaaa gctccttcga tccccagcct cgggcaagga aagggccttt 107820
ctctctgtga tgccacctgt gctcaggtgt gcactggatg gaactgtgtc ctagacccct 107880
cagctgtgat attgatccgc tgagattgtt tttcatctgt agaaatcaat aaattccttt 107940
ttggtgcagt gttttgtgaa cgggtgcact ctctcacccg gtcgctgtcc taagaattct 108000
ccttgacttc ggaactggcc ctccacgccc caggatccac ctgccaggag acccccagtg 108060
tgctctcaaa cccccaccca tctgagtggc ctggaaaggc tggtctgaag acctctcttc 108120
ccatgtctgc cgaccaggct ttgctctcca gggactttct gggaggggga gaacccacct 108180
cctgccaacg gccctgctgg cactccgagg acagcagagg gaaggaagcc aggggctggg 108240
gagccggcca cacaactgcc cagtgcctat ccttctcctg tgcccacaga tgctgagctg 108300
cctggagcac atgtaccacg acctcgggct ggtcagggac ttcagcatca accctgtcac 108360
cctcaggagg tggctggtga gtgccaaacc cgccttcggt tcttcctggg cacgtggttt 108420
catccagttc cacaggaatg gagggaatgg atcaccaggg caccttccgg atggcactgc 108480

-continued gctccctgtg agcagaggtg acatttcccc gggagttctg tgaggacact cagcctgtct 108540
ctgttcctcc ttccaccaaa accttcttta cgcccgagct actcctgctc tgataagcaa 108600
ggagtagctt atcagtgaga ctctgccatc atcaagcaaa gcagcatgtc ctaaagcagc 108660
ggtgtgtggg agcgtgtgtg tgtgtgtggg agcgtgtgtg tgtgtgagag tgagtatggg 108720
ggtgtggatg tgagtgtgtg tgagtgtggg gtgtggatgt gagcatgggg gtgtctgcat 108780
gtgtttgtga gtgggtgtgt ggatgtaaat gtgtgggagc gtgtgtgtgt gtgagtgtgg 108840
ggtgtgggtg tgagcatggg ggtatctgag tttacgggtg ggtgtgtgtg aatgtgtggt 108900
gggagtgtgt ggggtgggag taggagtgtg gaggtgtgtc tgtgtgtgtc agtgtggatg 108960
tgtgcatgtg tatatctgga tgtggggtgt gtctgtgtgt gggtgtgtgt gagggtgtgt 109020
gtgcatgtgt gtatctgtgg atgtgaggtg tgtgtgcatg tgtgtatctg gatgtggggg 109080
tgtgtgaggg tggatgtgtg catgtgtgtg tgtggatgtg gggtgtgtga gtgtgtggtg 109140
tgtgagtggg tgtgtgcatg tgggtgtctg cctgtgtgaa tatgtttggc agcaggtttt 109200
tttaatgaaa tattgctcag aaccaaatat taaaagccta ttaaaggttt catggtgact 109260
ggggacccag agctccctct tggagtctcc cctcccccca tcccctaact ttatgcccca 109320
ctgtggctcc tcagacacct ccggggagac cccagtcctt gactgcaggg tgaaacccct 109380
ggtgggagct ctgtccccac acctgccccg ggtgccgtgg tgtggcccgc tggacgttct 109440
cagggtccct gtgtcacctc attggtacct gtggtaaacc tggaacactg ttgacctctg 109500
gttgggatga gggtttggca gagaatgttc aaaccagcgc acagccttct gggtggcttt 109560
gggaggagag gtgggcgggc ccaggcacag ggtgactcgg acccccctgcc tcccgcagtt 109620 ctgcgtccac gacaactaca gaaacaaccc cttccacaac ttccggcact gcttctgcgt 109680
ggcccagatg atgtacagca tggtctggct ctgcagtctc caggtgggtc ctgcccgctg 109740
cacacccaga cctctactct cgggggtcag acggaggccc ccttccaggg agcggcagcc 109800
ccatcccacc aagagagcca caggcgtggg gtccccagcc gctccgcccc tcctagggac 109860
gcacccctgc ccaccgttgt cagtcacccc atgggcgagg ctgctcctag gattacgaga 109920
gcaggtgagt ccccgacctg gtcacccccc caaccccccac aggcaggccg atcctctccc 109980
accatgccag gagatgccag atggctgcag ggcctttgt cccccgctta ccactcaccc 110040
aattccaccc cccctcaccc catcccaccc tccgagtgaa gagagcaaac acctacgccc 110100
tgttttccaa tccaggagaa gttctcacaa acggatatcc tgatcctaat gacagcggcc 110160
atctgccacg atctggacca tcccggctac aacaacacgt atgtacagga ttttctcttt 110220
ttttcctttt aaaaggcacc ctggctactg gagggaacct gtcagcccaa ccctcagagc 110280
agttcccaga tggagctgtc aacgacggcc tcccagcccc caactctgcc tccactgaca 110340
cagctcctgg cttctggact ttgcccaggg ccttgggtct ccccggagta ggaactttca 110400
ggattatcaa accccagggg ctctttccca ctcctgtgcg ggcctggctt caggctcagg 110460
tgcacggcag atccctggcc ccgccggcgc cttctccacc ccaggcaggg agcaacacct 110520
gtccgcatgc agggatgggg gctccacacc cccctctcag gagctcgcct ctccctgggc 110580
aggctcccag ctggcttccg cagggaaagc acaggcagga gccagaagag agcagaagag 110640
ggggagaaga gggactgcag agggacagga ggtgggagtg aggtgtccct cgtggggcca 110700
gggatcagaa ggacagaccg ttgctccact cctgcctcca caggcacaga gttccgcccc 110760
atgtggcgga caaggtccag gccatgggct tgggtctgtg tcctcagtgg cgcagcagct 110820
ctctctgttg aactgtgtgt ttgtgtgatg tcatcacatg cctgagagct ctgctgccat 110880
gtgtcagcgc ctagtgggtt ccgaggtgtg gctgtcagcg ctcctcccgg ggccatcacc 110940
atgcacaccc atctgttccc cttttgctca tttcacactc acagtggccg gcacagcaca 111000
ggtcagcaga ggccttgacc acagcatccc agtgaacctc agcctcgttc tgcccacctg 111060
cctctggcac ctggtgacgt ttgataattt cacaagaggc cgtgatgcct cagggcctgt 111120
cccagggagc atgccgcttc ctcagaggtg tctgtctggt gggactgcag gagcatgggg 111180
acgtgcagtt gcaggggcag ctgagcggca ggagggacct cctggccagg ccagggcaca 111240
ggcagctccc ccagccccca cggcaccttc tcctgactct acttgctcca cttacatggc 111300
tgggtgttgc tcccccgtgc aggtacctgg tgagggcgcc tgagtctccc ctcactctct 111360
ccttgcctcc caggtaccag atcaatgccc gcacagagct ggcggtccgc tacaatgaca 111420
tctcaccgct ggagaaccac cactgcgccg tggccttcca gatcctcgcc gagcctgagt 111480
gcaacatctt ctccaacatc ccacctgatg ggttcaagca gatccgacag gtgtgtgggg 111540
tgagggccct cccaccggag tgggggcaca ttcagggaca gagcagcccc cactctccat 111600
tggctggaag ctcccagaag ctcctggcca cagcagtgcc ctggggaccc aagggaaccc 111660
ctccctcctt cctcacctcc tccagggccc agagtggagc cccaaaaaga gggtaccctc 111720
gccatgcgca cgtgcatccc actgacctgc acttcccagc ctgtatttaa ttcagccttc 111780
actggctccc tttgagataa atcctttgtc cctcttccag cccaagaaac tgaggcttag 111840
caaaggtagg gagcctgccc aaggagggga caggccctgg acagacacat ctgctgcatc 111900
caacatagga gagctgcccc ctgccccata accccagctg ctgtcacctg ccacccacag 111960
cccagtcagc ccccttcctt ttatttattt tttttcttt tgagacagag tctcgctctg 112020
ttgcccaggc tggagtgtaa tggcaggatc tcggctcact gcaacctcca cctcctgggt 112080
tcaagcaatt ctcctgcctc agcctcccaa atagctggga ttacaggcat gcgccaccaa 112140
gccggctaat tttcggtatt tttaatagag acggggtttc atcatgttgg ccaggctggt 112200
cttgaactcc agacctcagg tgatccacct gcctcgacct cccaaagtgc tgggattaca 112260
ggtgtgagcc accacgcccg gccacccctt ccattttaga taagggggct ttatgcctct 112320
cagggcgtga tgggaggaga gtgagaggat atctgcgtga gaggaagatg acctggtcca 112380
cctgccccag acaaacacct ccagctcacc gaaataacgc cccattccac acgggaattc 112440
ctcatcaaac cctcactctc tgacatttgc aggggaggga agctctcgga gtaaaccctg 112500
ggagaaatgt gttgggttga atagcagcgt ccttcaaaca aggtccacct cccgtgaatg 112560
tgatcttatt tggaaaaggg tctttgcatt tgtacttgtt aagatttcca gataagatca 112620
gtgtggattg tctaaggggg ccgtaaatcc aaagactagt gtccttggac gaggagacag 112680
agtagaaaac agcccagaca cagaggagaa ggccgcatga agacgcagtg attggagatt 112740
tgagtgatgc agccccaaac taagggactt cggggccccc aggagcagga ggagacaagg 112800
aaggaccctc ccctggagtc ttctttgaga gcagggccct gcccacactt tgatcttggt 112860
tctggcttcc agaactgtga gagaatgagt ttgttgtttt aagccgccta gtttgtggta 112920
ctttgtgtgg cggccccagg acactcaccc agggcaccgt cttctgcggt tccacaaggc 112980
agacctcagc cattcgaagt ctaagtggct tccttccaga ggcagcaaga aagactgcct 113040
ggacttcagc actgggaaga tactcaccac cctccaggcg tgctgctgag cctcccttta 113100
tcagagagca gcagcctctt ctaccatggc tttccaattt gtctacgctt ccaggaagtt 113160
caaagcccag tgtaaaaaac tgaagtcagt gaagcatttg ggaagctccc gaggaagcag 113220
catgctccct gggacggggc cctgaggcat cacggcctct tgcgaaattg tcaaatgcca 113280
ccatgtgcca gaggcagagg tgggcagaac caggctgtgg ttcattggga tgctgtggtc 113340
aaggcctctg ctggcctgtg ctgtgccagc cactgtgagt gtgaaatgag caggagaaca 113400
gatgggtgtg catggtgatg gccccgggag gagcgccgac agccgcacct cagaacccac 113460
tcggcgctga catacggcgg cagcgctctc gggcctgtga tgacatcatt gcacaaacat 113520
acacaattca atagacaatt tacagtcatt attgaatcac tggttcccag tacagttatc 113580
tccccttat ctataggctc tctggcctct cctccatgtt tgtgcccctc cccaccctgc 113640
aagcaggtgc cctgtgtggc tacgataagc tgtggcaaat cttcgtctgc agtaggtcaa 113700
ggagcaaccg tgaagagaga acgctgcatc tgccactgct accccagtgg ggagctcctc 113760
cagggacagg acctggggaa tcaaagcaag tgaacgcccc ttagtgtagg cctcgtccca 113820
ctgagccatg tcggagagca tcccgcaaga gaaggaggcg gcacctgatt ggaggagcag 113880
ccgctctgca caggggatcg ttctcgtgcc catccaccgt ggggacacac cagcattggc 113940
ctgcttcaaa tgcttcactg actgcaaaat atgactctcc tctgggggta aaattagttg 114000
tcccactttt ttaaaaatat attttgtcat ggaagatttc aggaataact gaataaatgc 114060
ttcactaata acacaattaa atgtttacag gaaaattgaa taattcaaga tacaagtgat 114120
ccccccaaaa aaatatatat atatacagtt gaaatgacct agattgatgg gtttgggttt 114180
tgtatctgat gcttgttgtt ttatttttctt ggaagaggaa aacatcatac ctggcacaga 114240
gatgtgttct gtaaatgctt gtggggtggg tgggtggatg gatggatgga tggatggatg 114300
gatggatgga tgggtggatg ggtggatgga caaatggatg gaagggtgga tggatggatg 114360
ggtggatggg tggatgaatg gacagatgga taaatgggtg gaaggatgga tggataaatg 114420
gatggaaggg cagatggatg ggtggatggg tagatggatg gaggatgaat gggtggatgg 114480
atggatgaat ggatgggttt ttgggtgggc agatggatgt gtggacaaat ggatgggtga 114540
tggatgcaca tatgaatcgg aataagagat acatgaaata atgtgtgcag ggggctcagt 114600
acacagtagg cctccgctga ataattgttc agactatacc cgtgttaaca cgttgttctc 114660
tcgctattta gggaatgatc acattaatct tggccactga catggcaaga catgcagaaa 114720
ttatggattc tttcaaagag aaaatggaga attttgacta cagcaacgag gagcacatga 114780
ccctggtgag tggcttattc tgcctgggtg ggcagccagg cggtgggctg gcgaagcagg 114840
tcatccatcc agctcacact ggaagccaag aagctgaaat tattagtctt cttggaacaa 114900
ggtgtctata aatctggttt tcaaggtcat gactcttact aggaaagtcc gggcagggcc 114960
tccctcctga tgggtcctcc ttcatggtca gaggcagcat tctcccattc ctccatctct 115020
tttggatttg aaggagataa gtgggtgaag gccgtgcatc tcgctctgct ttccagagaa 115080
taaaaccagc tctcccatga aggcacagcc ccagcatggc actctgaaag cccacctatg 115140
tgggggcaac tccaacacag ctcccgctcc ccaagccagc atcccccacc aggcccacac 115200
catagcccag cacccctcca taaccaggac aaggtggcca gagaaggggt agggggcctc 115260
ccccatgaga aggtgcactt aggttgccca gcatctgcct tttggaaagg acaggcactg 115320
ggcacaccaa ggcacacaag gaccagagca cgactcatgc ctggaatcca gcactttggg 115380
aggccacggc aggaggattg cttgagtcca aaagtttgag accagtctga gcaatattag 115440
caagactcca tctccacaaa aaaagaaaga aaaataaaaa aatcagtgca tatctgtggt 115500
cccaactgct tgggaggcag aggtgggagg atcgctggag cccaggtcca ggctgcagtg 115560
agccatggtc gttccactgc actccagcct gggcaacaga gcaagggtct gtctcagata 115620
acagagagag agagaggtgc atgagaactg ccctcccggc cttcagagag aaagctggtt 115680
ttgtggagcc ttgtctaagc atcaggtgca cccctggcat tcttactctg aaatttgatt 115740
atctgtttaa aatcaatagc atcactttcc acctccagag aggttgaaag atagggaact 115800
ctcggctcag gctgaccttc taaccatcca gtcccagtag gtagagtcat taggactcat 115860
cgctctctgg agctgaggtg cagttaattc ccaaagactg tgcgagagga tgggagctcc 115920
cgcaggcaag ggctggacag caggcaaacc tccccaggcc agggccacca gaagcccctt 115980
ccctaagagg gaaacagtca catagagcgg cttcctggca agcaagtttc ttgctcctga 116040
aaaaccaagg gaaggaggga ggcgccgcct tgtcctctaa gatatgagga aggcagagat 116100
ggacctgcag tcaggggtga cccaggcccc gccgatgcct tcctcctctg aggtgggagg 116160
agaggtcagg gaagagacgg ggaggggcag gatgccagag gatcgggtgc caggtggtca 116220
ggacaagtga acccagctga aggtccccac tcccacccca cccccagcct tacacactgc 116280
agctgtgcag accagaggca aagcgaggct cagagcccag ggttccgttt atcccaacga 116340
cctgcaccgc ggggtcagat gacaagcagc acggccaggc atcgtctcac tgctacggag 116400
ccccagacgg ggctttatga acacgggtgg aggacagagg ttggggtaag gtctcggggg 116460
aaaggttctg attcaaaatg ggccccaata gggaggcctc tgaggatagt gcgggccagc 116520
gtgggaggtg tgaggtgcag ggagtgtggc cggcagggcc tgggaccttg accttcccca 116580
gagacactgc tgccctggcc ctgccctagg tctggtgtcg ggacagctcc actgaggccg 116640
gccaggcaca ggctagtcat tgcctctgat ctggagccgg actccacaga ggagtcaaag 116700
aaaggcctga atggcttcct gggaactgat agggcaggga aaggaagggc gaccacagca 116760
ggatcccttc gaggtcctgc cgaggttgga aggcaggatc caccaagcat catgcagact 116820
ccgagctgaa ctgagctgct cctcacctag tcacgttccc caaaccagca ggtgcagccc 116880
gcagcccggg ggcatgtgcc tcagctgggc tttcctgtct aatcagcttc agagcctgga 116940
tggcaaccaa cactttggtc tggaaacctg gtgattccag acactcattt gtgcccggtg 117000
caggcagggc cacgggacgc cagccctcca cctcttgtcc tatggcgaca tccgggctag 117060
tttgggtgga agctgctgca ttcctgggcc tgccctatct cctcctgaag ctcctatggc 117120
atgcccaacc ctggccaagc tgagacagag ctacctgtcc cctgggaaga tgagcaatgc 117180
acccacctag ggaacagcag aaaatagggg gtgaccaggc acagggcagt gcttcagggg 117240
atatcacctg ggctggggtg gccagaaagg ctggaaggag gggacccaaa caggaccttg 117300
aaggttcatt ctccattgag aagggagcct gtcctccctg aaggcagcca agctcagttg 117360
catggtccag caggtcctcc gtctcttcct gcctgtaatg gcaagtccag acccgagcag 117420
cagcagcagg cccgtgttct acctcctgtt acctcaattc caaaatctct tctttcagct 117480
gaagatgatt ttgataaaat gctgtgatat ctctaacgag gtccgtccaa tggaagtcgc 117540
agagccttgg gtggactgtt tattagagga atattttatg caggtaagag tcttgcagag 117600
caatcaagcc tccagccact cttattagcc ccacttagta agggtttgcg ttaaacgagc 117660
acgcctgggt ggtcccgcat attccccggg ctgccgacag ttcagcctcc agaaagcctt 117720
cagggtaagc gtacatcaga aacaaaatag gttataattt gagacctgaa agacagtaac 117780
aatccagaaa agctaatact ctaaaactgt cacctgtcac tgctaattga gccattatta 117840
caagcagcct tgtcaaacaa attgcctgaa agtcaagaag caaggactgc agaagcagga 117900
gggggcccag gagggccgag acccagcagg tcagctcaca cagatggcca cggggaaggt 117960
cggggacata gaaaaccaag ccagctgaaa acaaccacca aatattaata caacagcttg 118020
atgaacccta ggagaagtcg ggaggctttc tgcaggacgc tgctgccgtc ctgggataca 118080
tccatccaac tcacctctgc ctatctctca ggtcggtctt cccagctaga cctgcacgcc 118140
cagctctgtt tagcactgaa gatagggtca ccttctcctt gttcttactg agacacattt 118200
gtggtgtggt ttggttggtt ggtggttaac tggcgcatct tgtctttctc tgagaacagc 118260
gatctggtta tggggcattt ctgtctctaa tgtcactgtc tgctgcattc cctgcagagc 118320
gaccgtgaga agtcagaagg ccttcctgtg gcaccgttca tggaccgaga caaagtgacc 118380
aaggccacag cccagattgg gttcatcaag tttgtcctga tcccaatgtt tgaaacagtg 118440
accaaggtga gtaactgtca ccacatgtca cacttgctta cactcagata catgcatgca 118500
cacacaggca cacacacata tacacatatg cacacaggta cacacagaca cacactcatg 118560
cacacacgta cacagataca cacagacgca catacaggca catacacata tacacacacg 118620
cacacagcta cacacaggca cacacacagg cacacacttg tgcacacagg tacacaggca 118680
cacaaatgca cacacacggc acacacaggc acacactcgt gcacacacat gtacacaggc 118740
acacacaggc acacaaatgt gcatgcaggt acacatgcac acaaggcacg caggtacaca 118800
tgcacacaag gcacacaggc acacacaggc acacaaatgc acacacaggc acacacacac 118860
acacacatgc acacaggtac acacaggcac acaaatgcac atgcaggtac acatgcacac 118920
acaggcacac acagggacac acaggcacac ataggcacac aaatgcacac acaggcacac 118980
acatacacac atgcacacag gtacacgcag gcacacacgt acagaggcac acacatgcac 119040
acacaggtat gcacatgcac gcacacaggt acacacaggc acacctgcac acctgcacat 119100
cctgagcagc ctcttccccg gctgtcgtgg tgaccgctgt ccctgttcca tccagagcct 119160
gctccccaca gcctggcccg tgaccccagc atctcccact ctgtgctgca ctccctgcct 119220
tgccttgctg ggccctgggg ggcccctcac tgccctcacc catcgctgcc ggccttcagg 119280
accctggagg cagcactggc tgtggactct cctgtcccca ctctgcgtcc cagttcctca 119340
cctgtggagg aacccctgag ctctgtgccc tcgagctgtg aagcccctgt ccagctccca 119400
gtctcaccgc acccagccac cgagaccttg ctccttgcac acagctcgtt cctgcccagc 119460
tccccccagg gcctctgagc tgcctgtggc cccctgccaa ggccccccacc tcaaggcacc 119520
cccagcatgt ccaaaacagg cccatctctt gttccccccg gggatctggg ctcacagcct 119580
cacaccctcc gaccttcctg ggctcctacg ctgcgcatcc ttctgctcta gggcatctct 119640
tggagccaac ccacccactt cccactccca ggaccctcag ccgggaggct gtcagctcct 119700
ttcccctgcc ccgtgtcttt gtaagaacct cccaacctgt cccccaccct catctcacgg 119760
gcacggggga cacaggaggc aggaagggga ctttctgtag gacctcatgg agggtgatga 119820
gggccagaga cagagccgca gtgggtggag gcagcagagc cggcacgagg gtgtccagga 119880
gctgggactg gcccagaggt ttccgcacgg agcacctgac acctgttttt ctccgacgtt 119940
tcccattgcc ttaagaacga gggactctga ataaatccgt gtgtctctcc cagctcttcc 120000
ccatggttga ggagatcatg ctgcagccac tttgggaatc ccgagatcgc tacgaggagc 120060
tgaagcggat agatgacgcc atgaaagagg taaaacacac tgagaagagc ctgccttcct 120120
tgcggcaagc aggcacgctg ccctccgcac tcccgactcc agaagcttgg acgtgccaag 120180
cagggcacca ctgaaggccc cgtggacagg cacacgtgta ccttccatca gaaagcctgg 120240
ctcagtaaaa ttagggaatg cgatgaggga aaccaaaact gcattcgcca agaacacgtc 120300
aggtctcagt accttcgagg gagtttactg gccgtgccct tcacaagaat cacaactgtc 120360
acccacacct gtggacaccc aggtgtcttt gggtgtatca gccgccgtta gagcatctgg 120420
gacccctcag agtacagtgc ctggcctggc cccagggctg acttgttcag aggaggccat 120480
ggggtagaaa ggggccctcc cctggcacgg ggacaaagcg accacccacc tgccagctcc 120540
cgggcccaga acacacaccg gcacctctca ggggccaggg agcctggggc tggctttagg 120600
ttgctgctgg atagatatca ttttggagga aggggtccag gtcacagcct cagggcccac 120660
gcagtctttc tacggattcc ccacggctgt ctgctgtcct gctgcccatg gtgtggcctc 120720
tgcccctccc agcctcctgc ctcctccctc cagcgccccc aggcagctag aacagtctta 120780
ctactcctgc agggtttgac ccctcctggc cttggccggt gttgcctctg ccacccccgc 120840
tccccacagt gccactgaag caccctccaa ggcccgtcag tcagggctcc cctagttact 120900
gtgcccacca ccccgtcttt tctgcctggg cgctcctgaa gcccatgtgg cccacaatgc 120960
ccttttgagc actgagccat tttccaggcg tagccttggg ttggtctcat ctccctcgac 121020
tgacggcccc gtgctcccca tgcccacacc cgcctggagc gccatgccag gcacatggta 121080
ggcgctcagc aattgcttag gagtccactg aaaatccaga ccagctgccc tgacttctcc 121140
agttgatgtc tcctactgga aagtcacaga aaggtctcta aacctctgga aggctgagag 121200
cacttatgca gagggacaga tgtagcaaga aggcttcccc cactccacaa ccccgcaaga 121260
gagctgaagg ggcttctgcc tctctcgtgg gccctccgag agccatagcc ctgatggcct 121320
tgagtctcta gtcctgagcc ctgctgccca gtaggggata gtagggttcc ttaaggcctc 121380
tgccttcccc cctgtcagcc cccacaaaaa ggagagacac gccaaagagg tgaaaaggcc 121440
aagcccaagc cgcaggctct gcacacacca ccagtccccg cggctgtggt ggctgcagct 121500
gggtgagctc actgtccagg ccccagatga ggcaccaagg gtagcgggac agggtatgca 121560
gagctgcctc tgaaaagccc atgtcaggag tgcttgggct cagaggggct ggggaccaca 121620
ggctttcacg ttgcagcacc tccaggcaac agaagctgct gggagagagg cagacactcc 121680
cctgctgtct cctgctccct gacttggcct tctctgtact ctgttccagt tacagaagaa 121740
gactgacagc ttgacgtctg gggccaccga gaagtccaga gagagaagca gagatgtgaa 121800
aaacagtgaa ggtaatgctt gctctgctga agtggcatct cagcgcatac aatgattctg 121860
acaaaggaca gaaggaaaga ggaaggggag aaaatctgaa ttttggaata cctttaaatg 121920
aatggaactt tttttttttt tgaaactaag tctcgctctt gttgcccagg ttggagtgcg 121980
atggcacgat ctcagctcac tacaacctct gtctcctgag ttcaagtgat tctcctgcct 122040
cagcccccta agtagctggg attacaggca tgagccacca tgcctggcta gtttttctat 122100
ttttagtaga gatggggttt caccatgttg gccaggctgg tcttgaactc ctgacctcag 122160
gtgatccacc cacctcggcc tcccaaagtg ctgggattac aggtgtgaga ttgcgcctga 122220
ccaaatgaat ggaaatttta tttcttgcaa ctaatcatta gaattaggct cttaaggctg 122280
gtggctcatg cctgcaatcc cagcactttg ggaggccaag gtgggcggat cacttgaggt 122340
caggagttca agacccagct tggccaacat ggtgaaaccc tgtctctact aaaaatacaa 122400
aaattagcca ggtgttgtgg cgtgcacctg tagtcccagc tacttgggag gctgaggcag 122460
gagagtcact tgaacctggg aggtggaggt tgcagtgagc ccacattgcg ccactgccct 122520
ccagcctgga gaacagtgag actccatctc aaaaaaaaaa aaaaaaaaaa gtgaggctct 122580
taaagaaggg gaacatgctt tagttaatag aaaaacatca ataattagca tatgtatcac 122640
ttataagagt aagtactttt taaaagtgca attgaagtac tgaaaacttt tcacaaatca 122700

```
cgtgtttgct ttatatggct ttgagcattt tcctctgtac ttgttgatac tagtcattca 122760
gctcacgggg aatgcagagc agccgtttgt tcacctcata ataaggtcac actaatggcc 122820
aggcacggtg gctcacgcct gtaatccaag cactttggga ggccaaggcg gcggatcacg 122880
aggagatcga gaccatcctg gctaacacgg tgaaaccccg tctctacttt aaacacaaaa 122940
aattagccgg gcgtggtggc gggtgcctgt agtcccagct acttgagagg ctgaggcagg 123000
agaatggagt gaacccagga ggcggagatt gccgtgagcc aagatcgcgc cactgcactc 123060
cagcctgggc aacagagcga gacttcgtct caaaaaataa aaataaataa ataagccggg 123120
cgcagtggct catgcctgta gtcccagcac tttgggaggc caaggtggac ggatcacaag 123180
gtcaggagat cgagaccatc ctggctaaca cggtgaaacc cttctctact aaaaatacaa 123240
aaaaaattag ccgggcgtgg tggtgggtgc ctgtattccc agctactcgg gaggctgagg 123300
cggagcttgc agtgagccaa gatcgtgcca ctgcactcca gcctgggtga cagagcgaga 123360
ctctgtctca aaaaaaatat aaataaataa gtaaataata aataaggtca gactccatct 123420
caaaaaaata taaataaata aataaacaat aaataaggtc acactctcca tgtctaacag 123480
ataattcaag agatagtgca tcaagcatgc aaggctcagg gcaggacaaa cgggacatgg 123540
ctcataagag gagctgcaac aggctttggc atccaacaca cctggttttg agtccaggct 123600
tgccaattac aagccgagag atgtgcacaa gtgtcccagc ctctctgaac ctcagagccc 123660
cagtctctaa gccagaggca ataataccat tgttactgct gttttagtga ttaaacagtc 123720
aaagtgcttg tctggtcccg atgaagtgct cagtcaatgt tgccatttaa tttttaagtc 123780
agttcatatt tttcagtggg tcagaaaaga gatcaatatt gttttacttt gtctaaatgt 123840
gttcagcaat atatctgatg gcctctttct tttaaaatgg tctgtgtgtc ggccgggcac 123900
ggtggttcac acctgtaatc ccagaacttt gggaggctga ggtgggcaga tcacttgagg 123960
tcaggagttc taaaccagcc tggccaacat ggtgaaaccc catctctact aaaaacacaa 124020
aaattagcca gctgtagtgg cgtgcacctg taatcccagc tacttgggag ccagaggcag 124080
gagaattgct tgaacccagg aggcggaggt tgcagtgagc cgagatcacg ccactgcacc 124140
ccaacctggg caacagagca agactccatc tcaaaaaaaa aaaaaaaagt ctgtgtataa 124200
tcctgtaacg tttctgcgac tgctggcact tttttttttc cttcttttgt gagacggagt 124260
ctcgctctgt tgcccaggct ggagtgcagt ggtgcaatct cggctcactg caatctccac 124320
ctcccgggtt caagcaattc tcctgtctca gcctcccgag tagctgggat tacaggtgtg 124380
tgccaccacg cctggctaat tttctattt ttagtagaga cagggtttca ccatgttggt 124440
cagcctggtc tcgaactcct gacctcgtga tccacccacc ttggtctctc aaagtgctgg 124500
gattaaaggt gtgagccacc gcgccctaat tctaacaaaa acaaatcagt catcgtttcc 124560
cttcttccag gagactgtgc ctgaggaaag cggggggcgt ggctgcagtt ctggacgggc 124620
tggccgagct gcgcgggatc cttgtgcagg gaagagctgc cctgggcacc tggcaccaca 124680
agaccatgtt ttctaagaac cattttgttc actgatacaa aaaaaaaaaa aggaattcat 124740
gatgctgtac agaattttat ttttaaactg tcttttaaat aatatattct tatacggaaa 124800
tgggtactgt acttcttctt tggtagagtt gtgtatgctg cttccggtaa gttctctcat 124860
ggagacgaag gacactgtgc ttttccccca gatgtatctt agagcaattg accagtgtga 124920
tgcggtgcgt acgtccctgt aaattcagca ttaaatgtca gcacggtgcc ctgagtgcaa 124980
ggacatgcac gggtcctgtg                                             125000
```

```
<210> SEQ ID NO 45
<211> LENGTH: 19
<212> TYPE: DNA
<213> ORGANISM: Homo sapiens

<400> SEQUENCE: 45

gcagagcgac cgtgagaag                                             19


<210> SEQ ID NO 46
<211> LENGTH: 24
<212> TYPE: DNA
<213> ORGANISM: Homo sapiens

<400> SEQUENCE: 46

aggacaaact tgatgaaccc aatc                                       24


<210> SEQ ID NO 47
<211> LENGTH: 34
<212> TYPE: DNA
<213> ORGANISM: Homo sapiens

<400> SEQUENCE: 47

cctgtggcac cgttcatgga ccgagactca cagg                            34


<210> SEQ ID NO 48
<211> LENGTH: 20
<212> TYPE: DNA
<213> ORGANISM: Homo sapiens

<400> SEQUENCE: 48

gcagcatgag aagtccaaga                                            20


<210> SEQ ID NO 49
<211> LENGTH: 20
<212> TYPE: DNA
<213> ORGANISM: Homo sapiens

<400> SEQUENCE: 49

tgtatgtgcc accgtgaaac                                            20


<210> SEQ ID NO 50
<211> LENGTH: 36
<212> TYPE: DNA
<213> ORGANISM: Homo sapiens

<400> SEQUENCE: 50

tcggtttctc ccaagctctc tccagtgata aaccga                          36
```